(12) United States Patent
Salvati et al.

(10) Patent No.: US 7,432,267 B2
(45) Date of Patent: Oct. 7, 2008

(54) FUSED CYCLIC MODULATORS OF NUCLEAR HORMONE RECEPTOR FUNCTION

(75) Inventors: Mark E. Salvati, Lawrenceville, NJ (US); James Aaron Balog, Lambertville, NJ (US); Weifang Shan, Princeton, NJ (US); Sören Giese, New Hope, PA (US); Lalgudi S. Harikrishnan, Princeton, NJ (US)

(73) Assignee: Bristol-Myers Squibb Comapny, Princeton, NJ (US)

( * ) Notice: Subject to any disclaimer, the term of this patent is extended or adjusted under 35 U.S.C. 154(b) by 370 days.

(21) Appl. No.: 11/168,223

(22) Filed: Jun. 28, 2005

(65) Prior Publication Data

US 2005/0282813 A1    Dec. 22, 2005

Related U.S. Application Data

(60) Division of application No. 10/322,306, filed on Dec. 18, 2002, now Pat. No. 7,001,911, which is a continuation-in-part of application No. 10/025,233, filed on Dec. 19, 2001, now abandoned, which is a continuation-in-part of application No. 09/885,798, filed on Jun. 20, 2001, now abandoned, and a continuation-in-part of application No. 09/885,827, filed on Jun. 20, 2001, now Pat. No. 6,960,474.

(60) Provisional application No. 60/284,617, filed on Apr. 18, 2001, provisional application No. 60/284,438, filed on Apr. 18, 2001, provisional application No. 60/214,392, filed on Jun. 28, 2000.

(51) Int. Cl.
*C07D 487/08*  (2006.01)
*A61K 31/498*  (2006.01)

(52) U.S. Cl. .................. 514/250; 544/346
(58) Field of Classification Search ........... 544/346; 514/250
See application file for complete search history.

(56) References Cited

U.S. PATENT DOCUMENTS 3,261,845 A   7/1966   Bockstahler
3,343,940 A   9/1967   Popoff et al.

(Continued)

FOREIGN PATENT DOCUMENTS

AU    A-16993-83    1/1984

(Continued)

OTHER PUBLICATIONS

Matsumoto et al. Reproductive Medicine and Biology 2007; 6: 11-17.*

Kucharczyk et al., J. Med. Chem., vol. 36, pp. 1654-1661, 1993.
Ben-Ishai et al., Tetrahedron, vol. 27, pp. 3119-3127, 1971.
Krow et al, Tetrahedron, vol. 30, p. 2977-2981 (1974).
Kucharczyk et al., J. Med. Chem., vol. 36, p. 1645-1661 (1993).
Ben-Ishai et al., Tetrahedron, vol. 27, p. 3119-3127 (1971).
Vincent et al., Tetrahedron Letters, vol. 33, No. 48, p. 7369-7372 (1992).

(Continued)

*Primary Examiner*—Kahsay T Habte
(74) *Attorney, Agent, or Firm*—Gary D. Greenblatt; Anastasia P. Winslow

(57) ABSTRACT

Disclosed are compounds having the formula (I):

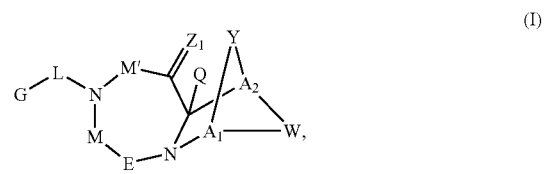

Figure 1:
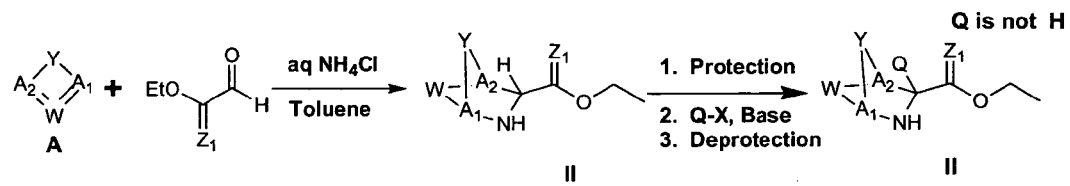

including compounds of formulae (Ia) and (Ib):

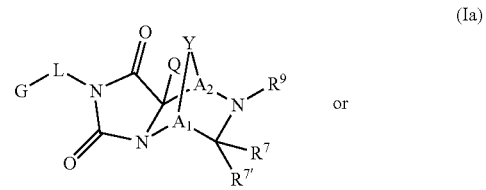

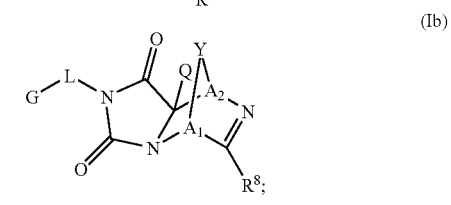

wherein G is an optionally substituted aryl or heterocyclo, L is an optional linker, M is a bond, O, $CR^7R^{7'}$ or $NR^{10}$, and M' is a bond or $NR^{10}$, with the proviso that at least one of M or M' must be a bond; E is $C=Z_2$, $CR^7CR^{7'}$, $SO_2$, $P=OR^2$, or $P=OOR^2$; $Z_1$ is O, S, NH, or $NR^6$; $A_1$ is $CR^7$ or N; $A_2$ is $CR^7$ or N; Y is J-J'-J" where J is $(CR^7R^{7'})n$ and n=0–3, J' is a bond or O, S, S=O, $SO_2$, NH, $NR^6$, C=O, CO=O, $NR^1C=O$, $CR^7R^{7'}$, $C=CR^8R^{8'}$, $R^2P=O$, $OPOOR^2$, $OPO_2$, $OSO_2$, C=N, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0–3; and W, Q, $R^2$, $R^6$, $R^7$, $R^{7'}$, $R^8$, $R^{8'}$, $R^9$, $R^{9'}$, and $R^{10}$ are as defined in the specification and/or claims herein, to methods of using such compounds in the treatment of nuclear hormone receptor-associated conditions such as cancer and immune disorders, and to pharmaceutical compositions containing such compounds.

14 Claims, No Drawings

U.S. PATENT DOCUMENTS

| | | | |
|---|---|---|---|
| 3,428,538 A | 2/1969 | Scheiner |
| 3,821,232 A | 6/1974 | Redmore |
| 3,906,102 A | 9/1975 | Tottori et al. |
| 3,923,490 A | 12/1975 | Redmore |
| 3,925,554 A | 12/1975 | Tottori et al. |
| 3,965,264 A | 6/1976 | Redmore |
| 3,997,293 A | 12/1976 | Redmore |
| 3,998,833 A | 12/1976 | Redmore |
| 4,089,650 A | 5/1978 | Redmore |
| 4,092,413 A | 5/1978 | Arth et al. |
| 4,097,578 A | 6/1978 | Perronnet |
| 4,191,775 A | 3/1980 | Glen |
| 4,234,736 A | 11/1980 | Bernauer et al. |
| 4,239,776 A | 12/1980 | Glen et al. |
| 4,397,857 A | 8/1983 | Vincent et al. |
| 4,472,382 A | 9/1984 | Labrie et al. |
| 4,473,393 A | 9/1984 | Nagpal |
| 4,476,184 A | 10/1984 | Lubowitz et al. |
| 4,507,303 A | 3/1985 | Ishizumi et al. |
| 4,533,737 A | 8/1985 | Ryang |
| 4,536,559 A | 8/1985 | Lubowitz et al. |
| 4,543,355 A | 9/1985 | Ishizumi et al. |
| 4,562,255 A | 12/1985 | Freed et al. |
| 4,584,364 A | 4/1986 | Lubowitz et al. |
| 4,598,072 A | 7/1986 | Schweikert et al. |
| 4,656,235 A | 4/1987 | Tesoro et al. |
| 4,659,695 A | 4/1987 | Labrie |
| 4,666,885 A | 5/1987 | Labrie |
| 4,673,748 A | 6/1987 | Rock et al. |
| 4,739,075 A | 4/1988 | Odagiri et al. |
| 4,753,957 A | 6/1988 | Chan |
| 4,760,053 A | 7/1988 | Labrie |
| 4,775,660 A | 10/1988 | Labrie et al. |
| 4,775,661 A | 10/1988 | Labrie |
| 4,851,495 A | 7/1989 | Sheppard et al. |
| 4,873,256 A | 10/1989 | Coussediere et al. |
| 4,892,578 A | 1/1990 | Chang et al. |
| 4,944,791 A | 7/1990 | Schroder et al. |
| 4,980,481 A | 12/1990 | Lubowitz et al. |
| 5,084,472 A | 1/1992 | Moguilewsky et al. |
| 5,093,500 A | 3/1992 | Wang |
| 5,098,888 A | 3/1992 | Vincent et al. |
| 5,104,967 A | 4/1992 | Sheppard et al. |
| 5,112,939 A | 5/1992 | Lubowitz et al. |
| 5,114,612 A | 5/1992 | Benicewicz et al. |
| 5,116,935 A | 5/1992 | Lubowitz et al. |
| 5,151,487 A | 9/1992 | Lubowitz et al. |
| 5,155,206 A | 10/1992 | Lubowitz et al. |
| 5,210,213 A | 5/1993 | Sheppard et al. |
| 5,239,046 A | 8/1993 | Lubowitz et al. |
| 5,367,083 A | 11/1994 | Sheppard et al. |
| 5,403,666 A | 4/1995 | Lubowitz et al. |
| 5,434,176 A | 7/1995 | Claussner et al. |
| 5,446,120 A | 8/1995 | Lubowitz et al. |
| 5,455,115 A | 10/1995 | Lubowitz et al. |
| 5,463,076 A | 10/1995 | Sheppard et al. |
| 5,482,921 A | 1/1996 | Secking et al. |
| 5,512,676 A | 4/1996 | Sheppard et al. |
| 5,516,876 A | 5/1996 | Lubowitz et al. |
| 5,530,089 A | 6/1996 | Sheppard et al. |
| 5,532,372 A | 7/1996 | Saji et al. |
| 5,550,107 A | 8/1996 | Labrie |
| 5,556,983 A | 9/1996 | Claussner et al. |
| 5,573,854 A | 11/1996 | Sheppard et al. |
| 5,587,105 A | 12/1996 | Sheppard et al. |
| 5,589,497 A | 12/1996 | Claussner et al. |
| 5,594,089 A | 1/1997 | Lubowitz et al. |
| 5,595,985 A | 1/1997 | Labrie |
| 5,610,317 A | 3/1997 | Lubowitz et al. |
| 5,627,201 A | 5/1997 | Gaillard-Kelley et al. |
| 5,643,855 A | 7/1997 | Kilama |
| 5,645,925 A | 7/1997 | Sheppard et al. |
| 5,693,741 A | 12/1997 | Sheppard et al. |
| 5,714,566 A | 2/1998 | Lubowitz et al. |
| 5,750,553 A | 5/1998 | Claussner et al. |
| 5,780,583 A | 7/1998 | Lubowitz et al. |
| 5,817,649 A | 10/1998 | Labrie |
| 5,817,744 A | 10/1998 | Sheppard et al. |
| RE35,956 E | 11/1998 | Gaillard-Kelly et al. |
| 5,929,146 A | 7/1999 | Amos et al. |
| 6,017,924 A | 1/2000 | Edwards et al. |
| 6,020,327 A | 2/2000 | Messenger |
| 6,054,487 A | 4/2000 | Sekut et al. |
| 6,071,957 A | 6/2000 | Miller et al. |
| 6,124,460 A | 9/2000 | Tomiyama et al. |
| 6,162,444 A | 12/2000 | Dubois |
| 6,200,573 B1 | 3/2001 | Locke |
| 6,242,611 B1 | 6/2001 | Claussner et al. |
| 6,670,386 B2 | 12/2003 | Sun et al. |
| 2001/0012839 A1 | 8/2001 | Miller et al. |
| 2001/0020002 A1 | 9/2001 | Lederman et al. |
| 2002/0173445 A1 | 11/2002 | Salvati et al. |
| 2003/0181728 A1 | 9/2003 | Salvati et al. |
| 2004/0019063 A1 | 1/2004 | Sun et al. |
| 2004/0077606 A1 | 4/2004 | Salvati et al. |
| 2004/0087548 A1 | 5/2004 | Salvati et al. |
| 2004/0181064 A1 | 9/2004 | Sun et al. |

FOREIGN PATENT DOCUMENTS

| | | |
|---|---|---|
| CN | 1050877 | 4/1991 |
| DE | 2365677 | 11/1975 |
| DE | 3227055 A1 | 7/1982 |
| EP | 0001813 A1 | 10/1978 |
| EP | 0051020 A1 | 5/1982 |
| EP | 0082402 B1 | 6/1982 |
| EP | 0091596 A2 | 3/1983 |
| EP | 0253503 B1 | 6/1987 |
| EP | 0277476 A2 | 1/1988 |
| EP | 0436426 A1 | 12/1990 |
| EP | 0494819 A1 | 1/1992 |
| EP | 0406119 B1 | 1/1994 |
| EP | 0678507 | 10/1995 |
| EP | 1008457 A1 | 6/2000 |
| FR | 2075751 | 1/1971 |
| FR | 2329276 | 11/1975 |
| GB | 2133066 B | 10/1986 |
| GB | 2290296 | 12/1995 |
| GB | 1039020 | 4/2001 |
| JP | 51088631 | 8/1976 |
| JP | 53-86035 | 7/1978 |
| JP | 64-6258 | 2/1989 |
| JP | 1-125381 | 5/1989 |
| JP | 7-144477 | 6/1995 |
| WO | WO98/32439 | 7/1978 |
| WO | WO98/16830 | 4/1988 |
| WO | WO98/29495 | 7/1988 |
| WO | WO95/18794 | 7/1995 |
| WO | WO96/19458 | 6/1996 |
| WO | WO97/49709 | 12/1997 |
| WO | WO 98/39303 | 9/1998 |
| WO | WO98/49555 | 11/1998 |
| WO | WO99/27365 | 6/1999 |
| WO | WO99/32463 | 7/1999 |
| WO | WO 99/42458 A1 | 8/1999 |
| WO | WO02/00617 | 1/2000 |
| WO | WO02/00653 | 1/2000 |
| WO | WO00/06525 | 2/2000 |
| WO | WO00/37430 | 6/2000 |
| WO | WO01/07052 | 2/2001 |
| WO | WO01/16108 | 3/2001 |
| WO | WO01/16133 | 3/2001 |
| WO | WO01/19831 | 3/2001 |
| WO | WO01/30781 | 5/2001 |

| WO | WO01/16139 | 3/2002 |
| WO | WO02/24702 | 3/2002 |

OTHER PUBLICATIONS

Goldstein et al., Tetrahedron Letters, vol. 31, p. 2631-2634 (1969).
Evnin et al., J. Org. Chem., vol. 35, No. 9, p. 3097-3106 (1970).
Kobayashi et al., Bull. Chem. Soc. Jpn., vol. 67, No. 11, p. 3082-3087 (1994).
Kobayashi et al., Bull. Chem. Soc. Jpn., vol. 65, p. 61-65 (1992).
Pons et al., Eur. J. Org. Chem., p. 853-859 (1998).
Pons et al., Pept. Proc. Am. Pept. Symp., 15th p. 176-177 (1999).
Reyniers et al., Bull. Soc. Chim. Belg. vol. 94(6), pp. 413-419 (1985).
Anteunis et al., Tetrahedron Lett., vol. 22(32), p. 3101-3104 (1981).
Mauger et al., J. Chem. Soc., Perkin Trans. 1, vol. 17, p. 2146-2148 (1972).
Mauger , J. Chem. Soc. d, vol. 1, p. 39-40 (1971).
Lee et al., Tetrahedron Lett., vol. 37(34), p. 6053-6056 (1996).
Verbruggen et al., Acta Crystallogr., Sect. C: Cryst. Struct. Commun., vol. C49(6), p. 1113-1116 (1993).
Shalati et al., Journal of Polymer Science: Polm. Chem. Ed., vol. 22(1), p. 107-120 (1984).
Van Poucke et al., Bull. Soc. Chim. Belg., vol. 91(3), p. 213-218 (1982).
Schrooten et al., Bull. Soc. Chim. Belg., vol. 89(8), p. 615-628 (1980).
Hausler et al., Chem. Ber. vol. 107(9), p. 2804-2815 (1974).
Vicar et al., Collect. Czech. Chem. Commun. vol. 38(7), p. 1940-1956 (1973).
Vicar et al., Collect. Czech. Chem. Commun. vol. 37(12), p. 4060-4071 (1972).
Kovtunenko et al., Ukr. Khim. Zh. (Russ. Ed), vol. 58(11), p. 1035-1040 (1992).
Kovtunenko et al., Ukr. Khim. Zh. (Russ. Ed), vol. 58(7), p. 588-592 (1992).
Kreher et al., Chem. Ber., vol. 125(1), p. 183-189 (1992).
Kovtunenko et al., Ukr. Khim. Zh. (Russ. Ed), vol. 57(1), p. 71-77 (1991).
Kovtunenko et al., Khim. Geterotsikl Soedin., vol (2), p. 190-202 (1990).
Kreher et al., Chem. Ber., vol. 123(2), p. 381-390 (1990).
Kreher et al., Chem.-Ztg., vol. 112(11), p. 335-342 (1988).
Kovtunenko et al., Ukr. Khim. Zh. (Russ. ed), vol. 55(1), p. 64-65 (1989).
Kovtunenko et al., Ukr. Khim. Zh. (Russ. ed), vol. 54(11), p. 1186-1190 (1988).
Kovtunenko et al., Ukr. Khim. Zh., vol. 54(2), p. 186-190 (1988).
Kreher et al., Chem.-Ztg., vol. 111(12), p. 349-356 (1987).
Kreher et al., Chem. Ber., vol/. 121(5), p. 927-934 (1988).
Kreher et al., Chem.-Ztg., vol. 110(10), p. 363-367 (1986).
Kovtunenko et al., Khim. Geterotsikl. Soedin., vol. 20(9), p. 1200-1205 (1984).
Kreher et al., Angew. Chem., vol. 96(7), p. 507-508 (1984).
Kovtunenko et al., Ukr. Khim. Zh., vol. 49(12), p. 1287-1293 (1983).
Kreher et al., Angew. Chem., vol. 94(8), p. 634-635 (1982).
Munoz et al., Biotechnol. Bioeng., vol. 71(1), p. 78-84 (2000).
Chen et al., Tetrahedron Lett., vol. 40(18), p. 3491-3494 (1999).
Srivastav et al., Natl. Acad. Sci. Lett., vol. 19(1&2), p. 16-18 (1996).
Tosunyan et al., Khim. Geterotsikl. Soedin., vol. (11), p. 1465-1471 (1992).
Kirby et al., J. Chem. Res., Synop., vol. (9), p. 273 (1985).
Krow et al., J. Heterocycl. Chem., vol. 22(1), p. 131-135 (1985).
Krow et al., J. Org. Chem., vol. 47(11), p. 1989-1993 (1982).
Knaus et al., J. Heterocycl. Chem., vol. 13(3), p. 481-486 (1976).
Lyle et al., J. Org. Chem., vol. 39(25), p. 3708-3711 (1974).
Lin et al., Journal of the Chinese Chemical Society, vol. 48, p. 49-53 (2001).
Kirby et al., J. Chem. Res. Miniprint, vol 9, p. 3089-3097 (1985).
Xu, Trends in Pharmacological Science, vol. 2 (10), p. 271-272 (1981).
Li et al., J. Pharm. Biomed. Anal. vol. 7(12), p. 1635-1639 (1989).
Cheng et al., Huaxue Shiji, vol. 15(1), p. 1-4 (1993).
Liu et al., Yaoxue Xuebao, vol. 18(10), p. 752-759 (1983).
Bockstahler et al., J. Med. Chem., vol. 11(3), p. 603-606 (1968).
Srivastava et al., Natl. Acad. Sci. Lett., vol. 15(2), p. 41-44 (1992).
Joshi et al., Indian J. Chem., Sect. B, vol. 22B(2), p. 131-135 (1983).
Fisera et al., Chem. Pap., vol. 49(4), p. 186-191 (1995).
Fang et al., Huaxue Tongbao, vol. (1), p. 27-30 (1994).
Wijnberg et al., Tetrahedron, vol. 38, p. 209-217 (1982).
Grogan et al., J. Med. Chem., vol. 6, p. 802-805 (1963).
Gringauz et al., J. Med. Chem., vol. 11, p. 611-612 (1968).
Chem. Abstr., vol. 65, p. 15325h (1966).
Dominianni, J. Med. Chem., vol. 14, No. 2, p. 175 (1971)
Chem. Abstr., vol. 57, p. 16561f (1962).
Jolivet, Ann. Chim., vol. 5, p. 1165-1217 (1960).
Maruyama et al., J. Org. Chem., vol. 46, p. 27-34 (1981).
Chem. Abstr., vol. 68, p. 39458j (1964).
Kwart, J. Amer. Chem. Soc., vol. 74 p. 3094-3097 (1952).
Berson et al., J. Amer. Chem. Soc., vol. 76, p. 4060-4067 (1954).
Yur'ev et al., J. Gen. Chem. (Engl. Transl.), vol. 30, p. 869-872 (1960).
Jolivet, C.R. Hebd. Seances Acad. Sci., vol. 243, p. 2085-2086 (1956).
Lin et al., Bioorganic Chemistry, vol. 28, p. 266-272 (2000).
Mel'nikow, Zh. Obshch. Khim., vol. 26, p. 227-232 (1956).
Mel'nikow, Zh. Obshch. Khim., vol. 29, p. 968,970 (1956).
Warrener et al., Tetrahedron Lett., vol. 36(42), p. 7753-7756 (1995).
Qimin et al., J. Pharm. Biomed. Anal., vol. 7(12), p. 1635-1639 (1989).
Maruyama et al., J. Org. Chem., vol. 46(1), p. 27-34 (1981).
Zawadowski et al., Rocz. Chem., vol. 51(3), p. 557-560 (1977).
Liu et al., Eur. J. Canada, vol. 31A, (6), p. 953-963 (1995).
Lin, Journal of Natural Toxins, vol. 4 (2), p. 147-153 (1995).
Walter et al., Biochemica et Biophysica Acta, 1155, p. 207-0226 (1993).
Walter, J. Pharm. Sci., vol. 78 (1), p. 66-67 (1989).
Yin et al., Chem. Chinese Chemical Society, No. 1, p. 27-30 (1994).
Bockstahler et al., J. Med. Chem., vol. 11 (3), p. 603-606 (1968).
Dominianni et al., J. Med. Chem., vol. 14 (2), p. 175 (1971).
Zhou et al., Acta Pharm. Sinica, vol. 18 (10), p. 725-729 (1983).
Wang, J. Ethnopharm., vol. 26, p. 147-162 (1989).
Honkanen, FEBS Letters, vol. 330 (3), p. 283-286 (1993).
Waller, Toxicol. Appl. Pharmacol., vol. 137 (2), p. 219-227 (1996).
Search Report "A" (Scifinder Jun. 23, 2000).
Search Report "B" (Scifinder Jun. 5, 2001).
Search Report "C" (Scifinder, Jun. 20, 2001).
Search Report "D" (Scifinder, Jun. 20, 2001).
Search Report "E" (Scifinder, Jun. 20, 2001).
Search Report "F" (Scifinder, Aug. 16, 2000).
Search Report "G" (Scifinder, Aug. 22, 2000).
Search Report "H" (Scifinder, Sep. 12, 2000).
Search Report "K" (Scifinder, Sep. 11, 2000).
Search Report "L" (Scifinder, Sep. 11, 2000).
Search Report "M" (Scifinder, Sep. 11, 2000).
Search Report "N" (Scifinder, Sep. 11, 2000).
Search Report "O" (Scifinder, Sep. 11, 2000).
Search Report "P" (Scifinder, Sep. 11, 2000).
Search Report "Q" (Scifinder, Sep. 11, 2000).
Search Report "R" (Scifinder, Sep. 11, 2000).
Search Report "S" (Scifinder, Sep. 11, 2000).
Search Report "T" (Scifinder, Sep. 11, 2000).
Search Report "U" (Scifinder, Sep. 11, 2000).
Search Report "V" (Scifinder, Sep. 11, 2000).
Search Report "Y" (Scifinder, Sep. 11, 2000).
Search Report "BB" (Scifinder, Sep. 11, 2000).
Tanaka et al., Tetrahedron, Elsevier Science Publishers, Amsterdam, NL, vol. 54 (34), p. 10029-10042 (1998).
Rosen et al., J. Med. Chem., vol. 31 (8), p. 1598-1611 (1988).
Remuzon et al., Journal of Medicinal Chemistry, American Chemican Society, vol. 35, (15), p. 2898-2909, 1992.
Evans, American Association for the Advancement of Science, vol. 240, No. 4854, p. 889-895 (1988).
Denison, J. Biol. Chem., vol. 270 (31), p. 18175-18178 (1995).
Furr, Eur. Urol., vol. 29 (Suppl. 2), 83-95 (1996).

Negro-Vilar, Journal of Clinical Endocrinology & Metabolism, vol. 84, No. 10, 3459-3462 (1999).
Reid et al., Investigational New Drugs, vol. 17, 271-284 (1999).
Avolos et al., Tetra. Ltrs., vol. 39, 9301-9304 (1998).

Rui et al., ACTA Pharmaceutica Sinica, vol. 10, 783-786 (1981).
Tsuchiya et al., Tetra., vol. 29, No. 18, 2747-2751 (1973).

* cited by examiner

FUSED CYCLIC MODULATORS OF NUCLEAR HORMONE RECEPTOR FUNCTION

This application is a divisional application of U.S. patent application 10/322,306, filed Dec. 18, 2002, issued as U.S. Pat. No. 7,001,911 B2, which claims priority from and is a continuation-in-part of U.S. application Ser. No. 10/025,233 filed Dec. 19, 2001, abandoned; which is a continuation-in-part of U.S. application Ser. No. 09/885,798, filed Jun. 20, 2001, abandoned, which claims priority from U.S. application Ser. No. 60/214,392, filed Jun. 28, 2000, from U.S. application Ser. No. 60/284,617, filed April 18, 2001, and from U.S. application Ser. No. 60/284,438, filed Apr. 18, 2001, which provisional applications are incorporated herein by reference in their entirety, and U.S. application Ser. No. 09/885,827, filed Jun. 20, 2001, issued as U.S. Pat. No. 6,960,474 B2, which claims priority from U.S. application Ser. No. 60/284,438, filed Apr. 18, 2001, which applications are incorporated herein by reference in their entirety.

FIELD OF THE INVENTION

The present invention relates to fused cyclic compounds, to methods of using such compounds in the treatment of nuclear hormone receptor-associated conditions such as cancer, and to pharmaceutical compositions containing such compounds.

BACKGROUND OF THE INVENTION

Applicants incorporate by reference the "Background of Invention" section of the parent case, i.e., U.S. patent application Ser. No. 10/322,306, filed Dec. 18, 2002, appearing at pages 1 to 4 thereof, as if fully set forth herein.

SUMMARY OF THE INVENTION

The present invention provides fused cyclic compounds and pharmaceutically acceptable salts, solvates, prodrugs and stereoisomers thereof, as set forth in the claims appended hereto and otherwise described in the formulae, Schemes and Examples hereof.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substitutents forming, in the latter case, groups such as a perfluoroalkyl group or an alkyl group bearing $Cl_3$ or $CF_3$), alkoxy, alkylthio, hydroxy, carboxy (i.e., —COOH), alkoxycarbonyl, alkylcarbonyloxy, amino (i.e., —$NH_2$), carbamoyl or substituted carbomoyl, carbamate or substituted carbamate, urea or substituted urea, amidinyl or substituted amidinyl, thiol (—SH), aryl, heterocycle, cycloalkyl, heterocycloalkyl, —S-aryl, —S-heterocycle, —S=O-aryl, —S=O-heterocycle, —S(O)$_2$-aryl, —S(O)$_2$-heterocycle, —NHS(O)$_2$-aryl, —NHS(O)$_2$-heterocycle, —NHS(O)$_2$NH-aryl, —NHS(O)$_2$NH-heterocycle, —P(O)$_2$-aryl, —P(O)$_2$-heterocycle, —NHP(O)$_2$-aryl, —NHP(O)$_2$-heterocycle, —NHP(O)$_2$NH-aryl, —NHP(O)$_2$NH-heterocycle, —O-aryl, —O-heterocycle, —NH-aryl, —NH-heterocycle, —NHC=O-aryl, —NHC=O-heterocycle, —OC=O-aryl, —OC=O-heterocycle, —NHC=ONH-aryl, —NHC=ONH-heterocycle, —OC=OO-aryl, —OC=OO-heterocycle, —OC=ONH-aryl, —OC=ONH-heterocycle, —NHC=OO-aryl, —NHC=OO-heterocycle, -C=ONH-aryl, -C=ONH-heterocycle, -C=OO-aryl, -C=OO-heterocycle, —N(alkyl)S(O)$_2$-aryl, —N(alkyl)S(O)$_2$-heterocycle, —N(alkyl)S(O)$_2$NH-aryl, N(alkyl)S(O)$_2$NH-heterocycle, —N(alkyl)P(O)$_2$-aryl, —N(alkyl)P(O)$_2$-heterocycle, —N(alkyl)P(O)$_2$NH-aryl, N(alkyl)P(O)$_2$NH-heterocycle, —N(alkyl)-aryl, —N(alkyl)-heterocycle, —N(alkyl)C=O-aryl, —N(alkyl)C=O-heterocycle, —N(alkyl)C=ONH-aryl, —N(alkyl)C=ONH-heterocycle, —OC=ON(alkyl)-aryl, —OC=ON(alkyl)-heterocycle, —N(alkyl)C=OO-aryl, —N(alkyl)C=OO-heterocycle, -C=ON(alkyl)-aryl, -C=ON(alkyl)-heterocycle, —NHS(O)$_2$N(alkyl)-aryl, NHS(O)$_2$N(alkyl)-heterocycle, NHP(O)$_2$N(alkyl)-aryl, NHP(O)$_2$N(alkyl)-heterocycle, —NHC=ON(alkyl)-aryl, —NHC=ON(alkyl)-heterocycle, —N(alkyl)S(O)$_2$N(alkyl)-aryl, —N(alkyl)S(O)$_2$N(alkyl)-heterocycle, —N(alkyl)P(O)$_2$N(alkyl)-aryl, —N(alkyl)P(O)$_2$ N(alkyl)-heterocycle, —N(alkyl)C=ON(alkyl)-aryl, and —N(alkyl)C=ON(alkyl)-heterocycle, as well as by $OR^{13}$ where $R^{13}$ is defined below in Scheme XV. In the aforementioned exemplary substitutents, groups such as "aryl" and "heterocycle" can themselves be optionally substituted.

The term "alkenyl" refers to a straight or branched chain hydrocarbon radical containing from 2 to 12 carbon atoms and at least one carbon-carbon double bond. Exemplary such groups includes ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkenyl or substituted cycloalkenyl.

The term "cycloalkenyl" refers to a partially unsaturated cyclic hydrocarbon group containing I to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point attachment. Exemplary substituents include but are not limited to nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkyl or substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl-S(O)$_m$— (m=0, 1 or 2), alkyl or substituted alkyl, as well as those groups recited above as exemplary alkyl substituents and as previously mentioned as preferred aryl substituents in the definition for G. Exemplary substituents also include fused cyclic substituents, such as heterocyclo or cycloalkenyl, or substituted heterocyclo or cycloalkenyl, groups.

"Carbamoyl" refers to the group —CONH— which is bonded on one end to the remainder of the molecule and on the other to hydrogen or an organic moiety (such as alkyl, substituted alkyl, aryl, substituted aryl, heterocycle, alkylcarbonyl, hydroxyl and substituted nitrogen). "Carbamate" refers to the group —O—CO—NH— which is bonded on one end to the remainder of the molecule and on the other to hydrogen or an organic moiety (such as those listed above). "Urea" refers to the group —NH—CO—NH— which is bonded on one end to the remainder of the molecule and on the other to hydrogen or an organic moiety (such as those listed above). "Amidinyl" refers to the group —C(=NH)(NH$_2$). "Substituted carbamoyl," "substituted carbamate," "substituted urea" and "substituted amidinyl" refer to carbamoyl, carbamate, urea or amidinyl groups as described above in which one more of the hydrogen groups are replaced by an organic moiety (such as those listed above).

The terms "heterocycle", heterocyclic" and "heterocyclo" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or firo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl-S(O)$_m$— (m =0, 1 or 2), alkyl or substituted alkyl, as well as those groups recited above as exemplary alkyl substituents, and as previously mentioned as preferred heterocyclo substituents in the definition for G.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethylhydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The terms "hydroxylamine" and "hydroxylamide" refer to the groups OH—NH— and OH—NH—CO—, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

When a term such as "(CRR)n" is used, it denotes an optionally substituted alkyl chain existing between the two fragments to which it is bonded, the length of which chain is defined by the range described for the term n. An example of this is n=0-3, implying from zero to three (CRR) units existing between the two fragments, which are attached to the primary and terminal (CRR) units. In the situation where the term n is set to zero (n =0) then a bond exists between the two fragments attached to (CRR).

Unless otherwise indicated, any heteroatom with unsatisfied valences is assumed to have hydrogen atoms sufficient to satisfy the valences.

Divalent groups, such as those in the definition of W (e.g., NR$^9$—CR$^7$R$^7$), may be bonded in either direction to the remainder of the molecule (e.g,

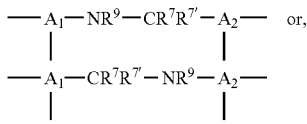

for the aforementioned group within the definition of W).

Carboxylate anion refers to a negatively charged group —COO—.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

Throughout the specifications, groups and substituents thereof may be chosen to provide stable moieties and compounds.

Methods of Preparation

The compounds of the present invention may be prepared by methods such as those illustrated in the following Schemes I to XV. Solvents, temperatures, pressures, and other reaction conditions may readily be selected by one of ordinary skill in the art. Starting materials are commercially available or readily prepared by one of ordinary skill in the art or prepared by methods illustrated in FIGS. 1 to 3. Combinatorial techniques may be employed in the preparation of compounds, for example, where the intermediates possess groups suitable for these techniques. See the following for alternative methods which may be employed in the preparation of compounds of the present invention: *Tetrahedron*, 27, 3119 (1971); *Tetrahedron*, 30, 2977 (1974); *Tetrahedron. Let*, 31, 2631 (1969); *J. Org. Chem.*, 35, 3097 (1970); *Bull. Chem. Soc. Jpn.*, 67, 3082 (1994); *Bull. Chem. Soc. Jpn.*, 65, 61 (1992); European Patent (EP) No. 406119; U.S. Pat. No. 4,397,857; Pons et al., *Eur. J. Org. Chem.*, 853-859 (1998); Kucharczyk et al., *J. Med. Chem.*, 1654-1661 (1993); and German Patent (DE) Document No. 3227055.

All documents cited in the present specification, such as those cited in this "Methods of Preparation" as well as other sections herein, are incorporated herein by reference in their entirety. Such documents are not admitted as prior art.

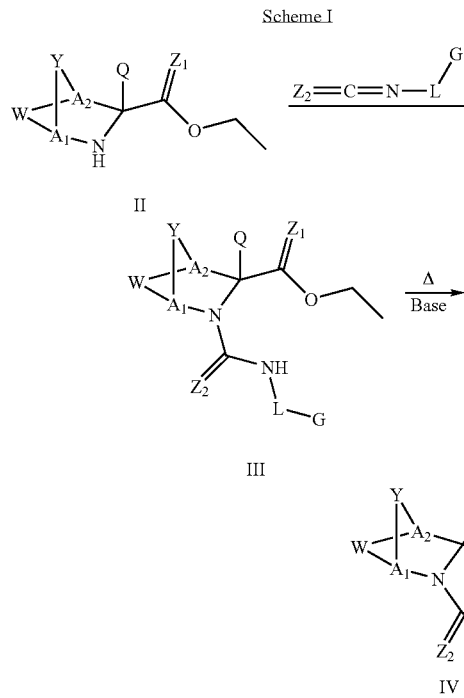

$Z_2$ = S, O, NH, $NR^6$

As illustrated in Scheme I, compounds of formula I can be obtained from azabicyclo-3-ethylcarboxylate intermediates of formula II. Intermediates of formula H can be prepared, for example, from the synthetic approaches described in *Bull. Chem. Soc. Jpn.*, 65, 61 (1992), *Tetrahedron Let.* 31, 2603 (1990), *Chem. Commun.* 597 (1999), *Tetrahedron Lett.* 38, 4021, (1997), *Tetrahedron Lett.* 40, 7929 (1999), *Synlett.* 1, 29 (1991), *J. Chem. Soc., Chem. Commun.* 1601 (1988), *J. Org. Chem.* 31, 1059 (1966), *Synthesis* 10, 925 (1990), *Tetrahedron Lett.* 40, 8447 (1999), U.S. Pat. No. 4,775,668 and EP No. 266576 and the references therein, by one of ordinary skill in the art (incorporated herein by reference in their entirety). In addition to a racemic mixture of a compound of formula H, individual antipodes can be synthesized, for example, in accordance with procedures set forth in the above documents. Exemplary methods for preparing compounds of the formula II are described further below in FIGS. 1 to 3.

Treatment of H with an intermediate of formula $Z_2$=C=N-L-G, yields an intermediate of formula m. The intermediates of formula $Z_2$=C=N-L-G can be obtained, for example, from commercially available isocyanates, thioisocyanates and carbodiimides or can be readily prepared by one skilled in the art. An intermediate of formula III can be heated with or without the presence of a base, such as DBU or triethylamine, to yield a compound of formula IV, which is compound of formula I where M' and M are each a bond and E is C=$Z_2$. The individual optical isomers of a compound of Formula IV (also known as antipodes) can be obtained, for example, by use of the corresponding individual antipodes of a compound of formula H or by separation of the racemic mixture by standard techniques. The individual α or β (endo or exo) isomers of a compound of formula IV can be obtained, for example, by separation of a resulting mixture by standard techniques.

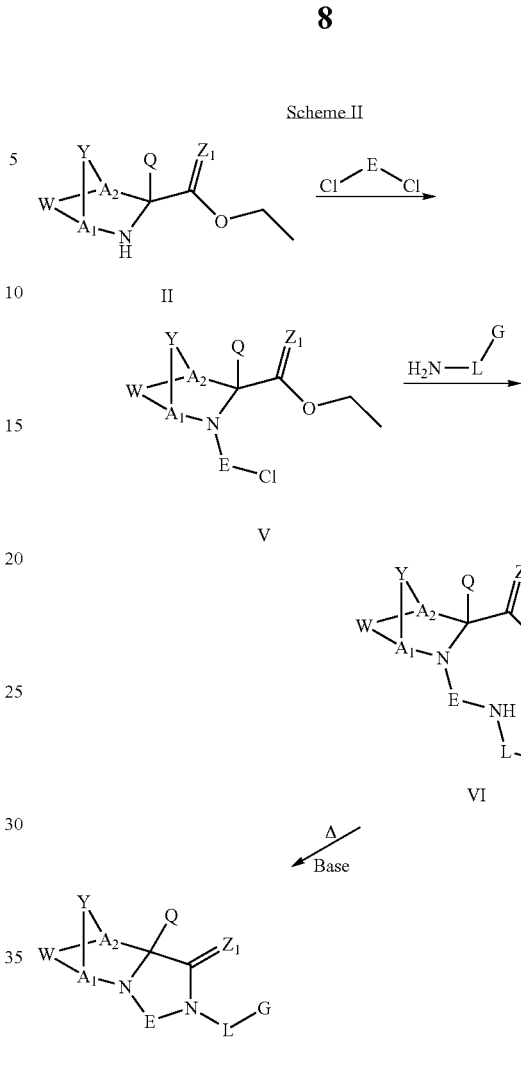

E = C=$Z_2$, $SO_2$, P=$OR^2$, P=$OOR^2$

Scheme II describes a method for preparing compounds of formula I wherein an intermediate of formula II is treated with a phosgene like reagent of formula Cl-E-Cl in the presence of a base, such as $NaHCO_3$, to yield an intermediate of formula V. The phosgene like intermediates of formula Cl-E-Cl can be obtained from commercially available sources or can readily be prepared by one skilled in the art. Phosgene equivalents such as carbonyldiimidazoles may alternatively be employed in this step, and elsewhere in these Schemes as appropriate, in place of Cl-E-Cl. The intermediate of formula V can be reacted with an amine of formula $H_2N$-L-G in the presence of a base, such as diusopropylamine or triethylamine, with or without a coupling reagent, such as DMAP, to give an intermediate of formula VI. The amine intermediates of formula $H_2N$-L-G can be obtained from commercially available sources or can readily be prepared by one skilled in the art. The intermediate of formula VI can be converted to a compound of formula VII by heating with or without the presence of a base, such as DBU or triethylamine. A compound of formula VII is a compound of formula I where M and M' are each a bond and E is C=$Z_2$, $SO_2$, P=$OR^2$ or P=$OOR^2$. The individual antipodes of a compound of formula VII can be

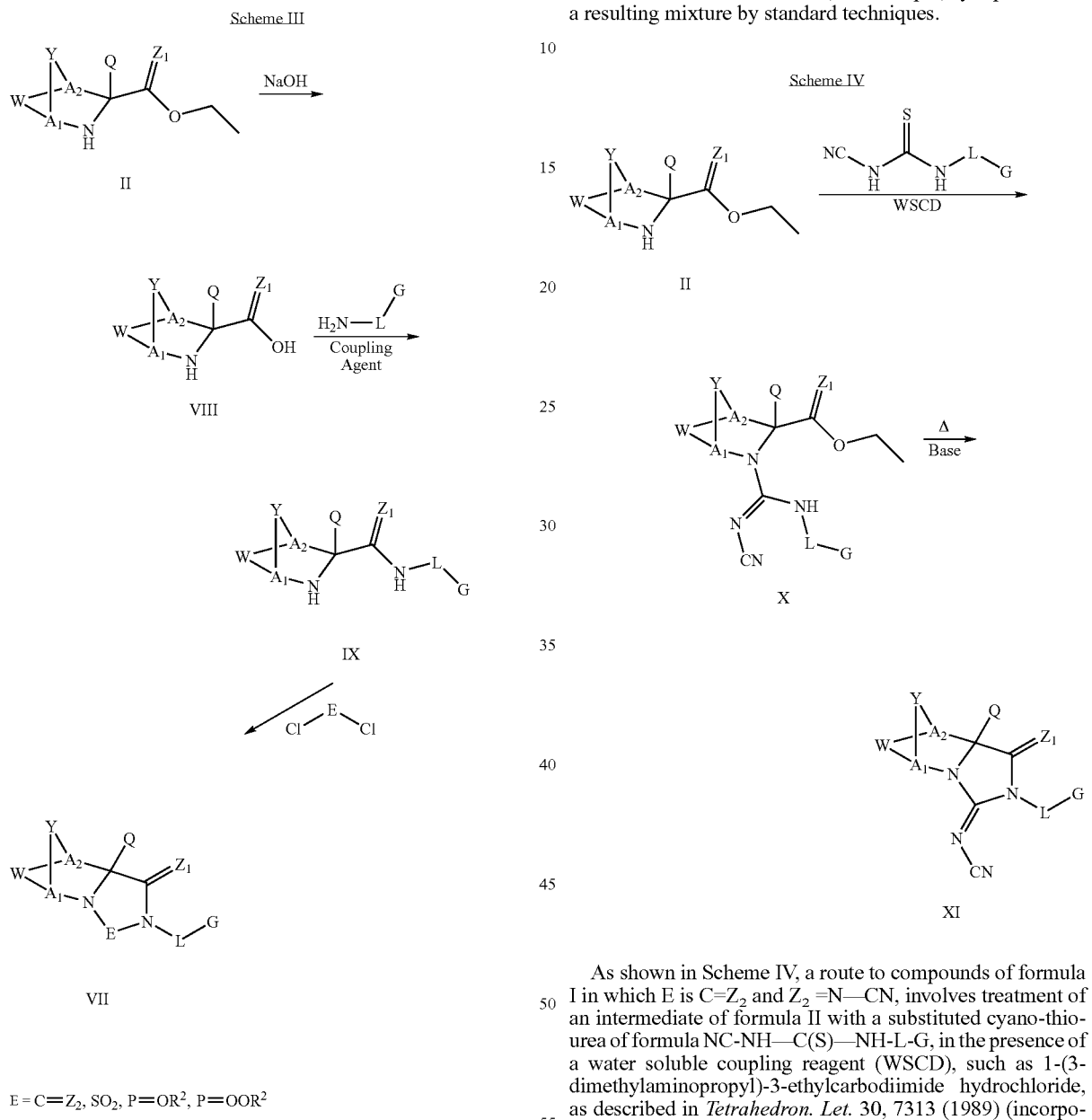

Scheme III describes a method for preparing compounds of formula I wherein an intermediate of formula II is saponified to an acid of formula VIII by treatment with a base, such as sodium hydroxide. The acid can then by coupled to an amine of formula H$_2$N-L-G via a variety of coupling reagents, for example, as described in The Practice of Peptide Synthesis, Springer-Verlag, 2$^{nd}$ Ed., Bodanszy, Miklos, 1993 (incorporated herein by reference in its entirety), to yield an amide intermediate of formula IX. The intermediate of formula IX can be heated, with or without the presence of a base such as triethylamine, with a phosgene like reagent of formula Cl-E-Cl, to yield a compound of formula VII, which is a compound of formula I where M and M' are each a bond and E is C=Z$_2$, SO$_2$, P=OR$^2$ or P=OOR$^2$. The individual antipodes of a compound of formula VII can be obtained, for example, by use of the corresponding individual antipodes of a compound of formula II or by separation of the racemic mixture by standard techniques. The individual isomers of a compound of formula VII can be obtained, for example, by separation of a resulting mixture by standard techniques.

As shown in Scheme IV, a route to compounds of formula I in which E is C=Z$_2$ and Z$_2$ =N—CN, involves treatment of an intermediate of formula II with a substituted cyano-thiourea of formula NC-NH—C(S)—NH-L-G, in the presence of a water soluble coupling reagent (WSCD), such as 1-(3-dimethylaminopropyl)-3-ethylcarbodiimide hydrochloride, as described in Tetrahedron. Let. 30, 7313 (1989) (incorporated herein by reference in its entirety), to yield an intermediate of formula X. The substituted cyano-thioureas of formula NC—NH—C(S)—NH-L-G can be obtained from commercially available sources or can readily be prepared by one skilled in the art. An intermediate of formula X can be heated with or without the presence of a base, such as DBU, to yield a compound of formula XI, which is a compound of formula I where, in addition to E being C=N—CN, M and M' are each a bond. The individual antipodes of a compound of formula XI can be obtained, for example, by use of the corresponding individual antipodes of a compound of formula II or by separation of the racemic mixture by standard techniques. The individual isomers of a compound of formula XI can be obtained, for example, by separation of a resulting mixture by standard techniques.

Scheme V

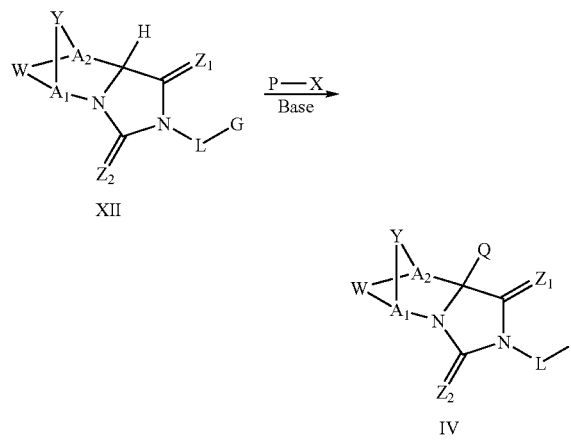

As illustrated in Scheme V, a compound of formula XII, which is a compound of formula I in which Q=H, can be converted to a compound of formula I where Q is equal to substituents as defined herein other than H, by treatment with a base such as LDA and an alkyl halide such as methyl iodide, preferably in a solvent such as tetrahydrofuran at low temperatures (e.g., −78° C.) to yield a compound of formula IV, which is a compound of formula I where M' and M are each a bond and E is C=$Z_2$. The individual antipodes of a compound of formula IV can be obtained, for example, by use of the corresponding individual antipodes of a compound of formula XII or by separation of the racemic mixture by standard techniques. The individual isomers of a compound of formula IV can be obtained, for example, by use of the corresponding individual endo or exo isomers of a compound of formula XII or by separation of a resulting mixture by standard techniques. Compounds of the formula XII may be obtained, for example, by employing the procedure of Scheme I wherein Q=H.

Scheme VI

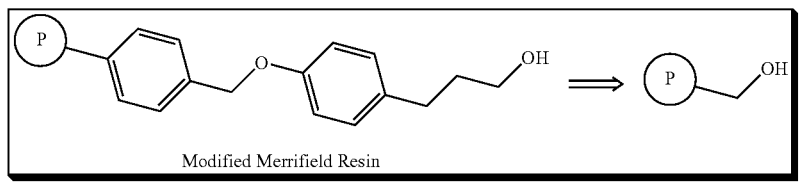

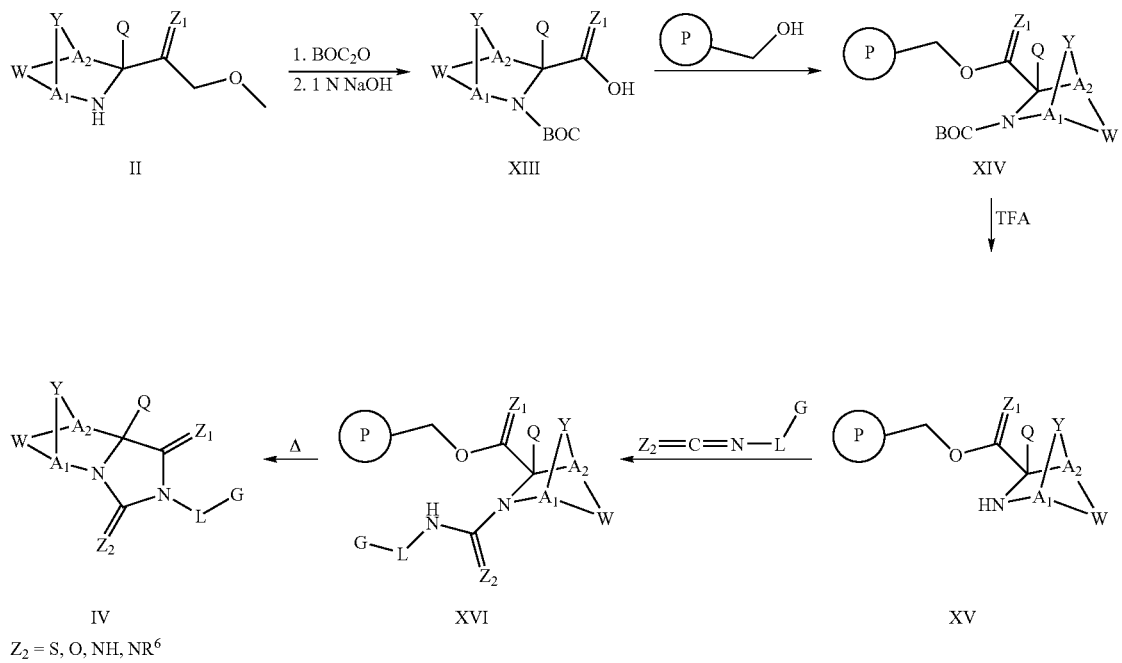

$Z_2$ = S, O, NH, $NR^6$

As shown in Scheme VI, compounds of formula I can be synthesized by means of a solid support route. As such, the above synthetic route allows for the synthesis of combinatorial libraries of compounds of formula I via, for example, standard procedures of automated solid phase synthesis. Treatment of a compound of formula II with a protecting agent such as di-tertbutylcarbonate, followed by hydrolysis of the ester group by treatment with a base, such as sodium compound of formula I where M' and M are each a bond and E is C=$Z_2$. The individual antipodes of a compound of formula IV can be obtained, for example, by use of the corresponding individual antipodes of a compound of formula II or by separation of the racemic mixture by standard techniques. The individual □ or □ isomers of a compound of formula IV can be obtained, for example, by separation of a resulting mixture by standard techniques.

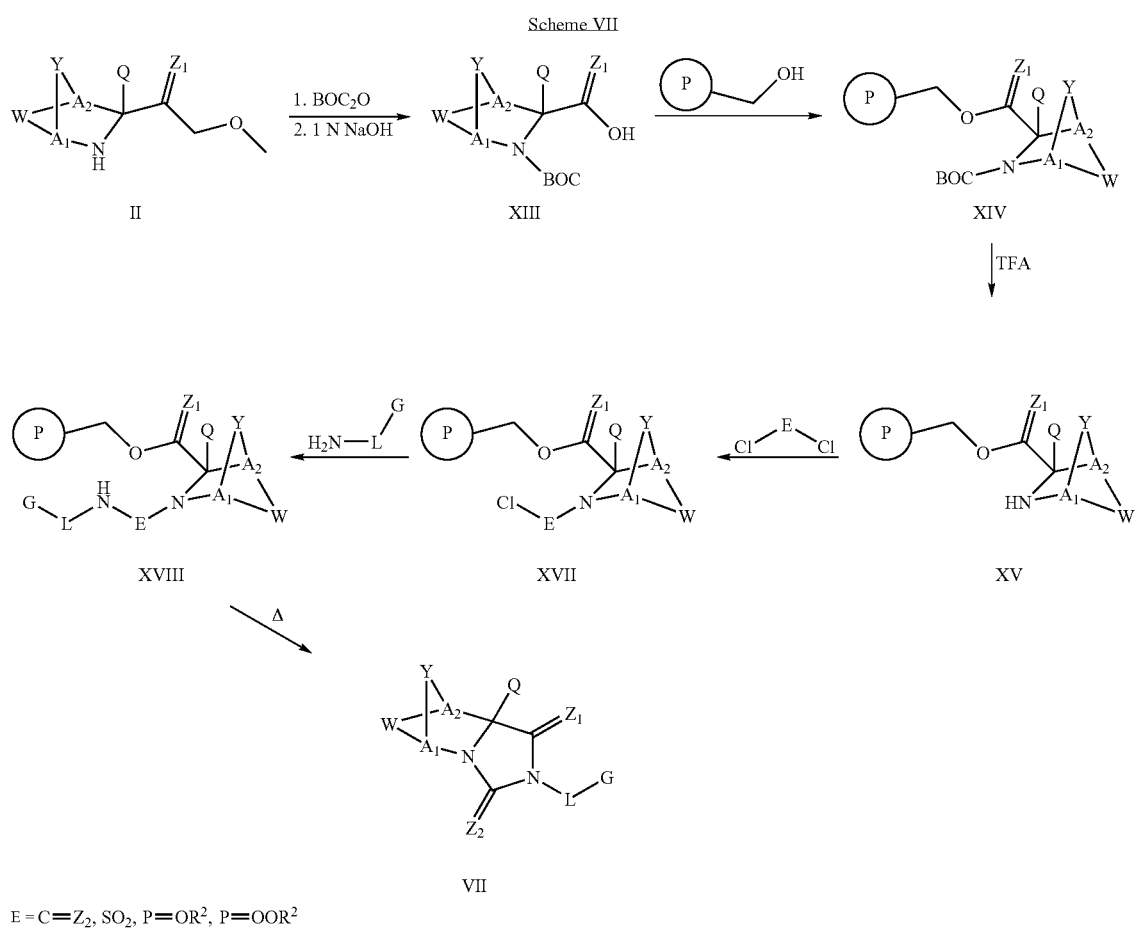

E = C=$Z_2$, $SO_2$, P=$OR^2$, P=$OOR^2$ hydroxide, yields an intermediate of formula XII. The intermediate of formula XIII can be attached to a solid support, such as a modified Merrifield resin, by treatment with a coupling reagent such as 2,6-dichloro-benzoyl chloride in the presence of pyridine and DMF, to yield a solid support intermediate of formula XIV. Removal of the protecting group can be achieved by treatment with an acid, such as trifluoroacetic acid in DMF with sonication, to yield a compound of formula XV, which can be reacted with an intermediate of formula $Z_2$=C=N-L-G, to yield an intermediate of formula XVI. The final product, IV, can be formed and liberated from the solid support by heating the intermediate of formula XVI with or without a base, such as DBU. A compound of formula IV is a Scheme VII shows an alternate approach to the synthesis of compounds of formula I on solid support. As described for Scheme VI, an intermediate of formula XV can readily be synthesized. The intermediate of formula XV can be treated, with or without the presence of a base such as triethylamine or NaHCO$_3$, with a phosgene like reagent of formula Cl-E-Cl, to yield an intermediate of formula XVII. The intermediate of formula XVII can be reacted with an amine of formula H$_2$N-L-G in the presence of a base, such as diusopropylamine, with or without a coupling reagent, such as 4-dimethylamino pyridine, to give an intermediate of formula XVIII. The final product VII can be formed and liberated from the solid support by heating the intermediate of formula XVIII with or without a base, such as DBU. A compound of formula VII is a compound of formula I where M and M' are each a bond and E is $C=Z_2$, $SO_2$, $P=OR^2$ or $P=OO^2$. The individual antipodes of a compound of formula VII can be obtained, for example, by use of the corresponding individual antipodes of a compound of formula II or by separation of the racemic mixture by standard techniques. The individual isomers of a compound of formula VII can be obtained, for example, by separation of a resulting mixture by standard techniques.

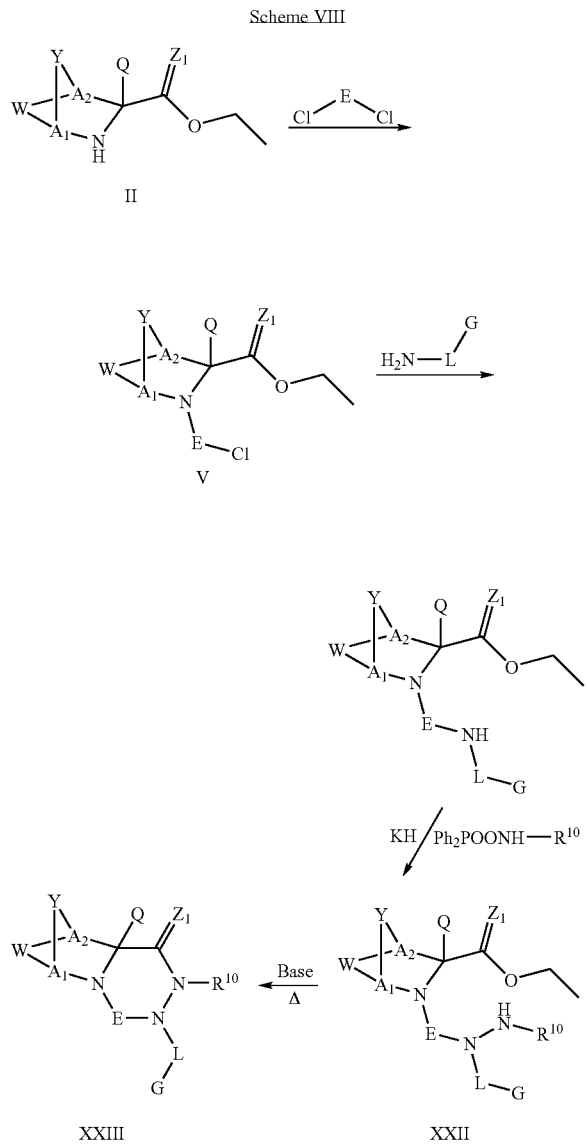

XXIII    XXII $E = C=Z_2$, $SO_2$, $P=OR^2$, $P=OOR^2$

As described in Scheme II, an intermediate of formula VI can be readily synthesized. As shown in Scheme VIII, treatment of an intermediate of formula VI with a substituted O-diphenylphosphinylhydroxylamine of formula $Ph_2POONH$—$R^{10}$, and potassium hydride as described in *Synthesis*, 7, 592 (1982) and *Tetrahedron Let.*, 29, 1777 (1988) (both incorporated herein by reference in their entirety), yields an intermediate of formula XXII. The intermediate of formula XXII can be heated with or without a base, such as triethylamine, to yield a compound of formula XXIII, which is a compound of formula I where M is a bond, M' is $NR^{10}$ and E is $C=Z_2$, $SO_2$, $P=OR2$ or $P=OOR^2$. The individual antipodes of a compound of formula XXII can be obtained, for example, by use of the corresponding individual antipodes of a compound of formula II or by separation of the racemic mixture by standard techniques. The individual isomers of a compound of formula XXIII can be obtained, for example, by separation of a resulting mixture by standard techniques.

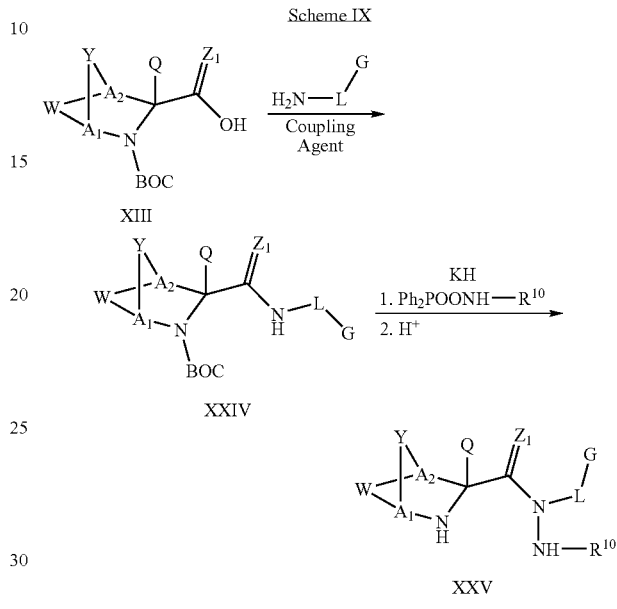

As described in Scheme VI, an intermediate of formula XIII can be readily synthesized. As shown in Scheme IX, the acid intermediate of formula XIII can be coupled to an amine of formula $H_2N$-L-G via use of a variety of coupling reagents, as described in Scheme III, to yield an amide intermediate of formula XXIV. Treatment of the intermediate of formula XXIV with potassium hydride and a substituted O-diphenylphosphinylhydroxylamine of formula $Ph_2POONH$—$R^{10}$, as described in Scheme VIII, followed by removal of the BOC protecting group by treatment with an acid, such as trifluoroacetic acid, yields an intermediate of formula XXV. The intermediate of formula XXV can be treated with a phosgene like reagent of formula Cl-E-Cl, to yield an intermediate which can be heated with or without a base, such as triethylamine, to yield a compound of formula XXVI, which is a compound of formula I where M' is a bond, M is $NR^{10}$ and E is $C=Z_2$, $SO_2$, $P=OR^2$ or $P=OR^2$. The individual antipodes of a compound of formula XXVI can be obtained, for example, by use of the corresponding individual antipodes of a compound of formula XIII or by separation of the racemic mixture by standard techniques. The individual isomers of a compound of formula XXVI can be obtained, for example, by separation of a resulting mixture by standard techniques.

Scheme X

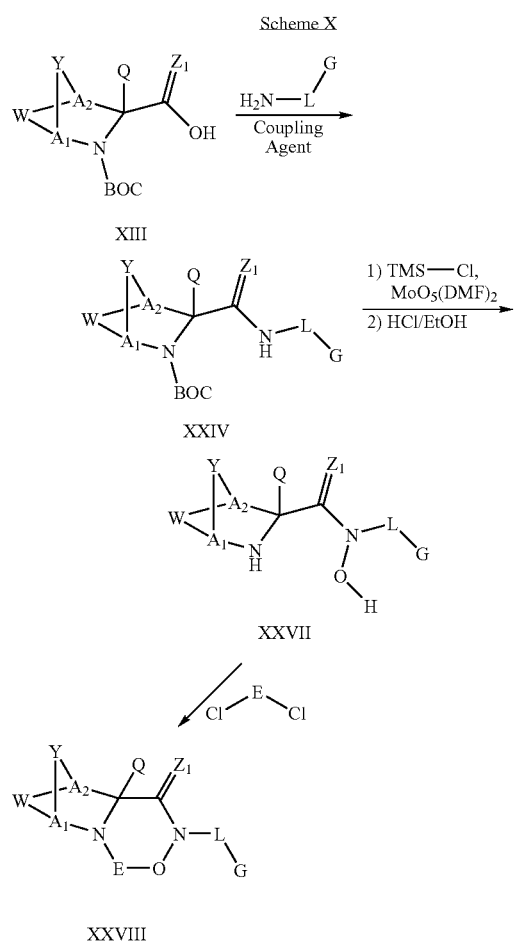

As described in Scheme IX, an intermediate of formula XXIV can be readily synthesized. As shown in Scheme X, treatment of an intermediate of formula XXIV with agents suitable for forming a hydroxylamide moiety, such as TMS-Cl followed by MoO$_5$(DMF)$_2$ as described in *J. Org. Chem.*, 54, 5852 (1989) and *J. Org. Chem.*, 59, 8065 (1994) (both incorporated herein by reference in their entirety), and for deprotection of a BOC group, such as ethanol saturated with HCl gas, results in the generation of a hydroxylamide intermediate of formula XXVII. The intermediate of formula XXVII can be treated with a phosgene like reagent of formula Cl-E-Cl, to yield a compound of formula XXVIII, which is a compound of formula I where M is O, M' is a bond, and E is C=Z$_2$, SO$_2$, P=OR$^2$ or P=OOR$^2$. The individual antipodes of a compound of formula XXVIII can be obtained, for example, by use of the corresponding individual antipodes of a compound of formula XIII or by separation of the racemic mixture by standard techniques. The individual isomers of a compound of formula XXVIII can be obtained, for example, by separation of a resulting mixture by standard techniques.

Scheme XI

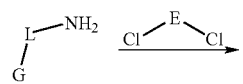

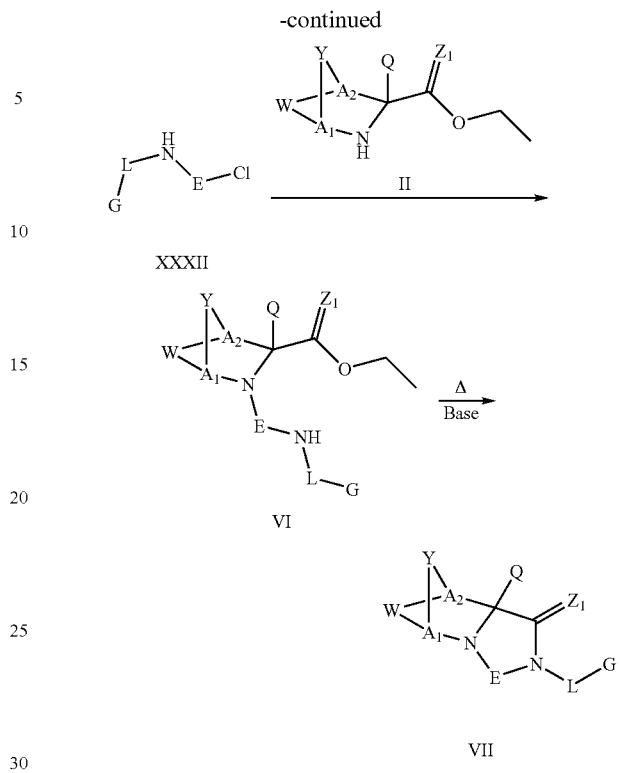

E = C=Z$_2$, SO$_2$, P=OR$^2$, P=OOR$^2$

As shown in Scheme XI, treatment of an intermediate of formula H$_2$N-L-G with a phosgene like reagent of formula Cl-E-Cl as described in *Oppi. Briefs* 17, 235 (1985), results in an intermediate of formula XXXII. The intermediate of formula XXXII can be reacted with an intermediate of formula II to yield an intermediate of formula VI. As described in Scheme II, an intermediate of formula VI can readily be converted to an intermediate of formula VII, which is a compound of formula I where M and M' are each a bond and E is C=Z$_2$, SO$_2$, P=OR$^2$ or P=OOR$^2$. The individual antipodes of a compound of formula VII can be obtained, for example, by use of the corresponding individual antipodes of a compound of formula II or by separation of the racemic mixture by standard techniques. The individual isomers of a compound of formula VII can be obtained, for example, by use of the corresponding individual endo or exo isomers of a compound of formula II or by separation of a resulting mixture by standard techniques.

Scheme XII

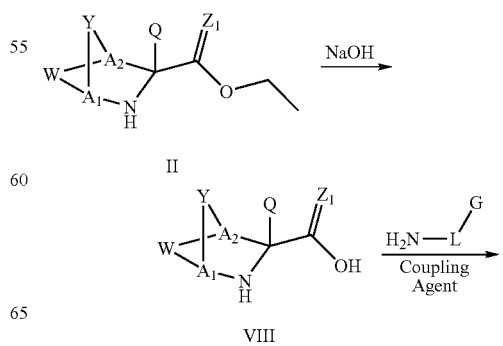

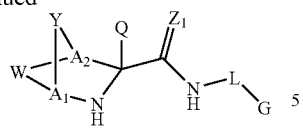

IX

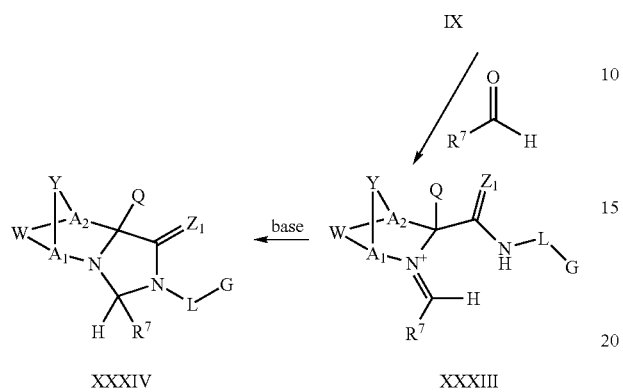

XXXIV   XXXIII

As described in Scheme IIII, a compound of formula IX can readily be made by the process described. As illustrated in Scheme XII, treatment of a compound of formula IX, with an aldehyde reagent of formula R$^7$CHO, which can be obtained from commercial sources or readily synthesized by one skilled in the art, yields an imine intermediate of formula XXXIII. Treatment of the intermediate of formula XXXIII, with a base such as DBU, results in a compound of formula XXXIV, which is a compound of formula I where M and M' are each a bond and E is CHR$^7$. The individual antipodes of a compound of formula XXXIV can be obtained, for example, by use of the corresponding individual antipodes of a compound of formula II or by separation of the racemic mixture by standard techniques. The individual α or β isomers of a compound of formula XXXIV can be obtained by separation of a resulting mixture by standard techniques.

Scheme XIII

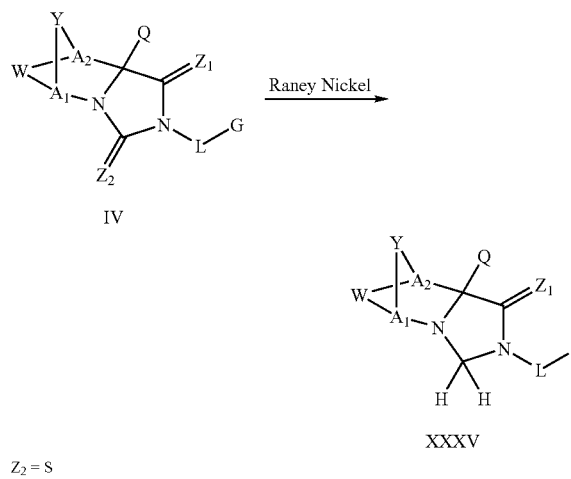

$Z_2 = S$

As described in Scheme I a compound of formula IV, where $Z_2$=S, can readily be made by the process described. As illustrated in Scheme XIII, treatment of a compound of formula IV, where $Z_2$=S, with an agent capable of reductively eliminating sulfur, such as Raney nickel, yields a compound of formula XXXV, which is a compound of formula I, where M and M' are each a bond and E is CH$_2$. The individual antipodes of a compound of formula XXXV can be obtained, for example, by use of the corresponding individual antipodes of a compound of formula II or by separation of the racemic mixture by standard techniques. The individual α or M isomers of a compound of formula XXXV can be obtained by separation of a resulting mixture by standard techniques.

Scheme XIV

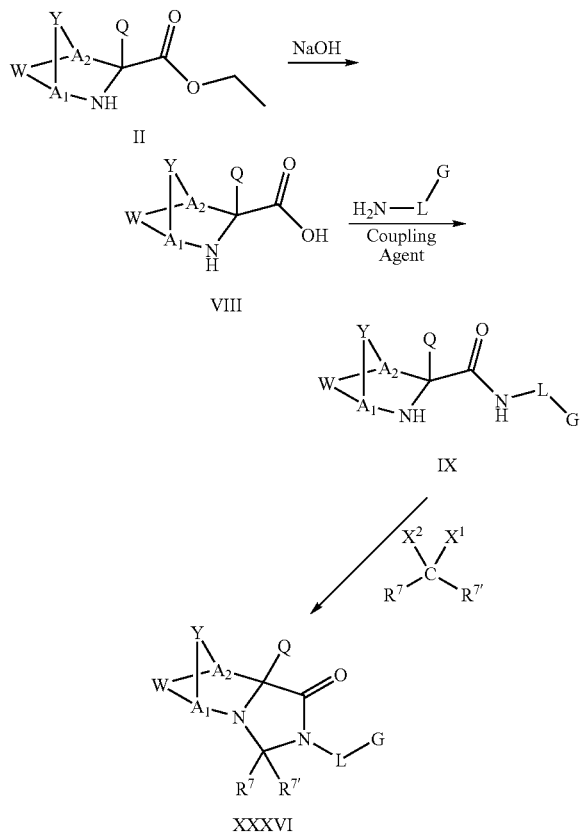

XXXVI

Scheme XIV describes a method for preparing compounds of formula I wherein an intermediate of formula II (where $Z_1$ is O) is saponified to an acid of formula VIII by treatment with a base, such as sodium hydroxide. The acid can then by coupled to an amine of formula H$_2$N-L-G via a variety of coupling reagents, for example, as described in The Practice of Peptide Synthesis, Springer-Verlag, 2$^{nd}$ Ed., Bodanszy, Miklos, 1993 (incorporated herein by reference in its entirety), to yield an amide intermediate of formula IX. The intermediate of formula IX can be treated with a reagent of formula R$^7$R$^{7'}$-C—X$^1$X$^2$ (where X$^1$ and X$^2$ are independently F, Br, Cl, or I, or X$^1$ and X$^2$ are taken together along with the carbon to which they are attached to form C=O), to yield a compound of formula XXXVI, which is a compound of formula I where $Z_1$ is O, M and M' are bonds and E is CR$^7$R$^{7'}$ (such as where one of R$^7$ and R$^{7'}$ is H, C$_{1-4}$alkyl or C$_{1-4}$haloalkyl and the other is R$^1$OC=O).

When the intermediate of formula R$^7$R$^{7'}$—C—X$^1$X$^2$ is a ketone (X$^1$ and X$^2$ are taken together with the attached carbon to form C=O), amines of formula IX can be condensed with these intermediate carbonyl compounds, for example, in the presence of sodium hydroxide in water at a temperature between 0° C. and 25° C. using the procedures described by D. A. Johnson et. al., *J. Org. Chem.* 31, 897 (1966) and Uozumi et. al., *Tetrahedron Letters*, 42 407-410 (2001). (See Scheme XII above for when the intermediate of formula $R^7R^{7'}$—C—$X^1X^2$ is an aldehyde). When the intermediate of formula $R^7R^{7'}$—C—$X^1X^2$ is a dihalide ($X^1$ and $X^2$ are halogens), the condensation can be conducted, for example, in the presence of a base by heating the mixture of IX and $R^7R^{7'}$—C—$X^1X^2$ in an inert solvent. Preferred dihalides of formula $R^7R^{7'}$—C—$X^1X^2$ are ethyl bromofluoroacetate and ethyl bromodifluoroacetate. Examples of suitable bases include alkali salts of carbonate, such as potassium, sodium and lithium, and hydride bases such as sodium hydride. Examples of inert solvents include ethers such as diethyl ether, tetrahydrofuran and dioxane; esters such as ethyl acetate; amides such as dimethylformamide; and acetonitrile. Although the cyclization of compounds of formula IX and $R^7R^{7'}$—C—$X^1X^2$ can proceed at room temperature, the reaction is preferably performed by heating above room temperature. Dihalides, aldehydes and ketones of formula $R^7R^{7'}$C—$X^1X^2$ can be prepared by known methods and many are commercially available. For example, see March, J. *Advanced Organic Chemistry;* 3rd ed., John Wiley: New York, 1985. Other synthetic routes which can be employed for the conversion of compounds of formula IX to compounds of formula XXXVI are analogous to those found in WO-94 14817, U.S. Pat. No. 5,643,855, WO-0107440, WO-9910313, WO-9910312 and JP-46016990 and the references therein. The individual optical isomers of a compound of formula XXXVI (also known as antipodes) can be obtained, for example, by use of the corresponding individual antipodes of a compound of formula II or by separation of the racemic mixture by standard techniques. The individual isomers of a compound of formula XXXVI can be isolated from the resulting mixture, for example, by standard techniques.

Scheme XV

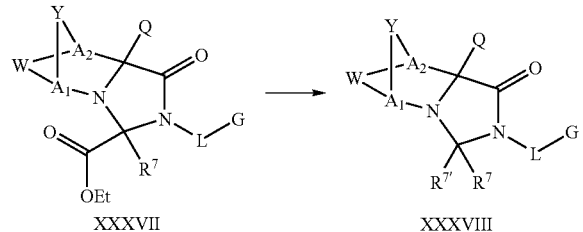

$R^{7'} = R^1$, $COOR^1$, $CONR^1R^{1'}$, Cl, F, Br, I, CN, $OR^1$, $R^1C$=O, $SO_2OR^1$, or $SO_2NR^1NR^{1'}$

As shown in Scheme XV, compounds of formula I where $Z_1$ is O, M and M' are bonds and E is $CR^7R^{7'}$ can be prepared by transforming the imidazolinones of formula XXVIII. The ester of formula XXXVII is hydrolyzed, for example, with sodium hydroxide in a solvent such as methanol or ethanol at about 0° C. to 50° C. to provide the corresponding carboxylic acid. The acid can be converted to the corresponding ester ($R^{7'}$=$COOR^1$) or amide ($R^{7'}$=$CONR^1R^{1'}$) of formula XXXVIII by treatment with thionyl chloride or oxalyl chloride to form the acid chloride followed by treatment with the appropriate alcohol $R^1$—OH or amine H—$NR^1R^{1'}$, respectively.

Treatment of the acid chloride with ammonia produces the unsubstituted amide, $R^{7'}$=$CONH_2$, which can be dehydrated such as by conventional methods to form the nitrile, $R^{7'}$=CN.

Alternatively, esterification of the carboxlic acid can be achieved by reacting the acid with an appropriate alkyl halide in the presence of a base such as potassium carbonate in an inert solvent such as dimethylformamide, for example, at about 0° C. to 60° C. to give the ester of formula XXXVII ($R^{7'}$=$COOR^1$).

The amide of compound XXXVIII ($R^{7'}$=$CONR^1R^{1'}$), can also be obtained by 1,3-dicyclohexylcarbodiimide (DCC) coupling between the carboxylic acid and the appropriate amine H—$NR^1R^{1'}$. The DCC coupling procedure is described by Bodanszky, M. and Bodanszky, A; in *Practice of Peptide Synthesis, Vol.* 21; Springer-Verlag, New York: (1984).

Reduction of the carboxylic acid or ester with a reducing agent such as aluminum hydride in solvent such as tetrahydrofuran, for example, at 0° C. to 80° C. produces the corresponding alcohol, a compound of formula XXXVIII wherein $R^{7'}$=$CH_2OH$.

Treatment of the alcohol with an $R^{13}$-halide (where $R^{13}$ is alkyl (e.g., $C_1$-$C_6$ alkyl) or substituted alkyl; alkenyl (e.g., $C_1$-$C_6$ alkenyl) or substituted alkenyl; cycloalkyl (e.g., $C_3$-$C_6$cycloalkyl) or substituted cycloalkyl; heterocycloalkyl or substituted heterocycloalkyl; aryl or substituted aryl (e.g., substituted by alkyl and additional substituents); heterocyclo or substituted heterocyclo (e.g., heteroaryl or substituted heteroaryl, such as heteroaryl substituted by alkyl and additional substituents), in the presence of a base such as potassium carbonate, in an inert solvent such as acetonitrile, produces compounds of formula XXXVIII, wherein $R^{7'}$=$CH_2OR^{13}$.

Other $R^{7'}$ substitutions are also obtainable from the $CO_2Et$ group of the compounds of formula XXXVII using functional group transformations, such as those known by one skilled in the art.

Scheme XVI

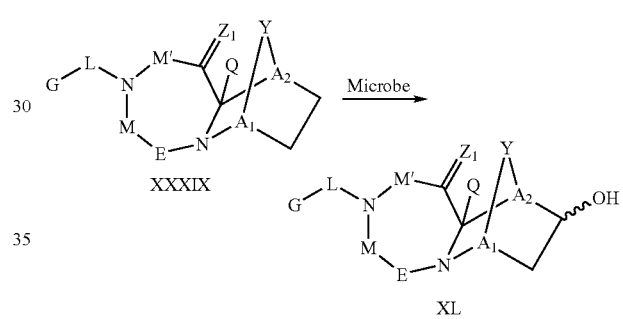

Scheme XVI describes another approach to incorporating additional substitution onto a compound of formula I. As illustrated in Scheme XVI, a compound of formula XXXIX, which can be prepared in accordance with the above Schemes, can be incubated in the presence of a suitable enzyme or microorganism resulting in the formation of a hydroxylated analog of formula XL. Such a process can be employed to yield regiospecific as well as enantiospecific incorporation of a hydroxyl group into a molecule of formula XXXIX by a specific microorganism or by a series of different microorganisms. Such microorganisms can, for example, be bacterial, yeast or fungal in nature and can be obtained from distributors such as ATCC or identified for use in this method such as by methods known to one skilled in the art. Compound XL is a compound of formula I where Y is as described above and A1 and $A_2$ are preferably $CR^7$.

Scheme XVII

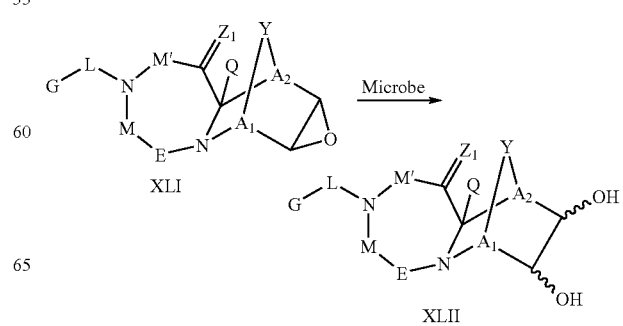

Scheme XVII describes another approach to incorporating additional substitution onto a compound of formula I. As illustrated in Scheme XVII, a compound of formula XLI, which can be prepared in accordance with the above Schemes, can be incubated in the presence of a suitable enzyme or microorganism resulting in the formation of a diol analog of formula XLII. Such a process can be employed to yield regiospecific as well as enantiospecific transformation of a compound of formula XLI to a 1-2 diol of formula XLII by a specific microorganism or by a series of different microorganisms. Such microorganisms can, for example, be bacterial, yeast or fungal in nature and can be obtained from distributors such as ATCC or identified for use in this method such as by methods known to one skilled in the art. Compound XLII is a compound of formula I where Y is as described above and $A_1$ and $A_2$ are preferably $CR^7$.

The present invention also provides the methods of Schemes XVI and XVII.

Thus, in one embodiment, the present invention provides a method for preparation of a compound of the following formula XL, or salt thereof:

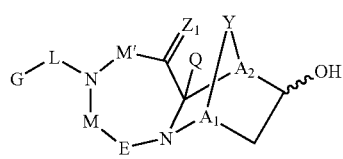

XL where the symbols are as defined herein, comprising the steps of contacting a compound of the following formula XXXIX, or salt thereof:

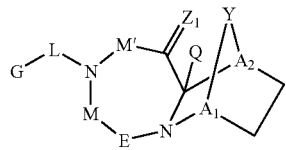

XXXIX where the symbols are as defined above;

with an enzyme or microorganism capable of catalyzing the hydroxylation of said compound XXXIX to form said compound XL, and effecting said hydroxylat In another preferred embodiment, the present invention provides a method for preparation of a compound of the following formula XLII, or salt thereof: ion.

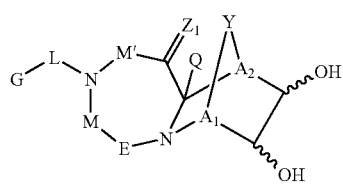

XLII where the symbols are as defined herein, comprising the steps of contacting a compound of the following formula XLI, or salt thereof:

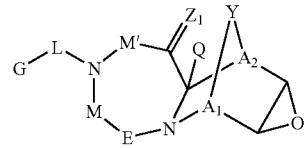

XLI where the symbols are as defined above;

with an enzyme or microorganism capable of catalyzing the opening of the epoxide ring of compound XLI to form the diol of said compound XLII, and effecting said ring opening and diol formation.

All stereoconfigurations of the unspecified chiral centers of the compounds of the formulae XXXIX, XL, XLI, and XLII are contemplated in the methods of the present invention, either alone (that is, substantially free of other stereoisomers) or in admixture with other stereoisomeric forms. Conversion of one isomer selectively (e.g., hydroxylation of the exo isomer preferentially to hydroxylation of the endo isomer) when contacting an isomeric mixture is a preferred embodiment of the invention. Conversion to one isomer selectively (e.g., hydroxylation on the exo face "exo isomer" preferentially to the endo face "endo isomer" or regioselective opening of an epoxide to form only one of two possible regioisomers of a trans diol) is a preferred embodiment of the invention. Hydroxylation of an achiral intermediate to form a single optical isomer of the hydroxylated product is also a preferred embodiment of the invention. Resolution of a recemic mixture of an intermediate by selective hydroxylation, or epoxide ring opening and diol formation, to generate one of the two possible optical isomers is also a preferred embodiment of the invention. The term "resolution" as used herein denotes partial, as well as, preferably, complete resolution.

The terms "enzymatic process" or "enzymatic method", as used herein, denote a process or method of the present invention employing an enzyme or microorganism. The term "hydroxylation", as used herein, denotes the addition of a hydroxyl group to a methylene group as described above. Hydroxylation can be achieved, for example, by contact with molecular oxygen according to the methods of the present invention. Diol formation can be achieved, for example, by contact with water according to the methods of the present invention. Use of "an enzyme or microorganism" in the present methods includes use of two or more, as well as a single, enzyme or microorganism.

The enzyme or microorganism employed in the present invention can be any enzyme or microorganism capable of catalyzing the enzymatic conversions described herein. The enyzmatic or microbial materials, regardless of origin or purity, can be employed in the free state or immobilized on a support such as by physical adsorption or entrapment. Microorganisms or enzymes suitable for use in the present invention can be selected by screening for the desired activity, for example, by contacting a candidate microorganism or enzyme with a starting compound XXXIX or XLI or salt thereof, and noting conversion to the corresponding compound XL or XLII or salt thereof. The enzyme may, for example, be in the form of animal or plant enzymes or mixtures thereof, cells of microorganisms, crushed cells, extracts of cells, or of synthetic origin.

Exemplary microorganisms include those within the genera: *Streptomyces* or *Amycolatopsis*. Particularly preferred microorganisms are those within the species *Streptomyces griseus*, especially *Streptomyces griseus* ATCC 10137, and *Amycolatopsis orientalis* such as ATCC 14930, ATCC 21425, ATCC 35165, ATCC 39444, ATCC 43333, ATCC 43490, ATCC 53550, ATCC 53630, and especially ATCC 43491. The term "ATCC" as used herein refers to the accession number of the American Type Culture Collection, 10801 University Blvd., Manassas Va. 20110-2209, the depository for the organism referred to. It should be understood that mutants of these organisms are also contemplated by the present invention, for use in the methods described herein, such as those modified by the use of chemical, physical (for example, X-rays) or biological means (for example, by molecular biology techniques).

Preferred enzymes include those derived from microorganisms, particularly those microorganisms described above. Enzymes may be isolated, for example, by extraction and purification methods such as by methods known to those of ordinary skill in the art. An enzyme may, for example, be used in its free state or in immobilized form. One embodiment of the invention is that where an enzyme is adsorbed onto a suitable carrier, e.g., diato-maceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. When employed to immobilize an enzyme, a carrier may control the enzyme particle size and prevent aggregation of the enzyme particles when used in an organic solvent. Immobilization can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. While it is desirable to use the least amount of enzyme possible, the amount of enzyme required will vary depending upon the specific activity of the enzyme used.

Hydroxylation as described above can occur in vivo. For example, liver enzyme can selectively, relative to the endo isomer, hydroxylate the exo isomer of a compound of the present invention. In conducting the methods of the present invention outside the body, liver microsomal hydroxylase can be employed as the enzyme for catalysis.

These processes may also be carried out using microbial cells containing an enzyme having the ability to catalyze the conversions. When using a microorganism to perform the conversion, these procedures are conveniently carried out by adding the cells and the starting material to the desired reaction medium.

Where microorganisms are employed, the cells may be used in the form of intact wet cells or dried cells such as lyophilized, spray-dried or heat-dried cells, or in the form of treated cell material such as ruptured cells or cell extracts. Cell extracts immobilized on Celite® or Accurel® polypropylene as described earlier may also be employed. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic methods of the present invention may be carried out subsequent to the fermentation of the microorganism (two-stage fermentation and conversion), or concurrently therewith, that is, in the latter case, by in situ fermentation and conversion (single-stage fermentation and conversion).

Growth of the microorganisms can be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources can include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources can include N-Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements can include magnesium, manganese, calcium, cobalt, nickel, iron, sodium and potassium salts. Phosphates may also be added in trace or, preferably, greater than trace amounts.

The medium employed can include more than one carbon or nitrogen source or other nutrient.

Preferred media for growth include aqueous media.

The agitation and aeration of the reaction mixture affects the amount of oxygen available during the conversion process when conducted, for example, in shake-flask cultures or fermentor tanks during growth of microorganisms.

Incubation of the reaction medium is preferably at a temperature between about 4 and about 60° C. The reaction time can be appropriately varied depending upon the amount of enzyme used and its specific activity. Reaction times may be reduced by increasing the reaction temperature and/or increasing the amount of enzyme added to the reaction solution.

It is also preferred to employ an aqueous liquid as the reaction medium, although an organic liquid, or a miscible or immiscible (biphasic) organic/aqueous liquid mixture, may also be employed. The amount of enzyme or microorganism employed relative to the starting material is selected to allow catalysis of the enzymatic conversions of the present invention.

Solvents for the organic phase of a biphasic solvent system may be any organic solvent immiscible in water, such as toluene, cyclohexane, xylene, trichlorotrifluoroethane and the like. The aqueous phase is conveniently of water, preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase, and most preferably contains at or about 20 percent by volume of organic phase and at or about 80 percent by volume of the aqueous phase.

An exemplary embodiment of such processes starts with preparation of an aqueous solution of the enzyme(s) or microbes to be used. For example, the preferred enzyme(s) or microbes can be added to a suitable amount of an aqueous solvent, such as phosphate buffer or the like. This mixture is preferably adjusted to and maintained at a desired pH.

The compounds XL and XLII produced by the processes of the present invention can be isolated and purified, for example, by methods such as extraction, distillation, crystallization, and column chromatography.

Other compounds of the formula I, such as compounds where M is $CR^7R^{7'}$ or compounds where one of M or M' is other than a bond and E is $CHR^7$, can be readily prepared by one of ordinary skill in the art, for example, by methods analogous to those described herein.

Compounds of formula I can also be made, wherever appropriate, by methods described in U.S. application Ser. No. 10/025,116, filed concurrently herewith by Mark Salvati et al., entitled "Fused Heterocyclic Succinimide Compounds and Analogs Thereof, Modulators of Nuclear Hormone Receptor Function", filed Dec. 19, 2001, now abandoned, by reference in its entirety, such as by microbial/enzymatic conversion and/or separation methods as described therein.

Exemplary methods for the preparation of compounds of the formula II (employed in the above Schemes) are illustrated in the following FIGS. 1 to 3.

As shown in FIG. 1, an ethyl glyoxylate derivative can be treated with saturated aq. $NH_4Cl$ and the appropriate diene of formula A to give the compound of formula II, where Q=H. Such a cyclization can be enhanced by the addition of metal salts, such as but not limited to Ytterbium (III) trifluoromethanesulfonate, as described in the documents cited previously. An intermediate of formula II can be made where Q≠H, by protection of the secondary nitrogen with a protection group such as a BOC, followed by treatment with reactive intermediates of formula Q-X, where X represents a leaving group or X is an electrophilic center which can react to ultimately make up the definition of Q as described earlier, in the presence of base, such as LDA, or a coupling agent as is readily known by one skilled in the art, followed by deprotection of the BOC group with an acid such as saturated ethanolic HCl.

Figure 2:
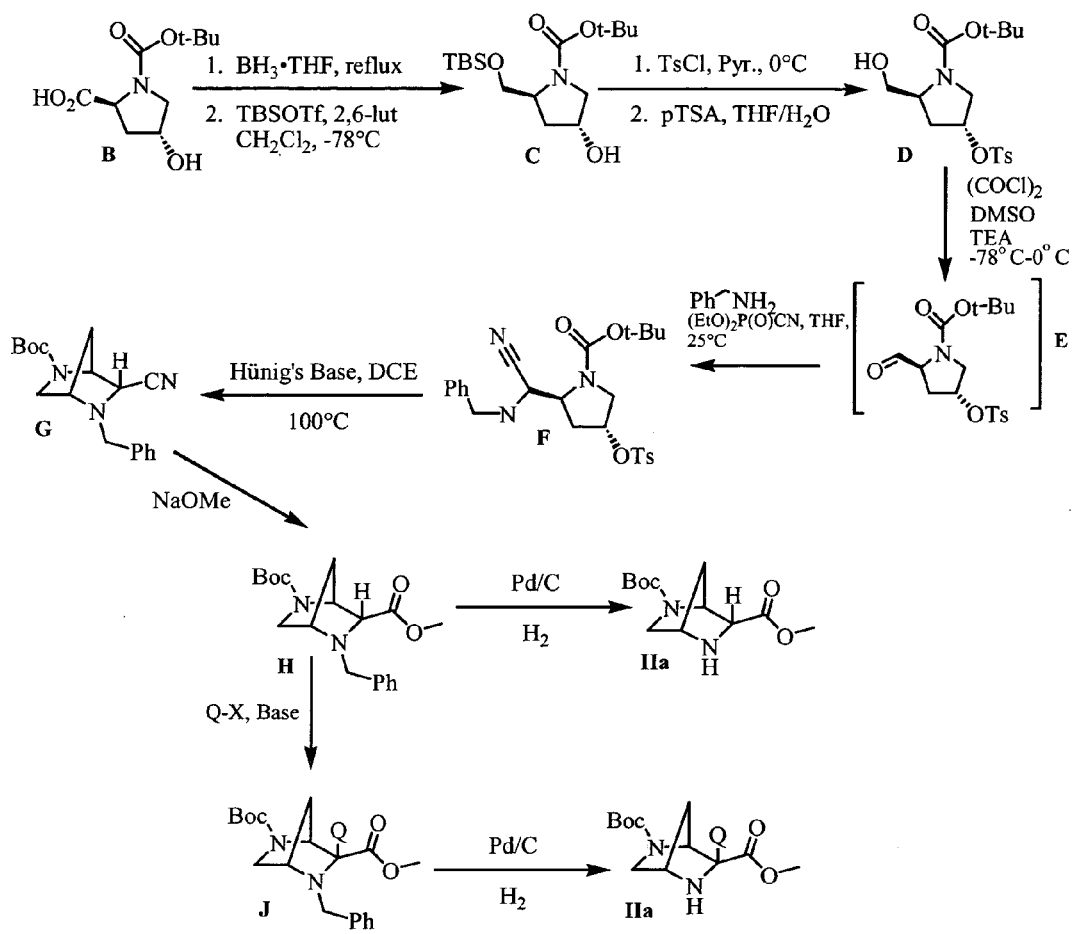

As shown in FIG. 2 (with preferred conditions indicated therein), the commercially available chiral (pure D or L) intermediate N-(tert-butoxycarbonyl)-L-4-hydroxyproline, B, can be treated with a reducing agent, such as BH₃.THF, to yield a primary alcohol, which can then be selectively protected with an agent such as TBSOTf, in the presence of base (e.g., 2,6-lutidine), to yield the intermediate alcohol C. The secondary alcohol of C can then be differentially protected by treatment with an agent such as TsCl, in the presence of a base (e.g., pyridine), followed by deprotection of the primary alcohol (which can be achieved by treatment with an acid, such as para-toluenesulphonic acid), to yield intermediate alcohol D. The resulting alcohol D can be oxidized, such as under standard Swern conditions, to yield the corresponding aldehyde intermediate E. The aldehyde intermediate E can be directly treated with benzylamine and diethyl cyanophosphonate to give intermediate F. Treatment of intermediate F with a base, such as Hüning's base, with heating, yields the bicyclic intermediate G. Treatment of G with a base, such as sodium methoxide, converts the nitrile intermediate G directly to the ester intermediate H. Treatment of intermediate H with an agent to remove the benzyl group, such as palladium on charcoal with hydrogen gas, results in the formation of an intermediate of Formula IIa where Q=Hydrogen. Alternatively, the intermediate of formula II can be treated with reactive intermediates of formula Q-X, where X represents a leaving group or X is an electrophilic center which can react to ultimately make up the definition of Q as described earlier, in the presence of base, such as LDA, or a coupling agent as is readily known by one skilled in the art, which, after treatment with an agent such as palladium on charcoal, yields an intermediate of formula IIa where Q≠H. The various intermediates of FIG. 2 can be purified, for example, by silica purification, or can, for example, be simply carried forward in situ to the next step (e.g., converting D to F without isolating E).

The method of FIG. 2 is novel, as are intermediates prepared therein, all of which form part of the present invention.

Thus, for example, the following method is novel as are the individual steps and intermediates produced therein (e.g., E, F, G, H, J and IIa): a method for the preparation of a compound of the following formula IIa:

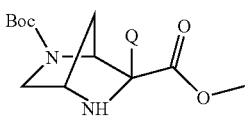

IIa where

BOC is t-butoxycarbonyl; and

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

comprising the steps of (i) treating a compound of the following formula B:

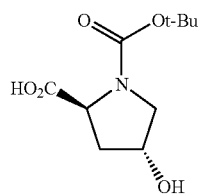

B with a reducing agent to reduce the carboxylic acid group to hydroxymethyl, followed by protection of said hydroxy to yield a compound of the following formula C:

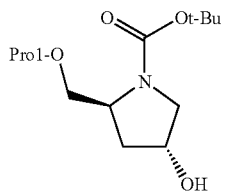

C where Pro I is a hydroxyl protecting group;

(ii) protecting the unprotected hydroxyl group of the compound of formula C, followed by deprotection of Pro1 —O— to form hydroxyl, yielding a compound of the following formula D:

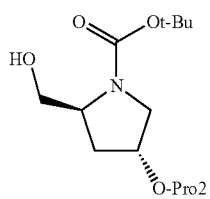

D where Pro2 is a protecting group;

(iii) oxidizing the hydroxymethyl group of D, yielding an aldehyde of the following formula E:

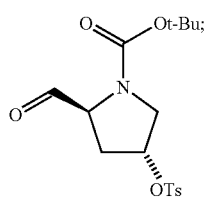

E (iii) treating E with benzylamine and diethyl cyanophosphonate, yielding a compound of the following formula F:

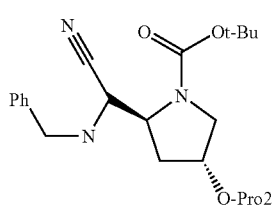

F (iv) treating said compound of the formula F with a base with heating to yield a compound of the following formula G:

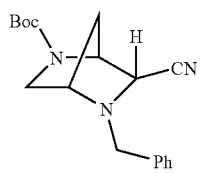

G (v) treating said compound of the formula G with a base to convert the nitrile group to methoxycarbonyl yielding a compound of the following formula H:

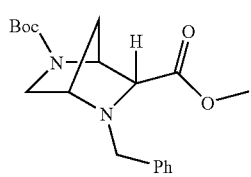

H and (vi) removing the benzyl group of said compound of the formula II to form said compound of the formula IIa,; wherein, optionally, said compound of the formula II is contacted with a compound Q-X, where X is a leaving group or X is an electrophilic center which can react to form a group Q, prior to said removal to form compounds of the formula IIa where Q is other than hydrogen.

The method of FIG. 2 is especially useful for the preparation of unnatural amino acids IIa which can be employed, by methods analogous to those using compounds of the formula II, in the preparation of the present compounds of formula I.

Figure 3:
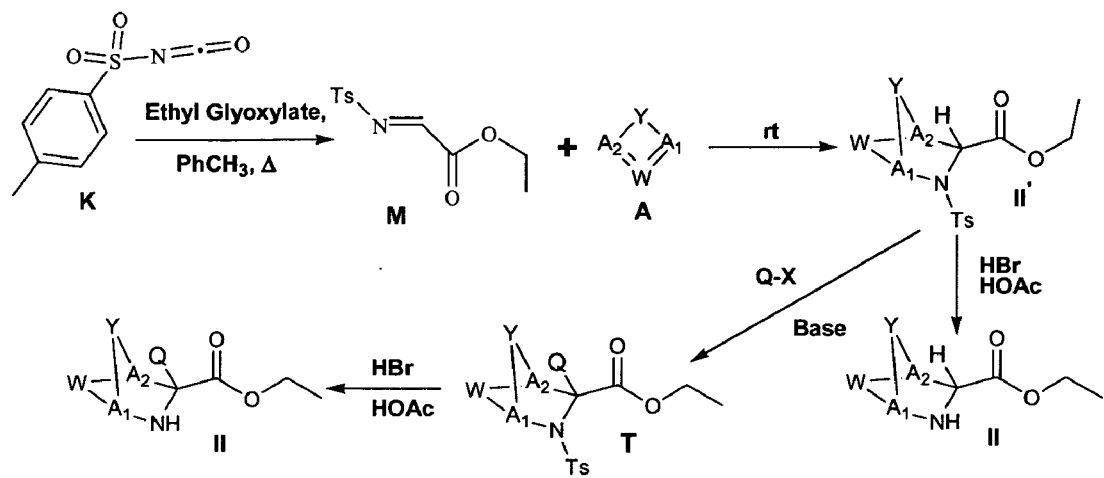

As shown in FIG. 3 (with preferred conditions indicated therein), the activated imine intermediate M can be generated by the reactions of an activated sulfonyl isocyanate, such as p-toluenesulfonyl isocyanate, with ethyl glyoxylate and heating. Imine M can undergo cyclization with an appropriate diene intermediate of formula A to give an intermediate of formula II'. Such a cyclization can be enhanced by the addition of metal salts, such as but not limited to Ytterbium (III) trifluoromethanesulfonate, as described in the references cited previously. The tosyl protecting group can be removed from intermediate II' by a number of reagents, such as those known to one skilled in the art, such as hydrogen bromide in acetic acid, to yield an intermediate of formula II. The intermediate of formula II' can be treated with reactive intermediates of formula Q-X, where X represents a leaving group or X is an electrophilic center which can react to ultimately make up the definition of Q as described earlier, in the presence of base, such as LDA, or a coupling agent as is readily known by one skilled in the art, to yield the intermediate of formula T. The tosyl protecting group can be removed from intermediate T by a number of reagents known to one skilled in the art, such as hydrogen bromide in acetic acid, to yield an intermediate of formula II, where Q≠H.

Preferred Compounds

A preferred subgenus of the compounds of the present invention includes compounds of the formula I or salts thereof wherein one or more, preferably all, of the following substituents are as defined below:

G is an aryl (especially, phenyl or naphthyl) or heterocyclo (e.g., heteroaryl) group, where said group is mono- or polycyclic, and which is optionally substituted at one or more positions, preferably with hydrogen, $C_{1-6}$ alkyl, alkyl substituted with one or more halogens (e.g., perfluoroalkyl), heterocyclo, alkyl substituted with hydroxy, allyl or substituted allyl, alkynyl, Cl, F, Br, I, CN, $R^1OC=O$, $R^1C=O$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^1O)P=O$, $(R^1)(R^1)P=O$, or $(R^{1'})(NHR^1)P=O$;

E is $C=Z_2$, $CHR^7$, $SO_2$, $P=OR^2$, or $P=OOR^2$;

$Z_1$ is O, S, or $NR^6$;

$Z_2$ is O, S, or $NR^6$;

$A_1$ is $CR^7$ (especially, CH);

$A_2$ is $CR^7$ (especially, CH);

Y is J-J'-J" where J is $(CR^7R^{7'})n$ and n=0-2, J' is a bond or NH, $NR^6$, C=O, cycloalkyl (especially, cyclopropyl or cyclobutyl), or cycloalkenyl (especially, cyclobutenyl or cyclopentenyl), and J" is $(CR^7R^{7'})n$ and n=1-2, where Y is not a bond;

W is $CR^7R^{7'}$—$CR^7R^{7'}$, $CR^8=CR^{8'}$, $CR^7R^{7'}$—C=O, $NR^9$—$CR^7R^{7'}$, cycloalkyl (especially, cyclopropyl or cyclobutyl) or cycloalkenyl (especially, cyclobutenyl or cyclopentenyl);

Q is H, $C_{1-6}$ alkyl, alkyl substituted with one or more halogens (e.g., perfluoroalkyl), $C_{1-6}$ alkyl substituted with hydroxy, alkenyl (e.g., allyl), alkynyl, Cl, F, Br, I, arylalkyl (e.g., benzyl) or substituted arylalkyl, CN, $R^1OC=O$, $R^4C=O$, $R^5R^6NC=O$, $HOCR^7R^{7'}$, $R^1OCH_2$, $R^1O$, $NH_2$, or $NR^4R^5$;

M is a bond or $NR^{10}$, and M' is a bond or $NR^{10}$, with the proviso that at least one of M or M' must be a bond;

L is a bond, $(CR^7R^{7'})n$, NH, or $NR^5$ where n=0-1;

$R^1$ and $R^{1'}$ are each independently H, alkyl, perfluoroalkyl, cycloalkyl, heterocyclo, cycloalkylalkyl, or heterocycloalkyl;

$R^2$ is alkyl, perfluoroalkyl, cycloalkyl, heterocyclo, cycloalkylalkyl, or heterocycloalkyl;

$R^3$ and $R^{3'}$ are each independently H, alkyl, perfluoroalkyl, cycloalkyl, heterocyclo, cycloalkylalkyl, heterocycloalkyl, Cl, F, Br, I, CN, alkoxy, amino, $NR^1R^2$, thiol, or alkylthio;

$R^4$ is H, alkyl, cycloalkyl, heterocyclo, cycloalkylalkyl, heterocycloalkyl, $R^1C=O$, $R^1NHC=O$, $SO_2OR^1$, or $SO_2NR^1R^{1'}$;

$R^5$ is alkyl, cycloalkyl, heterocyclo, cycloalkylalkyl, heterocycloalkyl, $R^1C=O$, $R^1NHC=O$, $SO_2OR^1$, or $SO_2NR^1R^{1'}$;

$R^6$ is alkyl or substituted alkyl, cycloalkyl or substituted cycloalkyl, heterocyclo or substituted heterocyclo, cycloalkylalkyl or substituted cycloalkylalkyl, heterocycloalkyl or substituted heterocycloalkyl, aryl or substituted aryl, arylalkyl or substituted arylalkyl, CN, OH, $OR^1$, $R^1C=O$, $R^1NHC=O$, $SO_2OR^1$, or $SO_2NR^1R^{1'}$;

$R^7$ and $R^{7'}$ are each independently H, alkyl, perfluoroalkyl, cycloalkyl, heterocyclo, cycloalkylalkyl, heterocycloalkyl, aryl, arylalkyl, Cl, F, Br, I, CN, $OR^1$, nitro, hydroxylamine, hydroxylamide, amino, $NHR^4$, $NR^2R^5$, $NOR^1$, thiol, alkylthio, $R^1C=O$, $R^1NHC=O$, $SO_2OR^1$, or $SO_2NR^1R^{1'}$;

$R^8$ and $R^{8'}$ are each independently H, alkyl or substituted alkyl, cycloalkyl or substituted cycloalkyl, heterocyclo or substituted heterocyclo, cycloalkylalkyl or substituted cycloalkyalkyl, heterocycloalkyl or substituted heterocycloalkyl, aryl or substituted aryl, arylalkyl or substituted arylalkyl, halo, CN, $OR^1$, amino, $NHR^4$, $NR^2R^5$, $NOR^1$, alkylthio or substituted alkylthio, $R^1C=O$, $R^1NHC=O$, $SO_2OR'$, or $SO_2NR^1R^{1'}$;

$R^9$ and $R^{9'}$ are each independently H, alkyl, alkenyl, cycloalkyl, heterocyclo, cycloalkylalkyl, heterocycloalkyl, aryl, arylalkyl, CN, OH, $OR^1$, $R^1C=O$, $R^1OC=O$, $R^1NHC=O$, $SO_2R^1$, $SO_2OR^1$, or $SO_2NR^1R^{1'}$; and $R^{10}$ is H, alkyl, cycloalkyl, heterocyclo, cycloalkylalkyl, heterocycloalkyl, aryl, arylalkyl, CN, OH, $OR^1$, $R^1C=O$, $R^1OC=O$, $R^1R^{1'}NC=O$, $SO_2OR^1$, or $SO_2NR^1R^{1'}$.

A more preferred subgenus of the compounds of the invention includes compounds of the formula I or salts thereof wherein one or more, preferably all, of the following substituents are as defined below:

G is an aryl or heteroaryl group, where said group is mono- or polycyclic, and which is optionally substituted at one or more positions with hydrogen, $C_1$-$C_3$ alkyl, allyl or substituted allyl, alkynyl, Cl, F, Br, I, CN, $R^1C=O$, $R^1HNC=O$, $R^1R^2NC=O$, haloalkyl (especially, perfluoroalkyl), $C_1$-$C_3$ hydroxyalkyl, $HOCR^3R^{3'}$, nitro, $R^1OCH_2$, $R^1O$, $NR^4R^5$, or $SR^1$;

E is $C=Z_2$, $CHR^7$ or $SO_2$;

$Z_1$ is O, S, or NCN;

$Z_2$ is O, S, or NCN;

$A_1$ is $CR^7$ (especially, CH);

$A_2$ is $CR^7$ (especially, CH);

Y is J, cyclopropyl, or cyclobutyl, where $J=(CR^7R^{7'})n$ and n=1-3;

W is $CR^7R^{7'}$—$CR^7R^{7'}$, $CR^8=CR^{8'}$, $CR^7R^{7'}$—C=O, cyclopropyl, or cyclobutyl;

Q is hydrogen, $C_1$-$C_4$ alkyl, alkynyl, Cl, F, Br, I, CN, $R^1OC=O$, $R^4C=O$, $R^5R^6NC=O$, haloalkyl (especially, perfluoroalkyl), $C_1$-$C_6$ hydroxyalkyl, $HOCR^7R^{7'}$, $R^1OCH_2$, $R^1O$, $NH_2$ or $NR^4R^5$;

M is a bond and M' is a bond;

L is a bond, $(CR^7R^{7'})n$, NH, or $NR^5$, where n=0-1;

$R^1$ and $R^{1'}$ are each independently H, alkyl, cycloalkyl, heterocycloalkyl, or perfluoroalkyl;

$R^2$ is alkyl, cycloalkyl, heterocycloalkyl, or perfluoroalkyl;

$R^3$ and $R^{3'}$ are each independently H, alkyl, perfluoroalkyl, Cl, F, Br, I, CN, alkoxy, amino, $NR^1R^2$, thiol, or alkylthio;

R⁴ is H, alkyl, cycloalkyl, heterocycloalkyl, R¹C=O, R¹NHC=O, SO₂OR¹, or SO₂NR¹R¹';

R⁵ is alkyl, cycloalkyl, heterocycloalkyl, R¹C=O, R¹NHC=O, SO₂OR¹, or SO₂NR¹R¹';

R⁷ and R⁷' are each independently H, alkyl, arylalkyl, heteroaryl, perfluoroalkyl, heteroarylalkyl, Cl, F, Br, I, CN, OR¹, amino, NHR⁴, NR²R⁵, NOR¹, thiol, alkylthio, R¹C=O, R¹NHC=O, SO₂OR¹, or SO₂NR¹R¹'; and R¹⁰ is H, alkyl, cycloalkyl, heterocycloalkyl (especially, heteroarylalkyl), aryl, heteroaryl (such as heteroarylium), arylalkyl, CN, R¹C=O, R¹R¹'NC=O, SO₂OR¹, or SO₂NR¹R¹'.

Another more preferred subgenus of the compounds of the invention includes compounds of the formula I or salts thereof wherein one or more, preferably all, of the following substituents are as defined below:

G is an aryl or heteroaryl group, where said group is mono- or polycyclic, and which is optionally substituted at one or more positions with hydrogen, $C_1$-$C_3$ alkyl, allyl or substituted allyl, alkynyl, Cl, F, Br, I, CN, R¹C=O, R¹HNC=O, haloalkyl (especially, perfluoroalkyl), $C_1$-$C_3$ hydroxyalkyl, HOCR³R³', nitro, R¹OCH₂, R¹O, NR⁴R⁵, or SR¹;

E is C=Z₂;

Z₁ is O;

Z₂ is O or NCN;

A₁ is CR⁷ (especially, CH);

A₂ is CR⁷ (especially, CH);

Y is J, where J=(CR⁷R⁷')n and n=1-3;

W is CR⁷R⁷'—CR⁷R⁷', CR⁸=CR⁸', or CR⁷R⁷'—C=O;

Q is hydrogen, $C_1$-$C_4$ alkyl, alkynyl, Cl, F, Br, I, CN, R⁴C=O, R⁵R⁶NC=O, haloalkyl (especially, perfluoroalkyl), $C_1$-$C_6$ hydroxyalkyl, HOCR⁷R⁷', R¹OCH₂, R¹O, NH₂ or NR⁴R⁵;

M is a bond and M' is a bond;

L is a bond;

R¹ and R¹' are each independently H, alkyl, or perfluoroalkyl;

R² is alkyl, or perfluoroalkyl;

R³ and R³' are each independently H, alkyl, perfluoroalkyl, Cl, F, Br, I, CN, alkoxy, amino, NR¹R², thiol, or alkylthio;

R⁴ is H, alkyl, R¹C=O, R¹NHC=O, or SO₂NR¹R¹';

R⁵ is alkyl, R¹C=O, R¹NHC=O, or SO₂NR¹R¹';

R⁷ and R⁷' are each independently H, alkyl, arylalkyl, heteroaryl, perfluoroalkyl, heteroarylalkyl, Cl, F, Br, I, CN, OR¹, amino, NHR⁴, NR²R⁵, NOR¹, R¹C=O, R¹NHC=O, or SO₂NR¹R¹'; and R¹⁰ is H, alkyl, aryl, heteroaryl, arylalkyl, heteroarylalkyl, CN, R¹C=O, R¹R¹'NC=O, or SO₂NR¹R⁴¹.

A particularly preferred subgenus of the compounds of the invention includes compounds of the formula I or salts thereof wherein one or more, preferably all, of the substituents are as defined below:

G is an aryl (especially, phenyl or naphthyl) or heterocyclo (especially benzo-fused heterocyclic groups such as indole, benzothiophene, benzothiazole, benzothiadiazole, benzisoxazole, benzoxadiazole, oxidobenzothiophene, benzofuran or benzopyran) group, where said group is mono- or polycyclic, and which is optionally substituted at one or more positions, such as 1 to 5 positions (preferably 1 to 2 positions), with substituents selected from one or more of hydrogen, NH₂, alkyl (especially having 1 to 4 carbons) or substituted alkyl (especially having 1 to 4 carbons and substituted with halo, such as the substituted alkyl group CF₃), halo (especially F, Cl, Br or I), heterocyclo (such as tetrazole or oxazole), CN, nitro, SR¹ or R¹O (especially where R¹ is alkyl);

E is C=Z₂ or CHR⁷ (especially where R⁷ is hydrogen);

Z₁ is O or S;

Z₂ is O, S, or NR⁶ (especially where R⁶ is CN or phenyl);

A₁ is CR⁷ (especially where R⁷ is hydrogen);

A₂ is CR⁷ (especially where R⁷ is hydrogen);

Y is (CR⁷R⁷')n and n=1-2 (especially where R⁷ and R⁷' are hydrogen);

W is CR⁷R⁷'—CR⁷R⁷', CR⁸=CR⁸', or NR⁹—CR⁷R⁷' (especially where R⁷, R⁷', R⁸ and R⁸' and hydrogen and R⁹ is as defined in this preferred subgenus);

Q is H, alkyl (especially having 1 to 4 carbons), alkenyl (especially having 1 to 4 carbon atoms), arylalkyl (especially benzyl) or substituted arylalkyl (especially substituted benzyl, such as halo-substituted benzyl);

M is a bond or NH (especially a bond), and M' is a bond;

L is a bond;

R¹ and R¹' are each independently alkyl (especially having 1 to 4 carbons) or substituted alkyl (especially having 1 to 4 carbons and substituted with halo), heterocyclo (such as imidazole or isoxazole) or substituted heterocyclo (such as imidazole substituted with methyl), aryl (especially phenyl) or substituted aryl (especially phenyl substituted with one or more of halo, nitro, halo-substituted alkyl such as CF₃, or alkyl having 1 to 4 carbons), arylalkyl (especially benzyl or phenethyl) or substituted arylalkyl (especially substituted benzyl such as halo- and/or nitro-substituted benzyl); and R⁹ and R⁹' are each independently H, alkyl (especially having 1 to 4 carbons), alkenyl (especially having 1 to 4 carbons), arylalkyl (especially benzyl), R¹C=O, R¹OC=O, R¹NHC=O, or SO₂R¹ (especially where each R¹ is independently as defined in this preferred subgenus).

In this particularly preferred subgenus, G-L- can be, for example, selected from optionally substituted phenyl, optionally substituted naphthyl and optionally substituted fused bicyclic heterocyclic groups such as optionally substituted benzo-fused heterocyclic groups (e.g., bonded to the remainder of the molecule through the benzene portion), especially such groups wherein the heterocyclic ring bonded to benzene has 5 members exemplified by benzoxazole, benzothiazole, benzothiadiazole, benzoxadiazole or benzothiophene, for example:

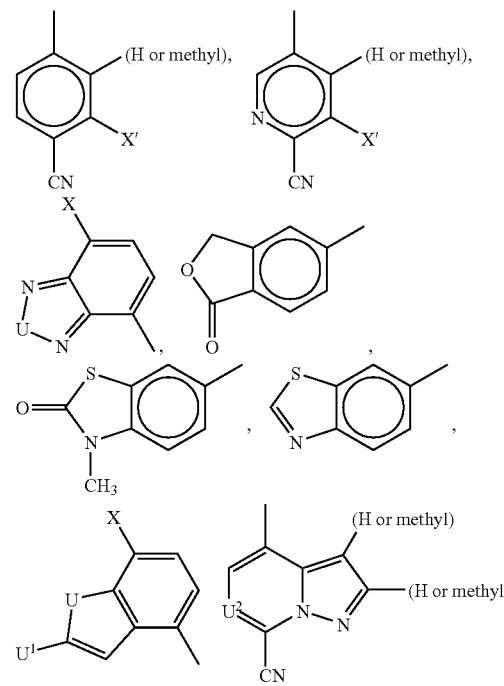

-continued

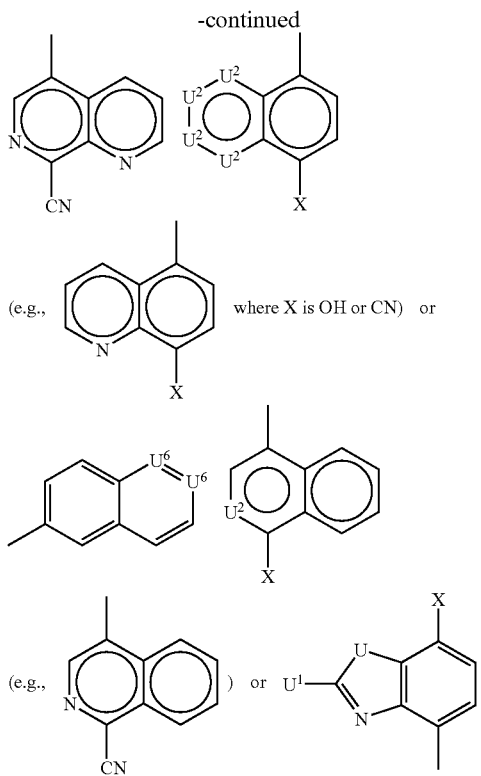

(e.g., <image of quinoline with methyl and X>) where X is OH or CN) or

<image of isoquinoline derivative with CN> where
X=halo (especially F, Cl), OH, CN, NO$_2$ or

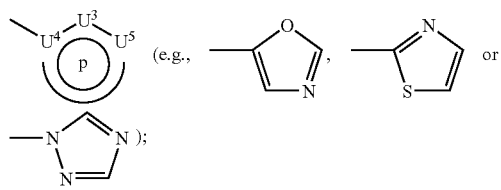

X'=halo (especially Cl, F, or I), CH$_3$, CF$_3$, CN or OCH$_3$;
U is O or S (where S can optionally be oxygenated, e.g., to SO);
U$^1$ is CH$_3$ or CF$_3$;
each U$^2$ is independently N, CH or CF;
U$^3$ is N, O or S;
U$^4$ and U$^5$, together with the atoms to which they are bonded, form an optionally substituted 5-membered heterocyclic ring which can be partially unsaturated or aromatic and which contains 1 to 3 ring heteroatoms;
each U$^6$ is independently CH or N; and <image of circle labeled p> denotes optional double bond(s) within the ring formed by U$^3$, U$^4$ and U$^5$.

Especially preferred are compounds of the formula I having the following structure, or salts thereof:

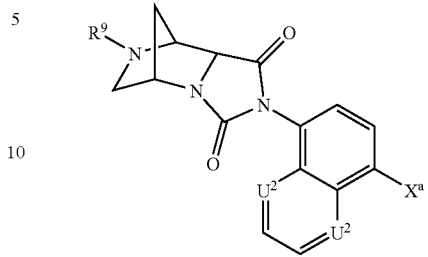

where R$^9$ and U$^2$ are as defined above, such as optionally substituted arylcarbonyl or optionally substituted aryloxycarbonyl, and X$^a$ is an aryl substituent, such as nitro.

Also especially preferred are compounds of the formula I having the following structure or salts thereof:

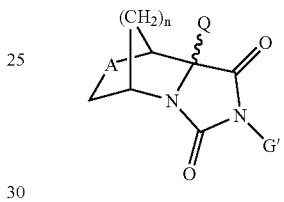

where
n is 1 or 2;
Q is H, methyl or ethyl;

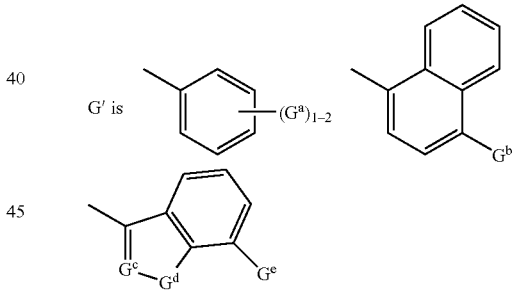

each G$^a$ is independently CN, NO$_2$, CF$_3$, Cl, Br, F, OCH$_3$, SCH$_3$, I, CH$_3$, C(O)—CH$_3$ or

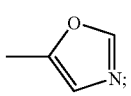

G$^b$ is CN, H, F, Br, NO$_2$ or

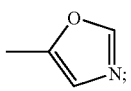

$G^c$ is CH or N;

$G^d$ is S or O;

$G^e$ is H or F;

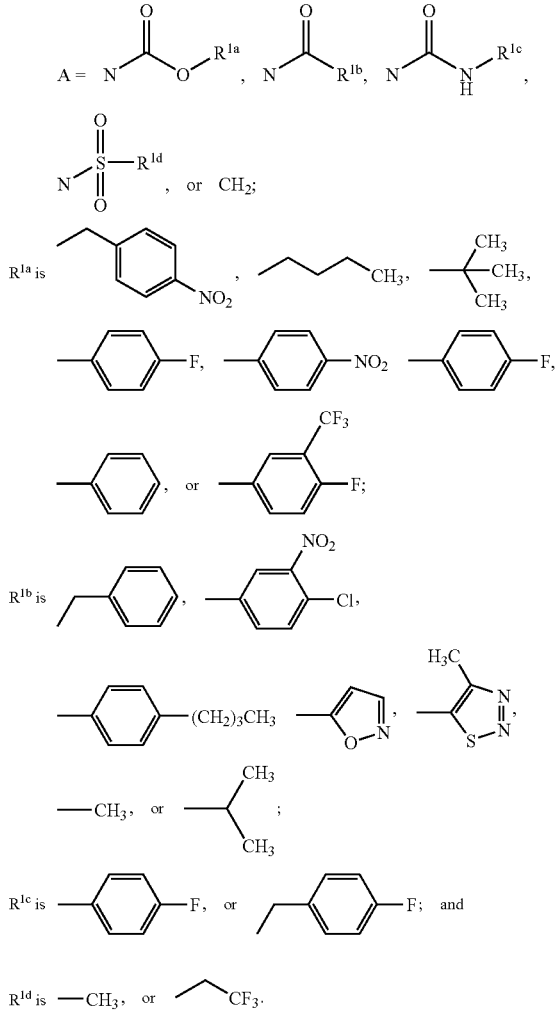

Use and Utility

Applicants incorporate by reference the "Use and Utility" Section of the parent application, U.S. patent application Ser. No. 10/322,306, filed Dec. 18, 2002, appearing at about pages 63 to 103 of said application, as if fully set forth herein at length. Compounds of the present invention modulate the function of nuclear hormone receptors (NHR), and include compounds which are, for example, agonists, partial agonists, antagonists or partial antagonists of the androgen receptor (AR).

EXAMPLES 1-3

Applicants incorporate by reference Examples 1-3 of the parent case hereof, i.e., U.S. patent application Ser. No. 10/322,306, filed Dec. 18, 2002, as if said examples were fully set forth herein at length.

EXAMPLE 4

(5α, 8α,8aα)-2,3,8.8a-Tetrahydro-2-[3-(trifluoromethyl)phenyl]-3-thioxo-5,8-methanoimidazo[1,5-a]pyridine-1,3(2H,5H)-one (4B)

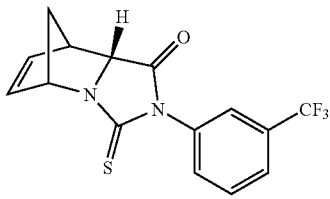

A. endo/exo-2-[[[3-(Trifluoromethyl)phenyl]amino]thioxomethyl]-2-azabicyclo[2.2.1]hept-5-ene-3-carboxylic acid, ethyl ester (4A)

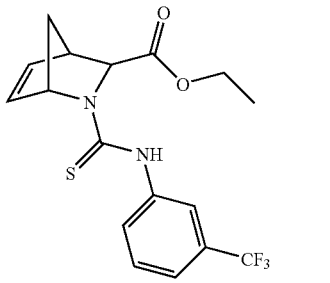

To a solution of 2-azabicyclo[2.2.1.]hept-5-ene-3-carboxylic acid, ethyl ester (0.253 g, 1.5 mmol) in toluene (7.0 mL) was added 3-(trifluoromethylphenyl)-isothiocyanate (0.339 g, 1.66 mmol). After 14 h at 25° C., the reaction was diluted with EtOAc and washed with 1N NaOH (2×10 mL). The organic layer was dried over anhydrous sodium sulfate and the crude material was purified by silica gel chromatography using a gradient of 0 to 20% acetone in hexane to yield 188 mg (34%) of intermediate compound 4B.

A. (5α,8α,8aα)-2,3,8,8a-Tetrahydro-2-[3-(trifluoromethyl)phenyl]-3-thioxo-5,8-methanoimidazo[1,5-a]pyridin-1(5H)-one (4B)

The intermediate compound 4A (180 mg, 0.5 mmol) was dissolved in anhydrous toluene (5 mL) and DBU (0.042 mL) was added. The reaction was heated at 80° C. for 1.5 h and then cooled to 25° C. The volatiles were removed in vacuo and the resulting residue was purified by flash chromatography on $SiO_2$ eluting with a gradient of 0 to 20% acetone/hexane giving pure compound 4B (67 mg) as a yellow oil. HPLC: 66.9% at 2.980 min (retention time) (YMC S5 ODS column 4.6×50 mm eluting with 10-90% aqueous methanol over 4 minutes containing 0.1% TFA, 4 mL/min, monitoring at 220 nM) MS (ES): m/z 343.07 $[M+H]^+$.

EXAMPLE 5

Applicants incorporate by reference Example 5 of the parent case hereof, i.e., U.S. aatent application Ser. No. 10/322,306, filed Dec. 18, 2002, as if said example was fully set forth herein at length.

EXAMPLE 6

(5α,8α,8aα)-2,3,8,8a-Tetrahydro-8a-methyl-3-thioxo-2-[3-(trifluoromethyl)phenyl]-5,8-methanoimidazo[1,5-a]pyridin-1(5H)-one (6)

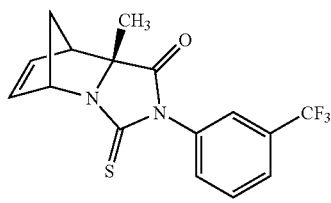

To a solution of Compound 4B (0.056 g, 0.173 mmol, Example 4) in THF at −78° C. was added lithium diisopropylamine (2.0 M soln in THF, 0.173 mL). After 2 h, MeI (0.022 mL, 0.35 mmol) was added and the reaction was warmed to 25° C. over 2 h. $H_2O$ was then added and the mixture extracted with $CH_2Cl_2$ (3×30 mL). The combined organic layers were dried over anhydrous sodium sulfate. The crude product was purified by flash chromatography on $SiO_2$ eluting with 10% acetone in hexanes to give 0.034 g of Compound 6 as white solid. HPLC: 90% at 4.023 min (retention time) (YMC S5 ODS column 4.6×50 mm eluting with 10-90% aqueous methanol over 4 minutes containing 0.2% phosphoric acid, 4 mL/min, monitoring at 220 mn) MS (ES): m/z 339.0 $[M+H]^+$.

EXAMPLES 7-12

Applicants incorporate by reference Examples 7-12 of the parent case hereof, i.e., U.S. patent application Ser. No. 10/322,306, filed Dec. 18, 2002, as if said examples were fully set forth herein at length.

EXAMPLE 13

(5α,8α,8aα) & (5α,8α,8aβ)-[[2-(3,4-Dichlorophenyl)octahydro-1-oxo-5,8-methanoimidazo[1,5-a]pyridin-3-ylidene]amino](13Bi & 13Bii, respectively)

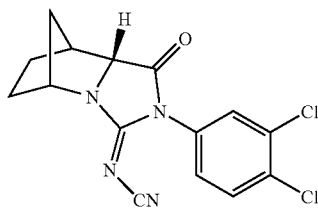

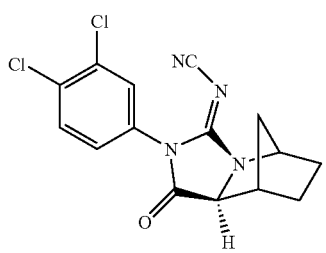

A. endo/exo-2-[(Cyanoimino)[(3,4-dichlorophenyl)amino]methyl]-2-azabicyclo[2.2.1]heptane-3-carboxylic acid ethyl ester (13A)

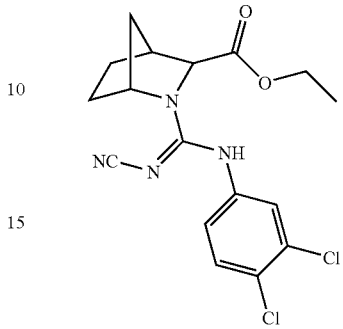

2-Azabicyclo[2.2.1.]heptane-3-carboxylic acid, ethyl ester (169 mg, 1.0 mmol, 1 eq) was combined in dimethylformamide with N-cyano-N'-(3,4-dichlorophenyl)-thiourea (246 mg, 1.0 mmol, 1 eq) and 1-[3-(dimethylamino)propyl]-3-ethylcarbodiimide hydrochloride (288 mg, 1.5 mmol, 1.5 eq). The mixture was stirred at ambient temperature overnight. The reaction was quenched with 1M aqueous citric acid and extracted with $CH_2Cl_2$. The combined organic extracts were dried and concentrated in vacuo. The crude material was purified by flash chromatography on silica gel eluting with 30% acetone in hexanes to provide 192 mg (50.4%) of Compound 13A as a white semi-solid. HPLC: 100% at 3.260 minutes (YMC Combiscreen ODS-A S5 column eluting with 10-90% aqueous methanol over a 4 minute gradient.) MS (ES): m/z 381. $[M+H]^+$.

B. [[2-(3,4-Dichlorophenyl)octahydro-1-oxo-5,8-methanoimidazo[1,5-a]pyridin-3-ylidene]amino] (13Bi & 13Bii)

Compound 13A (180 mg, 0.47 mmol, 1 eq) was combined in anhydrous toluene with DBU (72 mg, 0.47 mmol, 1 eq). The solution was heated at 60° C. for 1 h. TLC ($SiO_2$ plate, 1% $CH_3OH$ in $CH_2Cl_2$) showed no starting material remaining, while LC monitoring indicated a peak with the same retention time as the starting material. The reaction was quenched with saturated aqueous $NH_4Cl$ and extracted with $CH_2Cl_2$. The combined organic extracts were dried and concentrated in vacuo. The crude material was purified by flash chromatography on silica gel eluting with 0.5% $CH_3OH$ in $CH_2Cl_2$ to provide two isomers. Compound 13Bi was obtained in 52% yield (82 mg) as white semi-solid. HPLC: 100% at 3.297 minutes (YMC Combiscreen ODS-A S5 column eluting with 10-90% aqueous methanol over a 4 minute gradient.) MS(ES): 335.08 $[M^+]$. Compound 13Bii was obtained in 25% yield (40 mg) as white solid. HPLC: 100% at 3.323 minutes (YMC Combiscreen ODS-A S5 column eluting with 10-90% aqueous methanol over a 4 minute gradient.) MS (ES): m/z 335.06 $[M]^+$. & 337.07 $[M+2H]^+$.

EXAMPLE 14

Applicants incorporate by reference Example 14 of the parent case hereof, i.e., U.S. patent application Ser. No. 10/322,306, filed Dec. 18, 2002, as if said example was fully set forth herein at length.

EXAMPLE 15

(5α,8α,8aα)-Hexahydro-2-(2-naphthaleny)-3-(phenylimino)-5,8-methanoimidazo[1,5-a]pyridine-1(5H)-one (15B)

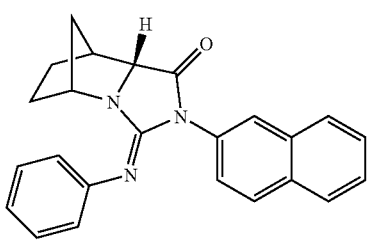

A. N-(2-Naphthalenyl)-2-azabicyclo[2.2.1.]heptane-3-carboxamide (15A)

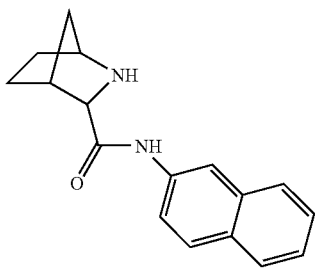

The intermediate Compound 9B (1.00 g, 4.15 mmol, as prepared in Example 9) was dissolved in CH$_2$Cl$_2$ (8.0 mL) and TEA (2.31 mL, 16.6 mmol) and 2,6-dichlorobenzoyl chloride (0.549 mL, 4.15 mmol) were added. The mixture was stirred for 14 h and 2-aminonapthal (0.593 g, 4.15 mmol) was added in CH$_2$Cl$_2$ followed by addition of 4-DMAP (0.010 g). After 3 h, the reaction was diluted with CH$_2$Cl$_2$ and washed once with 1N HCl (40 mL), once with sat aq NaHCO$_3$ (40 mL) and dried over anhydrous sodium sulfate. The crude intermediate (1.00 g, 2.73 mmol) was dissolved in CH$_2$Cl$_2$ (2.0 mL) and treated with TFA (2.0 mL) at 20° C. After 3 h, the reaction was quenched with saturated aq. NaHCO$_3$ and extracted with CH$_2$Cl$_2$ (3×30 mL) and dried over anhydrous sodium sulfate. The crude reaction was purified by preparative reverse phase HPLC to give 0.770 g of Compound 15A as a white solid.

B. (5α,8α,8aα)-Hexahydro-2-(2-naphthaleny)-3-(phenylimino)-5,8-methanoimidazo[1,5-a]pyridine-1(5H)-one (15B)

The intermediate Compound 15A (0.050 g, 0.188 mmol) was dissolved in dichloroethane (2.0 mL) and the phenyl isocyanide dichloride (0.026 mL, 0.188 mmol), 4-DMAP (0.010 g) and DBU (0.084 mL, 0.564 mmol) were added and the reaction was heated to 90° C. in a sealed tube. After 14 h, the reaction was cooled to room temperature and concentrated in vacuo. The residue was purified by preparative TLC on SiO$_2$ eluting with CH$_2$Cl$_2$/acetone (9:1) to give 0.063 g of Compound 15B as a tan oil. HPLC: 93% at 3.590 min (retention time) (YMC S5 ODS column 4.6×50 mm eluting with 10-90% aqueous methanol over 4 minutes containing 0.2% phosphoric acid, 4 mL/min, monitoring at 220 nm) MS (ES): m/z 368.37 [M+H]$^+$

EXAMPLE 16

Hexahydro-2-[3-(trifluoromethyl)phenyl]-5,8-methanoimidazo[15-a]pyridine-1 (5H)-one (16)

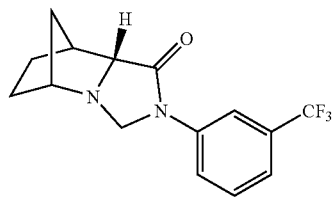

Compound 4B (0.020 g, 0.062 mmol, as described in Example 4) was dissolved in absolute EtOH (2.0 mL) and Ra-Ni (excess) was added. After 3 h at 25° C., the reaction was filtered thru celite rinsing with EtOH. The crude material was purified by preparative TLC eluting with 30% acetone in hexanes, yielding 0.6 mg of Compound 16 as a white solid. HPLC: 100% at 2.437 min (retention time) (YMC S5 ODS column 4.6×50 mm eluting with 10-90% aqueous methanol over 4 minutes containing 0.2% phosphoric acid, 4 mL/min, monitoring at 220 nm) MS (ES): m/z 297.3 [M+H]$^+$.

Alternative preparation of Compound 16

A. (5α,8α,8aα)-Hexahydro-3-thioxo-2-[3-(trifluoromethyl)phenyl]-5,8-methanoimidazo[1,5-a]pyridin-1(51H)-one (16A)

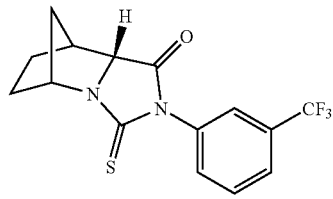

2-Azabicyclo[2.2.1.]hept-5-ene-3-carboxylic acid, ethyl ester (0.250 g, 0.15 mmol) was dissolved in toluene and 3-(trifluoromethylphenyl)isothiocyanate (0.334 g, 0.166 mmol) was added. The reaction was stirred at 25° C. for 14 h and then 1N NaOH (4 mL) was added. After half hour, the aqueous layer was extracted with dichloromethane (3×25 mL). The combined organic layers were washed with brine (50 mL) and dried over Na$_2$SO$_4$ and then the solvent was removed in vacuo. The resulting residue was purified by flash chromatography on SiO$_2$ eluting with 10%-30% acetone in hexanes to give 0.378 g of compound 16A as a yellow solid.

B. Hexahydro-2-[3-trifluoromethyl)phenyl]-5,8-methanoimidazo[1,5-a]pyridine-1(5H)-one (16b or 16)

Compound 16A (0.020 g, 0.062 mmol) was dissolved in ethanol (2 mL) and Ra-Ni (~0.020 g) was added. After 3 h, the reaction mixture was filtered through celite, concentrated, and the resulting residue purified by preparative TLC on silica eluting with 30% acetone in hexanes to give 0.8 mg of 16B as a white solid. HPLC: 99% at 2.437 min (retention time) (YMC S5 ODS column 4.6×50 mm eluting with 10-90% aqueous methanol over 4 minutes containing 0.1% TFA, 4 mL/min, monitoring at 220 nm) MS (ES): m/z 297.3 [M+H]$^+$.

EXAMPLE 17

Applicants incorporate by reference Example 17 of the parent case hereof, i.e., U.S. patent application Ser. No. 10/322,306, filed Dec. 18, 2002, as if said example was fully set forth herein at length.

EXAMPLE 18

(6α,9α,9aα)-Tetrahydro-2-[3-(trifluoromethyl)phenyl]-6.9-methano-2H-pyrido[1,2-d][1,2,4]triazine-1,4(3H,9aH)-dione (18D)

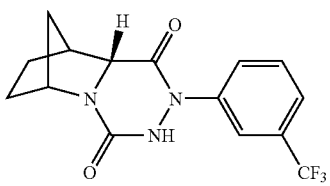

A. 3-[[[3-(Trifluoromethyl)phenyl]amino]carbonyl]-2-azabicyclo[2.2.1]heptane-2-carboxylic acid 1,1-dimethylethyl ester (18A)

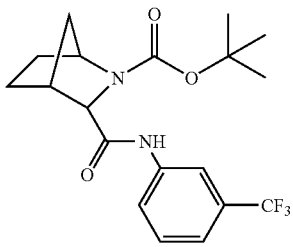

Intermediate Compound 9B (964 mg, 4 mmol, 1 eq, Example 9) was dissolved in 20 mL of tetrahydrofuran and 1-methyl-2-pyrrolidinone (487 µL, 4 mmol, 1 eq) was added followed by methyl chloroformate (309 µL, 4 mmol, 1 eq). The mixture was stirred at rt for 15 min. 3-(Trifluoromethyl)aniline (499 µL, 4 mmol, 1 eq) was then added, and the reaction was stirred at rt for 72 h. The reaction was quenched by addition of water and 0.1 M aqueous citric acid. The mixture was extracted with $CH_2Cl_2$. The combined organic extracts were dried, concentrated in vacuo, and purified by flash chromatography on silica gel eluting with 0.3% methanol in $CH_2Cl_2$ to provide 640 mg (41.6%) of intermediate Compound 18A.

B. 3-[[1-[3-(Trifluoromethyl)phenyl]hydrazino]carbonyl]-2-azabicyclo[2.2.1]heptane-2-carboxylic acid 1,1-dimethylethyl ester (18B)

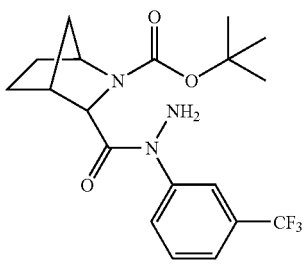

Compound 18A (308 mg, 0.8 mmol, 1 eq) was dissolved in 15 mL of tetrahydrofuran. Sodium hydride (60% in oil, 38 mg, 0.96 mmol, 1.2 eq) was added, and the mixture was stirred at rt for 15 min. O-Diphenylphosphinylhydroxylamine (224 mg, 0.96 mmol, 1.2 eq) was then added, and the reaction was stirred at rt for 1 h. LC analysis indicated that the starting material had been consumed. Water was added, and the reaction was extracted with $CH_2Cl_2$. The combined organic extracts were dried and concentrated in vacuo to provide Compound 18B as a semi-solid in quantitative yield. The compound was used without further purification. LC: R.T.=3.39 min (retention time) (YMC Combiscreen ODS-A S5 column eluting with 10-90% aqueous methanol over a 4 minute gradient.)

C. 2-Azabicyclo[2.2.1]heptane-3-carboxylic acid 1-[3-(trifluoromethyl)-phenyl]hydrazide (18C)

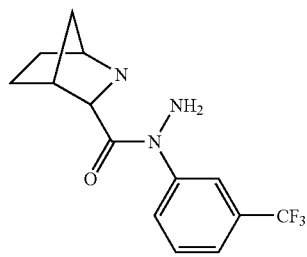

Compound 18B (136 mg, 0.34 mmol, 1 eq) was dissolved in 5 mL of $CH_2Cl_2$. Trifluoroacetic acid (2 mL) was added, and the mixture was stirred at rt for 1 h. LC analysis showed complete conversion to Compound 18C. The crude material was concentrated in vacuo and taken on to the next step.

D. (6α,9α,9α)-Tetrahydro-2-[3-(trifluoromethyl)phenyl]-6,9-methano-2H-pyrido[1,2-d][1,2,4]triazine-1,4(3H,9aH)-dione (18D)

Compound 18C was dissolved in 10 mL of $CH_2Cl_2$, and Hünig's base (10 eq) was added to bring the pH to 10. The mixture was cooled to 10° C. Triphosgene (approx. 1.5 eq) was dissolved in $CH_2Cl_2$ and added dropwise to the reaction mixture. The reaction was stirred at 0° C. and then allowed to stir at rt overnight. LC analysis indicated that the starting material had been consumed. The mixture was washed with saturated aqueous $NH_4Cl$ followed by saturated aqueous NaCl. The $CH_2Cl_2$ layer was dried, concentrated in vacuo and purified by flash chromatography on silica gel eluting with 2% methanol in $CH_2Cl_2$. The material was purified further by preparative LC to provide 15 mg (14%) of Compound 18D as a light yellow solid. HPLC: 100% at 2.523 min (retention time) (YMC Combiscreen ODS-A S5 column eluting with 10-90% aqueous methanol over a 4 minute gradient.) MS (APCI): m/z 326.2 $[M+H]^+$

EXAMPLES 19-21

Applicants incorporate by reference Examples 19-21 of the parent case hereof, i.e., U.S. patent application Ser. No. 10/322,306, filed Dec. 18, 2002, as if said examples were fully set forth herein at length.

EXAMPLES 22 TO 88

Using the procedures described herein or by modification of the procedures described herein readily available to one of ordinary skill in the art, the following additional compounds of Table 2 were prepared. Those of the following compounds which were prepared enantiomerically pure are so indicated in the structure box by the nomenclature (R) or (S). Those compounds not so indicated were racemic mixtures which can readily be separated by one of ordinary skill in the art or prepared enantiomerically pure by the procedures described herein.

For examples 22-35, 39-42, 46-47, and 52-88, applicants incorporate herein by reference said examples as reported in the parent case hereof, i.e., U.S. patent application Ser. No. 10/322,306, filed Dec. 18, 2002, as if said examples were fully set forth herein at length.

TABLE 2

The chromatography techniques used to determine the compound retention times of Table 2 are as follows:
LC = YMC S5 ODS column 4.6 × 50 mm eluting with 10-90% MeOH/H₂O over 4 minutes containing 0.2% phosphoric acid, 4 mL/mm, monitoring at 220 nm
LCMS = YMC S5 ODS column, 4.6 × 50 mm eluting with 10-90% MeOH/H₂O over 4 minutes containing 0.1% TFA; 4 mL/min, monitoring at 220 nm

| Ex. No. | Compound Structure | Compound Name | Retention Time Min. | Procedure of Example |
|---|---|---|---|---|
| 36. | 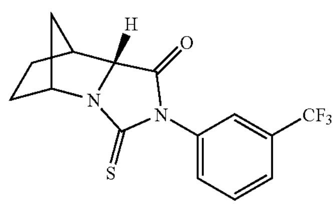 | (5α,8α,8αα)-Hexahydro-3-thioxo-2-[3-(trifluoromethyl)phenyl]-5,8-methanoimidazo[1,5-a]pyridine-1(5H)-one | 3.360 LC | 11 |
| 37. | 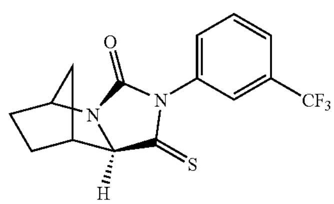 | (5α,8α,8αβ)-Hexahydro-3-thioxo-2-[3-(trifluoromethyl)phenyl]-5,8-methanoimidazo[1,5-a]pyridine-1(5H)-one | 3.443 LC | 11 |
| 38. | 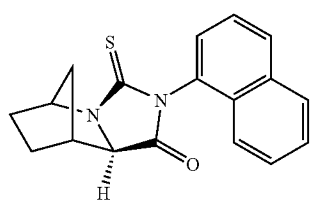 | (5α,8α,8αβ)-Hexahydro-2-(1-naphthaleny)-3-thioxo-5,8-methanoimidazo[1,5-a]pyridine-1(5H)-one | 3.487 LC | 11 |
| 43. | 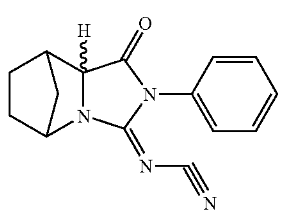 | [(Octahydro-1-oxo-2-phenyl-5,8-methanoimidazo[1,5-a]pyridin-3-ylidene)amino]carbonitrile | 2.357 LC | 13 |
| 44. | 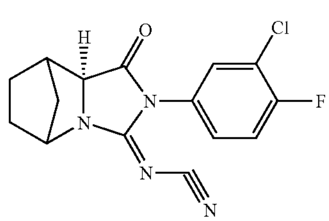 | (5α,8α,8αβ)-[[2-(3-Chloro-4-fluorophenyl)octahydro-1-oxo-5,8-methanoimidazo[1,5-a]pyridin-3-ylidene]amino]carbonitrile | 2.830 LCMS | 13 |

TABLE 2-continued

The chromatography techniques used to determine the compound retention times of Table 2 are as follows:
LC = YMC S5 ODS column 4.6 × 50 mm eluting with 10-90% MeOH/H$_2$O over 4 minutes containing 0.2% phosphoric acid, 4 mL/mm, monitoring at 220 nm
LCMS = YMC S5 ODS column, 4.6 × 50 mm eluting with 10-90% MeOH/H$_2$O over 4 minutes containing 0.1% TFA; 4 mL/min, monitoring at 220 nm

| Ex. No. | Compound Structure | Compound Name | Retention Time Min. | Procedure of Example |
|---|---|---|---|---|
| 45. | 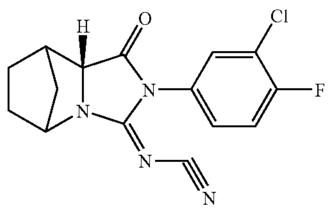 | (5α,8α,8aα)-[[2-(3-Chloro-4-fluorophenyl)octahydro-1-oxo-5,8-methanoimidazo[1,5-a]pyridin-3-ylidene]amino]carbonitrile | 2.833 LCMS | 13 |
| 48. | 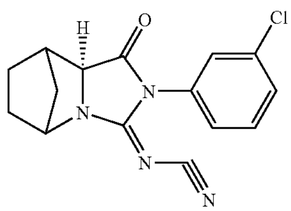 | (5α,8α,8αβ)-[[2-(3-Chlorophenyl)octahydro-1-oxo-5,8-methanoimidazo[1,5-a]pyridin-3-ylidene]-amino]carbonitrile | 2.727 LCMS | 13 |
| 49. | 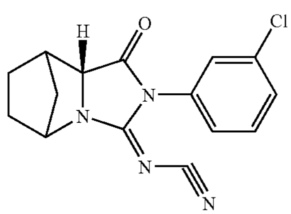 | (5α,8α,8αα)-[[2-(3-Chlorophenyl)octahydro-1-oxo-5,8-methanoimidazo[1,5-a]pyridin-3-ylidene]-amino]carbonitrile | 2.727 LCMS | 13 |
| 50. | 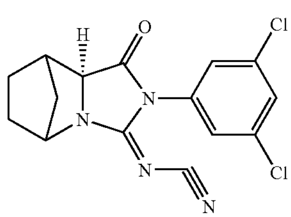 | (5α,8α,8αβ)-[[2-(3,5-Dichlorophenyl)octahydro-1-oxo-5,8-methanoimidazo[1,5-a]pyridin-3-ylidene]-amino]carbonitrile | 3.337 LCMS | 13 |
| 51. | 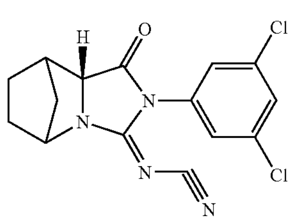 | (5α,8α,8αα)-[[2-(3,5-Dichlorophenyl)octahydro-1-oxo-5,8-methanoimidazo[1,5-a]pyridin-3-ylidene]-amino]carbonitrile | 3.413 LCMS | 13 |

EXAMPLE 89

(1S-exo)-2,5-Diazabicyclo[2.2.1]heptane-2,6-dicarboxylic acid 2-(1,1-dimethylethyl) 6-methyl ester & (1S-endo)-2,5-Diazabicyclo[2.2.1]heptane-2,6-dicarboxylic acid, 2-(1,1-dimethylethyl) 6-methyl ester

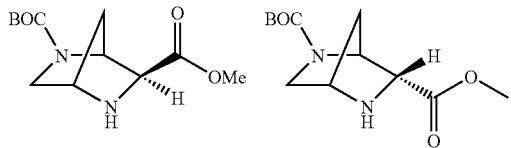

This example illustrates a preferred method for obtaining a compound of formula IIa, which compound is useful as an intermediate in the preparation of compounds of formula I (see, for example, FIG. 2 herein).

A. (2S-trans)-4-Hydroxy-2-[[[(1,1-dimethylethyl)dimethylsilyl]oxy]methyl]-1-pyrrolidinecarboxylic acid, 1,1-dimethylethyl ester (89A)

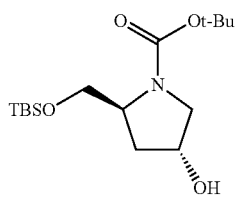

N-(tert-butoxycarbonyl)-L-4-hydroxyproline (10.0 g, 43.3 mmol) was dissolved in THF and cooled to 0° C. Borane/THF (1.0 M solution, 86.6 mL) was then added over a 15 min period. The reaction was then warmed to 25° C. followed by heating to reflux for 16 h. The reaction flask was then removed from the heat source and anhydrous methanol (35 mL) was added slowly. After cooling to 25° C., the solvent was removed in vacuo and the resulting crude diol intermediate was taken on directly. The crude diol (1.81 g, 8.34 mmol) was dissolved in methylene chloride (50 mL), 2,6-lutidine (1.46 mL, 12.51 mmol) was added and the mixture was cooled to −78° C. tert-Butyl dimethylsilyltrifluoro-methansulfonate (1.92 mL, 8.34 mmol) was then added. After 2 h, the mixture was poured into 1 N HCl (100 mL), extracted with methylene chloride (2×100 mL) and the organics were dried over anhydrous sodium sulfate. The resulting crude alcohol was purified by flash chromatography on SiO₂ eluting with acetone in chloroform (0-5-10% acetone) to give 1.011 g (37% for 2-steps) of the Compound 89A as a clear oil.

B. (2S-trans)-2-Hydroxymethyl4-[[(4-methylphenyl)sulfonyl]oxy]-1-pyrrolidinecarboxylic acid, 1,1-dimethylethyl ester (89B)

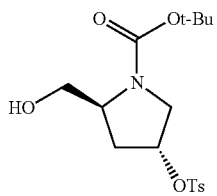

Intermediate Compound 89A (3.41 g, 10.3 mmol) was dissolved in anhydrous pyridine (30.0 mL) and cooled to 0° C. p-Toluenesulfonylchloride (5.89 g, 30.9 mmol) was then added in portions over a 10 minute period. The flask was then placed in a refrigerator at 4° C. for 48 h. The resulting solution was poured into 1 N HCl (300 mL), extracted with methylene chloride (3×200 mL) and the organics were dried over anhydrous sodium sulfate. The crude tosylate intermediate was dissolved in THF (50 mL), to which was added H₂O (0.5 mL) followed by pTSA-H₂O (1.03 mmol). Once the reaction was complete as determined by TLC, the mixture was poured into saturated aqueous NaHCO₃ (150 mL) and extracted with methylene chloride (3×50 mL). The combined organics were dried over sodium sulfate. The crude alcohol was purified by flash chromatography on SiO₂ eluting with acetone/chloroform (0-5-10% acetone) to give 2.71 g (71% for 2-steps) of intermediate Compound 89B as a clear oil.

C. (2S-trans)-2-[Cyano[(phenylmethyl)amino]methyl]-4-[[(4-methylphenyl)-sulfonyl]oxy]-1-pyrrolidinecarboxylic acid, 1,1-dimethylethyl ester (89C)

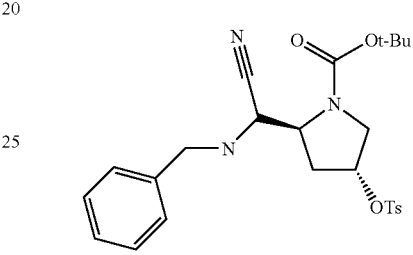

To a solution of oxalyl chloride (2.0 M soln in CH₂Cl₂, 2.82 mL) in CH₂Cl₂ (40 mL) at −78° C. was added anhydrous dimethylsulfoxide (0.462 µL, 6.51 mmol). The mixture was allowed to stand for 15 min, after which a solution of Compound 89B (1.61 g, 4.34 mmol) in CH₂Cl₂ (10 mL) was slowly added. After an additional 30 min, triethylamine (1.81 mL, 13.02 mmol) was added and the reaction was slowly warmed to 0° C. The reaction was then quenched with H₂O (25 mL) and diluted with CH₂Cl₂ (100 mL). The mixture was then washed sequentially with 1 N HCl (1×100 mL), saturated aqueous NaHCO₃ (50 mL), and water (2×50 mL). The organics were dried over anhydrous sodium sulfate and the volatile organics removed in vacuo. The crude aldehyde intermediate (1.60 g, 4.34 mmol) was dissolved in THF (25 mL) and diethyl cyanophosphonate (90%, 0.95 mL, 5.64 mmol) was added followed by benzyl amine (1.23 mL, 11.3 mmol). After 2 h, the reaction was complete, as observed by TLC and the volatile organics were removed in vacuo. The crude reaction mixture was purified by flash chromatography on SiO₂ eluting with acetone/chloroform (0-2-3% acetone) to give 1.48 g (70%) of intermediate Compound 89C as a white solid. Compound 89C was determined to be a ~1:1 mixture of diastereomers by NMR spectroscopy.

D. (1S-endo)-6-Cyano-5-(phenylmethyl)-2,5-diazabicyclo[2.2.1]heptane-2-carboxylic acid, 1,1-dimethylethyl ester (89Di); (1S-exo)-6-Cyano-5-(phenylmethyl)-2,5-diazabicyclo[2.2.1]heptane-2-carboxylic acid, 1,1-dimethylethyl ester (89Dii)

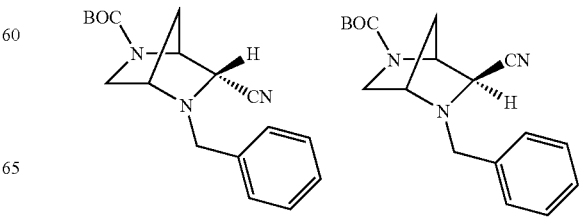

Intermediate Compound 89C (1.48 g, 3.05 mmol) was dissolved in dichloroethane (25 mL) and diisopropyl ethylamine (1.45 mL) was added. The mixture was heated to 100° C. in a sealed tube for 18 h. The volatiles were then removed in vacuo and the resulting crude material was purified by flash chromatography on $SiO_2$ eluting with acetone/chloroform (0-2-3% acetone), to yield a mixture of intermediate Compound 89Di (0.591 g, 62%) and intermediate Compound 89Dii (0.370 g, 38%) as clear oils. Structural assignments for Compounds 89Di and 89Dii were made after NOE, COESY and DEPT NMR experiments.

E. (1S-endo)-5-(Phenylmethyl)-2,5-diazabicyclo[2.2.1]heptane-2,6-dicarboxylic acid, 2-(1,1-dimethylethyl) 6-methyl ester (89E)

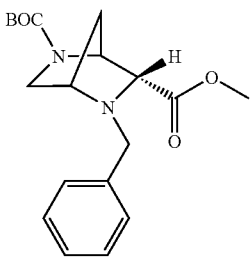

Intermediate Compound 89Di (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous $NaHCO_3$ (50 mL). The mixture was extracted with $CH_2Cl_2$ (3×50 mL) and the combined organics were dried over anhydrous sodium sulfate. The crude ester was purified by flash chromatography on $SiO_2$ eluting with chloroform/acetone (0-2-4% acetone) to give 0.320 g (0.92 mmol, 72%) of intermediate Compound 89E as a clear oil.

F. (1S-exo)-5-(Phenylmethyl)-2,5-diazabicyclo[2.2.1]heptane-2,6-dicarboxylic acid, 2-(1,1-dimethylethyl) 6-methyl ester (89F)

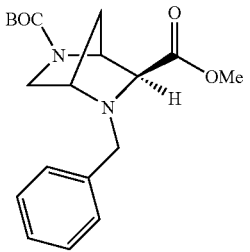

Intermediate Compound 89Dii (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous $NaHCO_3$ (50 mL). The mixture was extracted with $CH_2Cl_2$ (3×50 mL) and the combined organics were dried over anhydrous sodium sulfate. The crude ester was purified by flash chromatography on $SiO_2$ eluting with chloroform/acetone (0-2-4% acetone) to give 0.290g (0.85 mmol, 66%) of intermediate Compound 89F as a clear oil.

G. (1S-endo)-2,5-Diazabicyclo[2.2.1]heptane-2,6-dicarboxylic acid, 2-(1,1-dimethylethyl) 6-methyl ester (89G)

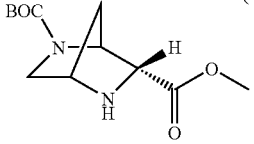

Intermediate Compound 89E (0.280 g, 0.81 mmol) was dissolved in absolute EtOH (10.0 mL) and Pd/C (10% Pd, 0.080 g) was added. An atmosphere of $H_2$ was introduced via a balloon and the reaction was stirred at 25° C. for 20 h. The Pd was removed by filtration through celite followed by rinsing with EtOAc. The volatiles were removed in vacuo to give Compound 89G (0.205 g, 99%) as viscous yellow oil. Compound 89G was taken on directly without purification. MS(ES)=m/z 257.18 $[M+H]^+$. HPLC RT =1.223 min (95%) (YMC S5 ODS column, 4.6×50 mm; 10-90% $MeOH/H_2O$ gradient,+0.1% TFA; 4 mL/min, 220 nM detection).

H. (1S-exo)-2,5-Diazabicyclo[2.2.1]heptane-2,6-dicarboxylic acid, 2-(1,1-dimethylethyl) 6-methyl ester (89H)

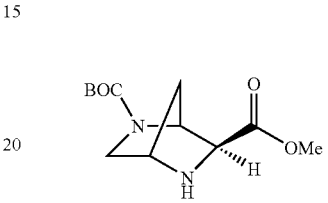

Intermediate Compound 89F (0.310 g, 0.89 mmol) was dissolved in absolute EtOH (10.0 mL) and Pd/C (10% Pd, 0.080 g) was added. An atmosphere of $H_2$ was introduced via a balloon and the reaction was stirred at 25° C. for 20 h. The Pd was removed by filtration through celite, followed by rinsing with EtOAc. The volatiles were removed in vacuo to give Compound 89H (0.210 g, 92%) as a viscous yellow oil. Compound 89H can be taken on directly without purification. MS(ES)=m/z 257.16 $[M+H]^+$ HPLC RT=1.293 min (90%) (YMC S5 ODS column, 4.6×50 mm; 10-90% $MeOH/H_2O$ gradient,+0.1% TFA; 4 mL/min, 220 nM detection).

EXAMPLE 90

[5S-(5α,8α,8aα)-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester, (90i)

[5S-(5α,8α,8aβ)]-2-[4-Cyano-3-(trifluoromethyl)phenyl]hexahydro-1,3-dioxo-5,8-methanoimidazo[1.5-a]pyrazine-7(8H)-carboxylic acid, 1,1-dimethylethyl ester, (90ii)

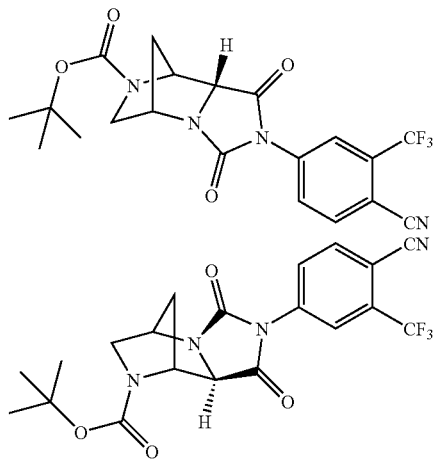

To a solution of 4-isocyanato-2-(trifluoromethyl)-benzonitrile (1.0 mmol) in toluene (4 mL) with activated 4 Å MS (0.300 g) was added Compound 89G (0.220 g, 0.856 mmol) in toluene (6 mL). After 10 h at 25° C., DBU (0.166 mL, 1.11 mmol) was added and the reaction was heated at 81° C. for 2 h. The reaction was then cooled to 25° C. and poured into 1 N HCl (50 mL). The solution was then extracted with methylene chloride (3×30 mL) and the combined organics were dried over anhydrous sodium sulfate. The resulting crude material was purified by flash chromatography on SiO$_2$ eluting with acetone/chloroform (0-2-4-8% acetone) to give Compound 90i (0.155 g, 42%) MS (ES): m/z 437.09 [M+H]$^+$. HPLC RT=3.280 min (100%) (YMC S5 ODS column, 4.6×50 mm; 10-90% MeOH/H$_2$O gradient, +0.1% TFA; 4 mL/min, 220 nM detection) and Compound 90ii (0.061 g, 16%) MS (ES): m/z 437.09 [M+H]$^+$. HPLC RT=3.133 min (100%) (YMC S5 ODS column, 4.6×50 mm; 10-90% MeOH/H$_2$O gradient,+0.1% TFA; 4 mL/min, 220 nM detection); both as white foams.

EXAMPLE 91

5S-(5α,8α,8aα)]-4-(Hexahydro-1,3-dioxo-5,8-methanoimidazo[1,5-a]pyrazin-2(3H)-yl)-2-(trifluoromethyl)benzonitrile (91)

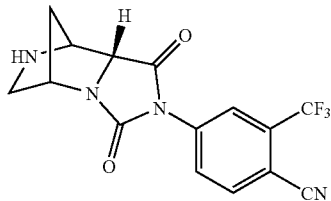

The Compound 90i (0.115 g, 0.264 mmol) was dissolved in anhydrous methylene chloride (3 mL) and anhydrous TFA (1.0 mL) was added at 25° C. After 1 h, the reaction was concentrated in vacuo and the resulting residue was dissolved in methylene chloride and poured into saturated aq NaHCO$_3$. This solution was then extracted with methylene chloride (3×10 mL) and the combined organics dried over anhydrous sodium sulfate. This gave 0.089 g (97%) of free Compound 91 as a yellow solid. MS (ES): m/z 359.09 [M+Na]$^+$. HPLC RT=1.477 min (100%) (YMC S5 ODS column, 4.6×50 mm; 10-90% MeOH/H$_2$O gradient,+0.1% TFA; 4 mL/min, 220 nM detection).

EXAMPLE 92

(1R-endo)-2,5-Diazabicyclo[2.2.1]heptane-2,6-dicarboxylic acid, 2-(1,1-dimethylethyl) 6-methyl ester (92H) & (1R-exo)-2,5-Diazabi-cyclo[2.2.1 1]heptane-2,6-dicarboxylic acid, 2-(1,1-dimethylethyl) 6-methyl ester 92I)

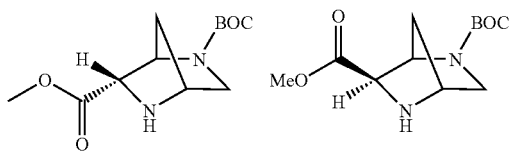

This example illustrates a preferred method for obtaining a compound of formula IIa, which compound is useful as an intermediate in the preparation of compounds of formula I (see, for example, FIG. 2 herein).

A. (2R-cis)-4-Hydroxy-1,2-pyrrolidinedicarboxylic acid, 1-(1,1-dimethylethyl)2-ethyl ester (92A)

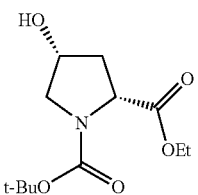

Cis-4-hydroxy-D-proline (10.0 g, 131.1 mmol) was suspended in absolute EtOH (100 mL) and anhydrous HCl (g) was bubbled through the reaction until a homogenous solution resulted. This was left at 25° C. for 1 h and then the volatiles organics were removed in vacuo. The resulting HCl salt was triturated with diethyl ether and filtered to give the crude ethyl ester as a white powder. The ethyl ester salt was used directly in the next reaction.

The salt (~12 g) was suspended in acetone and cooled to 0° C. 10% aq Na$_2$CO$_3$ (6.0 mL) was then added followed by BOC$_2$O (1.37 g, 6.29 mmol) and then the reaction was slowly warmed to 25° C. After 12 h, the reaction mixture was poured into water and extracted with methylene chloride (3×100 mL). The organics were then dried over anhydrous sodium sulfate and concentrated in vacuo to give the crude compound 92A as a white powder. This material was taken on without further purification.

B. (2R-trans)-4-[[(4-Methylphenyl)sulfonyl]oxy]-1, 2-pyrrolidinedicarboxylic acid, 1-(1,1-dimethylethyl) 2-ethyl ester (92B)

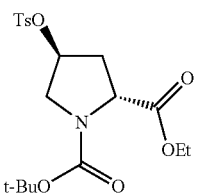

The crude compound 92A (1.41 g, 5.44 mmol) was dissolved in THF (50 mL) and Ph$_3$P (1.86 g, 70.8 mmol) was added. The mixture was cooled to 0° C. and DEAD (1.11 mL, 70.8 mmol) was added. After 15 min, methyl paratoluenesulfonate (1.32 g, 70.8 mmol) was then added and the solution was slowly warmed to 25° C. After 14 h, the reaction was concentrated in vacuo and purified by flash chromatography on silica eluting with acetone in chloroform (0-2-3% acetone) to give 0.845 g of the desired compound 92B as a yellow oil. HPLC RT=3.373 min (95%) (YMC S5 ODS column, 4.6×50 mm; 10-90% MeOH/H$_2$O gradient,+0.1% TFA; 4 mL/min, 220 nM detection). This material was taken on without further purification.

C. (2R-trans)-2-(Hydroxymethyl)-4-[[(4-methylphenyl)sulfonyl]oxy-1-pyrrolidinecarboxylic acid, 1,1-dimethyl ester (92C)

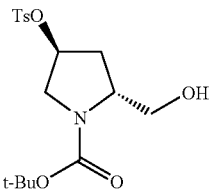

The crude compound 92B (5.50 g, 13.32 mmol) was dissolved in THF (150 mL) and cooled to 0° C. LiBH$_4$ (2.0 M in THF, 16.7 mL, 33.3 mmol) was then slowly added and the reaction was allowed to warm to 25° C. slowly. After 12 h, the mixture was cooled to 0° C. and the reaction was quenched with water (10 mL) and then AcOH (2.0 mL). After 15 min, the solution was poured into sat NaHCO$_3$ and extracted with methylene chloride (3×50 mL) and the combined organics were dried over anhydrous sodium sulfate. This gave the crude compound 92C (3.91 g) as a yellow oil, which was taken on without purification. HPLC RT=3.043 min (100%) (YMC S5 ODS column, 4.6×50 mm; 10-90% MeOH/H$_2$O gradient,+0.1% TFA; 4 mL/min, 220 nM detection).

D. (2R-trans)-2-[Cyano [(phenylmethyl)amino]methyl]-4-[[(4-methylphenyl)-sulfonyl]oxy]-1-pyrrolidinecarboxylic acid, 1,1-dimethylethyl ester (92D)

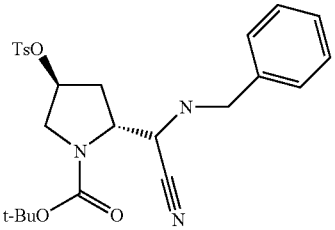

To a solution of oxalyl chloride (2.0 M soln in CH$_2$Cl$_2$, 2.82 mL) in CH$_2$Cl$_2$ (40 mL) at −78° C. was added anhydrous dimethylsulfoxide (0.462 mL, 6.51 mmol). The mixture was allowed to stand for 15 min, after which a solution of compound 92C (1.61 g, 4.34 mmol) in CH$_2$Cl$_2$ (10 mL) was slowly added. After an additional 30 min, triethylamine (1.81 mL, 13.02 mmol) was added and the reaction was slowly warmed to 0° C. The reaction was then quenched with H$_2$O (25 mL) and diluted with CH$_2$Cl$_2$ (100 mL). The mixture was then washed sequentially with 1 N HCl (1×100 mL), saturated aqueous NaHCO$_3$ (50 mL), and water (2×50 mL). The organics were dried over anhydrous sodium sulfate and the volatile organics removed in vacuo. The crude aldehyde intermediate (1.60 g, 4.34 mmol) was dissolved in THF (25 mL) and diethyl cyanophosphonate (90%, 0.95 mL, 5.64 mmol) was added followed by benzyl amine (1.23 mL, 11.3 mmol). After 2 h, the reaction was complete, as observed by TLC and the volatile organics were removed in vacuo. The crude reaction mixture was purified by flash chromatography on SiO$_2$ eluting with acetone/chloroform (0-2-3% acetone) to give 1.48 g (70%) of intermediate Compound 92D as a white solid. Compound 92D was determined to be a ~1:1 mixture of diastereomers by NMR spectroscopy.

E. (1R-endo)-6-Cyano-5-(phenylmethyl)-2,5-diazabicyclo[2.2.1]heptane-2-carboxylic acid, 1,1-dimethylethyl ester (92Ei); (1R-exo)-6-Cyano-5-(phenylmethyl)-2,5-diazabicyclo[2.2.1]heptane-2-carboxylic acid, 1,1-dimethylethyl ester (92Eii)

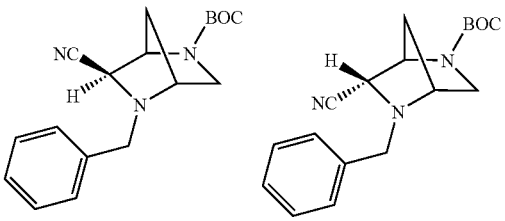

Intermediate compound 92D (1.48 g, 3.05 mmol) was dissolved in dichloroethane (25 mL) and diisopropyl ethylamine (1.45 mL) was added. The mixture was heated to 100° C. in a sealed tube for 18 h. The volatiles were then removed in vacuo and the resulting crude material was purified by flash chromatography on SiO$_2$ eluting with acetone/chloroform (0-2-3% acetone), to yield a mixture of intermediate compound 92Ei (0.591 g, 62%) and intermediate compound 92Eii (0.370 g, 38%) as clear oils. Structural assignments for Compounds 92Ei and 92Eii were made after NOE, COESY and DEPT NMR experiments.

F. (1R-endo)-5-(Phenylmethyl)-2,5-diazabicyclo[2.2.1]heptane-2,6-dicarboxylic acid, 2-(1,1-dimethylethyl)6-methyl ester (92F)

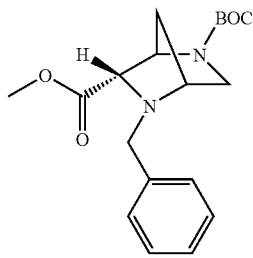

Intermediate Compound 92Ei (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO$_3$ (50 mL). The mixture was extracted with CH$_2$Cl$_2$ (3×50 mL) and the combined organics were dried over anhydrous sodium sulfate. The crude ester was purified by flash chromatography on SiO$_2$ eluting with chloroform/acetone (0-2-4% acetone) to give 0.320 g (0.92 mmol, 72%) of intermediate compound 92F as a clear oil.

G. (1R-exo)-5-(Phenylmethyl)-2,5-diazabicyclo[2.2.1]heptane-2,6-dicarboxylic acid, 2-(1,1-dimethylethyl)6-methyl ester (92G)

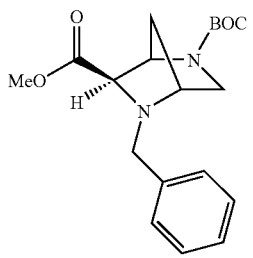

Intermediate compound 92Eii (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO₃ (50 mL). The mixture was extracted with CH₂Cl₂ (3×50 mL) and the combined organics were dried over anhydrous sodium sulfate. The crude ester was purified by flash chromatography on SiO₂ eluting with chloroform/acetone (0-2-4% acetone) to give 0.290 g (0.85 mmol, 66%) of intermediate compound 92G as a clear oil.

H. (1R-endo)-2,5-Diazabicyclo[2.2.1]heptane-2,6-dicarboxylic acid, 2-(1,1-dimethylethyl) 6-methyl ester (92H)

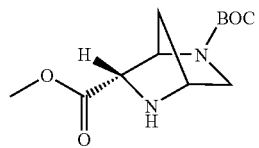

Intermediate compound 92F (0.280 g, 0.81 mmol) was dissolved in absolute EtOH (10.0 μL) and Pd/C (10% Pd, 0.080 g) was added. An atmosphere of H₂ was introduced via a balloon and the reaction was stirred at 25° C. for 20 h. The Pd was removed by filtration through celite followed by rinsing with EtOAc. The volatiles were removed in vacuo to give compound 92H (0.205 g, 99%) as viscous yellow oil. Compound 92H was taken on directly without purification. MS(ES)=m/z 257.18 [M+H]⁺. HPLC RT=1.223 min (95%) (YMC S5 ODS column, 4.6×50 mm; 10-90% MeOH/H₂O gradient,+0.1% TFA; 4 mL/min, 220 nM detection).

I. (1R-exo)-2,5-Diazabicyclo[2.2.1]heptane-2,6-dicarboxylic acid, 2-(1,1-dimethylethyl)6-methyl ester (92I)

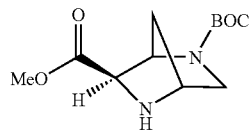

Intermediate compound 92G (0.310 g, 0.89 mmol) was dissolved in absolute EtOH (10.0 mL) and Pd/C (10% Pd, 0.080 g) was added. An atmosphere of H₂ was introduced via a balloon and the reaction was stirred at 25° C. for 20 h. The Pd was removed by filtration through celite, followed by rinsing with EtOAc. The volatiles were removed in vacuo to give compound 92I (0.210 g, 92%) as a viscous yellow oil. Compound 92I can be taken on directly without purification. MS(ES)=m/z 257.16 [M+H]⁺ HPLC RT=1.293 min (90%) (YMC S5 ODS column, 4.6×50 mm; 10-90% MeOH/H₂O gradient,+0.1% TFA; 4 mL/min, 220 nM detection).

EXAMPLE 93

[5R-(5α,8α,8aα)]-4-[Octahydro-7-[(1,1-dimethylethoxy)carbonyl]-1,3-dioxo-5,8-methanoimidazo[1,5-a]pyrazin-2-yl]-2-(trifluoromethyl)benzonitrile (93i)

[5R-(5α,8α,8aβ)]-4-[Octahydro-7-[(1,1-dimethylethoxy)carbonyl]-1,3-dioxo-5,8-methanoimidazo[1,5-a]pyrazin-2-yl]-2-(trifluoromethyl)benzonitrile (93ii)

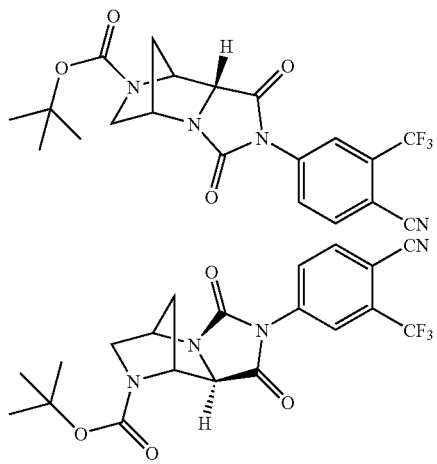

To a solution of 4-isocyanato-2-(trifluoromethyl)-benzonitrile (1.0 mmol) in toluene (4 mL) with activated 4 Å MS (0.300 g) was added Compound 92H or 92I (0.220 g, 0.856 mmol) (compounds epimerize to form same product) in toluene (6 mL). After 10 h at 25° C., DBU (0.166 mL, 1.11 mmol) was added and the reaction was heated at 81° C. for 2 h. The reaction was then cooled to 25° C. and poured into 1 N HCl (50 mL). The solution was then extracted with methylene chloride (3×30 mL) and the combined organics were dried over anhydrous sodium sulfate. The resulting crude material was purified by flash chromatography on SiO₂ eluting with acetone/chloroform (0-2-4-8% acetone) to give Compound 93i (0.155 g, 42%) MS (ES): m/z 437.09 [M+H]⁺. HPLC RT=3.280 min (100%) (YMC S5 ODS column, 4.6×50 mm; 10-90% MeOH/H₂O gradient, +0.1% TFA; 4 mL/min, 220 nM detection) and Compound 93ii (0.061 g, 16%) MS (ES): m/z 437.09 [M+H]⁺. HPLC RT=3.133 min (100%) (YMC S5 ODS column, 4.6×50 mm; 10-90% MeOH/H₂O gradient,+0.1% TFA; 4 mL/min, 220 nM detection); both as white foams.

EXAMPLE 94

[5S-(5α,8α,8aα)]Hexahydro-2-(4-nitro-1-naphthalenyl)-13-dioxo-5.8-methanoimidazo[1.5-a]pyrazine-7(8H)-carboxylic acid, 11-dimethylethyl ester (94)

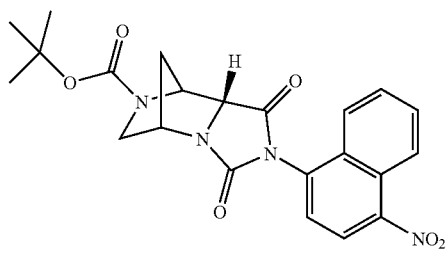

Compound 89G (0.220 g, 0.856 mmol) was added to a suspension of freshly activated 4 Å molecular sieves (0.300 g) in dry toluene (10.0 mL). To this mixture was added 4-nitronaphthal-1-isocyanate (0.214 g, 1.0 mmol). After stirring at 25° C. for 14 h, DBU (0.166 mL, 1.11 mmol) was added and the reaction was heated at 80° C. for 2 h. After 2 h, the reaction was cooled to 25° C. and then poured into 1 N HCl (50 mL). This solution was extracted with methylene chloride (3×30 mL) and the combined organics were dried over anhydrous sodium sulfate. The crude material was purified by flash chromatography on silica eluting with 0-2-6% acetone in chloroform to give 0.211 g of compound 94 as a yellow foam. HPLC: 95% at 3.130 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 439.19 [M+H]+.

EXAMPLE 95

[5S-(5α,8α,8aα)]-Tetrahydro-2-(4-nitro-1-naphthalenyl)-5,8methanoimidazo[1,5-a]pyrazine-1,3(2H,5H)-dione (95)

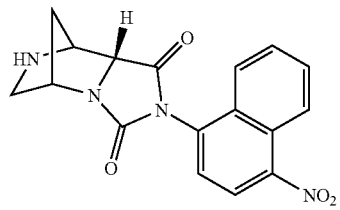

Compound 94 (0.160 g, 0.37 mmol) was dissolved in methylene chloride (5.0 mL) and TFA (1.5 mL) was added at 25° C. After 1.5 h, the reaction was concentrated in vacuo and redissolved in methylene chloride. This solution was washed with sat aq NaHCO₃. The aqueous layer was extracted with methylene chloride (3×25 mL). The combined organics were then dried over anhydrous sodium sulfate. Concentration in vacuo gave 0.115 g of compound 95 as a yellow solid. HPLC: 93% at 1.747 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 369.07 [M+MeOH]+.

EXAMPLE 96

[5S-(5α,8α,8aα)]-7-[(4-Fluorophenyl)sulfonyl]tetrahydro-2-(4-nitro-1-naphthalenyl)-5,8-methanoimidazo[1,5-a]pyrazine-1,3(2H,5H)-dione (96)

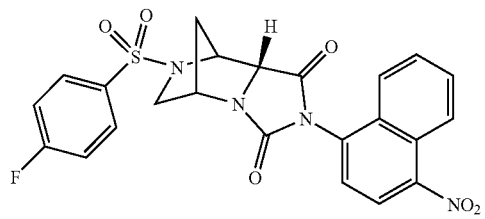

Compound 94 (0.025 g, 0.074 mmol) was dissolved in pyridine (0.5 mL) and then 4-fluorophenylsulfonyl chloride (0.028 g, 0.148 mmol) was added. After 16 h at 25° C., the reaction was concentrated in vacuo. The crude product was purified by flash chromatography on silica eluting with 5% acetone in chloroform to give 0.029 g of compound 96 as a yellow solid. HPLC: 99% at 3.107 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 497.2 [M+H]+.

EXAMPLE 97

Applicants incorporate by reference Example 97 of the parent case hereof, i.e., U.S. patent application Ser. No. 10/322,306, filed Dec. 18, 2002, as if said example was fully set forth herein at length.

EXAMPLE 98

[5S-(5α,8α,8aα)]-2-[4-Cyano-3-(trifluoromethyl)phenyl]hexahydro-8a-methyl-1,3-dioxo-5,8-methanoimidazo[1,5-a]pyrazine-7(8H)-carboxylic acid, 1,1-dimethylethyl ester (98)

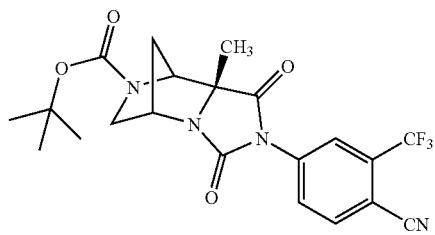

Compound 90i (0.100 g, 0.229 mmol) was added to freshly prepared LDA (0.048 mL diisopropyl amine, 0.186 mL, 1.6M BuLi) in THF (3.0 mL) at −78° C. After 30 min, methyl iodide (0.029 mL, 0.458 mmol) was added and the reaction was slowly warmed to −20° C. over 1 h and then quenched with sat aq ammonium chloride. The mixture was then extracted with methylene chloride (3×30 mL). The organics were dried over anhydrous sodium sulfate and concentrated in vacuo, to give 0.077 g of the crude compound 98 which was taken on without purification. HPLC: 93% at 3.243 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 473.12 [M+NaH]+.

EXAMPLE 99

[5S-(5α,8α,8aα)]-4-(Hexahydro-1,3-dioxo-8a-methyl-5,8-methanoimidazo[1.5-a]pyrazin-2(3H)-yl)-2-(trifluoromethyl)benzonitrile (99)

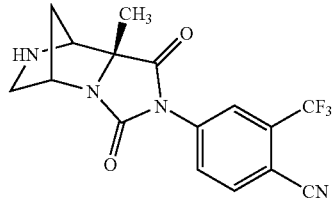

Compound 98 (0.070 g, 0.156 mmol) was dissolved in methylene chloride (2.0 mL) and TFA (0.75 mL) was added at 25° C. After 30 min, the reaction was quenched with sat aq NaHCO₃ and then extracted with methylene chloride (3×30 mL). The organics were then dried over anhydrous sodium sulfate and concentrated in vacuo. The crude material was purified by preparative TLC eluting with 25% acetone in chloroform to give 0.031 g of compound 99 as a white solid. HPLC: 86% at 1.817 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 351.15 [M+H]⁺.

EXAMPLE 100

[5S-(5α,8α,8aα)]-7-Benzoyl-2-[4-cyano-3-(trifluoromethyl)phenyl]tetrahydro-5,8-methanoimidazo[15-a]pyrazine-1.3(2H,5H)-dione. (100)

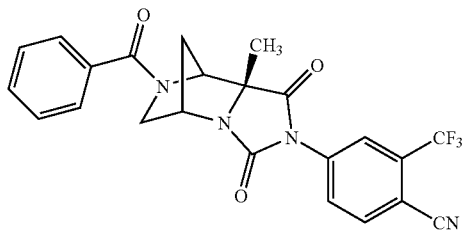

Compound 99 (0.023 g, 0.066 mmol) was dissolved in methylene chloride (2.0 mL) and then TEA (0.018 mL, 0.132 mmol) and 4-DMAP (cat) were added followed by benzoyl chloride (0.011 mL, 0.099 mmol). After 3 h, the reaction was concentrated in vacuo and then purified by preparative TLC on silica eluting with 7% acetone in chloroform to give 0.021 g of compound 100 as a white foam. HPLC: 100% at 2.927 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 455.10 [M+H]⁺.

EXAMPLE 101

[5S-(5α,8α,8aα)]-7-(4-Fluorobenzoyl)tetrahydro-2-(4-nitro-1-naphthalenyl)-5,8-methanoimidazo [1,5-a]pyrazine-1.3(2H,5H)-dione (101)

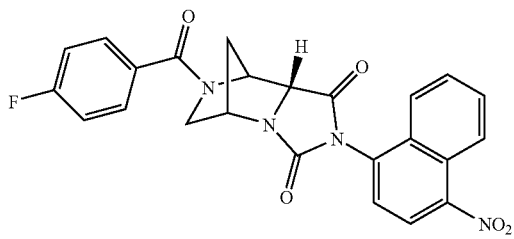

Compound 95 (0.077 g, 0.228 mmol) was dissolved in methylene chloride (2.0 mL) and TEA (0.127 mL, 0.912 mmol) and 4-DMAP (0.001 g) were added. The reaction was cooled to 0° C. and 4-fluorobenzoylchloride (0.040 mL, 0.342 mmol) was added. The reaction was then slowly warmed to 25° C. After 3 h, the reaction was diluted with methylene chloride (50 mL) and then washed successively with 1N HCl and sat aq NaHCO₃ then and dried over anhydrous sodium sulfate. The crude material was purified by preparative TLC on silica eluting with 5% acetone in chloroform to give 0.022 g of compound 101 as a yellow solid. HPLC: 100% at 2.960 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 461.07 [M+H]⁺.

EXAMPLE 102

[5S-(5α,8α,8aα)]-2-(4-Cyano-1-naphthalenyl)tetrahydro-7-(5-isoxazolylcarbonyl)-5,8-methanoimidazo[1,5-a]pyrazine-1,3(2H,5H)-dione (102A), [5S-(5α,8α,8aα)]-2-(4-Cyano-1-naphthalenyl) hexahydro-1,3-dioxo-5,8-methanoimidazo[1.5-a]pyrazine-7(8H)-carboxylic acid. 4-fluorophenyl ester (102B). [5S-(5α,8α,8aα)]-2-(4-Cyano-1-naphthalenyl)tetrahydro-7-[(1-methyl-1H-imidazol-4-yl)sulfonyl]-5,8-methanoimidazo [1.5-a]pyrazine-1,3(2H, 5H)-dione (102C) & [5S-(5α,8α,8aα)]-2-(4-Cyano-1-naphthalenyl)-N-(4-fluorophenyl)hexahydro-1,3-dioxo-5,8-methanoimidazo [1,5-a]pyrazine-7(8H)-carboxamide (102D)

Solution Phase Library Synthesis

The below procedure is a general approach to the synthesis of compounds of formula I in a solution phase library format. A more detailed description of individual compounds made via this combinatorial approach follows.

A series of free amine starting materials, analogous to the structure of [5S-(5α,8α,8aα)]-Tetrahydro-2-(4-nitro-1-naphthalenyl)-5,8 methanoimidazo[1,5-a]pyrazine-1,3(2H, 5H)-dione (0.05 mmol, prepared as described in Example 95) were dissolved in dichloromethane (1.5 mL) in a polystyrene tube with a coarse frit. N,N-(Diisopropyl)aminomethyl polystyrene (3.49 mmol/g, 60 mg) was then added to each reaction vessel followed by the addition of the desired acid chloride, isocyanate, chloroformate or sulfonyl chloride (0.10 mmol) in, 0.5 mL dichloroethane by automated synthesizer. The reaction vessels were shaken at 25° C. for 24 h and then Tris-(2-Aminoethyl)amine Polystyrene HL (200-400 mesh, 3.3 mmol/g, 75 mg) was added to each reaction vessel and the vessels shaken again for 18 h at 25° C. The liquid from each tube was drained into pretared 2.5 ml STR tubes and the resin was rinsed with dichloromethane (3×0.25 mL). The pretared tubes were then concentrated and analyzed by analytical HPLC and LC-MS. HPLC: (Phenomenex-Prime 5μ C-18 column 4.6×50 mm eluting with 10-90% aqueous methanol over 4 minutes containing 0.1% TFA, 4 mL/min, monitoring at 220 nm).

A. [5S-(5α,8α,8aα)]-2-(4-Cyano-1-naphthalenyl) tetrahydro-7-(5-isoxazolylcarbonyl)-5,8-methanoimidazo [1,5-a]pyrazine-1,3(2H,5H)-dione (102A)

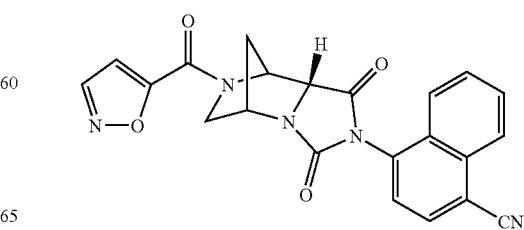

[5 S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of isoxazolacid chloride (0.025 g, 0.19 mmol). The tube was shaken at 25° C. for 24 h and then Tris-(2-Aminoethyl)amine Polystyrene HL (200-400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude compound 102A (0.058 g) as a yellow solid. No purification was necessary. HPLC: 100% at 2.237 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 414.11 [M+H]+.

B. [5S-(5α,8α,8aα)]-2-(4-Cyano-1-naphthalenyl) hexahydro-1,3-dioxo-5,8-methanoimidazo[1,5-a] pyrazine-7(8H)-carboxylic acid, 4-fluorophenyl ester (102B)

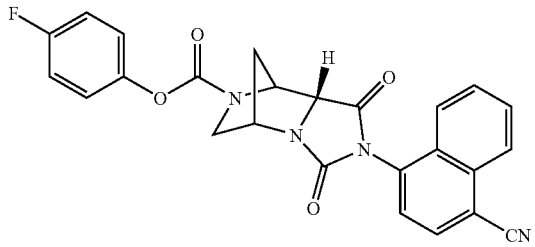

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylchloroformnate (0.033 g, 0.19 mmol). The tube was shaken at 25° C. for 24 h and then Tris-(2-Aminoethyl)amine Polystyrene HL (200-400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave crude compound 102B (0.053 g) as a yellow solid. No purification was necessary. HPLC: 93% at 2.987 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 457.07 [M+H]+.

C. [5S-(5α,8α,8aα)]-2-(4-Cyano-1-naphthalenyl) tetrahydro-7-[(1-methyl-1H-imidazol-4-yl)sulfonyl]-5,8-methanoimidazo [1,5-a]pyrazine-1,3(2H,5H)-dione (102C)

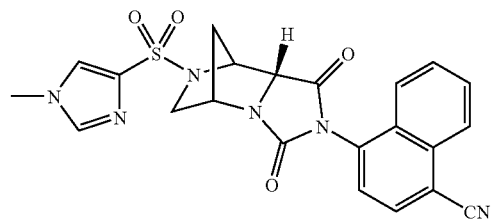

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of imidazolesulfonylchloride (0.034 g, 0.19 mmol). The tube was shaken at 25° C. for 24 h and then Tris-(2-Aminoethyl) amine Polystyrene HL (200-400 mesh, 3.3 mmol/g, 75 mg) was added to the reaction vessel and it was shaken again for 18 h at 25° C. The liquid was drained into pretared 2.5 ml STR tube and the resin was rinsed with dichloromethane (3×0.25 mL). Concentration in vacuo gave the crude compound 102C (0.043 g) as a yellow solid. No purification was necessary. HPLC: 70% at 1.603 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 463.07 [M+H]+.

D. [5S-(5α,8α,8aα)]-2-(4-Cyano-1-naphthalenyl)-N-(4-fluorophenyl)hexahydro-1,3-dioxo-5,8-methanoimidazo[1,5-a]pyrazine-7(8H)-carboxamide (102D)

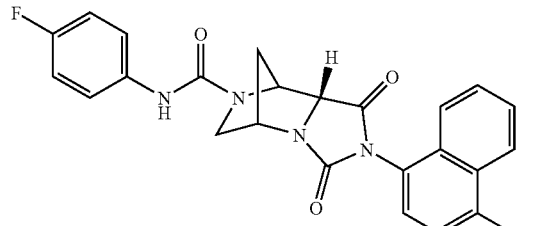

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylisocyanate (0.026 g, 0.19 mmol). The tube was shaken at 25° C. for 24 h and then Tris-(2-Aminoethyl)amine Polystyrene HL (200-400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude compound 102D (0.058 g) as a yellow solid. No purification was necessary. HPLC: 100% at 2.890 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 456.4 [M+H]+.

EXAMPLE 103

[5S-(5α,8α,8aα) -Tetrahydro-2-(4-nitro-1-naphthalenyl)-7-(phenylmethyl)-5,8-methanoimidazo [1,5-a] pyrazine-1,3(2H,5H)-dione (103)

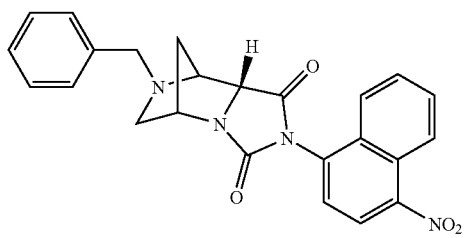

The TFA salt of the compound 95 (0.010 g, 0.022 mmol) was dissolved in DMF (0.5 mL) followed by addition of K$_2$CO$_3$ (0.009 g, 0.088 mmol) and benzyl bromide (0.005 mL, 0.044 mmol). After 1 h, the DMF was removed in vacuo and the crude product was purified by flash chromatography on silica eluting with 5% acetone in chloroform. This gave 0.008 g of compound 103 as a yellow solid. Proton NMR showed an intact hydantoin ring system. HPLC: 100% at 2.280 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 461.12 [M+H+MeOH]$^+$.

EXAMPLES 104 TO 199

Additional compounds of the present invention were prepared by procedures analogous to those described above. The compounds of Examples 104 to 199 have the following structure (L is a bond):

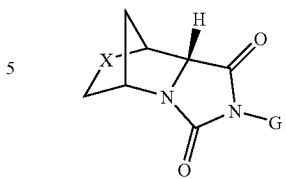

where G, X, the compound name, retention time, molecular mass, and the procedure employed, are set forth in Table 3. The chromatography techniques used to determine the compound retention times of Table 3 are as follows: LCMS=YMC S5 ODS column, 4.6×50 mm eluting with 10-90% MeOH/H$_2$O over 4 minutes containing 0.1% TFA; 4 mL/min, monitoring at 220 nm. LCMS*=YMC S5 ODS column, 4.6×50 mm eluting with 10-90% MeOH/H$_2$O over 2 minutes containing 0.1% TFA; 4 m-L/min, monitoring at 220 nm. LC=YMC S5 ODS column 4.6×50 mm eluting with 10-90% MeOH/H$_2$O over 4 minutes containing 0.2% phosphoric acid, 4 mL/min, monitoring at 220 nm. The molecular mass of the compounds listed in Table 3 were determined by MS (ES) by the formula m/z.

For examples 110, 114, 124, 125, 131 and 132, applicants incorporate herein by reference said examples as reported in the parent case hereof, i.e., U.S. patent application Ser. No. 10/322,306, filed Dec. 18, 2002, as if said examples were fully set forth herein at length.

TABLE 3

| Ex. No | G | X | Compound Name | Retention Time Min./ Molecular Mass | Procedure of Ex. |
|---|---|---|---|---|---|
| 104 | (4-CF$_3$, 2-CN phenyl; methyl substituent) | N-C(=O)-O-C(CH$_3$)$_2$-CH$_3$ (Boc) | [5R-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 1,1-dimethylethyl ester. | 3.13 LC | 93 |
| 105 | (4-nitro-1-naphthalenyl; methyl substituent) | N-C(=O)-O-C(CH$_3$)$_2$-CH$_3$ (Boc) | [5R-(5α,8α,8aα)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.13 LC | 93, 94 |
| 106 | (4-nitro-1-naphthalenyl; methyl substituent) | NH | [5R-(5α,8α,8aα)]-Tetrahydro-2-(4-nitro-1-naphthalenyl)-5,8-methanoimidazo[1,5-a]pyrazine-1,3(2H,5H)-dione. | 1.76 LC | 93, 95 |

TABLE 3-continued

| Ex. No | G | X | Compound Name | Retention Time Min./ Molecular Mass | Procedure of Ex. |
|---|---|---|---|---|---|
| 107 | 4-CN, 2-CF₃ phenyl (methyl) | NH | [5R-(5α,8α,8aα)]-4-(Hexahydro-1,3-dioxo-5,8-methanoimidazo[1,5-a]pyrazin-2(3H)-yl)-2-(trifluoromethyl)-benzonitrile. | 3.29 LC | 93, 91 |
| 108 | 4-CN, 2-CF₃ phenyl (methyl) | N-C(=O)-phenyl | [5S-(5α,8α,8aα)]-4-(7-Benzoylhexahydro-1,3-dioxo-5,8-methanoimidazo[1,5-a]pyrazin-2(3H)-yl)-2-(trifluoromethyl)-benzonitrile. | 2.98 LC | 100 |
| 109 | 4-CN, 2-CF₃ phenyl (methyl) | N-C(=O)-O-CH₂-phenyl | [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, phenylmethyl ester. | 3.12 LC | 102B |
| 111 | 4-CN, 2-CF₃ phenyl (methyl) | N—CH₃ | [5S-(5α,8α,8aα)]-4-(Hexahydro-7-methyl-1,3-dioxo-5,8-methanoimidazo[1,5-a]pyrazin-2(3H)-yl)-2-(trifluoromethyl)-benzonitrile. | 1.94 LC | 99 |
| 112 | 4-NO₂-1-naphthalenyl (methyl) | N-C(=O)-phenyl | [5S-(5α,8α,8aα)]-7-Benzoyltetrahydro-2-(4-nitro-1-naphthalenyl)-5,8-methanoimidazo[1,5-a]pyrazine-1,3(2H,5H)-dione. | 2.86 LC | 98A |
| 113 | 4-NO₂-1-naphthalenyl (methyl) | N-C(=O)-O-CH₂-phenyl | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, phenylmethyl ester. | 3.27 LC | 98B |
| 115 | 4-NO₂-1-naphthalenyl (methyl) | N—CH₃ | [5S-(5α,8α,8aα)]-Tetrahydro-7-methyl-2-(4-nitro-1-naphthalenyl)-5,8-methanoimidazo[1,5-a]pyridine-1,3(2H,5H)-dione. | 1.79 LC | 103 |

TABLE 3-continued

| Ex. No | G | X | Compound Name | Retention Time Min./ Molecular Mass | Procedure of Ex. |
|---|---|---|---|---|---|
| 116 | 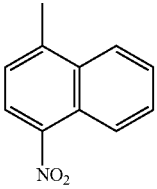 | 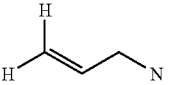 | [5S-(5α,8α,8aα)]-Tetrahydro-2-(4-nitro-1-naphthalenyl)-7-(2-propenyl)-5,8-methanoimidazo[1,5-a]pyrazine-1,3(2H,5H)-dione. | 3.11 LC | 103 |
| 117 | 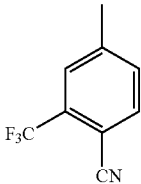 | 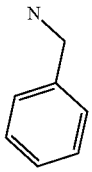 | [5S-(5α,8α,8aα)]-4-[Hexahydro-1,3-dioxo-7-(phenylmethyl)-5,8-methanoimidazo[1,5-a]pyrazin-2(3H)-yl]-2-(trifluoromethyl)-benzonitrile | 2.81 LC | 103 |
| 118 | 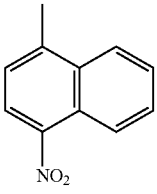 | 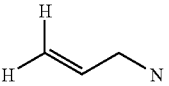 | [5R-(5α,8α,8aα)]-Tetrahydro-2-(4-nitro-1-naphthalenyl)-7-(2-propenyl)-5,8-methanoimidazo[1,5-a]pyrazine-1,3(2H,5H)-dione. | 3.06 LC | 103 |
| 119 | 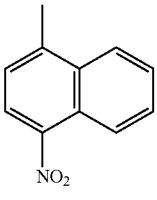 | 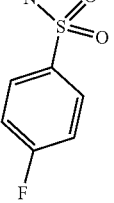 | [5R-(5α,8α,8aα)]-7-[(4-Fluorophenyl)sulfonyl]-tetrahydro-2-(4-nitro-1-naphthalenyl)-5,8-methanoimidazo[1,5-a]pyrazine-1,3(2H,5H)-dione. | 3.08 LC | 102C |
| 120 | 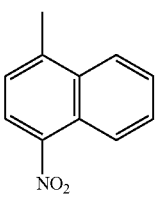 | 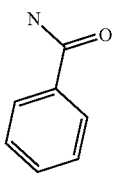 | [5R-(5α,8α,8aα)]-7-Benzoyltetrahydro-2-(4-nitro-1-naphthalenyl)-5,8-methanoimidazo[1,5-a]pyrazine-1,3(2H,5H)-dione. | 2.82 LC | 102A |
| 121 | 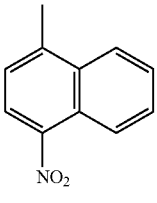 |  | [5S-(5α,8α,8aα)]-Tetrahydro-2-(4-nitro-1-naphthalenyl)-7-[(phenylmethyl)sulfonyl]-5,8-methanoimidazo[1,5-a]pyrazine-1,3(2H,5H)-dione. | 2.98 LC | 102C |
| 122 | 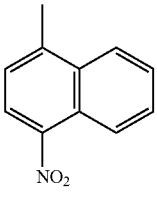 | 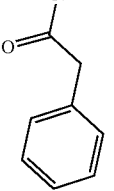 | [5S-(5α,8α,8aα)]-Tetrahydro-2-(4-nitro-1-naphthalenyl)-7-(phenylacetyl)-5,8-methanoimidazo[1,5-a]pyrazine-1,3(2H,5H)-dione. | 3.04 LC | 102A |

TABLE 3-continued

| Ex. No | G | X | Compound Name | Retention Time Min./ Molecular Mass | Procedure of Ex. |
|---|---|---|---|---|---|
| 123 | 4-methyl-1-nitronaphthalene (G substituent) | N-C(=O)-CH2-CH2-phenyl | [5S-(5α,8α,8aα)]-Tetrahydro-2-(4-nitro-1-naphthalenyl)-7-(3-phenyl-1-oxopropyl)-5,8-methanoimidazo[1,5-a]pyrazine-1,3(2H,5H)-dione. | 3.24 LC | 102A |
| 126 | 4-methyl-1-cyanonaphthalene | N-C(=O)-O-C(CH3)3 | [5S-(5α,5α,8aα)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester. | 3.00 LC | 94 |
| 127 | 4-methyl-1-cyanonaphthalene | NH | [5S-(5α,8α,8aα)]-4-(Hexahydro-1,3-dioxo-5,8-methanoimidazo[1,5-a]pyrazin-2(3H)-yl)-1-naphthalenecarbonitrile. | 1.65 LC | 95 |
| 128 | 4-methyl-1-cyanonaphthalene | N-C(=O)-CH(CH3)2 | [5S-(5α,8α,8aα)]-4-[Hexahydro-7-(2-methyl-1-oxopropyl)-1,3-dioxo-5,8-methanoimidazo[1,5-a]pyrazin-2(3H)-yl]-1-naphthalenecarbonitrile. | 2.49 LC | 102A |
| 129 | 4-methyl-2-iodobenzonitrile | N-C(=O)-O-C(CH3)3 | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 1,1-dimethylethyl ester. | 2.95 LC | 90 |
| 130 | 4-methyl-2-iodobenzonitrile | NH | [5S-(5α,8α,8aα)]-4-(Hexahydro-1,3-dioxo-5,8-methanoimidazo[1,5-a]pyrazin-2(3H)-yl)-2-iodobenzonitrile. | 1.34 LC | 91 |
| 133 | 4-methyl-1-nitronaphthalene | N-C(=O)-CH3 | [5S-(5α,8α,8aα)]-7-Acetyltetrahydro-2-(4-nitro-1-naphthalenyl)-5,8-methanoimidazo[1,5-a]pyrazine-1,3(2H,5H)-dione. | 2.76 LC 379.33 [M − H]+ | 98A |

TABLE 3-continued

| Ex. No | G | X | Compound Name | Retention Time Min./ Molecular Mass | Procedure of Ex. |
|---|---|---|---|---|---|
| 134 | 1-methyl-4-nitronaphthalenyl | (CH3)2CH-C(=O)-N | [5S-(5α,8α,8aα)]-Tetrahydro-7-(2-methyl-1-oxopropyl)-2-(4-nitro-1-naphthalenyl)-5,8-methanoixnidazo[1,5-a]pyrazine-1,3(2H,5H)-dione. | 3.16 LC 407.36 [M − H]+ | 102A |
| 135 | 1-methyl-4-nitronaphthalenyl | 4-fluoro-3-(trifluoromethyl)benzoyl-N | [5S-(5α,8α,8aα)]-7-[4-Fluoro-3-(trifluoromethyl)benzoyl]-tetrahydro-2-(4-nitro-1-naphthalenyl)-5,8-methanoimidazo[1,5-a]pyrazine-1,3(2H,5H)-dione. | 3.8 LC 529.35 [M + H]+ | 102A |
| 136 | 1-methyl-4-nitronaphthalenyl | 4-chloro-3-nitrobenzoyl-N | [5S-(5α,8α,8aα)]-7-(4-Chloro-3-nitrobenzoyl)tetrahydro-2-(4-nitro-1-naphthalenyl)-5,8-methanoimidazo[1,5-a]pyrazine-1,3(2H,5H)-dione. | 3.27 LC 522.33 [M + H]+ | 102A |
| 137 | 1-methyl-4-nitronaphthalenyl | 5-isoxazolylcarbonyl-N | [5S-(5α,8α,8aα)]-Tetrahydro-7-(5-isoxazolylcarbonyl)-2-(4-nitro-1-naphthalenyl)-5,8-methanoimidazo[1,5-a]pyrazine-1,3(2H,5H)-dione. | 2.4 LC 434.37 [M + H]+ | 102A |
| 138 | 1-methyl-4-nitronaphthalenyl | 4-butylbenzoyl-N | [5S-(5α,8α,8aα)]-7-(4-Butylbenzoyl)tetrahydro-2-(4-nitro-1-naphthalenyl)-5,8-methanoimidazo[1,5-a]pyrazine-1,3(2H,5H)-dione. | 3.69 LC 499.45 [M + H]+ | 102A |
| 139 | 1-methyl-4-nitronaphthalenyl | (3-chloro-4-fluorophenyl)NH-C(=O)-N | [5S-(5α,8α,8aα)]-N-(3-Chloro-4-fluorophenyl)hexahydro-2-(4-nitro-1-naphthalenyl)-1,3-dioxo-5,8-methanoimidazo[1,5-a]pyrazine-7(8H)-carboxamide. | 3.30 LC 510.34 [M + H]+ | 102D |

TABLE 3-continued

| Ex. No | G | X | Compound Name | Retention Time Min./ Molecular Mass | Procedure of Ex. |
|---|---|---|---|---|---|
| 140 | 1-methyl-4-nitronaphthalenyl | 4-(trifluoromethyl)phenyl-NH-C(=O)-N | [5S-(5α,8α,8aα)]-Tetrahydro-2-(4-nitro-1-naphthalenyl)-7-[4-(trifluoromethyl)benzoyl]-5,8-methanoimidazo[1,5-a]pyrazine-1,3(2H,5H)-dione. | 3.78 LC 526.38 [M + H]⁺ | 102D |
| 141 | 1-methyl-4-nitronaphthalenyl | (CH₃)₂CH-NH-C(=O)-N | [5S-(5α,8α,8aα)]-Hexahydro-N-(1-methylethyl)-2-(4-nitro-1-naphthalenyl)-1,3-dioxo-5,8-methanoimidazo[1,5-a]pyrazine-7(8H)-carboxamide. | 3.07 LC 424.43 [M + H]⁺ | 102D |
| 142 | 1-methyl-4-nitronaphthalenyl | 4-fluorophenyl-NH-C(=O)-N | [5S-(5α,8α,8aα)]-N-(4-Fluorophenyl)hexahydro-2-(4-nitro-1-naphthalenyl)-1,3-dioxo-5,8-methanoimidazo[1,5-a]pyrazine-7(8H)-carboxamide. | 3.00 LC 476.37 [M + H]⁺ | 102D |
| 143 | 1-methyl-4-nitronaphthalenyl | 4-fluorobenzyl-NH-C(=O)-N | [5S-(5α,8α,8aα)]-N-[(4-Fluorophenyl)methyl]-hexahydro-2-(4-nitro-1-naphthalenyl)-1,3-dioxo-5,8-methanoimidazo[1,5-a]pyrazine-7(8H)-carboxamide. | 3.43 LC 490.39 [M + H]⁺ | 102D |
| 144 | 1-methyl-4-nitronaphthalenyl | 4-nitrophenyl-O-C(=O)-N | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-nitrophenyl ester. | 3.23 LC 536.40 [M + MeOH]⁺ | 102B |
| 145 | 1-methyl-4-nitronaphthalenyl | 4-fluorophenyl-O-C(=O)-N | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-fluorophenyl ester. | 3.21 LC 477.38 [M + H]⁺ | 102B |

TABLE 3-continued

| Ex. No | G | X | Compound Name | Retention Time Min./ Molecular Mass | Procedure of Ex. |
|---|---|---|---|---|---|
| 146 | 1-methyl-4-nitronaphthalenyl | 4-nitrobenzyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-(nitrophenyl)methyl ester. | 3.01 LC 518.38 [M + H]$^+$ | 102B |
| 147 | 1-methyl-4-nitronaphthalenyl | butyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, butyl ester. | 3.22 LC 439.43 [M + H]$^+$ | 102B |
| 148 | 1-methyl-4-nitronaphthalenyl | (1-methyl-1H-imidazol-4-yl)sulfonyl | [5S-(5α,8α,8aα)]-Tetrahydro-7-[(1-methyl-1H-imidazol-4-yl)sulfonyl]-2-(4-nitro-1-naphthalenyl)-5,8-methanoimidazo[1,5-a]pyrazine-1,3(2H,5H)-dione. | 2.45 LC 483.39 [M + H]$^+$ | 102C |
| 149 | 1-methyl-4-nitronaphthalenyl | (4-chloro-3-nitrophenyl)sulfonyl | [5S-(5α,8α,8aα)]-7-[(4-Chloro-3-nitrophenyl)sulfonyl]-tetrahydro-2-(4-nitro-1-naphthalenyl)-5,8-methanoimidazo[1,5-a]pyrazine-1,3(2H,5H)-dione. | 3.43 LC 556.26 [M − H]$^+$ | 102C |
| 150 | 1-methyl-4-nitronaphthalenyl | (2,2,2-trifluoroethyl)sulfonyl | [5S-(5α,8α,8aα)]-Tetrahydro-2-(4-nitro-1-naphthalenyl)-7-[(2,2,2-trifluoroethyl)sulfonyl]-5,8-methanoimidazo[1,5-a]pyrazine-1,3(2H,5H)-dione. | 2.90 LC 483.17 [M − H]$^+$ | 102C |
| 151 | 1-methyl-4-cyanonaphthalenyl | acetyl | [5S-(5α,8α,8aα)]-7-Acetyl-2-(4-cyano-1-naphthalenyl)tetrahydro-5,8-methanoimidazo[1,5-a]pyrazine-1,3(2H,5H)-dione. | 2.07 LC 359.35 [M − H]$^+$ | 102A |

TABLE 3-continued

| Ex. No | G | X | Compound Name | Retention Time Min./ Molecular Mass | Procedure of Ex. |
|---|---|---|---|---|---|
| 152 | (4-methyl-1-naphthyl with CN) | isobutyryl (H₃C-CH(CH₃)-C(=O)-N) | [5S-(5α,8α,8aα)]-2-(4-Cyano-1-naphthalenyl)tetrahydro-7-(2-methyl-1-oxopropyl)-5,8-methanoimidazo[1,5-a]pyrazine-1,3(2H,5H)-dione | 2.52 LC 389.44 [M + H]⁺ | 102A |
| 153 | (4-methyl-1-naphthyl with CN) | 4-fluoro-3-(trifluoromethyl)benzoyl | [5S-(5α,8α,8aα)]-2-(4-Cyano-1-naphthalenyl)-7-[4-fluoro-3-(trifluoromethyl)benzoyl]tetrahydro-5,8-methanoimidazo[1,5-a]pyrazine-1,3(2H,5H)-dione. | 3.24 LC 509.40 [M + H]⁺ | 102A |
| 154 | (4-methyl-1-naphthyl with CN) | 4-chloro-3-nitrobenzoyl | [5S-(5α,8α,8aα)]-7-(4-Chloro-3-nitrobenzoyl)-2-(4-cyano-1-naphthalenyl)tetrahydro-5,8-methanoimidazo[1,5-a]pyrazine-1,3(2H,5H)-dione. | 3.11 LC 502.33 [M + H]⁺ | 102A |
| 155 | (4-methyl-1-naphthyl with CN) | 4-butylbenzoyl | [5S-(5α,8α,8aα)]-7-(4-Butylbenzoyl)-2-(4-cyano-1-naphthalenyl)tetrahydro-5,8-methanoimidazo[1,5-a]pyrazine-1,3(2H,5H)-dione. | 3.58 LC 479.47 [M + H]⁺ | 102A |
| 156 | (4-methyl-1-naphthyl with CN) | N-(3-chloro-4-fluorophenyl)carbamoyl | [5S-(5α,8α,8aα)]-N-(3-Chloro-4-fluorophenyl)-2-(4-cyano-1-naphthalenyl)hexahydro-1,3-dioxo-5,8-methanoimidazo[1,5-a]pyrazine-7(8H)-carboxamide. | 3.20 LC 488.36 [M − H]⁺ | 102D |
| 157 | (4-methyl-1-naphthyl with CN) | N-[4-(trifluoromethyl)phenyl]carbamoyl | [5S-(5α,8α,8aα)]-2-(4-Cyano-1-naphthalenyl)hexahydro-1,3-dioxo-N-[4-(trifluoromethyl)phenyl]-5,8-methanoimidazo[1,5-a]pyrazine-7(8H)-carboxamide. | 3.29 LC 504.38 [M − H]⁺ | 102D |

TABLE 3-continued

| Ex. No | G | X | Compound Name | Retention Time Min./ Molecular Mass | Procedure of Ex. |
|---|---|---|---|---|---|
| 158 | 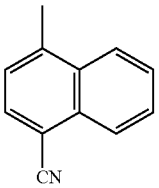 | 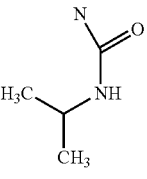 | [5S-(5α,8α,8aα)]-2-(4-Cyano-1-naphthalenyl)hexahydro-N-(1-methylethyl)-1,3-dioxo-5,8-methanoimidazo[1,5-a]pyrazine-7(8H)-carboxamide. | 2.48 LC 404.43 [M − H]+ | 102D |
| 159 | 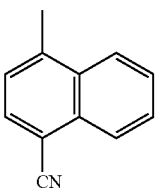 | 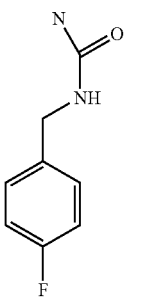 | [5S-(5α,8α,8aα)]-2-(4-Cyano-1-naphthalenyl)-N-[(4-fluorophenyl)methyl]hexahydro-1,3-dioxo-5,8-methanoimidazo[1,5-a]pyrazine-7(8H)-carboxamide. | 2.89 LC 470.41 [M + H]+ | 102D |
| 160 | 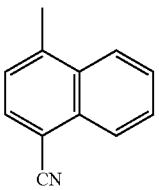 | 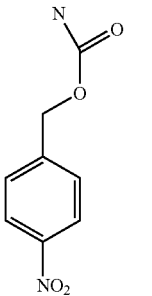 | [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 4-(nitrophenyl)methyl ester. | 2.88 LC 496.36 [M − H]+ | 102B |
| 161 | 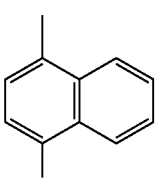 | 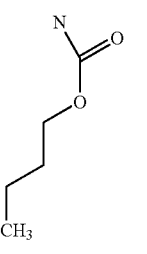 | [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, butyl ester. | 3.09 LC 417.39 [M − H]+ | 102B |
| 162 | 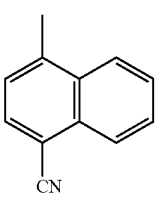 | 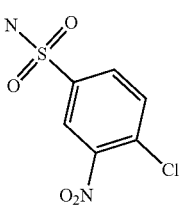 | [5S-(5α,8α,8aα)]-7-[(4-Chloro-3-nitrophenyl)sulfonyl]-2-(4-cyano-1-naphthalenyl)tetrahydro-5,8-methanoimidazo[1,5-a]pyrazine-1,3(2H,5H)-dione. | 3.31 LC 536.28 [M − H]+ | 102C |
| 163 | 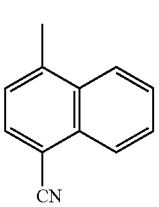 | 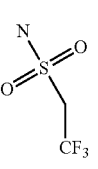 | [5S-(5α,8α,8aα)]-2-(4-Cyano-1-naphthalenyl)tetrahydro-7-[(2,2,2-trifluoroethyl)-sulfonyl]-5,8-methanoimidazo[1,5-a]pyrazine-1,3(2H,5H)-dione. | 2.72 LC 463.31 [M − H]+ | 102C |

TABLE 3-continued

| Ex. No | G | X | Compound Name | Retention Time Min./ Molecular Mass | Procedure of Ex. |
|---|---|---|---|---|---|
| 164 | (4-methyl-2-trifluoromethyl-phenyl with CN) | N-acetyl (H3C-C(=O)-NH-) | [5S-(5α,8α,8aα)]-7-Acetyl-2-[4-cyano-3-(trifluoromethyl)phenyl]-tetrahydro-5,8-methanoimidazo[1,5-a]pyrazine-1,3(2H,5H)-dione. | 2.26 LC 377.32 [M − H]+ | 102A |
| 165 | (4-methyl-2-trifluoromethyl-phenyl with CN) | isobutyryl | [5S-(5α,8α,8aα)]-2-[4-Cyano-3-(trifluoromethyl)phenyl]-tetrahydro-7-(2-methyl-1-oxopropyl)-5,8-methanoimidazo[1,5-a]pyrazine-1,3(2H,5H)-dione. | 2.82 LC 405.36 [M − H]+ | 102A |
| 166 | (4-methyl-2-trifluoromethyl-phenyl with CN) | 4-fluoro-3-(trifluoromethyl)benzoyl | [5S-(5α,8α,8aα)]-2-[4-Cyano-3-(trifluoromethyl)phenyl]-7-[4-fluoro-3-(trifluoromethyl)benzoyl]-tetrahydro-5,8-methanoimidazo[1,5-a]pyrazine-1,3(2H,5H)-dione. | 3.38 LC 525.31 [M − H]+ | 102A |
| 167 | (4-methyl-2-trifluoromethyl-phenyl with CN) | 4-chloro-3-nitrobenzoyl | [5S-(5α,8α,8aα)]-7-(4-Chloro-3-nitrobenzoyl)-2-[4-cyano-3-(trifluoromethyl)phenyl]-tetrahydro-5,8-methanoimidazo[1,5-a]pyrazine-1,3(2H,5H)-dione. | 3.24 LC 518.30 [M − H]+ | 102A |
| 168 | (4-methyl-2-trifluoromethyl-phenyl with CN) | 5-isoxazolylcarbonyl | [5S-(5α,8α,8aα)]-2-[4-Cyano-3-(trifluoromethyl)phenyl]-tetrahydro-7-(5-isoxazolylcarbonyl)-5,8-methanoimidazo[1,5-a]pyrazine-1,3(2H,5H)-dione. | 2.40 LC 430.34 [M − H]+ | 102A |
| 169 | (4-methyl-2-trifluoromethyl-phenyl with CN) | 4-butylbenzoyl | [5S-(5α,8α,8aα)]-7-(4-Butylbenzoyl)-2-[4-cyano-3-(trifluoromethyl)phenyl-]tetrahydro-5,8-methanoimidazo[1,5-a]pyrazine-1,3(2H,5H)-dione. | 3.65 LC 495.42 [M − H]+ | 102A |

TABLE 3-continued

| Ex. No | G | X | Compound Name | Retention Time Min./ Molecular Mass | Procedure of Ex. |
|---|---|---|---|---|---|
| 170 | 4-methyl-2-(trifluoromethyl)benzonitrile (F₃C, CN substituents) | N-(3-chloro-4-fluorophenyl)urea group | [5S-(5α,8α,8aα)]-N-(3-Chloro-4-fluorophenyl)-2-[4-cyano-3-(trifluoromethyl)phenyl]-hexahydro-1,3-dioxo-5,8-methanoimidazo[1,5-a]pyrazine-7(8H)-carboxamide. | 3.24 LC 508.31 [M + H]⁺ | 102D |
| 171 | 4-methyl-2-(trifluoromethyl)benzonitrile | N-[4-(trifluoromethyl)phenyl]urea group | [5S-(5α,8α,8aα)]-2-[4-Cyano-3-(trifluoromethyl)phenyl]-hexahydro-1,3-dioxo-N-[4-(trifluoromethyl)phenyl]-5,8-methanoimidazo[1,5-a]pyrazine-7(8H)-carboxamide. | 3.34 LC 522.33 [M − H]⁺ | 102D |
| 172 | 4-methyl-2-(trifluoromethyl)benzonitrile | N-(1-methylethyl)urea group | [5S-(5α,8α,8aα)]-2-[4-Cyano-3-(trifluoromethyl)phenyl]-hexahydro-N-(1-methylethyl)-1,3-dioxo-5,8-methanoimidazo[1,5-a]pyrazine-7(8H)-carboxamide. | 2.63 LC 422.40 [M + H]⁺ | 102D |
| 173 | 4-methyl-2-(trifluoromethyl)benzonitrile | N-(4-fluorophenyl)urea group | [5S-(5α,8α,8aα)]-2-[4-Cyano-3-(trifluoromethyl)phenyl]-N-(4-fluorophenyl)-hexahydro-1,3-dioxo-5,8-methanoimidazo[1,5-a]pyrazine-7(8H)-carboxamide. | 3.02 LC 472.35 [M − H]⁺ | 102D |
| 174 | 4-methyl-2-(trifluoromethyl)benzonitrile | N-[(4-fluorophenyl)methyl]urea group | [5S-(5α,8α,8aα)]-2-[4-Cyano-3-(trifluoromethyl)phenyl]-N-[(4-fluorophenyl)-methyl]hexahydro-1,3-dioxo-5,8-methanoimidazo[1,5-a]pyrazine-7(8H)-carboxamide. | 3.09 LC 488.38 [M + H]⁺ | 102D |
| 175 | 4-methyl-2-(trifluoromethyl)benzonitrile | 4-nitrophenyl carbamate group | [5S-(5α,5α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-nitrophenyl ester. | 3.19 LC 534.37 [M + MeOH]⁺ | 102B |

TABLE 3-continued

| Ex. No | G | X | Compound Name | Retention Time Min./ Molecular Mass | Procedure of Ex. |
|---|---|---|---|---|---|
| 176 | 4-methyl-2-(trifluoromethyl)benzonitrile | 4-fluorophenyl carbamate | [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-fluorophenyl ester. | 3.20 LC 507.38 [M + MeOH]⁺ | 102B |
| 177 | 4-methyl-2-(trifluoromethyl)benzonitrile | 4-nitrobenzyl carbamate | [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-(nitrophenyl)methyl ester. | 3.06 LC 546.34 [M + MeOH]⁺ | 102B |
| 178 | 4-methyl-2-(trifluoromethyl)benzonitrile | butyl carbamate | [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, butyl ester. | 3.22 LC 469.43 [M + MeOH]⁺ | 102B |
| 179 | 4-methyl-2-(trifluoromethyl)benzonitrile | 1-methyl-1H-imidazol-4-yl sulfonyl | [5S-(5α,8α,8aα)]-2-[4-Cyano-3-(trifluoromethyl)phenyl]-tetrahydro-7-[(1-methyl-1H-imidazol-4-yl)sulfonyl]-5,8-methanoimidazo[1,5-a]pyrazine-1,3(2H,5H)-dione. | 2.35 LC 481.33 [M + H]⁺ | 102C |
| 180 | 4-methyl-2-(trifluoromethyl)benzonitrile | 4-chloro-3-nitrophenyl sulfonyl | [5S-(5α,8α,8aα)]-7-[(4-Chloro-3-nitrophenyl)sulfonyl]-2-[4-cyano-3-(trifluoromethyl)phenyl]-tetrahydro-5,8-methanoimidazo[1,5-a]pyrazine-1,3(2H,5H)-dione. | 3.29 LC 554.25 [M − H]⁺ | 102C |
| 181 | 4-methyl-2-(trifluoromethyl)benzonitrile | 2,2,2-trifluoroethyl sulfonyl | [5S-(5α,8α,8aα)]-2-[4-Cyano-3-(trifluoromethyl)phenyl]-tetrahydro-7-[(2,2,2-trifluoroethyl)sulfonyl]-5,8-methanoimidazo[1,5-a]pyrazine-1,3(2H,5H)-dione. | 4.32 LC 481.29 [M − H]⁺ | 102C |

TABLE 3-continued

| Ex. No | G | X | Compound Name | Retention Time Min./ Molecular Mass | Procedure of Ex. |
|---|---|---|---|---|---|
| 182 |  | 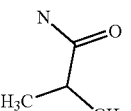 | [5S-(5α,8α,8aα)]-7-Acetyl-2-(4-cyano-3-iodophenyl)tetrahydro-5,8-methanoimidazo[1,5-a]pyrazine-1,3(2H,5H)-dione. | 2.07 LC 435.24 [M − H]+ | 102A |
| 183 |  | 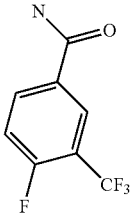 | [5S-(5α,8α,8aα)]-2-(4-Cyano-3-iodophenyl)tetrahydro-7-(2-methyl-1-oxopropyl)-5,8-methanoimidazo[1,5-a]pyrazine-1,3(2H,5H)-dione. | 2.48 LC 463.26 [M − H]+ | 102A |
| 184 |  | 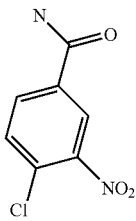 | [5S-(5α,8α,8aα)]-2-(4-Cyano-3-iodophenyl)-7-[4-fluoro-3-(trifluoromethyl)benzoyl]-tetrahydro-5,8-methanoimidazo[1,5-a]pyrazine-1,3(2H,5H)-dione. | 3.32 LC 583.21 [M − H]+ | 102A |
| 185 |  | 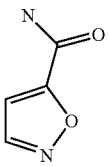 | [5S-(5α,8α,8aα)]-7-(4-Chloro-3-nitrobenzoyl)-2-(4-cyano-3-iodophenyl)-tetrahydro-5,8-methanoimidazo[1,5-a]pyrazine-1,3(2H,5H)-dione. | 3.10 LC 576.18 [M − H]+ | 102A |
| 186 |  | 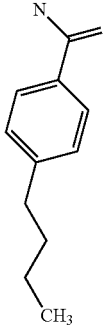 | [5S-(5α,8α,8aα)]-2-(4-Cyano-3-iodophenyl)tetrahydro-7-(5-isoxazolylcarbonyl)-5,8-methanoimidazo[1,5-a]pyrazine-1,3(2H,5H)-dione. | 2.22 LC 488.24 [M − H]+ | 102A |
| 187 |  | | [5S-(5α,8α,8aα)]-7-(4-Butylbenzoyl)-2-(4-cyano-3-iodophenyl)tetrahydro-5,8-methanoimidazo[1,5-a]pyrazine-1,3(2H,5H)-dione. | 3.58 LC 553.29 [M − H]+ | 102A |

TABLE 3-continued

| Ex. No | G | X | Compound Name | Retention Time Min./ Molecular Mass | Procedure of Ex. |
|---|---|---|---|---|---|
| 188 | (4-methyl-2-iodo-benzonitrile group) | (N-(3-chloro-4-fluorophenyl) urea group) | [5S-(5α,8α,8aα)]-N-(3-Chloro-4-fluorophenyl)-2-(4-cyano-3-iodophenyl)hexahydro-1,3-dioxo-5,8-methanoimidazo[1,5-a]pyrazine-7(8H)-carboxamide. | 3.09 LC 566.22 [M + H]⁺ | 102D |
| 189 | (4-methyl-2-iodo-benzonitrile group) | (N-(4-trifluoromethylphenyl) urea group) | [5S-(5α,8α,8aα)]-2-(4-Cyano-3-iodophenyl)hexahydro-1,3-dioxo-N-[4-(trifluoromethyl)phenyl]-5,8-methanoimidazo[1,5-a]pyrazine-7(8H)-carboxamide. | 3.21 LC 580.21 [M − H]⁺ | 102D |
| 190 | (4-methyl-2-iodo-benzonitrile group) | (N-isopropyl urea group) | [5S-(5α,8α,8aα)]-2-(4-Cyano-3-iodophenyl)hexahydro-N-(1-methylethyl)-1,3-dioxo-5,8-methanoimidazo[1,5-a]pyrazine-7(8H)-carboxamide. | 2.39 LC 480.31 [M + H]⁺ | 102D |
| 191 | (4-methyl-2-iodo-benzonitrile group) | (N-(4-fluorophenyl) urea group) | [5S-(5α,8α,8aα)]-2-(4-Cyano-3-iodophenyl)-N-(4-fluorophenyl)hexahydro-1,3-dioxo-5,8-methanoimidazo[1,5-a]pyrazine-7(8H)-carboxamide. | 2.90 LC 530.23 [M − H]⁺ | 102D |
| 192 | (4-methyl-2-iodo-benzonitrile group) | (N-(4-fluorobenzyl) urea group) | [5S-(5α,8α,8aα)]-2-(4-Cyano-3-iodophenyl)-N-[(4-fluorophenyl)methyl]hexahydro-1,3-dioxo-5,8-methanoimidazo[1,5-a]pyrazine-7(8H)-carboxamide. | 2.75 LC 544.26 [M − H]⁺ | 102D |
| 193 | (4-methyl-2-iodo-benzonitrile group) | (4-nitrophenyl carbamate group) | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 4-nitrophenyl ester. | 2.99 LC 590.25 [M + MeOH]⁺ | 102B |

TABLE 3-continued

| Ex. No | G | X | Compound Name | Retention Time Min./ Molecular Mass | Procedure of Ex. |
|---|---|---|---|---|---|
| 194 | 4-methyl-2-iodo-benzonitrile | 4-fluorophenyl carbamate | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 4-fluorophenyl ester. | 3.02 LC 565.26 [M + MeOH]⁺ | 102B |
| 195 | 4-methyl-2-iodo-benzonitrile | (4-nitrophenyl)methyl carbamate | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, (4-nitrophenyl)methyl ester. | 2.89 LC 572.22 [M − H]⁺ | 102B |
| 196 | 4-methyl-2-iodo-benzonitrile | butyl carbamate | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, butyl ester. | 3.04 LC 493.28 [M − H]⁺ | 102B |
| 197 | 4-methyl-2-iodo-benzonitrile | (1-methyl-1H-imidazol-4-yl)sulfonyl | [5S-(5α,8α,8aα)]-2-(4-Cyano-3-iodophenyl)tetrahydro-7-[(1-methyl-1H-imidazol-4-yl)sulfonyl]-5,8-methanoimidazo[1,5-a]pyrazine-1,3(2H,5H)-dione. | 2.16 LC 539.22 [M + H]⁺ | 102D |
| 198 | 4-methyl-2-iodo-benzonitrile | (4-chloro-3-nitrophenyl)sulfonyl | [5S-(5α,8α,8aα)]-7-[(4-Chloro-3-nitrophenyl)sulfonyl]-2-(4-cyano-3-iodophenyl)tetrahydro-5,8-methanoimidazo[1,5-a]pyrazine-1,3(2H,5H)-dione. | 3.13 LC 612.15 [M − H]⁺ | 102D |
| 199 | 4-methyl-2-iodo-benzonitrile | methylsulfonyl | [5S-(5α,8α,8aα)]-2-(4-Cyano-3-iodophenyl)tetrahydro-7-(methylsulfonyl)-5,8-methanoimidazo[1,5-a]pyrazine-1,3(2H,5H)-dione. | 2.11 LC 471.20 [M − H]⁺ | 102D |

EXAMPLES 200 TO 217

Additional compounds of the present invention were prepared by procedures analogous to those described above. The compounds of Examples 200 to 217 have the following structure (L is a bond):

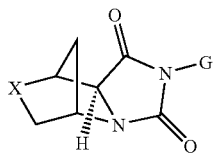

where G, X, the compound name, retention time, molecular mass, and the procedure employed, are set forth in Table 4.

The chromatography techniques used to determine the compound retention times of Table 4 are as follows: LCMS=YMC S5 ODS column, 4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with 10-90% MeOH/$H_2O$ over 2 minutes containing 0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm. The molecular mass of the compounds listed in Table 4 were determined by MS (ES) by the formula m/z.

For examples 208, 210, 211, 212, 215 and 217, applicants incorporate herein by reference said examples as reported in the parent case hereof, i.e., U.S. patent application Ser. No. 10/322,306, filed Dec. 18, 2002, as if said examples were fully set forth herein at length.

TABLE 4

| Ex. No | G | x | Compound Name | Retention Time Min./ Molecular Mass | Procedure of Ex. |
|---|---|---|---|---|---|
| 200 | 3-CF3-4-CN-phenyl | NH | [5S-(5α,8α,8aβ)]-4-(Hexahydro-1,3-dioxo-5,8-methanoimidazo[1,5-a]pyrazin-2(3H)-yl)-2-(trifluoromethyl)benzonitrile. | 1.46 LC | 91 |
| 201 | 3-CF3-4-CN-phenyl | N-C(=O)-O-C(CH3)3 (Boc) | [5R-(5α,8α,8aβ)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.29 LC | 93 |
| 202 | 3-CF3-4-CN-phenyl | N-C(=O)-O-C(CH3)3 (Boc) | [5S-(5α,8α,8aβ)]-2-[4-Cyano-3-(trifluoromethyl)phenyl]-hexahydro-1,3-dioxo-5,8-methanoimidazo[1,5-a]pyrazine-7(8H)-carboxylic acid, 1,1-dimethylethyl ester. | 3.28 LC | 90 |
| 203 | 4-NO2-naphthalen-1-yl | NH | [5S-(5α,8α,8aβ)]-Tetrahydro-2-(4-nitro-1-naphthalenyl)-5,8-methanoimidazo[1,5-a]pyrazine-1,3(2H,5H)-dione, trifluoroacetate (1:1). | 1.83 LC | 95 |
| 204 | 3-CF3-4-CN-phenyl | N-C(=O)-O-C(CH3)3 (Boc) | [5R-(5α,8α,8aβ)]-2-[4-Cyano-3-(trifluoromethyl)phenyl]-hexahydro-1,3-dioxo-5,8-methanoimidazo[1,5-a]pyrazine-7(8H)-carboxylic acid, 1,1-dimethylethyl ester. | 3.29 LC | 93 |

TABLE 4-continued

| Ex. No | G | x | Compound Name | Retention Time Min./ Molecular Mass | Procedure of Ex. |
|---|---|---|---|---|---|
| 205 | 4-methyl-1-nitronaphthalenyl | N-C(=O)-O-C(CH3)2-CH3 (Boc-like) | [5S-(5α,8α,8aβ)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.35 LC | 94 |
| 206 | 4-methyl-2-(trifluoromethyl)benzonitrile | NH | [5R-(5α,8α,8aβ)]-4-(Hexahydro-1,3-dioxo-5,8-methanoimidazo[1,5-a]pyrazin-2(1H)-yl)-2-(trifluoromethyl)benzonitrile. | 3.29 LC | 91 |
| 207 | 4-methyl-2-(trifluoromethyl)benzonitrile | N-C(=O)-phenyl | [5S-(5α,8α,8aβ)]-4-(7-Benzoylhexahydro-1,3-dioxo-5,8-methanoimidazo[1,5-a]pyrazin-2(3H)-yl)-2-(trifluoromethyl)benzonitrile. | 3.09 LC | 102A |
| 209 | 4-methyl-1-nitronaphthalenyl | N-C(=O)-phenyl | [5S-(5α,8α,8aβ)]-7-Benzoyltetrahydro-2-(4-nitro-1-naphthalenyl)-5,8-methanoimidazo[1,5-a]pyrazine-1,3(2H,5H)-dione. | 2.97 LC | 102A |
| 213 | 4-methyl-1-cyanonaphthalenyl | N-C(=O)-O-C(CH3)2-CH3 | [5S-(5α,8α,8aβ)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester. | 3.17 LC | 94 |
| 214 | 4-methyl-2-iodobenzonitrile | N-C(=O)-O-C(CH3)2-CH3 | [5S-(5α,8α,8aβ)]-2-(4-Cyano-3-iodophenyl)hexahydro-1,3-dioxo-5,8-methanoimidazo[1,5-a]pyrazine-7(8H)-carboxylic acid, 1,1-dimethylethyl ester. | 3.22 LC | 90 |
| 216 | 3,5-dichloro-methylphenyl | N-C(=O)-O-C(CH3)2-CH3 | [5S-(5α,8α,8aβ)]-2-(3,5-Dichlorophenyl)hexahydro-1,3-dioxo-5,8-methanoimidazo[1,5-a]pyrazine-7(8H)-carboxylic acid, 1,1-dimethylethyl ester. | 3.59 LC | 90 |

EXAMPLE 218

4-Isocyanato-2-trifluoromethyl benzonitrile

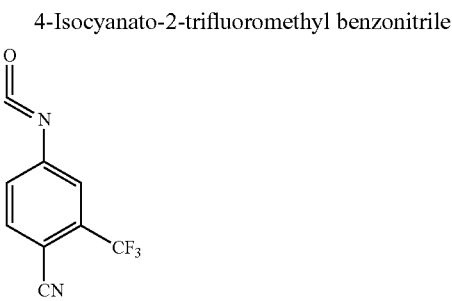

A. General Procedure for the Conversion of Anilines to Isocyanates: (218A)

To a solution of aryl/heteroaryl amine (5 mmol, 1.0 eq) in anhydrous methylene chloride (200 mL) at 0° C. was added sodium bicarbonate (50 mmol, 10.0 eq). To this stirred suspension was added a solution of phosgene (20 mmol, 20% solution in toluene). The reaction mixture was allowed to warm up to rt over 1 h and continued to stir at rt until the reaction was complete. The reaction was monitored by removing aliquots that were filtered and concentrated in vacuo to remove excess phosgene. The residue was reacted with excess piperidine in methylene chloride. The ratio of starting aniline to urea (as determined by LC-MS) indicated the progress of the reaction. When the reaction was complete by (LCMS), the reaction mixture was filtered to get rid of the inorganics and the filtrate was concentrated in vacuo to obtain the crude isocyanate that was used in the next step without further purification.

B. 4-Isocyanato-2-trifluoromethyl benzonitrile (218B)

To a solution of 3-trifluoromethyl-phenylamine (0.372 g, 2 mmol) in anhydrous dichloromethane (50 mL) at 0° C. was added sodium bicarbonate (1.7 g, 20 mmol) followed by a solution of phosgene (4 mL, 20% solution in toluene). The reaction mixture was warmed up to rt over 1 h and stirred for an additional 3 h. The reaction mixture was concentrated in vacuo to generate compound 218B which was used directly in the next step without further purification.

EXAMPLE 219

[5S-(5α,8α,8aα)]-2-[3-(Trifluoromethyl)phenyl]hexahydro-1,3-dioxo-5,8-methanoimidazo[1,5-a]pyrazine-7(8H)-carboxylic acid. 1,1-dimethylethyl ester & [5S-(5α,8α,8aβ)]-2-[3-(Trifluoromethyl)phenyl]hexahydro-1,3-dioxo-5,8-methanoimidazo[1,5-a]pyrazine-7(8H)-carboxylic acid. 1,1-dimethylethyl ester (219Bi & 219Bii)

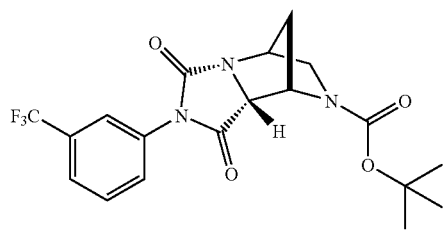

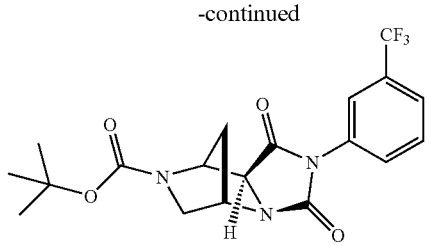

A. General Procedure for Formation of Hydantoin System: (219Aii & 219Aiii)

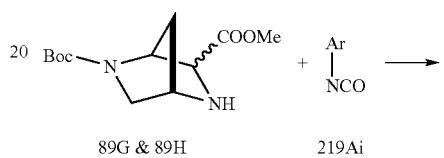

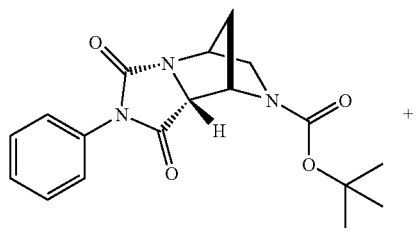

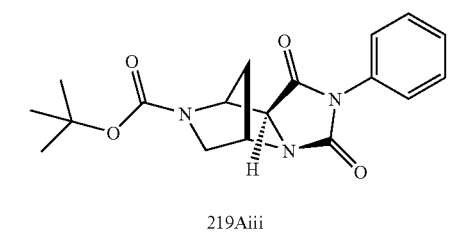

To a solution of a mixture of compounds 89G & 89H (5 mmol, 1.0 eq) in anhydrous chloroform (50 mL) was added molecular sieves (1 g, 4 Å, activated, crushed). To this stirred suspension was added a solution of the aryl/heteroaryl isocyanate, compound 219Ai (5 mmol, 1.0 eq, made as described in example 218) in anhydrous toluene (50 mL). After compounds 89G & 89H were converted to the intermediate urea, as determined by LCMS, 1,5,7-triazabicyclo[4.4.0]dec-5-ene-7-yl polystyrene (2.5 g, 7.5 mmol, Novabiochem Product No. 01-64-0332, Batch# A26683, 2.7 mmol/g) was added. In cases where the reaction was slow, the reaction mixture was heated to 55° C. for 1 h. After the intermediate urea was consumed, (as determined by LC-MS), the reaction mixture was cooled and filtered through celite and washed with EtOAc. The combined filtrate was concentrated in vacuo. Purification by flash chromatography on SiO$_2$ eluting with EtOAc/hexanes gave compounds 219Aii & 219Aiii.

B. [5S-(5α,8α,8aα)]-2-[3-(Trifluoromethyl)phenyl]hexahydro-1,3-dioxo-5,8-methanoimidazo[1,5-a]pyrazine-7(8H)-carboxylic acid, 1,1-dimethylethyl ester & [5S-(5α,8α,8aβ)]-2-[3-(Trifluoromethyl)phenyl]hexahydro-1,3-dioxo-5,8-methanoimidazo[1,5-a]pyrazine-7(8H)-carboxylic acid, 1,1-dimethylethyl ester (219Bi 219Bii)

To a solution containing a mixture of compounds 89G & 89H (1.28 g, 5 mmol) in anhydrous chloroform (50 mL) was added molecular sieves (1 g, 4 Å, activated). To this stirred suspension was added a solution of 3-trifluoromethylphenyl isocyanate (0.935 g, 5 mmol) in anhydrous toluene (50 mL). After compounds 89G & 89H were consumed (as determined by LC-MS), 1,5,7-triazabicyclo[4.4.0]dec-5-ene-7-yl polystyrene (2.5 g, 7.5 mmol, Novabiochem Product No. 01-64-0332, Batch# A26683, 2.7 mmol/g) was added and stirred at rt. After the intermediate urea was consumed (as determined by LC-MS), the reaction was filtered through celite and washed with EtOAc. The combined filtrate was concentrated in vacuo. Purification by flash chromatography on SiO$_2$ eluting with 10% to 50% EtOAc/hexanes gave compound 219Bi (0.50 g) and compound 219Bii (0.96 g) adding up to 1.46 g (3.55 mmol, 71% yield). Compound 219Bi: HPLC: 100% at 3.41 min (retention time). Compound 219Bii: 100% at 3.21 min (retention time) (YMC ODS-A column 4.6×50 mm eluting with 10-90% aqueous methanol over 4 minutes containing 0.1% trifluoroacetic acid, 4 mL/min, monitoring at 220 nm). MS (ES): m/z 434.03 [M+Na]$^+$.

EXAMPLE 220

[5 S-(5α,8α,8aα)]-Tetrahydro-2-(3-(trifluoromethyl)phenyl)-5,8-methanoimidazo[1,5-a]pyrazine-1,3(2H,5H)-dione & [5S-(5α,8α,8aβ)]-Tetrahydro-2-(3-(trifluoromethyl)phenyl)-5,8-methanoimidazo[1.5-a]pyrazine-1,3(2H,5H)-dione (220Bi & 220Bii)

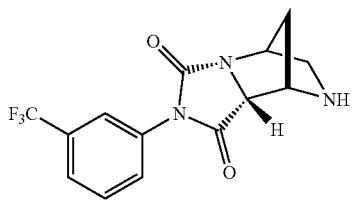

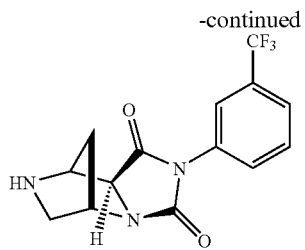

A. General Procedure for the Removal of Boc-Group: (220A)

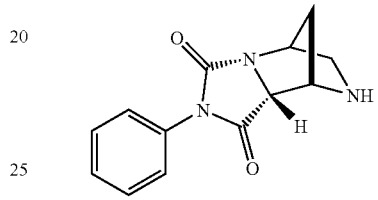

To a dry sample of compound 219Bi (2 mmol, 1.0 eq) was added excess trifluoroacetic acid (25 mL, 20% solution in methylene chloride). After compound 219Bi was consumed, (as determined by LCMS), the reaction mixture was concentrated in vacuo to yield the TFA salt of the free amine. The residue was dissolved in methylene chloride (50 mL) and extracted with saturated aqueous sodium bicarbonate (50 mL). The aqueous layer was extracted with methylene chloride (3×25 mL). The combined organic layers were dried over anhydrous sodium sulfate and concentrated in vacuo to yield the free base of compound 220A, which was used in the next step without further purification.

B. [5S-(5α,8α,8aα)]-Tetrahydro-2-(3-(trifluoromethyl)phenyl)-5,8-methanoimidazo[1,5-a]pyrazine-1,3(2H,5H)-dione & [5S-(5α,8α,8aβ)]-Tetrahydro-2-(3-(trifluoromethyl)phenyl)-5,8-methanoimidazo[1,5-a]pyrazine-1,3(2H,5H)-dione (220Bi & 220Bii)

Trifluoroacetic acid (20% in methylene chloride, 12 mL) was added to a flask containing compound 219Bi (0.50 g, 1.2 mmol). The reaction mixture was stirred at rt for 1 h. After the starting material was consumed (as determined by LC-MS), the reaction mixture was concentrated in vacuo to yield the TFA salt of compound 220Bi. The residue was dissolved in methylene chloride (50 mL) and extracted with saturated aqueous sodium bicarbonate (50 mL). The aqueous layer was extracted with methylene chloride (3×25 mL). The combined organic layers were dried over anhydrous sodium sulfate and concentrated in vacuo to yield compound 220Bi (0.37 g, 99% yield). HPLC: 100% at 1.94 min (retention times) (YMC ODS-A column 4.6×50 mm eluting with 10-90% aqueous methanol over 4 minutes containing 0.1% trifluoroacetic acid, 4 mL/min, monitoring at 220 nm). MS (ES): m/z 312.1 [M+H]$^+$. Compound 220Bii was synthesized as described above. MS (ES): m/z 312.1 [M+H]$^+$.

EXAMPLE 221

[5S-(5α,8α,8aα)-N-1,3-Benzodioxol-5-ylhexahydro-1,3-dioxo-2-[3-(trifluoromethyl)phenyl]-5,8-methanoimidazo[1,5-a]pyrazine-7(1H)-carbothioamide & [5S-(5α,8α,8aα)]-2-(4-Cyano-3-(trifluoromethyl)phenyl)-N-(1,1-dimethylethyl)hexahydro-1,3-dioxo-5,8-methanoimidazo[1,5-a]pyrazine-7(1H)-carboxamide, [5S-(5α,8α,8aα)]-2-[4-Cyano-3-(trifluoromethyl)phenyl]octahydro-1,3-dioxo-7-(1-oxopropyl)-5,8-methanoimidazo[1,5-a]pyrazine[5S-(5α,8α,8aα)]-2-[4-Cyano-3-(trifluoromethyl)phenyl] hexahydro-1,3-dioxo-5,8-methanoimidazo[1,5-a]pyrazine-7(1H)-carboxylic acid, 1-methyl ester, [5S-(5α,8α,8aα)]-7-[(1-Methylethyl)sulfonyl]tetrahydro-2-[3-(trifluoromethyl)phenyl]-5,8-methanoimidazo[1,5-a]pyrazine-1,3(2H,5H)-dione (221Bi & 221Bii, 221Ci, 221Cii, 221D)

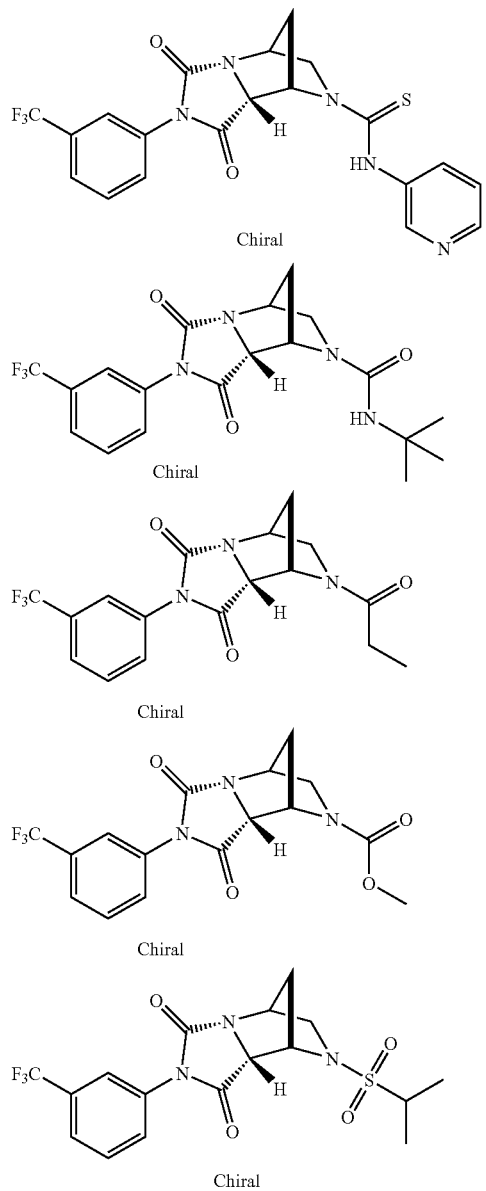

A. General Procedure for the Library Synthesis: (221 A)

Stock solutions (0.1 M in anhydrous methylene chloride) of acid chlorides, chloroformates, sulfonyl chlorides, isocyanates, isothiocyanates, anhydrides and carbamoyl chlorides were prepared. A stock solution (0.1 M in anhydrous methylene chloride) of compounds 220Bi was also prepared. All reactions were performed in Bohdan mini blocks. All reactions were agitated on an Innova 2100 shaker at 400 rpm for 24 h. Preparative HPLCs were performed using Shimadzu VP-ODS 20×50 mm column, using 10% to 90% aqueous methanol containing 0.1% TFA as the eluent, at a flow rate of 20 mL per min, using Mass Spec detection. All purified products were weighed and characterized by LS-MS. Proton NMR of random samples were obtained to ensure identity and purity.

Acronyms:

PVP=Poly(4-vinylpyridine), 2% crosslinked

STR=Synthesis Tube Rack (2.5 mL capacity, 96 well format).

PS-DMAP =DMAP equivalent, Polymer-bound, 1.5 mmol/g, Argonaut

B. Synthesis of thioureas and urea [5S-(5α,8α,8aα)]-N-1,3-Benzodioxol-5-ylhexahydro-1,3-dioxo-2-[3-(trifluoromethyl)phenyl]-5,8-methanoimidazo[1,5-a]pyrazine-7(1H)-carbothioamide & (221Bi & 221Bii)

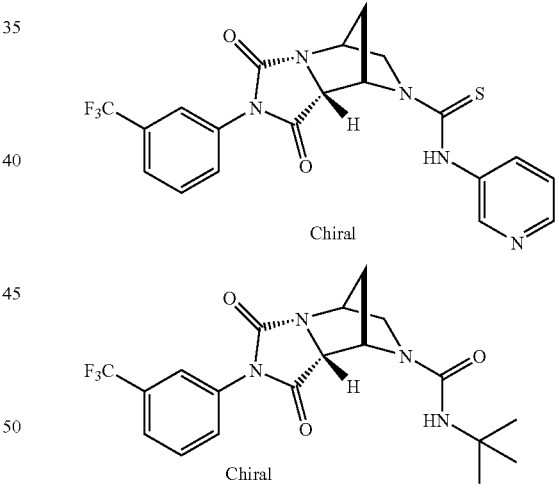

To the wells of a miniblock was added a stock solution of compounds 220Bi (300 uL, 0.1 M, 30 umol) followed by a solution of the isocyanate or isothicyanate (300 uL, 0.1 M, 30 umol). The wells were capped with a teflon lined rubber mat and agitated at rt for 24 h. The reaction mixture was drained into a synthesis tube rack. The wells of the mini-block were washed with methylene chloride (3×300 uL) and drained into the STR. The solvents were evaporated in vacuo. The crude products were purified by preparative HPLC. Compound 221Bi: retention time: 1.10 min. MS (ES): m/z 448.38 [M+H]$^+$. Compound 221Bii: Retention time: 1.45 min. MS (ES): m/z 411.45 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | B |
| Detector: | ELS |

C. Synthesis of amides and carbamates [5S-(5α,8α, 8aα)]-2-[4-Cyano-3-(trifluoromethyl)phenyl]octahydro-1,3-dioxo-7-(1-oxopropyl)-5,8-methanoimidazo [1,5-a]pyrazine & [5S-(5α,8α,8aα)]-2-[4-Cyano-3-(trifluoromethyl)phenyl]hexahydro-1,3-dioxo-5,8-methanoimidazo[1,5-a]pyrazine-7(1 H)-carboxylic acid, 1-methyl ester (221 Ci & 221 Cii)

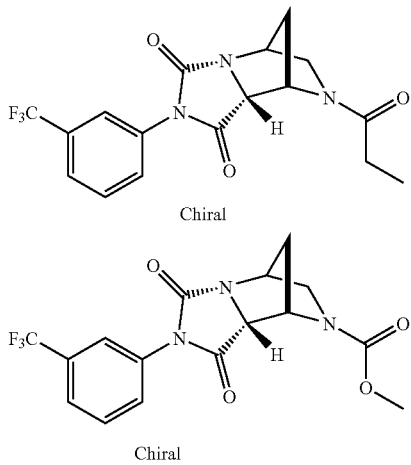

Chiral

Chiral

To the wells of the miniblock was added PVP (100 mg, 1 mmol), a stock solution of compounds 220Bi (300 uL, 0.1 M, 30 umol) followed by a stock solution of the acid chloride, chloroformate or anhydride (600 uL, 0.1 M, 60 umol). The wells were capped with a teflon lined rubber mat and agitated at rt for 24 h. The reaction mixture was drained into a synthesis tube rack. The resin was washed with methylene chloride (3×300 uL) and drained into the STR. The solvents were evaporated under reduced pressure. The crude products were purified by preparative HPLC. Compound 221Ci: Retention time: 1.22 min. MS (ES): m/z 368.41 [M+H]$^+$. Compound 221Cii: Retention time: 1.23 min. MS (ES): m/z 370.38 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | B |
| Detector: | ELS |

D. Synthesis of sulfonamides [5S-(5α,8α,8aα)]-7-[(1-Methylethyl)sulfonyl]tetrahydro-2-[3-(trifluoromethyl)phenyl]-5,8-methanoimidazo[1,5-a]pyrazine-1,3(2H,5H)-dione (221D)

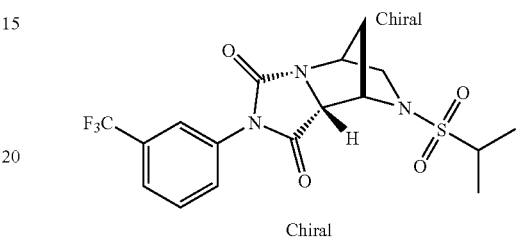

Chiral

To the wells of the miniblock was added PVP (100 mg, 1 mmol), PS-DMAP (25 mg, 37 umol), a stock solution of compounds 220Bi (300 uL, 0.1 M, 30 umol) followed by a solution of the sulfonyl chloride (600 uL, 0.1 M, 60 umol). The wells were capped with a teflon lined rubber mat and agitated at rt for 24 h. The reaction mixture was drained into a synthesis tube rack. The resin was washed with methylene chloride (3×300 uL) and drained into the STR. The solvents were evaporated under reduced pressure. The crude products were purified by preparative HPLC. Compound 221D: Retention time: 1.34 min. MS (ES): m/z 418.40 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | B |
| Detector: | ELS |

EXAMPLES 222 AND 223

Applicants incorporate by reference Examples 222 and 223 of the parent case hereof, i.e., U.S.pPatent application Ser. No. 10/322,306, filed Dec. 18, 2002, as if said examples were fully set forth herein at length.

EXAMPLES 224 TO 491

Additional compounds of the present invention were prepared by procedures analogous to those described above. The compounds of Examples 224 to 491 have the structure, compound name, retention time, molecular mass, and the procedure employed, as set forth in Table 5. The absolute configuration for the following compounds was not determined. For simplicity in nomenclature, compound 222i is designated herein as having an "R" configuration and compound 222ii as having an "S" configuration. Enantiomerically pure products derived from compound 222i are designated herein as having an "R" configuration and enantiomerically pure products derived from compound 222ii are designated herein as having an "S" configuration.

The chromatography techniques used to determine the compound retention times of Table 5 are as follows:

| | |
|---|---|
| A | Flow inject MS, HPLC-UV detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | A |
| Detector: | UV, 220 nm |
| B | Flow inject MS, HPLC-ELS detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | B |
| Detector: | ELS |
| Detector: | UV, 220 nm |
| C | LC(uv)-MS |
| Instrument: | LVL-L3604 LCMS |
| Source: | MetECN_Data\Data0001\52827-040-01_File0002.LCMS |
| Method: | C:\CLASS-VP\METHODS\WELLER.MET |
| Column: | PrimeSphere 5u C18-HC 30 × 4.6(2 min) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Detector: | UV, 220 nm |
| D | MS data from LCMS, HPLC-UV detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | A |
| Detector: | UV, 220 nm |
| E | MS data from LCMS, HPLC-ELS detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Channel: | B |
| Detector: | ELS |
| Detector: | UV, 220 nm |
| F | A. LC(uv)-MS |
| Instrument: | LVL-L3604 LCMS |
| Source: | MetECN Data\Data0001\52827-040-01_File0002.LCMS |
| Method: | C:\CLASS-VP\METHODS\WELLER.MET |
| Column: | Phenom-Prime S5 C18 4.6 × 30 mm (2 min. grad) |
| Solvents: | 10% MeOH - 90% H2O - 0.1% TFA, 90% MeOH - 10% H2O - 0.1% TFA |
| Flow Rate: | 5 ml/min |
| Gradient Time: | 2 min |
| Detector: | UV, 220 nm |
| G | B. LC(uv)-MS |
| Source: | MetECN_Data\Data0001\52827-040-01_File0002.LCMS |
| Method: | C:\CLASS-VP\METHODS\WELLER.MET |
| Column: | YMC S5 ODS column, 4.6 × 50 mm (4 min. grad) |
| Solvents: | 10% MeOH - 90% H2O - 0.1% TFA, 90% MeOH - 10% H2O - 0.1% TFA |
| Flow Rate: | 4 ml/min |
| Gradient Time: | 220 min |
| Detector: | UV, 220 nm |

The molecular mass of the compounds listed in Table 5 were determined by MS (ES) by the formula m/z.

TABLE 5

| Ex. No | Structure | Compound Name | Retention Time Min./ Molecular Mass | Proc. of Ex. | LC & MS Con. |
|---|---|---|---|---|---|
| 224 | 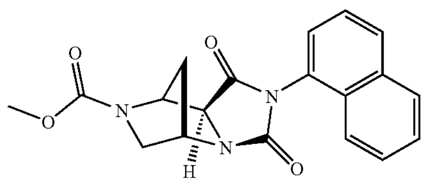 | [5S-(5α,8α,8aβ)]-Hexahydro-2-(1-naphthalenyl)-1,3-dioxo-5,8-methanoimidazo[1,5-a]pyrazine-7(1H)-carboxylic acid, methyl ester. | 1.36 LCMS [M + H]⁺ = 352.45 | 221Ci | B |
| 225 | 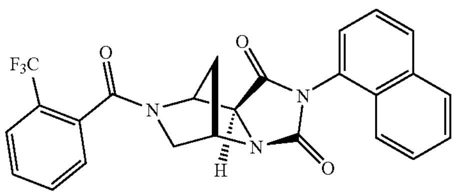 | [5S-(5α,8α,8aβ)]-Tetrahydro-2-(1-naphthalenyl)-7-[2-(trifluoromethyl)benzoyl]-5,8-methanoimidazo[1,5-a]pyrazine-1,3(2H,5H)-dione. | 1.65 LCMS [M + H]⁺ = 466.40 | 221Ci | B |
| 226 | 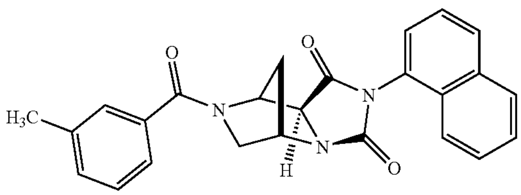 | [5S-(5α,8α,8aβ)]-Tetrahydro-7-(3-methylbenzoyl)-2-(1-naphthalenyl)-5,8-methanoimidazo[1,5-a]pyrazine-1,3(2H,5H)-dione. | 1.65 LCMS [M + H]⁺ = 412.42 | 221Ci | B |
| 227 | 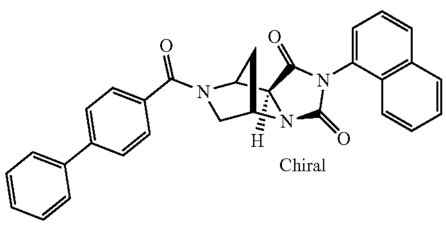 | [5S-(5α,8α,8aβ)]-7-([1,1'-Biphenyl]-4-ylcarbonyl)tetrahydro-2-(1-naphthalenyl)-5,8-methanoimidazo[1,5-a]pyrazine-1,3(2H,5H)-dione. | 1.87 LCMS [M + H]⁺ = 474.46 | 221Ci | B |
| 228 | 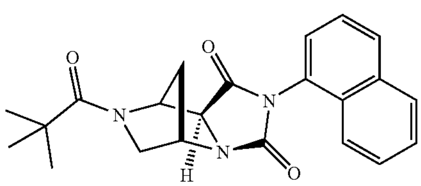 | [5S-(5α,8α,8aβ)]-7-(2,2-Dimethyl-1-oxopropyl)tetrahydro-2-(1-naphthalenyl)-5,8-methanoimidazo[1,5-a]pyrazine-1,3(2H,5H)-dione. | 1.58 LCMS [M + H]⁺ = 378.48 | 221Ci | B |
| 229 | 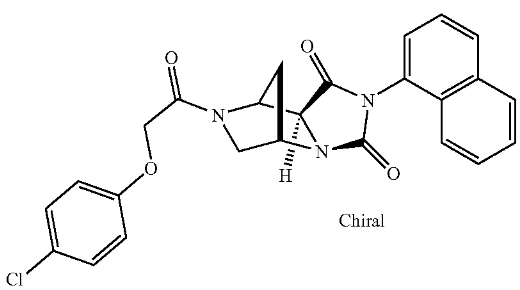 | [5S-(5α,8α,8aβ)]-7-[(4-Chlorophenoxy)-acetyl]tetrahydro-2-(1-naphthalenyl)-5,8-methanoimidazo[1,5-a]pyrazine-1,3(2H,5H)-dione. | 1.81 LCMS [M + H]⁺ = 462.37 | 221Ci | B |

TABLE 5-continued

| | | | | | |
|---|---|---|---|---|---|
| 230 | | [5S-(5α,8α,8aβ)]-Tetrahydro-7-(methoxyacetyl)-2-(1-naphthalenyl)-5,8-methanoimidazo[1,5-a]pyrazine-1,3(2H,5H)-dione. | 1.29 LCMS [M + H]$^+$ = 366.44 | 221Ci | B |
| 231 | | [5S-(5α,8α,8aβ)]-7-(3,3-Dimethyl-1-oxobutyl)tetrahydro-2-(1-naphthalenyl)-5,8-methanoimidazo[1,5-a]pyrazine-1,3(2H,5H)-dione. | 1.68 LCMS [M + H]$^+$ = 392.48 | 221Ci | B |
| 232 | | [5S-(5α,8α,8aβ)]-Tetrahydro-2-(1-naphthalenyl)-7-(1-oxopropyl)-5,8-methanoimidazo[1,5-a]pyrazine-1,3(2H,5H)-dione. | 1.36 LCMS [M + H]$^+$ = 350.41 | 221Ci | B |
| 233 | | [5S-(5α,8α,8aβ)]-Hexahydro-2-(1-naphthalenyl)-gamma,1,3-trioxo-5,8-methanoimidazo[1,5-a]pyrazine-7(1H)-butanoic acid, methyl ester. | 1.37 LCMS [M + H]$^+$ = 408.42 | 221Ci | B |
| 234 | | [5S-(5α,8α,8aβ)]-7-(Cyclopropylcarbonyl)tetrahydro-2-(1-naphthalenyl)-5,8-methanoimidazo[1,5-a]pyrazine-1,3(2H,5H)-dione. | 1.41 LCMS [M + H]$^+$ = 362.45 | 221Ci | B |
| 235 | | [5S-(5α,8α,8aβ)]-7-[(3,4-Dimethoxyphenyl)acetyl]-tetrahydro-2-(1-naphthalenyl)-5,8-methanoimidazo[1,5-a]pyrazine-1,3(2H,5H)-dione. | 1.51 LCMS [M + H]$^+$ = 472.45 | 221Ci | B |

TABLE 5-continued

| | | | | | |
|---|---|---|---|---|---|
| 236 | 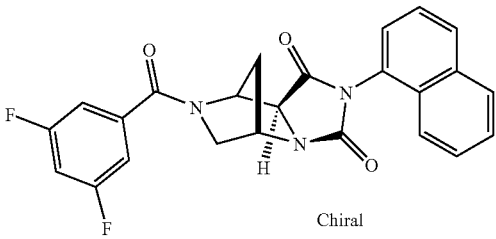 Chiral | [5S-(5α,8α,8aβ)]-7-(3,5-Difluorobenoyl)tetrahydro-2-(1-naphthalenyl)-5,8-methanoimidazo[1,5-a]pyrazine-1,3(2H,5H)-dione. | 1.63 LCMS [M + H]⁺ = 434.42 | 221Ci | B |
| 237 | 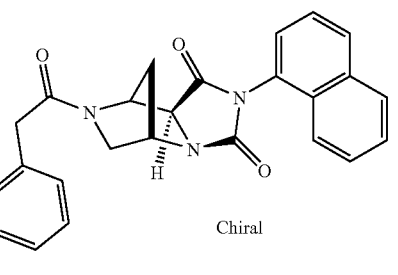 Chiral | [5S-(5α,8α,8aβ)]-Tetrahydro-7-[(3-methoxyphenyl)acetyl]-2-(1-naphthalenyl)-5,8-methanoimidazo[1,5-a]pyrazine-1,3(2H,5H)-dione. | 1.64 LCMS [M + H]⁺ = 442.44 | 221Ci | B |
| 238 | 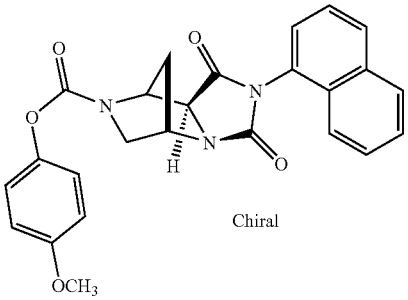 Chiral | [5S-(5α,8α,8aβ)]-Hexahydro-2-(1-naphthalenyl)-1,3-dioxo-5,8-methanoimidazo[1,5-a]pyrazine-7(1H)-carboxylic acid, 4-methoxyphenyl ester. | 1.69 LCMS [M + H]⁺ = 444.42 | 221Cii | B |
| 239 | 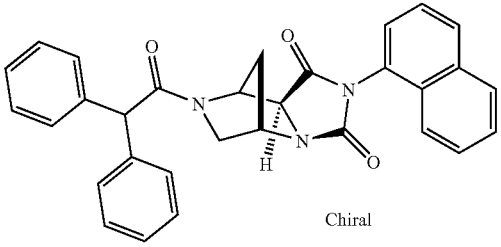 Chiral | [5S-(5α,8α,8aβ)]-7-(Diphenylacetyl)-tetrahydro-2-(1-naphthalenyl)-5,8-methanoimidazo[1,5-a]pyrazine-1,3(2H,5H)-dione. | 1.85 LCMS [M + H]⁺ = 488.48 | 221Ci | B |
| 240 | 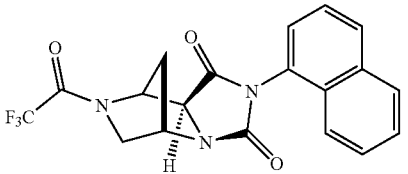 Chiral | [5S-(5α,8α,8aβ)]-Tetrahydro-2-(1-naphthalenyl)-7-(trifluoroacetyl)-5,8-methanoimidazo[1,5-a]pyrazine-1,3(2H,5H)-dione. | 1.52 LCMS [M + H]⁺ = 390.39 | 221Ci | B |
| 241 | 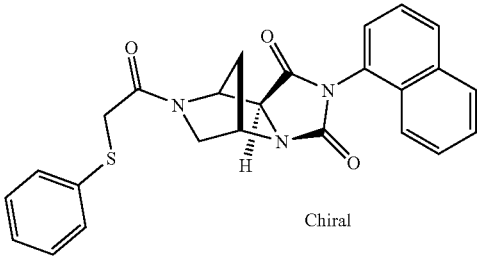 Chiral | [5S-(5α,8α,8aβ)]-Tetrahydro-2-(1-naphthalenyl)-7-[(phenylthio)acetyl]-5,8-methanoimidazo[1,5-a]pyrazine-1,3(2H,5H)-dione. | 1.70 LCMS [M + H]⁺ = 444.39 | 221Ci | B |

TABLE 5-continued

| | | | | | |
|---|---|---|---|---|---|
| 242 | | [5S-(5α,8α,8aβ)]-Hexahydro-2-(1-naphthalenyl)-1,3-dioxo-5,8-methanoimidazo[1,5-a]pyrazine-7(1H)-carboxylic acid, 1-methylethyl ester. | 1.63 LCMS [M + H]$^+$ = 402.41 | 221Cii | B |
| 243 | | [5S-(5α,8α,8aβ)]-7-[[3-(1,1-Dimethylethyl)-1-(phenylmethyl)-1H-pyrazol-5-yl]carbonyl]tetrahydro-2-(1-naphthalenyl)-5,8-methanoimidazo[1,5-a]pyrazine-1,3(2H,5H)-dione. | 1.96 LCMS [M + H]$^+$ = 534.50 | 221Ci | B |
| 244 | | [5S-(5α,8α,8aβ)]-7-[[3-(1,1-Dimethylethyl)-1-methyl-1H-pyrazol-5-yl]carbonyl]-tetrahydro-2-(1-naphthalenyl)-5,8-methanoimidazo[1,5-a]pyrazine-1,3(2H,5H)-dione. | 1.78 LCMS [M + H]$^+$ = 458.50 | 221Ci | B |
| 245 | | [5S-(5α,8α,8aβ)]-Tetrahydro-7-[(5-methyl-3-isoxazolyl)carbonyl]-2-(1-naphthalenyl)-5,8-methanoimidazo[1,5-a]pyrazine-1,3(2H,5H)-dione. | 1.53 LCMS [M + H]$^+$ = 403.43 | 221Ci | B |
| 246 | | [5S-(5α,8α,8aβ)]-Hexahydro-2-(1-naphthalenyl)-1,3-dioxo-5,8-methanoimidazo[1,5-a]pyrazine-7(1H)-carboxylic acid, (2-chlorophenyl)methyl ester. | 1.86 LCMS [M + H]$^+$ = 484.37 | 221Cii | B |
| 247 | | [5S-(5α,8α,8aβ)]-Tetrahydro-2-(1-naphthalenyl)-7-(2,2,3,3,4,4,5,5,5-nonafluoro-1-oxopentyl)-5,8-methanoimidazo[1,5-a]pyrazine-1,3(2H,5H)-dione. | 1.92 LCMS [M + H]$^+$ = 540.32 | 221Ci | B |

TABLE 5-continued

| | | | | | |
|---|---|---|---|---|---|
| 248 | | [5S-(5α,8α,8aβ)]-7-(3-Bromobenzoyl)tetrahydro-2-(1-naphthalenyl)-5,8-methanoimidazo[1,5-a]pyrazine-1,3(2H,5H)-dione. | 1.72 LCMS [M + H]$^+$ = 476.34 | 221Ci | B |
| 249 | | [5S-(5α,8α,8aβ)]-Tetrahydro-2-(1-naphthalenyl)-7-(2,2,3,3,4,4,5,5,6,6,7,7,8,8,8-pentadecafluoro-1-oxooctyl)-5,8-methanoimidazo[1,5-a]pyrazine-1,3(2H,5H)-dione. | 2.16 LCMS [M + H]$^+$ = 690.34 | 221Ci | B |
| 250 | | [5S-(5α,8α,8aβ)]-7-(2,2,3,3,4,4,4-Heptafluoro-1-oxobutyl)tetrahydro-2-(1-naphthalenyl)-5,8-methanoimidazo[1,5-a]pyrazine-1,3(2H,5H)-dione. | 1.82 LCMS [M + H]$^+$ = 490.37 | 221Ci | B |
| 251 | | [5S-(5α,8α,8aβ)]-Hexahydro-2-(1-naphthalenyl)-alpha,1,3-trioxo-5,8-methanoimidazo[1,5-a]pyrazine-7(1H)-acetic acid, methyl ester. | 1.36 LCMS [M + H]$^+$ = 380.41 | 221Ci | B |
| 252 | | [5S-(5α,8α,8aβ)]-Tetrahydro-7-[(1-methylethyl)sulfonyl]-2-(1-naphthalenyl)-5,8-methanoimidazo-[1,5-a]pyrazine-1,3(2H,5H)-dione. | 1.50 LCMS [M + H]$^+$ = 400.40 | 221D | B |
| 253 | | [5S-(5α,8α,8aβ)]-7-(Ethylsulfonyl)-tetrahydro-2-(1-naphthalenyl)-5,8-methanoimidazo[1,5-a]pyrazine-1,3(2H,5H)-dione. | 1.41 LCMS [M + H]$^+$ = 386.40 | 221D | B |

TABLE 5-continued

| | | | | | |
|---|---|---|---|---|---|
| 254 | (structure) Chiral | [5S-(5α,8α,8aβ)]-7-[(2-Fluorophenyl)sulfonyl]tetrahydro-2-(1-naphthalenyl)-5,8-methanoimidazo[1,5-a]pyrazine-1,3(2H,5H)-dione. | 1.63 LCMS [M + H]$^+$ = 474.36 | 221D | B |
| 255 | (structure) Chiral | [5S-(5α,8α,8aβ)]-Tetrahydro-7-(methylsulfonyl)-2-(1-naphthalenyl)-5,8-methanoimidazo[1,5-a]pyrazine-1,3(2H,5H)-dione. | 1.34 LCMS [M + H]$^+$ = 394.37 | 221D | B |
| 256 | (structure) Chiral | [5S-(5α,8α,8aβ)]-Hexahydro-N,N-dimethyl-2-(1-naphthalenyl)-1,3-dioxo-5,8-methanoimidazo[1,5-a]pyrazine-7(1H)-sulfonamide. | 1.48 LCMS [M + H]$^+$ = 423.38 | 221D | B |
| 257 | (structure) Chiral | [5S-(5α,8α,8aβ)]-N-(1,1-Dimethylethyl)-hexahydro-2-(1-naphthalenyl)-1,3-dioxo-5,8-methanoimidazo[1,5-a]pyriazine-7(1H)-carboxamide. | 1.62 LCMS [M + H]$^+$ = 393.47 | 221Bii | B |
| 258 | (structure) Chiral | [5S-(5α,8α,8aβ)]-Hexahydro-2-(1-naphthalenyl)-N-(3-nitrophenyl)-1,3-dioxo-5,8-methanoimidazo[1,5-a[pyrazine-7(1H)-carboxamide. | 1.69 LCMS [M + H]$^+$ = 458.42 | 221Bii | B |
| 259 | (structure) Chiral | [5S-(5α,8α,8aβ)]-N-(3,5-Dimethoxyphenyl)-hexahydro-2-(1-naphthalenyl)-1,3-dioxo-5,8-methanoimidazo[1,5-a]pyrazine-7(1H)-carboxamide. | 1.68 LCMS [M + H]$^+$ = 473.46 | 221Bii | B |

TABLE 5-continued

| 260 | 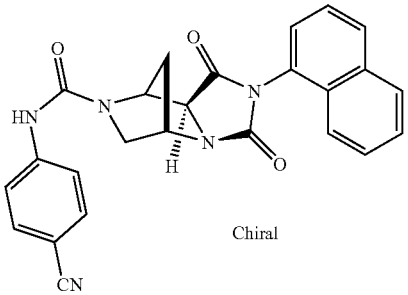 Chiral | [5S-(5α,8α,8aβ)]-N-(4-Cyanophenyl)-hexahydro-2-(1-naphthalenyl)-1,3-dioxo-5,8-methanoimidazo[1,5-a]pyrazine-7(1H)-carboxamide. | 1.60 LCMS $[M + H]^+$ = 438.40 | 221Bii | B |
|---|---|---|---|---|---|
| 261 | 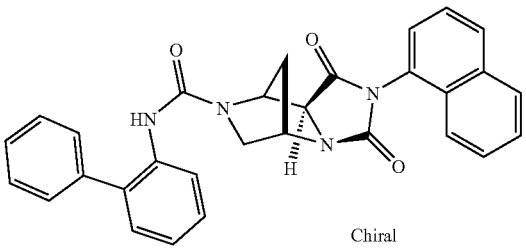 Chiral | [5S-(5α,8α,8aβ)]-N-[1,1'-Biphenyl]-2-ylhexahydro-2-(1-naphthalenyl)-1,3-dioxo-5,8-methanoimidazo[1,5-a]pyrazine-7(1H)-carboxamide. | 1.83 LCMS $[M + H]^+$ = 489.45 | 221Bii | B |
| 262 | 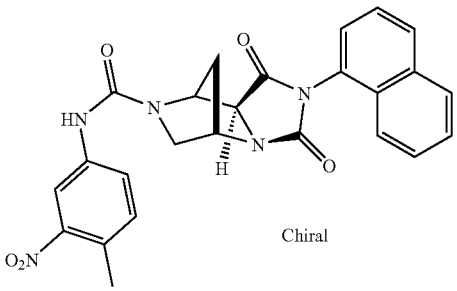 Chiral | [5S-(5α,8α,8aβ)]-Hexahydro-N-(4-methyl-3-nitrophenyl)-2-(1-naphthalenyl)-1,3-dioxo-5,8-methanoimidazo[1,5-a]pyrazine-7(1H)-carboxamide. | 1.75 LCMS $[M + H]^+$ = 472.43 | 221Bii | B |
| 263 | 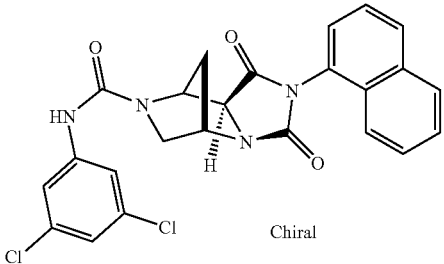 Chiral | [5S-(5α,8α,8aβ)]-N-(3,5-Dichlorophenyl)-hexahydro-2-(1-naphthalenyl)-1,3-dioxo-5,8-methanoimidazo[1,5-a]pyrazine-7(1H)-carboxamide. | 1.98 LCMS $[M + H]^+$ = 481.36 | 221Bii | B |
| 264 | 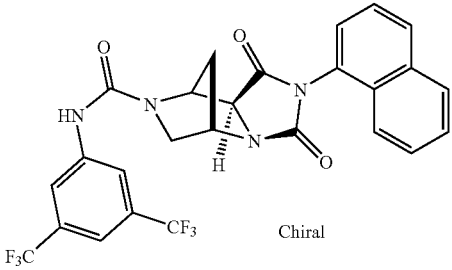 Chiral | [5S-(5α,8α,8aβ)]-N-[3,5-Bis(trifluoro-methyl)phenyl]hexahydro-2-(1-naphthalenyl)-1,3-dioxo-5,8-methanoimidazo[1,5-a]pyrazine-7(1H)-carboxamide. | 2.03 LCMS $[M + H]^+$ = 549.39 | 221Bii | B |

TABLE 5-continued

| | | | | | |
|---|---|---|---|---|---|
| 265 | | [5S-(5α,8α,8aβ)]-N-(4-Bromo-3-methylphenyl)hexahydro-2-(1-naphthalenyl)-1,3-dioxo-5,8-methanoimidazo[1,5-a]pyriazine-7(1H)-carboxamide. | 1.91 LCMS [M + H]$^+$ = 505.35 | 221Bii | B |
| 266 | | [5S-(5α,8α,8aβ)]-Hexahydro-N,2-di-1-naphthalenyl-1,3-dioxo-5,8-methanoimidazo[1,5-a]pyrazine-7(1H)-carboxamide. | 1.71 LCMS [M + H]$^+$ = 463.45 | 221Bii | B |
| 267 | | [5S-(5α,8α,8aβ)]-Hexahydro-2-(1-naphthalenyl)-1,3-dioxo-N-[3-(trifluoromethyl)-phenyl]-5,8-methanoimidazo[1,5-a]pyrazine-7(1H)-carboxamide. | 1.84 LCMS [M + H]$^+$ = 481.43 | 221Bii | B |
| 268 | | [5S-(5α,8α,8aβ)]-Hexahydro-N-[(4-methylphenyl)sulfonyl]-2-(1-naphthalenyl)-1,3-dioxo-5,8-methanoimidazo[1,5-a]pyrazine-7(1H)-carboxamide. | 1.57 LCMS [M + H]$^+$ = 491.41 | 221Bii | B |
| 269 | | [5S-(5α,8α,8aβ)]-Hexahydro-N-(2-methylpropyl)-2-(1-naphthalenyl)-1,3-dioxo-5,8-methanoimidazo[1,5-a]pyrazine-7(1H)-carbothioamide. | 1.72 LCMS [M + H]$^+$ = 409.45 | 221Bi | B |

TABLE 5-continued

| | | | | | |
|---|---|---|---|---|---|
| 270 | 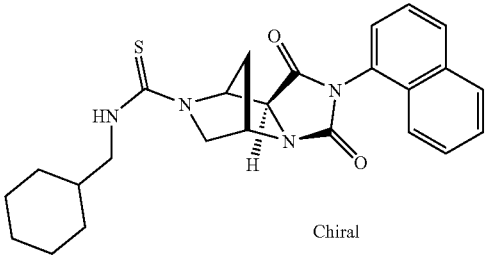 Chiral | [5S-(5α,8α,8aβ)]-N-(Cyclohexylmethyl)hexahydro-2-(1-naphthalenyl)-1,3-dioxo-5,8-methanoimidazo[1,5-a]pyrazine-7(1H)-carbothioamide. | 1.93 LCMS [M + H]⁺ = 449.49 | 221Bi | B |
| 271 | 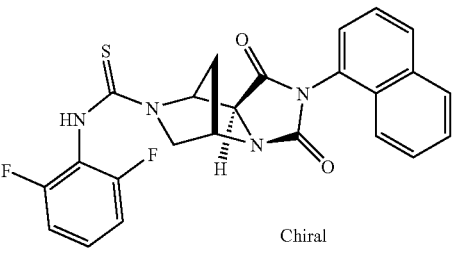 Chiral | [5S-(5α,8α,8aβ)]-N-(2,6-Difluorophenyl)hexahydro-2-(1-naphthalenyl)-1,3-dioxo-5,8-methanoimidazo[1,5-a]pyrazine-7(1H)-carbothioamide. | 1.61 LCMS [M + H]⁺ = 465.39 | 221Bi | B |
| 272 | 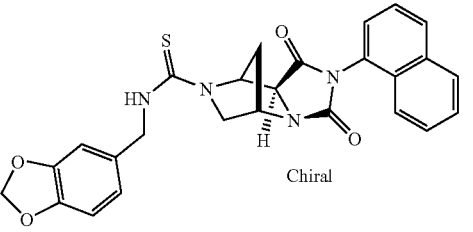 Chiral | [5S-(5α,8α,8aβ)]-N-(2,3-Benzodioxol-5-ylmethyl)hexahydro-2-(1-naphthalenyl)-1,3-dioxo-5,8-methanoimidazo[1,5-a]pyrazine-7(1H)-carbothioamide. | 1.73 LCMS [M + H]⁺ = 487.41 | 221Bi | B |
| 273 | 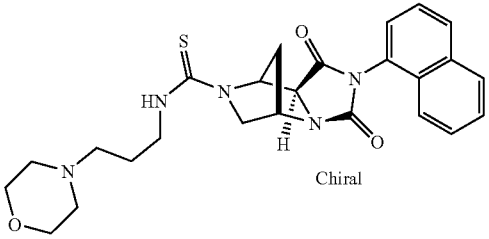 Chiral | [5S-(5α,8α,8aβ)]-Hexahydro-N-[3-(4-morpholinyl)propyl]-2-(1-naphthalenyl)-1,3-dioxo-5,8-methanoimidazo[1,5-a]pyrazine-7(1H)-carbothioamide. | 1.31 LCMS [M + H]⁺ = 480.50 | 221Bi | B |
| 274 | 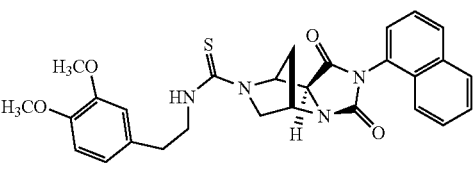 Chiral | [5S-(5α,8α,8aβ)]-N-[2-(3,4-Dimethoxyphenyl)ethyl]hexahydro-2-(1-naphthalenyl)-1,3-dioxo-5,8-methanoimidazo[1,5-a]pyrazine-7(1H)-carbothioamide. | 1.72 LCMS [M + H]⁺ = 517.47 | 221Bi | B |
| 275 | 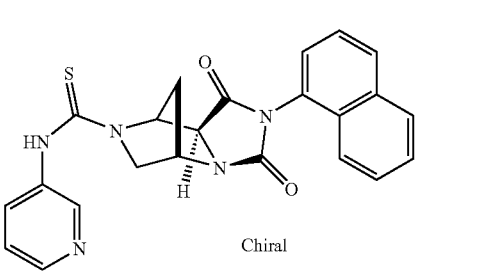 Chiral | [5S-(5α,8α,8aβ)]-Hexahydro-2-(1-naphthalenyl)-1,3-dioxo-N-3-pyridinyl-5,8-methanoimidazo[1,5-a]pyrazine-7(1H)-carbothioamide. | 1.32 LCMS [M + H]⁺ = 430.40 | 221Bi | B |

TABLE 5-continued

| | | | | | |
|---|---|---|---|---|---|
| 276 | (structure) | [5S-(5α,8α,8aβ)]-N-1,3-Benzodioxol-5-ylhexahydro-2-(1-naphthalenyl)-1,3-dioxo-5,8-methanoimidazo[1,5-a]pyrazine-7(1H)-carbothioamide. | 1.61 LCMS [M + H]$^+$ = 473.39 | 221Bi | B |
| 277 | (structure) | [5S-(5α,8α,8aβ)]-Tetrahydro-7-[2-(trifluoromethyl)benzoyl]-2-[3-(trifluoromethyl)phenyl]-5,8-methanoimidazo[1,5-a]pyrazine-1,3(2H,5H)-dione. | 1.47 LCMS [M + H]$^+$ = 484.37 | 221Ci | B |
| 278 | (structure) | [5S-(5α,8α,8aα)]-Tetrahydro-7-(3-methylbenzoyl)-2-[3-(trifluoromethyl)-phenyl]-5,8-methanoimidazo[1,5-a]pyrazine-1,3(2H,5H)-dione. | 1.53 LCMS [M + H]$^+$ = 430.41 | 221Ci | B |
| 279 | (structure) | [5S-(5α,8α,8aα)]-7-([1,1'-Biphenyl]-4-ylcarbonyl)-tetrahydro-2-[3-(trifluoromethyl)phenyl]-5,8-methanoimidazo[1,5-a]pyrazine-1,3(2H,5H)-dione. | 1.77 LCMS [M + H]$^+$ = 492.41 | 221Ci | B |
| 280 | (structure) | [5S-(5α,8α,8aα)]-7-(2,2-Dimethyl-1-oxopropyl)tetrahydr-2-[3-(trifluoromethyl)phenyl]-5,8-methanoimidazo[1,5-a]pyrazine-1,3(2H,5H)-dione. | 1.46 LCMS [M + H]$^+$ = 396.41 | 221Ci | B |

TABLE 5-continued

| | | | | | |
|---|---|---|---|---|---|
| 281 | 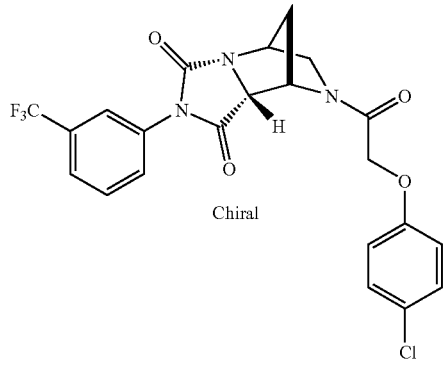 Chiral | [5S-(5α,8α,8aα)]-7-[(4-Chlorophenoxy)acetyl]tetrahydr-2-[3-(trifluoro-methyl)phenyl]-5,8-methanoimidazo[1,5-a]pyrazine-1,3(2H,5H)-dione. | 1.66 LCMS $[M + H]^+$ = 480.36 | 221Ci | B |
| 282 | 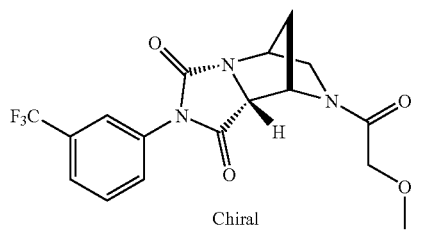 Chiral | [5S-(5α,8α,8aα)]-Tetrahydro-7-(methoxyacetyl)-2-[3-(trifluoro-methyl)phenyl]-5,8-methanoimidazo[1,5-a]pyrazine-1,3(2H,5H)-dione. | 1.12 LCMS $[M + H]^+$ = 384.40 | 221Ci | B |
| 283 | 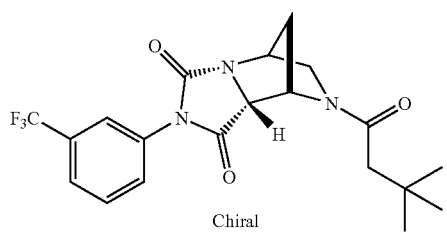 Chiral | [5S-(5α,8α,8aα)]-7-(3,3-Dimethyl-1-oxobutyl)tetrahydro-2-[3-(trifluoro-methyl)phenyl]-5,8-methanoimidazo[1,5-a]pyrazine-1,3(2H,5H)-dione. | 1.57 LCMS $[M + H]^+$ = 410.44 | 221Ci | B |
| 284 | 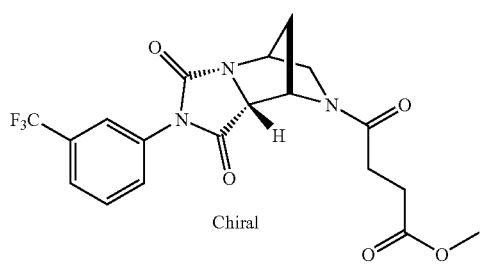 Chiral | [5S-(5α,8α,8aα)]-Hexahydro-gamma,1,3-trioxo-2-[3-(trifluoromethyl)phenyl]-5,8-methanoimidazo[1,5-a]pyrazine-7(1H)-butanoic acid, methyl ester. | 1.25 LCMS $[M + H]^+$ = 426.40 | 221 Ci | B |
| 285 | 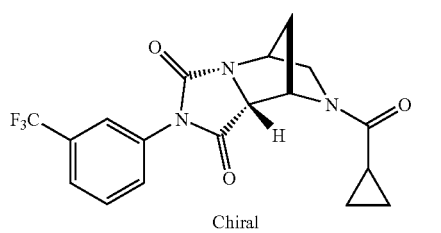 Chiral | [5S-(5α,8α,8aα)]-7-Cyclopropyl-carbonyl)tetra-hydro-2-[3-(trifluoromethyl)phenyl]-5,8-methanoimidazo-[1,5-a]pyrazine-1,3(2H,5H)-dione. | 1.24 LCMS $[M + H]^+$ = 380.42 | 221Ci | B |
| 286 | 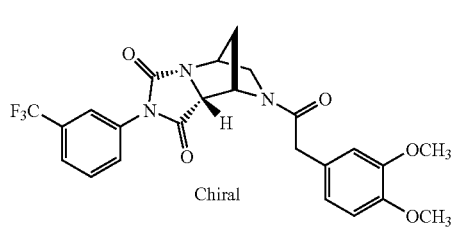 Chiral | [5S-(5α,8α,8aα)]-7-[(3,4-Dimethoxy-phenyl)acetyl]-tetrahydro-2-[3-(trifluoromethyl)phenyl]-5,8-methanoimidazo[1,5-a]pyrazine-1,3(2H,5H)-dione. | 1.35 LCMS $[M + H]^+$ = 490.41 | 221Ci | B |

TABLE 5-continued

| | | | | | |
|---|---|---|---|---|---|
| 287 | 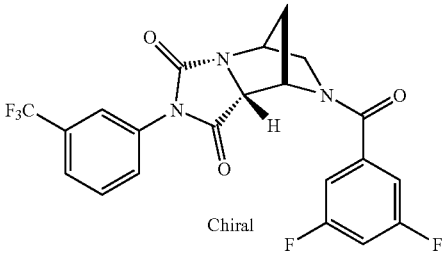 Chiral | [5S-(5α,8α,8aα)]-7-(3,5-Difluorobenzoyl)-tetrahydro-2-[3-(trifluoromethyl)phenyl]-5,8-methanoimidazo[1,5-a]pyrazine-1,3(2H,5H)-dione. | 1.52 LCMS [M + H]$^+$ = 452.36 | 221Ci | B |
| 288 | 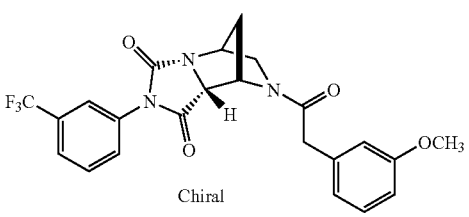 Chiral | [5S-(5α,8α,8aα)]-Tetrahydro-7-[(3-methoxyphenyl)acetyl]-2-[3-(trifluoromethyl)-phenyl]-5,8-methanoimidazo[1,5-a]pyrazine-1,3(2H,5H)-dione. | 1.49 LCMS [M + H]$^+$ = 460.41 | 221Ci | B |
| 289 | 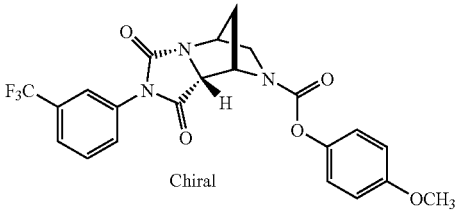 Chiral | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, 4-methoxyphenyl ester. | 1.51 LCMS [M + H]$^+$ = 462.41 | 221Cii | B |
| 290 | 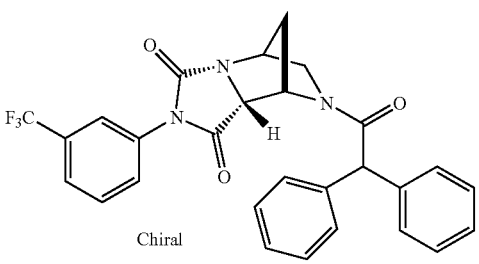 Chiral | [5S-(5α,8α,8aα)]-7-(Diphenylacetyl)tetrahydro-2-[3-(trifluoromethyl)-phenyl]-5,8-methanoimidazo[1,5-a]pyrazine-1,3(2H,5H)-dione. | 1.72 LCMS [M + H]$^+$ = 506.43 | 221Ci | B |
| 291 | 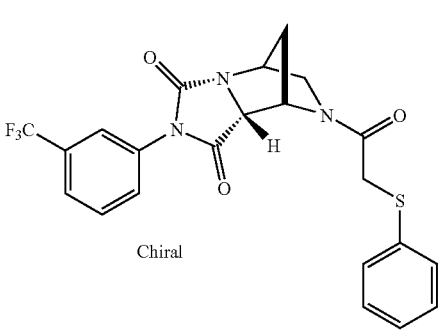 Chiral | [5S-(5α,8α,8aα)]-Tetrahydro-7-[(phenylthio)acetyl]-2-[3-(trifluoromethyl)phenyl]-5,8-methanoimidazo[1,5-a]pyrazine-1,3(2H,5H)-dione. | 1.55 LCMS [M + H]$^+$ = 462.39 | 221Ci | B |
| 292 | 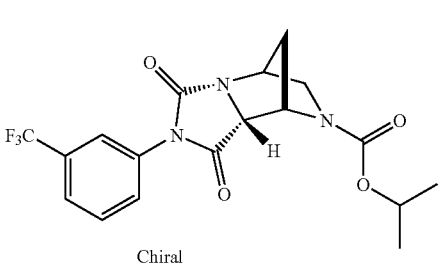 Chiral | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, 1-methylethyl ester. | 1.44 LCMS [M + H]$^+$ = 420.41 | 221Cii | B |

TABLE 5-continued

| | | | | | |
|---|---|---|---|---|---|
| 293 | 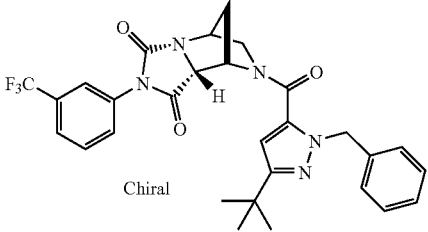 | [5S-(5α,8α,8aα)]-7-[[3-(1,1-Dimethyl-ethyl)-1-(phenyl-methyl)-1H-pyrazol-5-yl]carbonyl]-tetrahydro-2-[3-(trifluoromethyl)phenyl]-5,8-methanoimidazo[1,5-a]pyrazine-1,3(2H,5H)-dione. | 1.87 LCMS $[M+H]^+ =$ 552.45 | 221Ci | B |
| 294 | 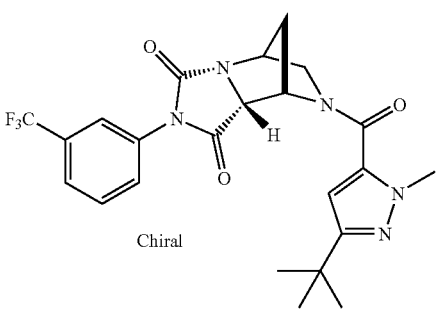 | [5S-(5α,8α,8aα)]-7-[[3-(1,1-Dimethyl-ethyl)-1-methyl-1H-pyrazol-5-yl]-carbonyl]tetrahydro-2-[3-(trifluoromethyl)-phenyl]-5,8-methanoimidazo[1,5-a]pyrazine-1,3(2H,5H)-dione. | 1.65 LCMS $[M+H]^+ =$ 476.45 | 221Ci | B |
| 295 | 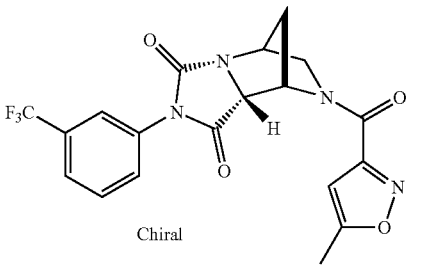 | [5S-(5α,8α,8aα)]-Tetrahydro-7-[(5-methyl-3-isoxazolyl)carbonyl]-2-[3-(trifluoro-methyl)phenyl]-5,8-methanoimidiazo[1,5-a]pyrazine-1,3(2H,5H)-dione. | 1.29 LCMS $[M+H]^+ =$ 421.37 | 221Ci | A |
| 296 | 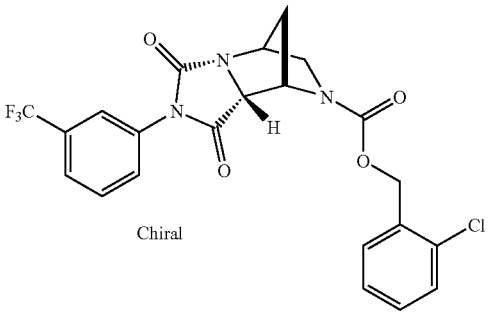 | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, (2-chlorophenyl)methyl ester. | 1.69 LCMS $[M+H]^+ =$ 502.33 | 221Cii | B |
| 297 | 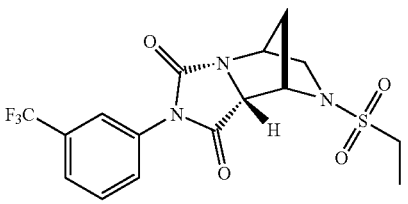 | [5S-(5α,8α,8aα)]-7-(Ethylsulfonyl)-tetrahydro-2-[3-(trifluoromethyl)phenyl]-5,8-methanoimidazo[1,5-a]pyrazine-1,3(2H,5H)-dione. | 1.22 LCMS $[M+H]^+ =$ 404.35 | 221D | B |

TABLE 5-continued

| | | | | | |
|---|---|---|---|---|---|
| 298 | 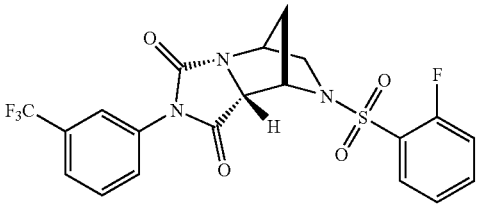 Chiral | [5S-(5α,8α,8aα)]-7-[(2-Fluorophenyl)sulfonyl]tetrahydro-2-[3-(trifluoromethyl)phenyl]-5,8-methanoimidazo[1,5-a]pyrazine-1,3(2H,5H)-dione. | 1.41 LCMS [M + H]$^+$ = 470.35 | 221D | A |
| 299 | 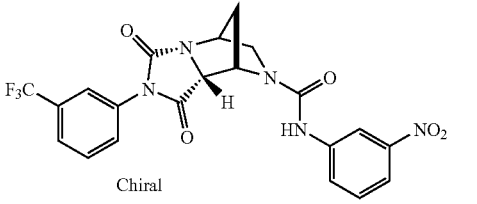 Chiral | [5S-(5α,8α,8aα)]-Hexahydro-N-(3-nitrophenyl)-1,3-dioxo-2-[3-(trifluoromethyl)phenyl]-5,8-methanoimidazo[1,5-a]pyrazine-7(1H)-carboxamide. | 1.46 LCMS [M + H]$^+$ = 476.36 | 221Bii | B |
| 300 | 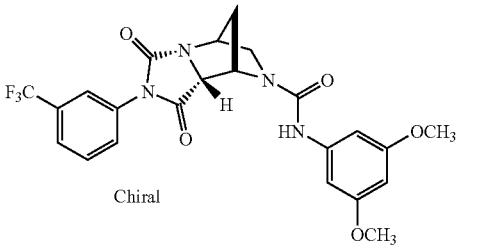 Chiral | [5S-(5α,8α,8aα)]-N-(3,5-Dimethoxyphenyl)hexahydro-1,3-dioxo-2-[3-(trifluoromethyl)phenyl]-5,8-methanoimidazo[1,5-a]pyrazine-7(1H)-carboxamide. | 1.45 LCMS [M + H]$^+$ = 491.42 | 221Bii | B |
| 301 | 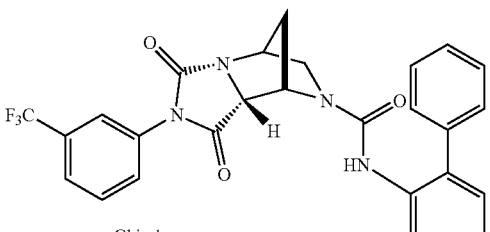 Chiral | [5S-(5α,8α,8aα)]-N-[1,1'-Biphenyl]-2-ylhexahydro-1,3-dioxo-2-[3-(trifluoromethyl)phenyl]-5,8-methanoimidazo[1,5-a]pyrazine-7(1H)-carboxamide. | 1.69 LCMS [M + H]$^+$ = 507.43 | 221Bii | B |
| 302 | 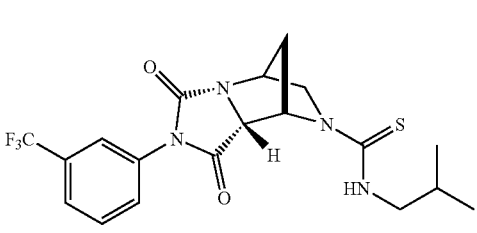 Chiral | [5S-(5α,8α,8aα)]-Hexahydro-N-(2-methylpropyl)-1,3-dioxo-2-[3-(trifluoromethyl)phenyl]-5,8-methanoimidazo[1,5-a]pyrazine-7(1H)-carbothioamide. | 1.52 LCMS [M + H]$^+$ = 427.42 | 221Bi | B |
| 303 | 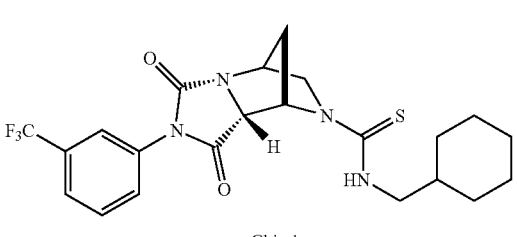 Chiral | [5S-(5α,8α,8aα)]-N-(Cyclohexylmethyl)hexahydro-1,3-dioxo-2-[3-(trifluormethyl)phenyl]-5,8-methanoimidazo[1,5-a]pyrazine-7(1H)-carbothioamide. | 1.75 LCMS [M + H]$^+$ = 467.44 | 221Bi | B |

TABLE 5-continued

| | | | | | |
|---|---|---|---|---|---|
| 304 | 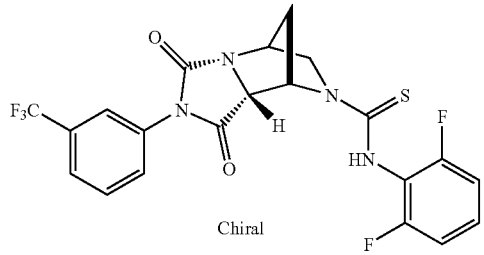 Chiral | [5S-(5α,8α,8aα)]-N-(2,6-Difluorophenyl)-hexahydro-1,3-dioxo-2-[3-(trifluoromethyl)phenyl]-5,8-methanoimidazo[1,5-a]pyrazine-7(1H)-carbothioamide. | 1.34 LCMS [M + H]$^+$ = 483.34 | 221Bi | B |
| 305 | 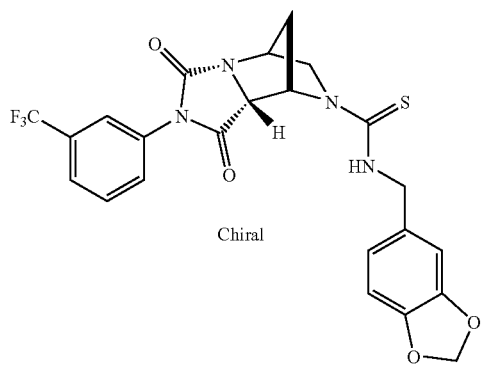 Chiral | [5S-(5α,8α,8aα)]-N-(1,3-Benzodioxol-5-ylmethyl)hexahydro-1,3-dioxo-2-[3-(trifluoromethyl)phenyl]-5,8-methanoimidazo[1,5-a]pyrazine-7(1H)-carbothioamide. | 1.52 LCMS [M + H]$^+$ = 505.40 | 221Bi | B |
| 306 | 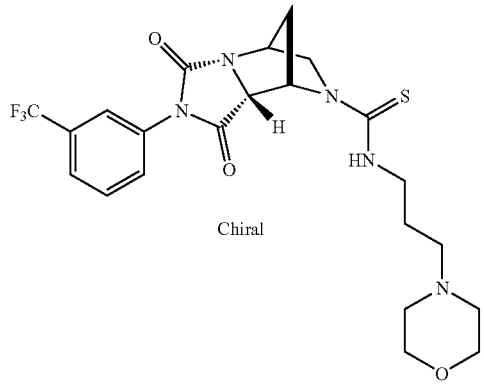 Chiral | [5S-(5α,8α,8aα)]-Hexahydro-N-[3-(4-morpholinyl)propyl]-1,3-dioxo-2-[3-(trifluoromethyl)phenyl]-5,8-methanoimidazo[1,5-a]pyrazine-7(1H)-carbothioamide. | 1.02 LCMS [M + H]$^+$ = 498.45 | 221Bi | B |
| 307 | 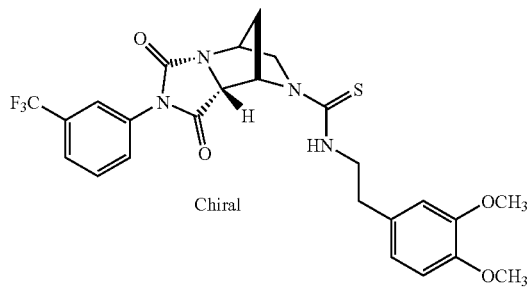 Chiral | [5S-(5α,8α,8aα)]-N-[2-(3,4-Dimethoxyphenyl)-ethyl]hexahydro-1,3-dioxo-2-[3-(trifluoromethyl)phenyl]-5,8-methanoimidazo[1,5-a]pyrazine-7(1H)-carbothioamide. | 1.48 LCMS [M + H]$^+$ = 535.41 | 221Bi | B |
| 308 | 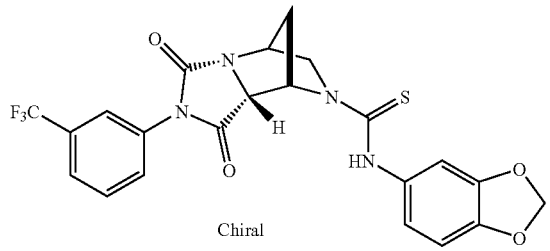 Chiral | [5S-(5α,8α,8aα)]-N-1,3-Benzodioxol-5-ylhexahydro-1,3-dioxo-2-[3-(trifluoromethyl)phenyl]-5,8-methanoimidazo[1,5-a]pyrazine-7(1H)-carbothioamide. | 1.37 LCMS [M + H]$^+$ = 491.38 | 221Bi | B |

TABLE 5-continued

| | | | | | |
|---|---|---|---|---|---|
| 309 | 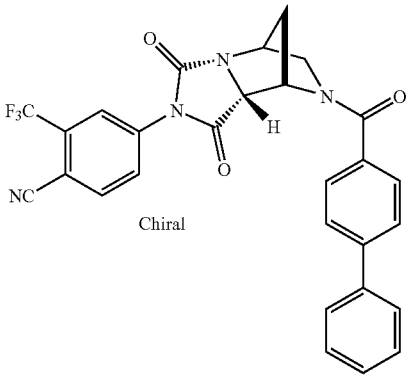 Chiral | [5S-(5α,8α,8aα)]-7-([1,1'-Biphenyl]-4-ylcarbonyl)-2-[4-cyano-3-(tri-fluoromethyl)phenyl]-octahydro-1,3-dioxo-5,8-methanoimidazo[1,5-a]pyrazine. | 1.93 LCMS [M + H]+ = 517.43 | 221Ci | B |
| 310 | 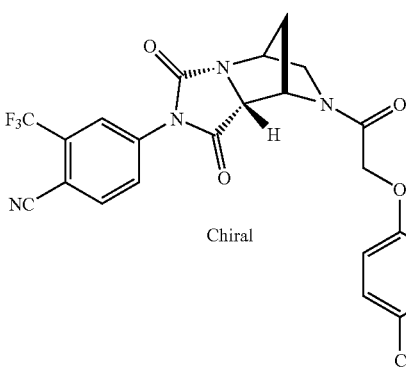 Chiral | [5S-(5α,8α,8aα)]-7-[(4-Chlorophenoxy)acetyl]-2-[4-cyano-3-(trifluoromethyl)phenyl]-octahydro-1,3-dioxo-5,8-methanoimidazo[1,5-a]pyrazine. | 1.89 LCMS [M + H]+ = 505.35 | 221Ci | B |
| 311 | 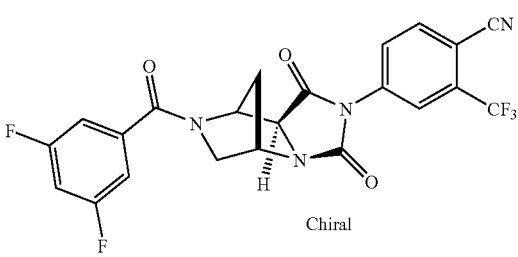 Chiral | [5S-(5α,8α,8aβ)]-2-[4-Cyano-3-(trifluoromethyl)-phenyl]-7-(3,5-difluorobenzoyl)-octahydro-1,3-dioxo-5,8-methanoimidazo[1,5-a]pyrazine. | 1.68 LCMS [M + H]+ = 477.41 | 221Ci | B |
| 312 | 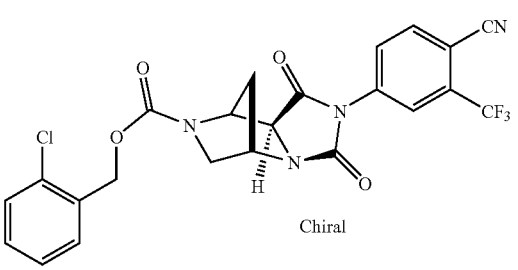 Chiral | [5S-(5α,8α,8aβ)]-2-[4-Cyano-3-(trifluoromethyl)-phenyl]hexahydro-1,3-dioxo-5,8-methanoimidazo[1,5-a]pyrazine-7(1H)-carboxylic acid, (2-chlorophenyl) methyl ester. | 1.85 LCMS [M + H]+ = 505.37 | 221Cii | B |
| 313 | 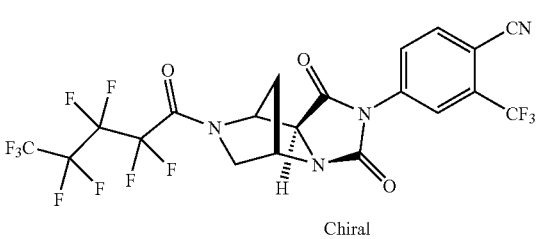 Chiral | [5S-(5α,8α,8aβ)]-2-[4-Cyano-3-(trifluoromethyl)-phenyl]octahydro-7-(2,2,3,3,4,4,5,5,5-nonafluoro-1-oxopentyl)-1,3-dioxo-5,8-methanoimidazo[1,5-a]pyrazine. | 1.92 LCMS [M + H]+ = 581.22 | 221Ci | B |

TABLE 5-continued

| | | | | | |
|---|---|---|---|---|---|
| 314 | 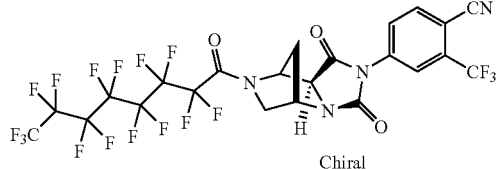 Chiral | [5S-(5α,8α,8aβ)]-2-[4-Cyano-3-(trifluoromethyl)phenyl]octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.12 LCMS [M + H]⁺ = 731.31 | 221Ci | B |
| 315 | 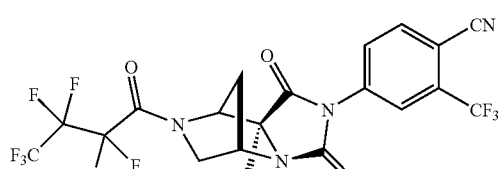 Chiral | [5S-(5α,8α,8aβ)]-2-[4-Cyano-3-(trifluoromethyl)phenyl]-7-(2,2,3,3,4,4,4-heptafluoro-1-oxobutyl)octahydro-1,3-dioxo-5,8-methanoimidazo[1,5-a]pyrazine. | 1.82 LCMS [M + H]⁺ = 531.25 | 221Ci | B |
| 316 | 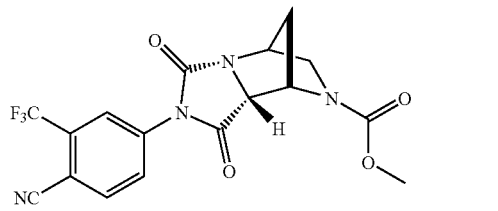 Chiral | [5S-(5α,8α,8aα)]-2-[4-Cyano-3-(trifluoromethyl)phenyl]-hexahydro-1,3-dioxo-5,8-methanoimidazo[1,5-a]pyrazine-7(1H)-carboxylic acid, methyl ester. | 1.45 LCMS [M + H]⁺ = 393.31 | 221Cii | B |
| 317 | 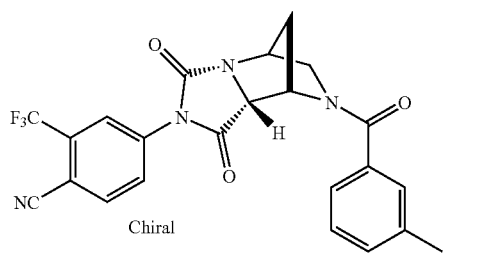 Chiral | [5S-(5α,8α,8aα)]-2-[4-Cyano-3-(trifluoromethyl)phenyl]octahydro-7-(3-methylbenzoyl)-1,3-dioxo-5,8-methanoimidazo[1,5-a]pyrazine. | 1.74 LCMS [M + H]⁺ = 455.43 | 221Ci | B |
| 318 | 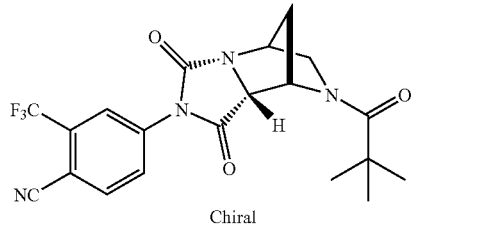 Chiral | [5S-(5α,8α,8aα)]-2-[4-Cyano-3-(trifluoromethyl)phenyl]-7-(2,2-dimethyl-1-oxopropyl)octahydro-1,3-dioxo-5,8-methanoimidazo[1,5-a]pyrazine. | 1.66 LCMS [M + H]⁺ = 421.43 | 221Ci | B |
| 319 | 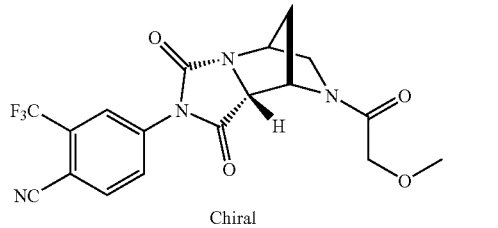 Chiral | [5S-(5α,8α,8aα)]-2-[4-Cyano-3-(trifluoromethyl)phenyl]octahydro-7-(methoxyacetyl)-1,3-dioxo-5,8-methanoimidazo[1,5-a]pyrazine. | 1.38 LCMS [M + H]⁺ = 409.40 | 221Ci | B |

TABLE 5-continued

| | | | | | |
|---|---|---|---|---|---|
| 320 | | [5S-(5α,8α,8aα)]-2-[4-Cyano-3-(trifluoromethyl)phenyl]-7-(3,3-dimethyl-1-oxobutyl)octahydro-1,3-dioxo-5,8-methanoimidazo[1,5-a]pyrazine. | 1.74 LCMS [M + H]⁺ = 435.44 | 221Ci | |
| 321 | | [5S-(5α,8α,8aα)]-2-[4-Cyano-3-(tri-fluoromethyl)phenyl]-octahydro-1,3-dioxo-7-(1-oxopropyl)-5,8-methanoimidazo[1,5-a]pyrazine. | 1.45 LCMS [M + H]⁺ = 393.41 | 221Ci | B |
| 322 | | [5S-(5α,8α,8aβ)]-2-[4-Cyano-3-(trifluoromethyl)phenyl]-hexahydro-gamma,1,3-trioxo-5,8-methanoimidazo[1,5-a]pyrazine-7(1H)-butanoic acid, methyl ester. | 1.42 LCMS [M + H]⁺ = 451.41 | 221Ci | B |
| 323 | | [5S-(5α,8α,8aβ)]-2-[4-Cyano-3-(trifluoromethyl)phenyl]-7-(cyclopropylcarbonyl)-octahydro-1,3-dioxo-5,8-methanoimidazo[1,5-a]pyrazine. | 1.41 LCMS [M + H]⁺ = 405.38 | 221Ci | B |
| 324 | | [5S-(5α,8α,8aβ)]-2-[4-Cyano-3-(trifluoromethyl)phenyl]-octahydro-7-[(3-methoxyphenyl)acetyl]-1,3-dioxo-5,8-methanoimidazo[1,5-a]pyrazine. | 1.61 LCMS [M + H]⁺ = 485.44 | 221Ci | B |
| 325 | | [5S-(5α,8α,8aβ)]-2-[4-Cyano-3-(trifluoromethyl)phenyl]-hexahydro-1,3-dioxo-5,8-methanoimidazo[1,5-a]pyrazine-7(1H)-carboxylic acid, 4-methoxyphenyl ester. | 1.68 LCMS [M + H]⁺ = 487.41 | 221Cii | B |

TABLE 5-continued

| | | | | | |
|---|---|---|---|---|---|
| 326 | 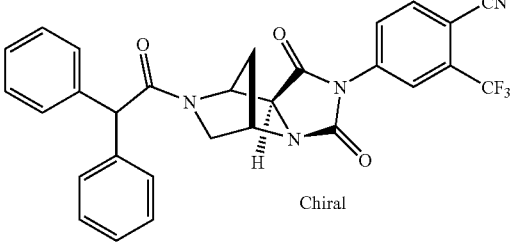 Chiral | [5S-(5α,8α,8aβ)]-2-[4-Cyano-3-(trifluoromethyl)phenyl]-7-(diphenylacetyl)-octahydro-1,3-dioxo-5,8-methanoimidazo[1,5-a]pyrazine. | 1.87 LCMS [M + H]⁺ = 531.44 | 221Ci | B |
| 327 | 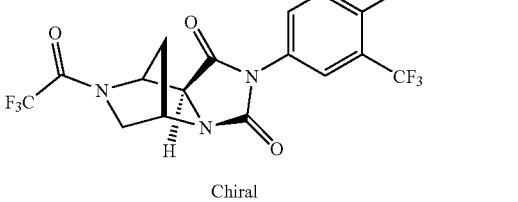 Chiral | [5S-(5α,8α,8aβ)]-2-[4-Cyano-3-(trifluoromethyl)phenyl]-octahydro-1,3-dioxo-7-(trifluoroacetyl)-5,8-methanoimidazo[1,5-a]pyrazine. | 1.54 LCMS [M + H]⁺ = 431.27 | 221Ci | B |
| 328 | 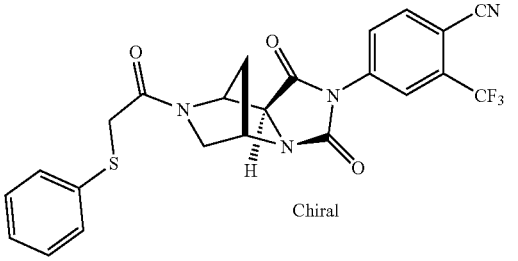 Chiral | [5S-(5α,8α,8aβ)]-2-[4-Cyano-3-(trifluoromethyl)phenyl]-octahydro-1,3-dioxo-7-[(phenylthio)acetyl]-5,8-methanoimidazo[1,5-a]pyrazine. | 1.71 LCMS [M + H]⁺ = 487.38 | 221Ci | B |
| 329 | 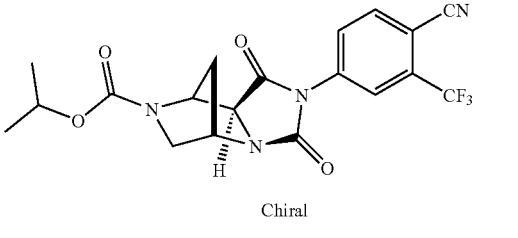 Chiral | [5S-(5α,8α,8aβ)]-2-[4-Cyano-3-(trifluoromethyl)phenyl]-hexahydro-1,3-dioxo-5,8-methanoimidazo[1,5-a]pyrazine-7(1H)-carboxylic acid, 1-methylethyl ester. | 1.64 LCMS [M + H]⁺ = 421.34 | 221Cii | B |
| 330 | 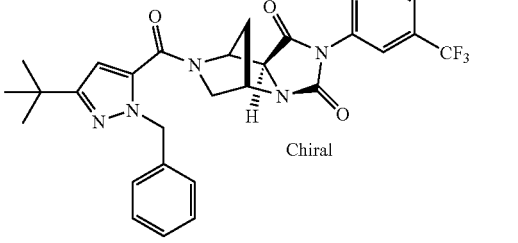 Chiral | [5S-(5α,8α,8aβ)]-2-[4-Cyano-3-(trifluoromethyl)phenyl]-7-[[3-(1,1-dimethylethyl)-1-(phenylmethyl)-1H-pyrazol-5-yl]carbonyl]-octahydro-1,3-dioxo-5,8methanoimidazo[1,5-a]pyrazine. | 1.98 LCMS [M + H]⁺ = 577.48 | 221Ci | B |
| 331 | 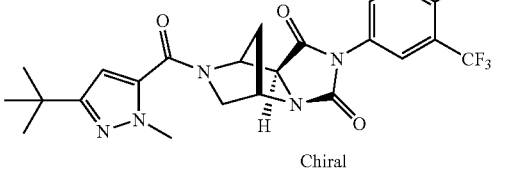 Chiral | [5S-(5α,8α,8aβ)]-2-[4-Cyano-3-(trifluoromethyl)phenyl]-7-[[3-(1,1-dimethylethyl)-1-methyl-1H-pyrazol-5-yl]carbonyl]octahydro-1,3-dioxo-5,8-methanoimidazo[1,5-a]pyrazine. | 1.79 LCMS [M + H]⁺ = 501.48 | 221Ci | B |

TABLE 5-continued

| | | | | | |
|---|---|---|---|---|---|
| 332 | | [5S-(5α,8α,8aβ)]-2-[4-Cyano-3-(trifluoromethyl)phenyl]-octahydro-7-[(5-methyl-3-isoxazolyl)-carbonyl]-1,3-dioxo-5,8-methanoimidazo[1,5-a]pyrazine. | 1.48 LCMS [M + H]$^+$ = 446.41 | 221Ci | B |
| 333 | | [5S-(5α,8α,8aβ)]-7-(3-Bromobenzoyl)-2-[4-cyano-3-(trifluoromethyl)phenyl]-octahydro-1,3-dioxo-5,8-methanoimidazo[1,5-a]pyrazine. | 1.75 LCMS [M + H]$^+$ = 519.31 | 221Ci | B |
| 334 | | [5S-(5α,8α,8aβ)]-2-[4-Cyano-3-(trifluoromethyl)phenyl]-hexahydro-alpha-1,3-trioxo-5,8-methanoimidzo[1,5-a]pyrazine-7(1H)-acetic acid, methyl ester. | 1.31 LCMS [M + H]$^+$ = 423.38 | 221Ci | B |
| 335 | | [5S-(5α,8α,8aα)]-2-[4-Cyano-3-(trifluoromethyl)phenyl]-octahydro-1,3-dioxo-7-[2-(trifluoromethyl)benzoyl]-5,8-methanoimidazo[1,5-a]pyrazine. | 1.75 LCMS [M + H]$^+$ = 509.38 | 221Ci | B |
| 336 | | [5S-(5α,8α,8aβ)]-2-[4-Cyano-3-(trifluoromethyl)phenyl]-7-[(3,4-dimethoxyphenyl)-acetyl]octahydro-1,3-dioxo-5,8-methanoimidazo[1,5-a]pyrazine. | 1.48 LCMS [M + H]$^+$ = 515.43 | 221Ci | B |
| 337 | | [5S-(5α,8α,8aβ)]-2-[4-Cyano-3-(trifluoromethyl)phenyl]-octahydro-1,3-dioxo-7-[(trifluoromethyl)sulfonyl]-5,8-methanoimidazo[1,5-a]pyrazine. | 1.72 LCMS [M + H]$^+$ = 467.26 | 221D | B |

TABLE 5-continued

| | | | | | |
|---|---|---|---|---|---|
| 338 | | [5S-(5α,8α,8aβ)]-2-(8-Cyano-5-quinolinyl)octahydro-1,3-dioxo-7-[2-(trifluoromethyl)-benzoyl]-5,8-methanoimidazo[1,5-a]pyrazine. | 1.33 LCMS [M + H]+ = 492.39 | 221Ci | B |
| 339 | | [5S-(5α,8α,8aβ)]-2-(8-Cyano-5-quinolinyl)hexahydro-1,3-dioxo-5,8-methanoimidazo[1,5-a]pyrazine-7(1H)-carboxylic acid, 2-propynyl ester. | 1.04 LCMS [M + H]+ = 402.38 | 221Cii | B |
| 340 | | [5S-(5α,8α,8aβ)]-7-([1,1'-Biphenyl]-4-ylcarbonyl)-2-(8-cyano-5-quinolinyl)octahydro-1,3-dioxo-5,8-methanoimidazo[1,5-a]pyrazine. | 1.67 LCMS [M + H]+ = 500.43 | 221Ci | B |
| 341 | | [5S-(5α,8α,8aβ)]-2-(8-Cyano-5-quinolinyl)-7-(2,2-dimethyl-1-oxopropyl)octahydro-1,3-dioxo-5,8-methanoimidazo[1,5-a]pyrazine. | 1.24 LCMS [M + H]+ = 404.44 | 221Ci | B |
| 342 | | [5S-(5α,8α,8aβ)]-7-[(4-Chlorophenoxy)-acetyl]-2-(8-cyano-5-quinolinyl)octahydro-1,3-dioxo-5,8-methanoimidazo[1,5-a]pyrazine. | 1.49 LCMS [M + H]+ = 488.38 | 221Ci | B |
| 343 | | [5S-(5α,8α,8aβ)]-2-(8-Cyano-5-quinolinyl)octahydro-7-(methoxyacetyl)-1,3-dioxo-5,8-methanoimidazo[1,5-a]pyrazine. | 0.85 LCMS [M + H]+ = 392.42 | 221Ci | B |
| 344 | | [5S-(5α,8α,8aβ)]-(8-Cyano-5-quinolinyl)-7-(3,3-dimethyl-1-oxobutyl)octahydro-1,3-dioxo-5,8-methanoimidazo[1,5-a]pyrazine. | 1.40 LCMS [M + H]+ = 418.45 | 221Ci | B |

TABLE 5-continued

| # | Structure | Name | LCMS | Ref | Grade |
|---|---|---|---|---|---|
| 345 | (Chiral structure) | [5S-(5α,8α,8aβ)]-2-(8-Cyano-5-quinolinyl)octahydro-1,3-dioxo-7-(1-oxopropyl)-5,8-methanoimidazo[1,5-a]pyrazine. | 0.96 LCMS [M + H]⁺ = 376.43 | 221Ci | B |
| 346 | (Chiral structure) | [5S-(5α,8α,8aβ)]-2-(8-Cyano-5-quinolinyl)hexahydro-gamma,1,3-trioxo-5,8-methanoimidazo[1,5-a]pyrazine-7(1H)-butanoic acid, methyl ester. | 0.98 LCMS [M + H]⁺ = 434.42 | 221Ci | B |
| 347 | (Chiral structure) | [5S-(5α,8α,8aβ)]-2-(8-Cyano-5-quinolinyl)-7-(cyclopropyl-carbonyl)octahydro-1,3-dioxo-5,8-methanoimidazo[1,5-a]pyrazine. | 0.98 LCMS [M + H]⁺ = 388.44 | 221Ci | B |
| 348 | (Chiral structure) | [5S-(5α,8α,8aβ)]-2-(8-Cyano-5-quinolinyl)-7-[(3,4-dimethoxyphenyl)-acetyl]octahydro-1,3-dioxo-5,8-methanoimidazo[1,5-a]pyrazine. | 1.17 LCMS [M + H]⁺ = 498.44 | 221Ci | B |
| 349 | (Chiral structure) | [5S-(5α,8α,8aβ)]-2-(8-Cyano-5-quinolinyl)-7-(3,5-difluoro-benzoyl)octahydro-1,3-dioxo-5,8-methanoimidazo[1,5-a]pyrazine. | 1.35 LCMS [M + H]⁺ = 460.41 | 221Ci | B |
| 350 | (Chiral structure) | [5S-(5α,8α,8aβ)]-2-(8-Cyano-5-quinolinyl)-octahydro-7-[(3-methoxyphenyl)acetyl]-1,3-dioxo-5,8-methanoimidazo[1,5-a]pyrazine. | 1.31 LCMS [M + H]⁺ = 468.43 | 221Ci | B |
| 351 | (Chiral structure) | [5S-(5α,8α,8aβ)]-2-(8-Cyano-5-quinolinyl)-hexahydro-1,3-dioxo-5,8-methanoimidazo[1,5-a]pyrazine-7(1H)-carboxylic acid, 4-methoxyphenyl ester. | 1.38 LCMS [M + H]⁺ = 470.41 | 221Cii | B |

TABLE 5-continued

| | | | | | | |
|---|---|---|---|---|---|---|
| 352 | 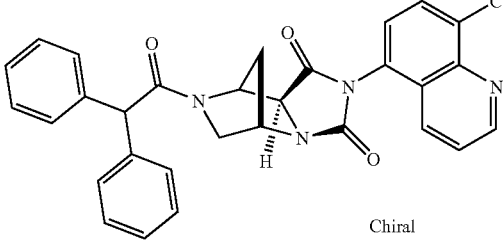 Chiral | [5S-(5α,8α,8aβ)]-2-(8-Cyano-5-quinolinyl)-7-(diphenylacetyl)-octahydro-1,3-dioxo-5,8-methanoimidazo[1,5-a]pyrazine. | 1.66 LCMS [M + H]$^+$ = 514.46 | 221Ci | B |
| 353 | 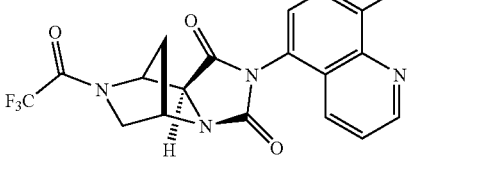 Chiral | [5S-(5α,8α,8aβ)]-2-(8-Cyano-5-quinolinyl)-octahydro-1,3-dioxo-7-(trifluoroacetyl)-5,8-methanoimidazo[1,5-a]pyrazine. | 1.15 LCMS [M + H]$^+$ = 416.36 | 221Ci | B |
| 354 | 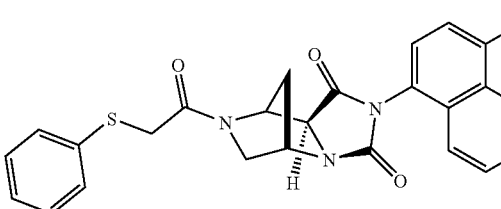 Chiral | [5S-(5α,8α,8aβ)]-2-(8-Cyano-5-quinolinyl)-octahydro-1,3-dioxo-7-[(phenylthio)acetyl]-5,8-methanoimidazo[1,5-a]pyrazine. | 1.40 LCMS [M + H]$^+$ = 470.38 | 221Ci | B |
| 355 | 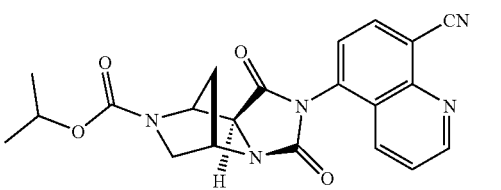 Chiral | [5S-(5α,8α,8aβ)]-2-(8-Cyano-5-quinolinyl)-hexahydro-1,3-dioxo-5,8-methanoimidazo[1,5-a]pyrazine-7(1H)-carboxylic acid, 1-methylethyl ester. | 1.24 LCMS [M + H]$^+$ = 406.41 | 221Cii | B |
| 356 | 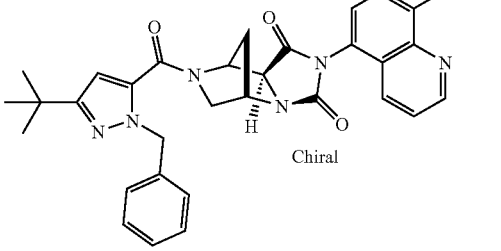 Chiral | [5S-(5α,8α,8aβ)]-2-(8-Cyano-5-quinolinyl)-7-[[3-(1,1-dimethylethyl)-1-(phenylmethyl)-1H-pyrazol-5-yl]carbonyl] octahydro-1,3-dioxo-5,8-methanoimidazo[1,5-a]pyrazine. | 1.79 LCMS [M + H]$^+$ = 560.47 | 221Ci | B |
| 357 | 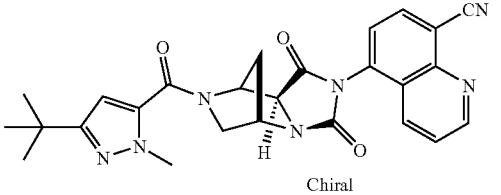 Chiral | [5S-(5α,8α,8aβ)]-2-(8-Cyano-5-quinolinyl)-7-[[3-(1,1-dimethylethyl)-1-methyl-1H-pyrazol-5-yl]carbonyl] octahydro-1,3-dioxo-5,8-methanoimidazo[1,5-a]pyrazine. 1.50 LCMS [M + H]$^+$ = 484.48 | | 221Ci | B |

TABLE 5-continued

| | Structure | Name | LCMS | Ref | Activity |
|---|---|---|---|---|---|
| 358 | (5-methylisoxazol-3-yl carbonyl compound, Chiral) | [5S-(5α,8α,8aβ)]-2-(8-Cyano-5-quinolinyl)-octahydro-7-[(5-methyl-3-isoxazolyl)carbonyl]-1,3-dioxo-5,8-methanoimidazo[1,5-a]pyrazine. | 1.13 LCMS [M + H]⁺ = 429.40 | 221Ci | B |
| 359 | (2-chlorobenzyl carbamate compound, Chiral) | [5S-(5α,8α,8aβ)]-2-(8-Cyano-5-quinolinyl)-hexahydro-1,3-dioxo-5,8-methanoimidazo[1,5-a]pyrazine-7(1H)-carboxylic acid, (2-chlorophenyl)methyl ester. | 1.57 LCMS [M + H]⁺ = 488.39 | 221Cii | B |
| 360 | (nonafluoropentanoyl compound, Chiral) | [5S-(5α,8α,8aβ)]-2-(8-Cyano-5-quinolinyl)octahydro-7-(2,2,3,3,4,4,5,5,5-nonafluoro-1-oxopentyl)-1,3-dioxo-5,8-methanoimidazo[1,5-a]pyrazine. | 1.72 LCMS [M + H]⁺ = 566.33 | 221Ci | B |
| 361 | (3-bromobenzoyl compound, Chiral) | [5S-(5α,8α,8aβ)]-7-(3-Bromobenzoyl)-2-(8-cyano-5-quinolinyl)octahydro-1,3-dioxo-5,8-methanoimidazo[1,5-a]pyrazine. | 1.43 LCMS [M + H]⁺ = 502.31 | 221Ci | B |
| 362 | (pentadecafluorooctanoyl compound, Chiral) | [5S-(5α,8α,8aβ)]-2-8-Cyano-5-quinolinyl)octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.03 LCMS [M + H]⁺ = 716.32 | 221Ci | B |

| | | | | | |
|---|---|---|---|---|---|
| 363 | 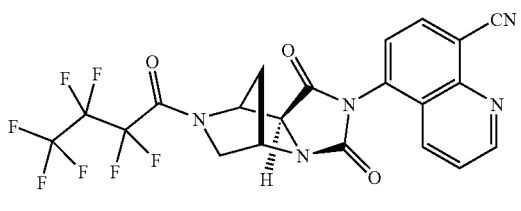 Chiral | [5S-(5α,8α,8aβ)]-2-(8-Cyano-5-quinolinyl)-7-(2,2,3,3,4,4,4-heptafluoro-1-oxobutyl)octahydro-1,3-dioxo-5,8-methanoimidzo[1,5-a]pyrazine. | 1.58 LCMS [M + H]$^+$ = 516.35 | 221Ci | B |
| 364 | 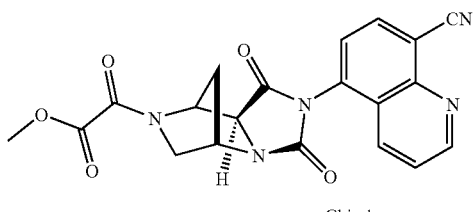 Chiral | [5S-(5α,8α,8aβ)]-2-(8-Cyano-5-quinolinyl)hexahydro-alpha,1,3-trioxo-5,8-methanoimidazo[1,5-a]pyrazine-7(1H)-acetic acid, methyl ester. | 0.91 LCMS [M + H]$^+$ = 406.39 | 221Ci | B |
| 365 | 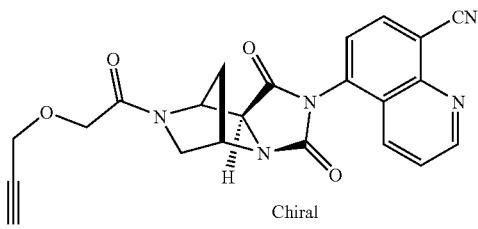 Chiral | [5S-(5α,8α,8aβ)]-2-(8-Cyano-5-quinolinyl)hexahydro-1,3-dioxo-5,8-methanoimidazo[1,5-a]pyrazine-7(1H)-carboxylic acid, 3-butynyl ester. | 1.10 LCMS [M + H]$^+$ = 416.41 | 221Cii | A |
| 366 | 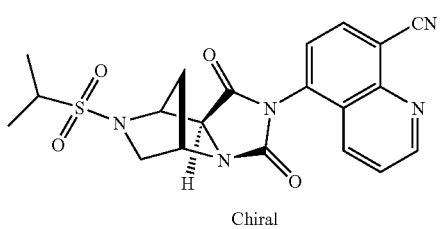 Chiral | [5S-(5α,8α,8aβ)]-2-(8-Cyano-5-quinolinyl)octahydro-7-[(1-methylethyl)-sulfonyl]-1,3-dioxo-5,8-methanoimidazo[1,5-a]pyrazine. | 2.25 LCMS [M + H]$^+$ = 426.40 | 221D | A |
| 367 | 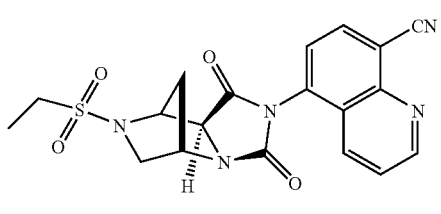 Chiral | [5S-(5α,8α,8aβ)]-2-(8-Cyano-5-quinolinyl)-7-(ethylsulfonyl)-octahydro-1,3-dioxo-5,8-methanoimidazo[1,5-a]pyrazine. | 0.97 LCMS [M + H]$^+$ = 412.39 | 221D | B |
| 368 | 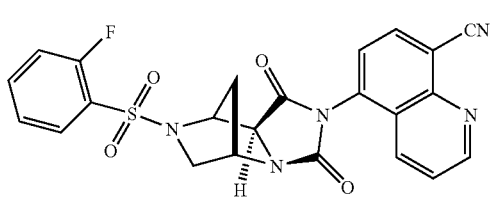 Chiral | [5S-(5α,8α,8aβ)]-2-(8-Cyano-5-quinolinyl)-7-[(2-fluorophenyl)sulfonyl]-octahydro-1,3-dioxo-5,8-methanoimidazo[1,5-a]pyrazine. | 1.32 LCMS [M + H]$^+$ = 478.38 | 221D | B |

| | | | | | |
|---|---|---|---|---|---|
| 369 | | [5S-(5α,8α,8aβ)]-2-(8-Cyano-5-quinolinyl)octahydro-7-(methylsulfonyl)-1,3-dioxo-5,8-methanoimidazo[1,5-a]pyrazine. | 0.85 LCMS [M + H]$^+$ = 398.38 | 221D | B |
| 370 | | [5S-(5α,8α,8aβ)]-2-(8-Cyano-5-quinolinyl)hexahydro-N,N-dimethyl-1,3-dioxo-5,8-methanoimidazo[1,5-a]pyrazine-7(1H)-sulfonamide. | 1.08 LCMS [M + H]$^+$ = 427.38 | 221D | B |
| 371 | | [5S-(5α,8α,8aβ)]-2-(8-Cyano-5-quinolinyl)-N-(1,1-dimethylethyl)hexahydro-1,3-dioxo-5,8-methanoimidazo]1,5-a]pyrazine-7(1H)-carboxamide. | 1.23 LCMS [M + H]$^+$ = 419.46 | 221Bii | B |
| 372 | | [5S-(5α,8α,8aβ)]-2-(8-Cyano-5-quinolinyl)hexahydro-N-(2-methylpropyl)-1,3-dioxo-5,8-methanoimidazo[1,5-a]pyrazine-7(1H)-carbothioamide. | 1.39 LCMS [M + H]$^+$ = 435.43 | 221Bi | B |
| 373 | | [5S-(5α,8α,8aβ)]-N-(4-Cyanophenyl)-2-(8-Cyano-5-quinolinyl)hexahydro-1,3-dioxo-5,8-methanoimidazo[1,5-a]pyrazine-7(1H)-carboxamide. | 1.15 LCMS [M + H]$^+$ = 464.45 | 221Bii | B |
| 374 | | [5S-(5α,8α,8aβ)]-N-[1,1'-Biphenyl]-2-yl-2-(8-cyano-5-quinolinyl)hexahydro-1,3-dioxo-5,8-methanoimidazo[1,5-a]pyrazine-7(1H)-carboxamide. | 1.62 LCMS [M + H]$^+$ = 515.45 | 221Bii | B |

| | | | | | |
|---|---|---|---|---|---|
| 375 | | [5S-(5α,8α,8aβ)]-2-(8-Cyano-5-quinolinyl)hexahydro-1,3-dioxo-N-2-propynyl-5,8-methanoimidazo[1,5-a]pyrazine-7(1H)-carbothioamide. | 0.77 LCMS $[M + H]^+ =$ 417.37 | 221Bi | A |
| 376 | | [5S-(5α,8α,8aβ)]-N-[3,5-Bis(tri-fluoromethyl)phenyl]-2-(8-cyano-5-quinolinyl)hexahydro-1,3-dioxo-5,8-methanoimidazo[1,5-a]pyrazine-7(1H)-carboxamide. | 1.90 LCMS $[M + H]^+ =$ 575.39 | 221Bii | B |
| 377 | | [5S-(5α,8α,8aβ)]-2-(8-Cyano-5-quinolinyl)hexahydro-N-1-naphthalenyl-1,3-dioxo-5,8-methanoimidazo[1,5-a]pyrazine-7(1H)-carboxamide. | 1.41 LCMS $[M + H]^+ =$ 489.45 | 221Bii | A |
| 378 | | [5S-(5α,8α,8aβ)]-2-(8-Cyano-5-quinolinyl)hexahydro-1,3-dioxo-N-[3-(trifluoromethyl)phenyl]-5,8-methanoimidazo[1,5-a]pyrazine-7(1H)-carboxamide. | 1.52 LCMS $[M + H]^+ =$ 507.41 | 221Bii | B |
| 379 | | [5S-(5α,8α,8aβ)]-2-(8-Cyano-5-quinolinyl)hexahydro-N-[3-(4-morpholinyl)propyl]-1,3-dioxo-5,8-methanoimidazo[1,5-a]pyrazine-7(1H)-carbothioamide. | 0.94 LCMS $[M + H]^+ =$ 506.47 | 221Bi | B |
| 380 | | [5S-(5α,8α,8aβ)]-2-(8-Cyano-5-quinolinyl)-N-(cyclohexylmethyl)-hexahydro-1,3-dioxo-5,8-methanoimidazo[1,5-a]pyrazine-7(1H)-carbothioamide. | 1.76 LCMS $[M + H]^+ =$ 475.47 | 221Bi | B |
| 381 | | [5S-(5α,8α,8aβ)]-2-(3-Chloro-4-cyano-2-methylphenyl)-hexahydro-N-(2-methylpropyl)-1,3-dioxo-5,8-methanoimidazo[1,5-a]pyrazine-7(1H)-carbothioamide. | 1.69 LCMS $[M + H]^+ =$ 432.17 | 221Bi | E |

-continued

| | | | | | |
|---|---|---|---|---|---|
| 382 | 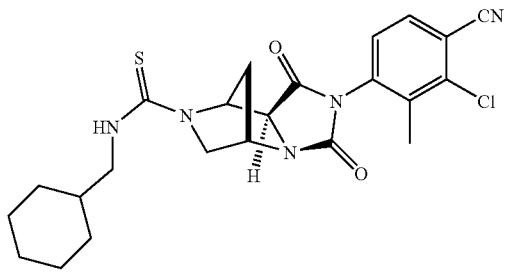 | [5S-(5α,8α,8aβ)]-2-(3-Chloro-4-cyano-2-methylphenyl)-N-(cyclohexylmethyl)-hexahydro-1,3-dioxo-5,8-methanoimidazo[1,5-a]pyrazine-7(1H)-carbothioamide. | 1.91 LCMS [M + H]⁺ = 472.16 | 221Bi | E |
| 383 | 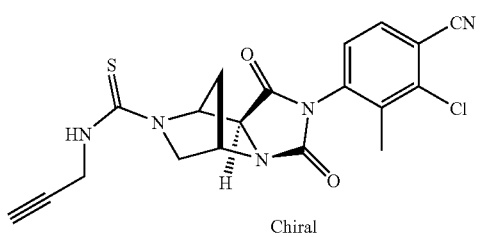  Chiral | [5S-(5α,8α,8aβ)]-2-(3-Chloro-4-cyano-2-methylphenyl)-hexahydro-1,3-dioxo-N-2-propynyl-5,8-methanoimidazo[1,5-a]pyrazine-7(1H)-carbothioamide. | 1.11 LCMS [M + H]⁺ = 414.14 | 221Bi | F |
| 384 | 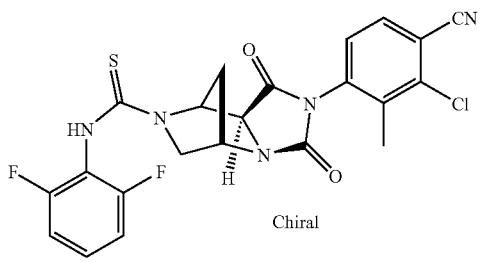  Chiral | [5S-(5α,8α,8aβ)]-2-(3-Chloro-4-cyano-2-methylphenyl)-N-(2,6-difluorophenyl)-hexahydro-1,3-dioxo-5,8-methanoimidazo[1,5-a]pyrazine-7(1H)-carbothioamide. | 1.49 LCMS [M + H]⁺ = 488.10 | 221Bi | F |
| 385 | 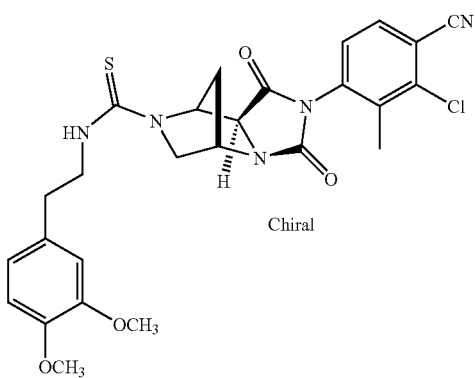  Chiral | [5S-(5α,8α,8aβ)]-2-(3-Chloro-4-cyano-2-methylphenyl)-N-[2-(3,4-dimethoxyphenyl)-ethyl]hexahydro-1,3-dioxo-5,8-methanoimidazo[1,5-a]pyrazine-7(1H)-carbothioamide. | 1.63 LCMS [M + H]⁺ = 538.15 | 221Bi | F |
| 386 | 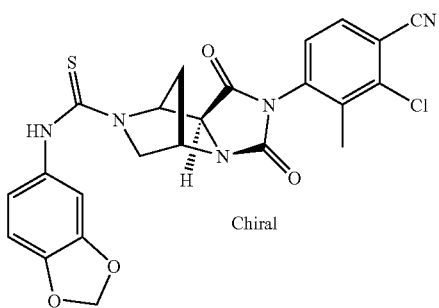  Chiral | [5S-(5α,8α,8aβ)]-N-1,3-Benzodioxol-5-yl-2-(3-chloro-4-cyano-2-methylphenyl)-hexahydro-1,3-dioxo-5,8-methanoimidazo[1,5-a]pyrazine-7(1H)-carbothioamide. | 1.51 LCMS [M + H]⁺ = 496.10 | 221Bi | F |

| | | | | | |
|---|---|---|---|---|---|
| 387 | 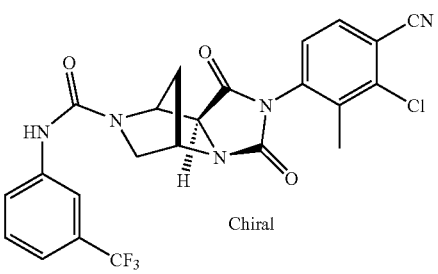 Chiral | [5S-(5α,8α,8aβ)]-2-(3-Chloro-4-cyano-2-methylphenyl)-hexahydro-1,3-dioxo-N-[3-(trifluoromethyl)phenyl]-5,8-methanoimidazo[1,5-a]pyrazine-7(1H)-carboxamide. | 1.75 LCMS [M + H]⁺ = 504.13 | 221Bii | F |
| 388 | 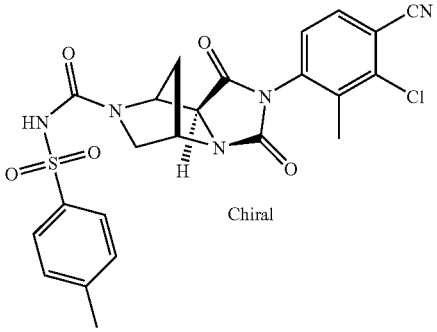 Chiral | [5S-(5α,8α,8aβ)]-2-(3-Chloro-4-cyano-2-methylphenyl)-hexahydro-N-[(4-methylphenyl)sulfonyl]-1,3-dioxo-5,8-methanoimidazo[1,5-a]pyrazine-7(1H)-carboxamide. | 1.53 LCMS [M + H]⁺ = 514.10 | 221Bii | F |
| 389 | 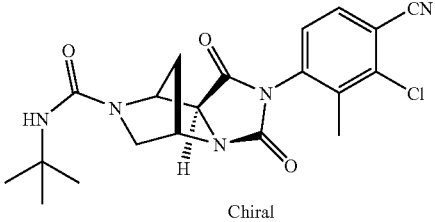 Chiral | [5S-(5α,8α,8aβ)]-2-(3-Chloro-4-cyano-2-methylphenyl)-N-(1,1-dimethylethyl)-hexahydro-1,3-dioxo-5,8-methanoimidazo[1,5-a]pyrazine-7(1H)-carboxamide. | 1.55 LCMS [M + H]⁺ = 416.20 | 221Bii | F |
| 390 | 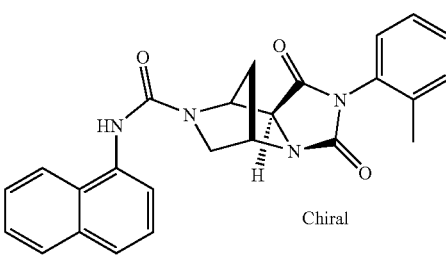 Chiral | [5S-(5α,8α,8aβ)]-2-(3-Chloro-4-cyano-2-methylphenyl)-hexahydro-N-1-naphthalenyl-1,3-dioxo-5,8-methanoimidazo[1,5-a]pyrazine-7(1H)-carboxamide. | 1.63 LCMS [M + H]⁺ = 486.16 | 221Bii | F |
| 391 | 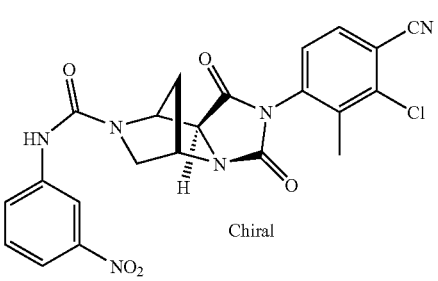 Chiral | [5S-(5α,8α,8aβ)]-2-(3-Chloro-4-cyano-2-methylphenyl)-hexahydro-N-(3-nitrophenyl)-1,3-dioxo-5,8-methanoimidazo[1,5-a]pyrazine-7(1H)-carboxamide | 1.55 LCMS [M + H]⁺ = 481.12 | 221Bii | F |

-continued

| | | | | | |
|---|---|---|---|---|---|
| 392 | 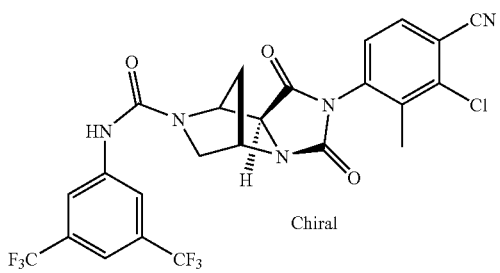 Chiral | [5S-(5α,8α,8aβ)]-N-[3,5-Bis(trifluoro-methyl)phenyl]-2-(3-chloro-4-cyano-2-methyl-phenyl)hexahydro-1,3-dioxo-5,8-methanoimidazo[1,5-a]pyrazine-7(1H)-carboxamide. | 2.01 LCMS [M + H]+ = 572.11 | 221Bii | E |
| 393 | 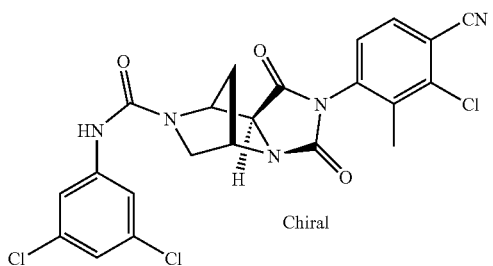 Chiral | [5S-(5α,8α,8aβ)]-2-(3-Chloro-4-cyano-2-methylphenyl)-N-(3,5-dichlorophenyl)-hexahydro-1,3-dioxo-5,8-methanoimidazo[1,5-a]pyrazine-7(1H)-carboxamide. | 1.92 LCMS [M + H]+ = 504.04 | 221Bii | F |
| 394 | 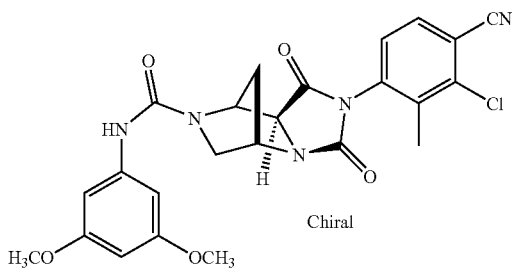 Chiral | [5S-(5α,8α,8aβ)]-2-(3-Chloro-4-cyano-2-methylphenyl)-N-(3,5-dimethoxyphenyl)-hexahydro-1,3-dioxo-5,8-methanoimidazo[1,5-a]pyrazine-7(1H)-carboxamide. | 1.57 LCMS [M + H]+ = 496.14 | 221Bii | E |
| 395 | 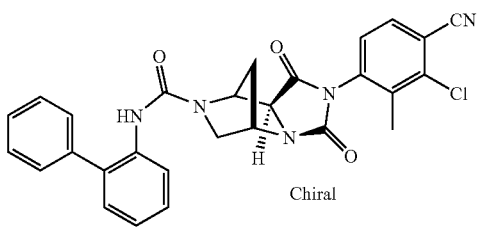 Chiral | [5S-(5α,8α,8aβ)]-N-[1,1'-Biphenyl]-2-yl-2-(3-chloro-4-cyano-2-methyl-phenyl)hexahydro-1,3-dioxo-5,8-methanoimidazo]1,5-a]pyrazine-7(1H)-carboxamide. | 1.79 LCMS [M + H]+ = 512.18 | 221Bii | E |
| 396 | 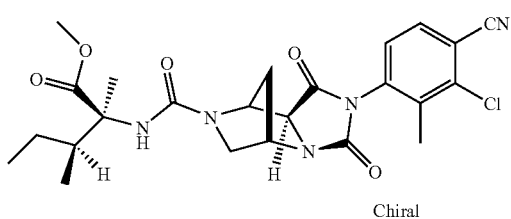 Chiral | [5S-(5α,8α,8aβ)]-N-[[2-(3-Chloro-4-cyano-2-methylphenyl)hexahydro-1,3-dioxo-5,8-methanoimidazo[1,5-a]pyrazin-7(1H)-yl]carbonyl-]isoleucine, methyl ester. | 1.66 LCMS [M + H]+ = 488.23 | 221Bii | E |
| 397 | 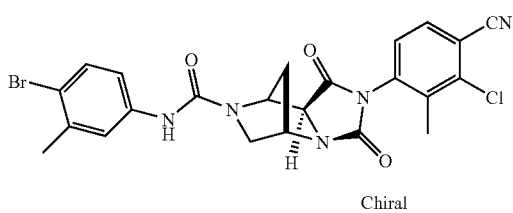 Chiral | [5S-(5α,8α,8aβ)]-N-(4-Bromo-3-methylphenyl)-2-(3-chloro-4-cyano-2-methylphenyl)-hexahydro-1,3-dioxo-5,8-methanoimidazo[1,5-a]pyrazine-7(1H)-carboxamide. | 1.86 LCMS [M + H]+ = 530.06 | 221Bii | E |

-continued

| | | | | | |
|---|---|---|---|---|---|
| 398 | | [5S-(5α,8α,8aβ)]-2-(3-Chloro-4-cyano-2-methylphenyl)-hexahydro-N-(4-methyl-3-nitrophenyl)-1,3-dioxo-5,8-methanoimidazo[1,5-a]pyrazine-7(1H)-carboxamide. | 1.68 LCMS [M + H]$^+$ = 495.14 | 221Bii | E |
| 399 | | [5S-(5α,8α,8aβ)]-2-(3-Chloro-4-cyano-2-methylphenyl)-7-[(2-fluorophenyl)-sulfonyl]octahydro-1,3-dioxo-5,8-methanoimidazo[1,5-a]pyrazine. | 1.62 LCMS [M + H]$^+$ = 473.19 | 221D | E |
| 400 | | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carboxylic acid, methyl ester. | 1.30 LCMS [M + H]$^+$ = 375.16 | 221Cii | F |
| 401 | | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carboxylic acid, 4-methoxyphenyl ester. | 1.62 LCMS [M + H]$^+$ = 467.14 | 221Cii | F |
| 402 | | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carboxylic acid, 3-butynyl ester. | 1.45 LCMS [M + H]$^+$ = 413.16 | 221Cii | F |
| 403 | | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carobxylic acid, 4-fluorophenyl ester. | 1.67 LCMS [M + H]$^+$ = 455.13 | 221Cii | F |

| | | | | | |
|---|---|---|---|---|---|
| 404 | | [5S-(5α,8α,8aβ)]-2-(3-Chloro-4-cyano-2-methylphenyl) hexahydro-1,3-dioxo-5,8-methanoimidazo[1,5-a]pyrazine-7(1H)-carboxylic acid, 4-nitrophenyl ester. | 1.65 LCMS [M + H]⁺ = 482.09 | 221Cii | F |
| 405 | | [5S-(5α,8α,8aβ)]-2-(3-Chloro-4-cyano-2-methylphenyl)-7-(cyclopropylcarbonyl)-octahydro-1,3-dioxo-5,8-methanoimidazo[1,5-a]pyrazine. | 1.35 LCMS [M + H]⁺ = 385.18 | 221Ci | E |
| 406 | | [5S-(5α,8α,8aβ)]-2-(3-Chloro-4-cyano-2-methylphenyl)-7-[(3,4-dimethoxyphenyl)-acetyl]octahydro-1,3-dioxo-5,8-methanoimidazo[1,5-a]pyrazine. | 1.46 LCMS [M + H]⁺ = 495.15 | 221Ci | E |
| 407 | | [5S-(5α,8α,8aβ)]-2-(3-Chloro-4-cyano-2-methylphenyl) hexahydro-1,3-dioxo-5,8-methanoimidazo[1,5-a]pyrazine-7(1H)-carboxylic acid, (1S,2R,5S)-5-methyl-2-(1-methylethyl)-cyclohexyl ester. | 2.12 LCMS [M + H]⁺ = 497.37 | 221Cii | D |
| 408 | | [5S-(5α,8α,8aβ)]-2-(3-Chloro-4-cyano-2-methylphenyl)-7-(3,5-difluorobenzoyl)-octahydro-1,3-dioxo-5,8-methanoimidazo[1,5-a]pyrazine. | 1.63 LCMS [M + H]⁺ = 457.13 | 221Ci | F |
| 409 | | [5S-(5α,8α,8aβ)]-2-(3-Chloro-4-cyano-2-methylphenyl)-octahydro-7-[(3-methoxyphenyl)acetyl]-1,3-dioxo-5,8-methanoimidazo[1,5-a]pyrazine. | 1.58 LCMS [M + H]⁺ = 465.19 | 221Ci | F |

-continued

| | | | | | | |
|---|---|---|---|---|---|---|
| 410 | 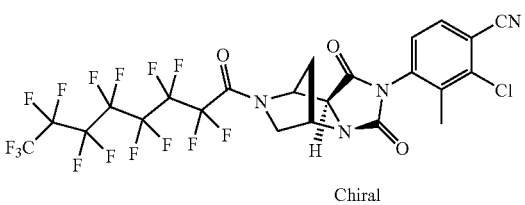 Chiral | [5S-(5α,8α,8aβ)]-2-(3-Chloro-4-cyano-2-methylphenyl) octahydro-1,3-dioxo-7-(2,2,3,3,4,4,5,5,6,6,7,7,8,8,8-pentadecafluoro-1-oxooctyl)-5,8methanoimidazo[1,5a]pyrazine. | 2.18 LCMS [M + H]$^+$ = 734.97 | 221Ci | E |
| 411 | 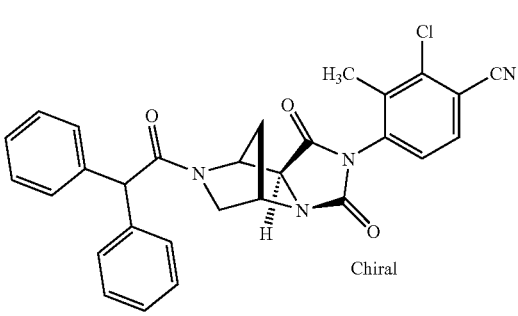 Chiral | [5S-(5α,8α,8aβ)]-2-(3-Chloro-4-cyano-2-methylphenyl) 7-(diphenylacetyl) octahydro-1,3-dioxo-5,8-methanoimidazo[1,5-a]pyrazine. | 1.83 LCMS [M + H]$^+$ = 511.18 | 221Ci | F |
| 412 | 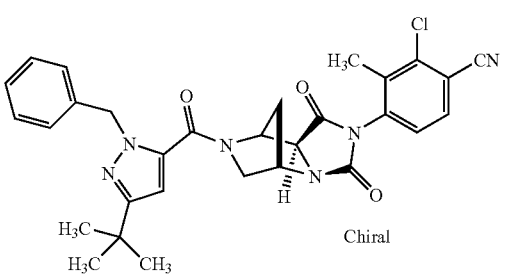 Chiral | [5S-(5α,8α,8aβ)]-2-(3-Chloro-4-cyano-2-methylphenyl)-7-[[3-(1,1-dimethylethyl)-1-(phenylmethyl)-1H-pyrazol-5-yl]carbonyl] octahydro-1,3-dioxo-5,8-methanoimidazo[1,5-a]pyrazine. | 2.00 LCMS [M + H]$^+$ = 557.26 | 221Ci | E |
| 413 | 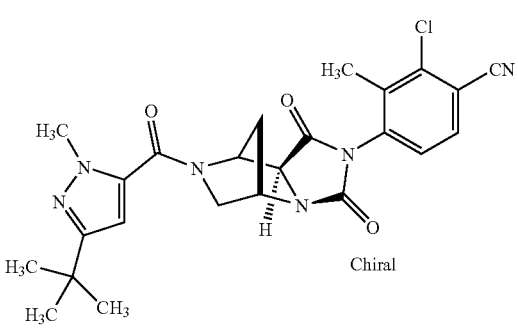 Chiral | [5S-(5α,8α,8aβ)]-2-(3-Chloro-4-cyano-2-methylphenyl)-7-[[3-(1,1-dimethylethyl)-1-methyl-1H-pyrazol-5-yl]carbonyl] octahydro-1,3-dioxo-5,8-methanoimidazo[1,5-a]pyrazine. | 1.76 LCMS [M + H]$^+$ = 481.25 | 221Ci | F |
| 414 | 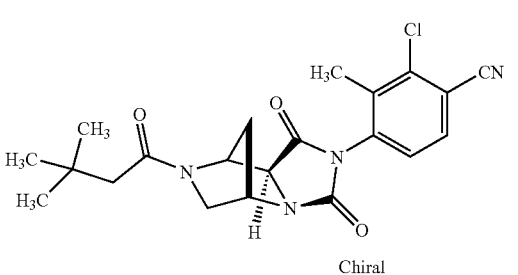 Chiral | [5S-(5α,8α,8aβ)]-2-(3-Chloro-4-cyano-2-methylphenyl)-7-(3,3-dimethyl-1-oxobutyl)octahydro-1,3-dioxo-5,8-methanoimidazo[1,5-a]pyrazine. | 1.67 LCMS [M + H]$^+$ = 415.23 | 221Ci | E |

-continued

| | | | | | |
|---|---|---|---|---|---|
| 415 | 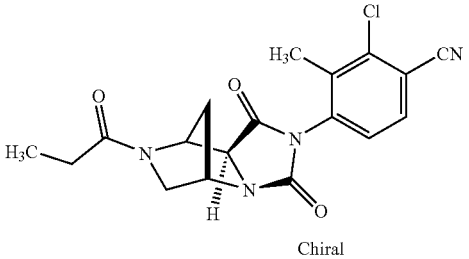<br>Chiral | [5S-(5α,8α,8aβ)]-2-(3-Chloro-4-cyano-2-methylphenyl)-octahydro-1,3-dioxo-7-(1-oxopropyl)-5,8-methanoimidazo[1,5-a]pyrazine. | 1.28 LCMS [M + H]+ = 373.15 | 221Ci | F |
| 416 | 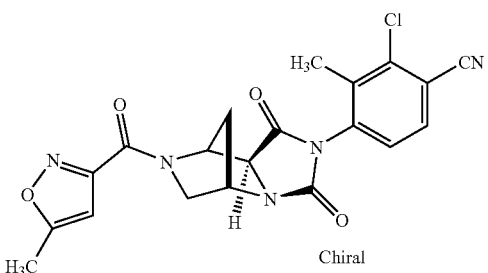<br>Chiral | [5S-(5α,8α,8aβ)]-2-(3-Chloro-4-cyano-2-methylphenyl)-octahydro-7-[(5-methyl-3-isoxazolyl)-carbonyl]-1,3-dioxo-5,8-methanoimidazo[1,5-a]pyrazine. | 1.43 LCMS [M + H]+ = 426.12 | 221Ci | F |
| 417 | 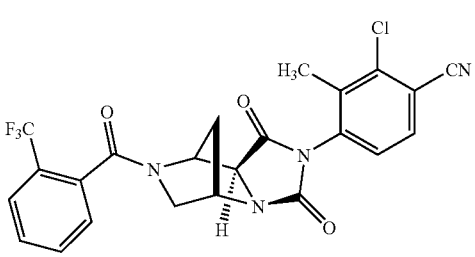<br>Chiral | [5S-(5α,8α,8aβ)]-2-(3-Chloro-4-cyano-2-methylphenyl)-octahydro-1,3-dioxo-7-[2-(trifluoromethyl)benzoyl]-5,8-methanoimidazo[1,5-a]pyrazine. | 1.60 LCMS [M + H]+ = 489.19 | 221Ci | E |
| 418 | 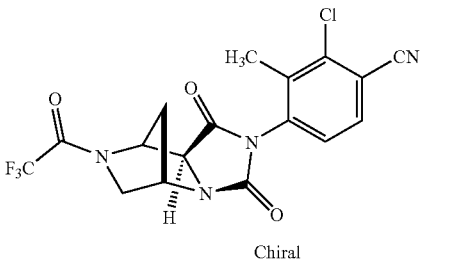<br>Chiral | [5S-(5α,8α,8aβ)]-2-(3-Chloro-4-cyano-2-methylphenyl)-octahydro-1,3-dioxo-7-(trifluoroacetyl)-5,8-methanoimidazo[1,5a]pyrazine. | 1.55 LCMS [M + H]+ = 413.31 | 221Ci | F |
| 419 | 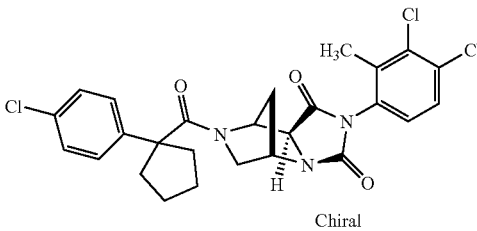<br>Chiral | [5S-(5α,8α,8aβ)]-2-(3-Chloro-4-cyano-2-methylphenyl)--7-[[1-(4-chlorophenyl)cyclopentyl]-carbonyl]octahydro-1,3-dioxo-5,8-methanoimidazo[1,5-a]pyrazine | 2.00 LCMS [M + H]+ = 523.14 | 221Ci | E |
| 420 | 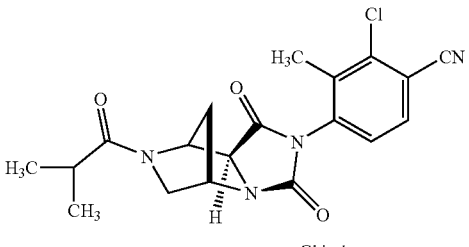<br>Chiral | [5S-(5α,8α,8aβ)]-2-(3-Chloro-4-cyano-2-methylphenyl)-octahydro-7-(2-methyl-1-oxopropyl)-1,3-dioxo-5,8-methanoimidazo[1,5-a]pyrazine. | 1.40 LCMS [M + H]+ = 387.20 | 221Ci | F |

-continued

| | | | | | |
|---|---|---|---|---|---|
| 421 | 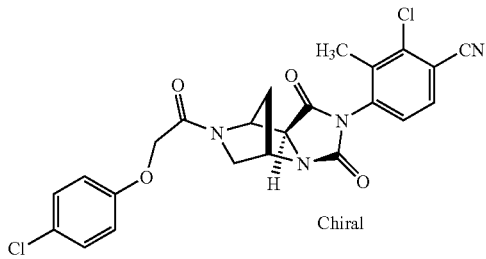 Chiral | [5S-(5α,8α,8aβ)]-2-(3-Chloro-4-cyano-2-methylphenyl)-7-[(4-chlorophenoxy)-acetyl]octahydro-1,3-dioxo-5,8-methanoimidazo[1,5-a]pyrazine. | 1.75 LCMS [M + H]$^+$ = 485.11 | 221Ci | F |
| 422 | 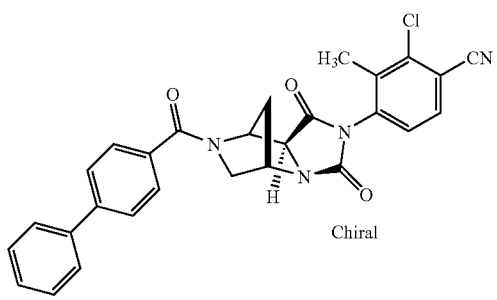 Chiral | [5S-(5α,8α,8aβ)]-7-([1,1'-Biphenyl]-4-ylcarbonyl)-2-(3-chloro-4-cyano-2-methylphenyl)-octahydro-1,3-dioxo-5,8-methanoimidazo[1,5-a]pyrazine. | 1.87 LCMS [M + H]$^+$ = 497.16 | 221Ci | E |
| 423 | 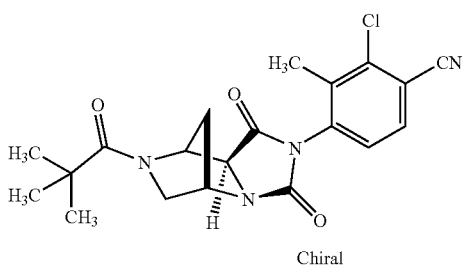 Chiral | [5S-(5α,8α,8aβ)]-2-(3-Chloro-4-cyano-2-methylphenyl)-7-(2,2-dimethyl-1-oxopropyl)octahydro-1,3-dioxo-5,8-methanoimidazo[1,5-a]pyrazine. | 1.56 LCMS [M + H]$^+$ = 401.22 | 221Ci | E |
| 424 | 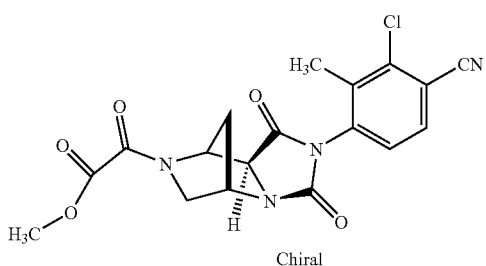 Chiral | [5S-(5α,8α,8aβ)]-2-(3-Chloro-4-cyano-2-methylphenyl)-hexahydro-alpha, 1,3-trioxo-5,8-methanoimidazo[1,5-a]pyrazine-7(1H)-acetic acid, methyl ester. | 1.32 LCMS [M + H]$^+$ = 403.15 | 221Ci | E |
| 425 | 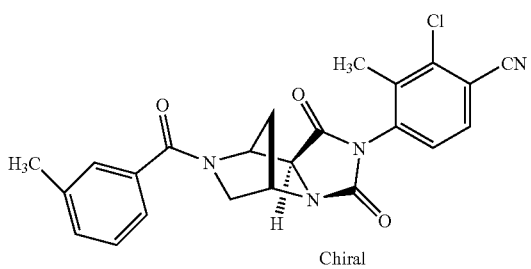 Chiral | [5S-(5α,8α,8aβ)]-2-(3-Chloro-4-cyano-2-methylphenyl)-octahydro-7-(3-methylbenzoyl)-1,3-dioxo-5,8-methanoimidazo[1,5-a]pyrazine. | 1.65 LCMS [M + H]$^+$ = 435.16 | 221Ci | E |

| | | | | | |
|---|---|---|---|---|---|
| 426 | 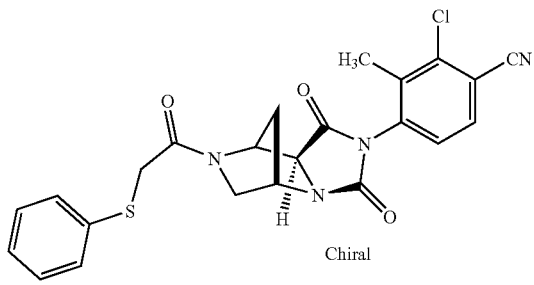 | [5S-(5α,8α,8aβ)]-2-(3-Chloro-4-cyano-2-methylphenyl)-octahydro-1,3-dioxo-7-[(phenylthio)acetyl]-5,8-methanoimidazo[1,5-a]pyrazine. | 1.66 LCMS $[M + H]^+$ = 467.10 | 221Ci | F |
| 427 | 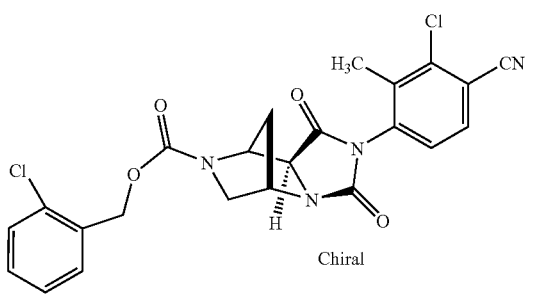 | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carboxylic acid, (2-chlorophenyl)methyl ester. | 1.82 LCMS $[M + H]^+$ = 485.06 | 221Cii | E |
| 428 | 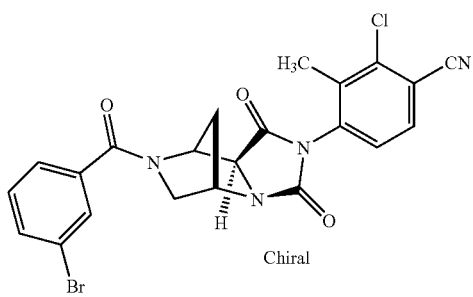 | [5S-(5α,8α,8aβ)]-7-(3-(Bromobenzoyl)-2-(3-chloro-4-cyano-2-methylphenyl)-octahydro-1,3-dioxo-5,8-methanoimidazo[1,5-a]pyrazine. | 1.72 LCMS $[M + H]^+$ = 501.01 | 221Ci | E |
| 429 | 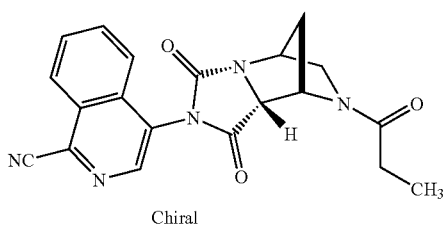 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, methyl ester. | 1.21 LCMS $[M + H]^+$ = 378.19 | 221Cii | C |
| 430 | 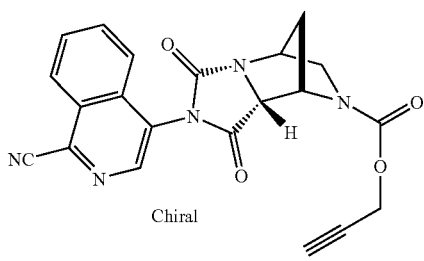 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, 2-propynyl ester. | 1.23 LCMS $[M + H]^+$ = 402.18 | 221Cii | C |

-continued

| | | | | | |
|---|---|---|---|---|---|
| 431 | 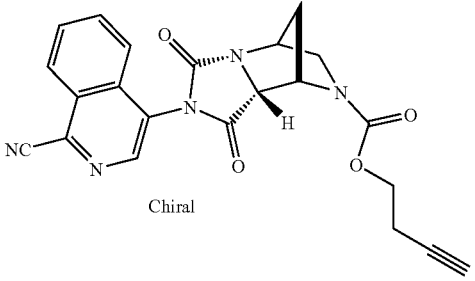 Chiral | [5S-(5α,8α,8aα)]-2-(1-Cyano-4-isoquinolinyl) hexahydro-1,3-dioxo-5,8-methanoimidazo[1,5-a]pyrazine-7(1H)-carboxylic acid, 3-butynyl ester. | 1.35 LCMS [M + H]$^+$ = 416.18 | 221Cii | C |
| 432 | 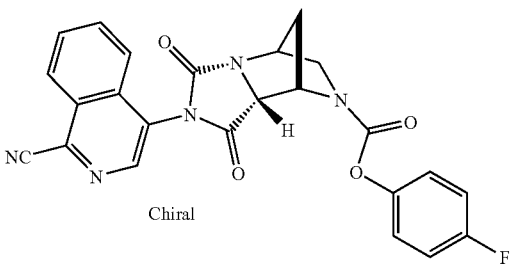 Chiral | [5S-(5α,8α,8aα)]-2-(1-Cyano-4-isoquinolinyl) hexahydro-1,3-dioxo-5,8-methanoimidazo[1,5-a]pyrazine-7(1H)-carboxylic acid, 4-fluorophenyl ester. | 1.59 LCMS [M + H]$^+$ = 458.23 | 221Cii | C |
| 433 | 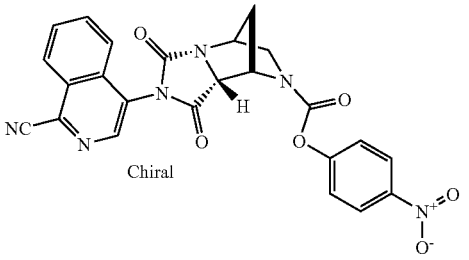 Chiral | [5S-(5α,8α,8aα)]-2-(1-Cyano-4-isoquinolinyl) hexahydro-1,3-dioxo-5,8-methanoimidazo[1,5-a]pyrazine-7(1H)-carboxylic acid, 4-nitrophenyl ester. | 1.57 LCMS [M + H]$^+$ = 485.23 | 221Cii | C |
| 434 | 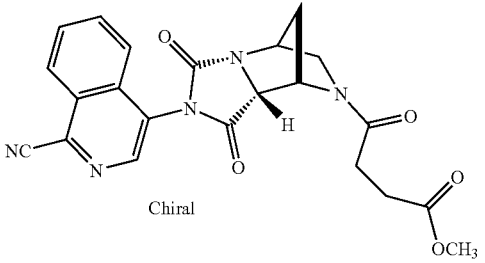 Chiral | [5S-(5α,8α,8aα)]-2-(1-Cyano-4-isoquinolinyl) hexahydro-gamma, 1,3-trioxo-5,8-methanoimidazo[1,5-a]pyrazine-7(1H)butanoic acid, methyl ester. | 1.20 LCMS [M + H]$^+$ = 434.20 | 221Ci | C |
| 435 | 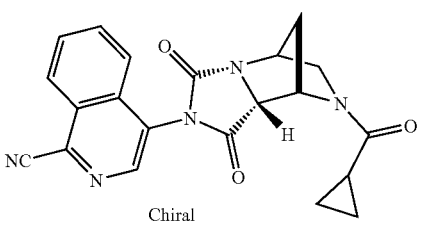 Chiral | [5S-(5α,8α,8aα)]-2-(1-Cyano-4-isoquinolinyl)-7-(cyclopropylcarbonyl) octahydro-1,3-dioxo-5,8-methanoimidazo[1,5-a]pyrazine. | 1.21 LCMS [M + H]$^+$ = 388.21 | 221Ci | C |
| 436 | 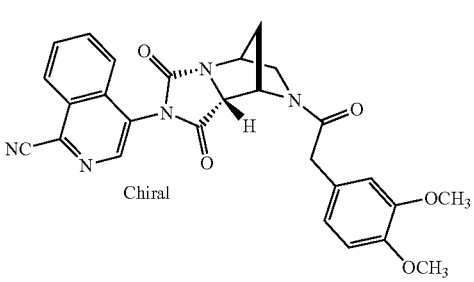 Chiral | [5S-(5α,8α,8aα)]-2-(1-Cyano-4-isoquinolinyl)-7-[(3,4-dimethoxyphenyl)-acetyl]octahydro-1,3-dioxo-5,8-methanoimidazo[1,5-a]pyrazine. | 1.37 LCMS [M + H]$^+$ = 498.25 | 221Ci | C |

| | | | | |
|---|---|---|---|---|
| 437 | | [5S-(5α,8α,8aα)]-2-(1-Cyano-4-isoquinolinyl) hexahydro-1,3-dioxo-5,8-methanoimidazo[1,5-a]pyrazine-7(1H)-carboxylic acid, (1S,2R,5S)-5-methyl-2-(1-methylethyl)-cyclohexyl ester. | 2.03 LCMS [M + H]⁺ = 502.32 | 221Cii D |
| 438 | | [5S-(5α,8α,8aβ)]-2-(1-Cyano-4-isoquinolinyl)-7-(3,5-difluorobenzoyl)-octahydro-1,3-dioxo-5,8-methanoimidazo[1,5-a]pyrazine. | 1.54 LCMS [M + H]⁺ = 460.22 | 221Ci C |
| 439 | | [5S-(5α,8α,8aβ)]-2-(1-Cyano-4-isoquinolinyl) octahydro-7-[(3-methoxyphenyl)-acetyl]-1,3-dioxo-5,8-methanoimidazo[1,5-a]pyrazine. | 1.51 LCMS [M + H]⁺ = 468.28 | 221Ci C |
| 440 | | [5S-(5α,8α,8aβ)]-2-(1-Cyano-4-isoquinolinyl) octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.06 LCMS LCMS [M + H]⁺ = 716.14 | 221Ci C |
| 441 | | [5S-(5α,8α,8aβ)]-2-(1-Cyano-4-isoquinolinyl)-7-(diphenylacetyl)-octahydro-1,3-dioxo-5,8-methanoimidazo[1,5-a]pyrazine. | 1.79 LCMS [M + H]⁺ = 514.21 | 221Ci C |
| 442 | | [5S-(5α,8α,8aβ)]-2-(1-Cyano-4-isoquinolinyl) hexahydro-1,3-dioxo-5,8-methanoimidazo[1,5-a]pyrazine-7(1H)-carboxylic acid, 1-methylethyl ester. | 1.43 LCMS [M + H]⁺ = 406.20 | 221Cii C |

| | | | | | |
|---|---|---|---|---|---|
| 443 | 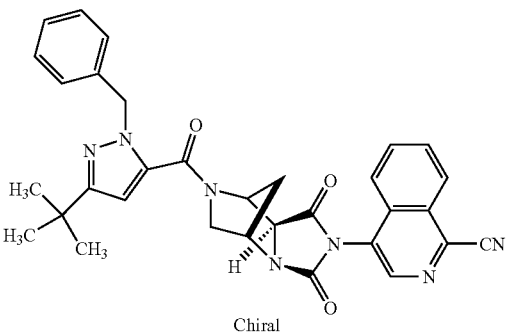 Chiral | [5S-(5α,8α,8aβ)]-2-(1-Cyano-4-isoquinolinyl)-7-[[3-(1,1-dimethylethyl)-1-(phenylmethyl)-1H-pyrazol-5-yl]carbonyl]octahydro-1,3-dioxo-5,8-methanoimidazo[1,5-a]pyrazine. | 1.93 LCMS $[M + H]^+ =$ 560.35 | 221Ci | C |
| 444 | 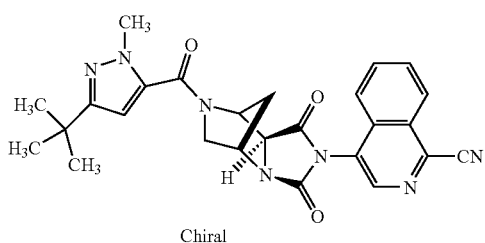 Chiral | [5S-(5α,8α,8aβ)]-2-(1-Cyano-4-isoquinolinyl)-7-[[3-(1,1-dimethylethyl)-1-methyl-1H-pyrazol-5-yl]carbonyl]-octahydro-1,3-dioxo-5,8-methanoimidazo[1,5-a]pyrazine. | 1.69 LCMS $[M + H]^+ =$ 484.28 | 221Ci | C |
| 445 | 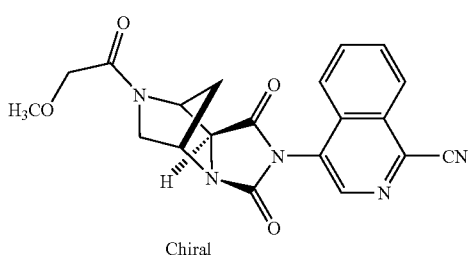 Chiral | [5S-(5α,8α,8aβ)]-2-(1-Cyano-4-isoquinolinyl)octahydro-7-(methoxyacetyl)-1,3-dioxo-5,8-methanoimidazo[1,5-a]pyrazine. | 1.07 LCMS $[M + H]^+ =$ 392.19 | 221Ci | C |
| 446 | 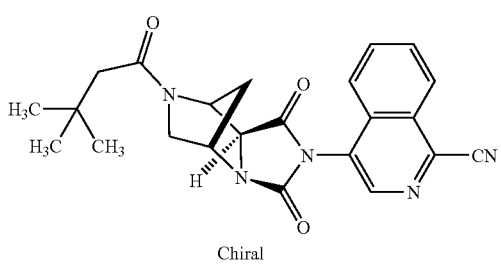 Chiral | [5S-(5α,8α,8aβ)]-2-(1-Cyano-4-isoquinolinyl)-7-(3,3-dimethyl-1-oxobutyl)octahydro-1,3-dioxo-5,8-methanoimidazo[1,5-a]pyrazine. | 1.58 LCMS $[M + H]^+ =$ 418.21 | 221Ci | C |
| 447 | 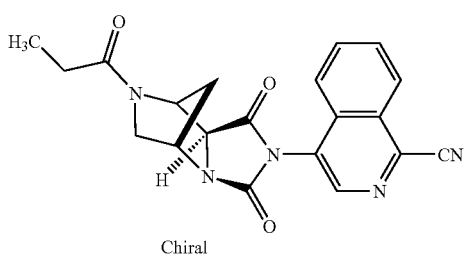 Chiral | [5S-(5α,8α,8aβ)]-2-(1-Cyano-4-isoquinolinyl)octahydro-1,3-dioxo-7-(1-oxopropyl)-5,8-methanoimidazo[1,5-a]pyrazine. | 1.20 LCMS $[M + H]^+ =$ 376.22 | 221Ci | C |

-continued

| | | | | | |
|---|---|---|---|---|---|
| 448 | 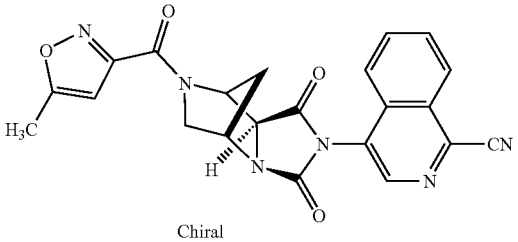 Chiral | [5S-(5α,8α,8aβ)]-2-(1-Cyano-4-isoquinolinyl) octahydro-7-[(5-methyl-3-isoxazolyl)-carbonyl]-1,3-dioxo-5,8-methanoimidazo[1,5-a]pyrazine. | 1.32 LCMS [M + H]+ = 429.17 | 221Ci | C |
| 449 | 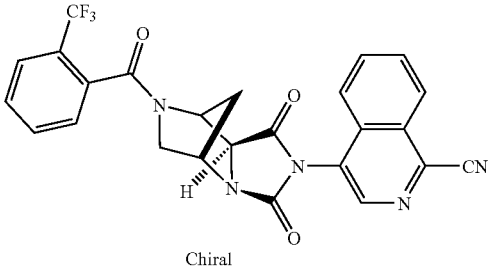 Chiral | [5S-(5α,8α,8aβ)]-2-(1-Cyano-4-isoquinolinyl) octahydro-1,3-dioxo-7-[2-(trifluoromethyl)-benzoyl]-5,8-methanoimidazo[1,5-a]pyrazine. | 1.50 LCMS [M + H]+ = 492.19 | 221Ci | C |
| 450 | 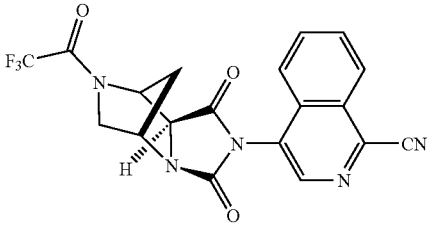 Chiral | [5S-(5α,8α,8aβ)]-2-(1-Cyano-4-isoquinolinyl) octahydro-1,3-dioxo-7-(trifluoroacetyl)-5,8-methanoimidazo[1,5-a]pyrazine. | 1.36 LCMS [M + H]+ = 416.13 | 221Ci | C |
| 451 | 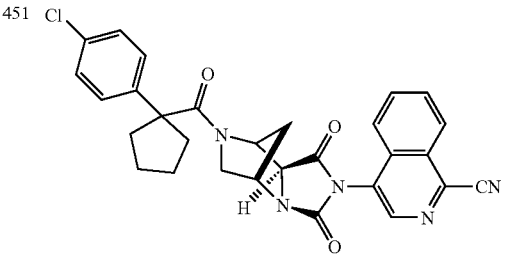 Chiral | [5S-(5α,8α,8aβ)]-7-[[1-(4-Chlorophenyl)-cyclopentyl]carbonyl]-2-(1-cyano-4-isoquinolinyl) octahydro-1,3-dioxo-5,8-methanoimidazo[1,5-a]pyrazine. | 1.89 LCMS [M + H]+ = 526.20 | 221Ci | C |
| 452 | 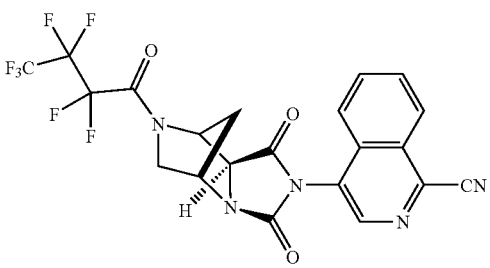 Chiral | [5S-(5α,8α,8aβ)]-2-(1-Cyano-4-isoquinolinyl)-7-(2,2,3,3,4,4,4-heptafluoro-1-oxobutyl)octahydro-1,3-dioxo-5,8-methanoimidazo[1,5-a]pyrazine. | 1.74 LCMS [M + H]+ = 516.12 | 221Ci | C |

-continued

| | | | | | |
|---|---|---|---|---|---|
| 453 | 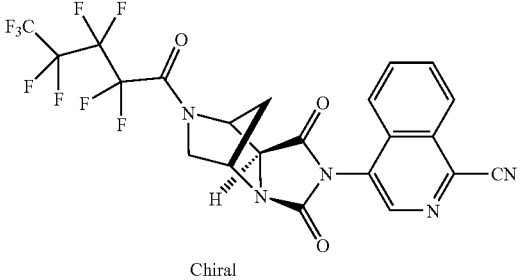<br>Chiral | [5S-(5α,8α,8aβ)]-2-(1-Cyano-4-isoquinolinyl) octahydro-7-(2,2,3,3,4,4,5,5,5-nonafluoro-1-oxopentyl)-1,3-dioxo-5,8-methanoimidazo[1,5-a]pyrazine. | 1.85 LCMS [M + H]$^+$ = 566.20 | 221Ci | C |
| 454 | 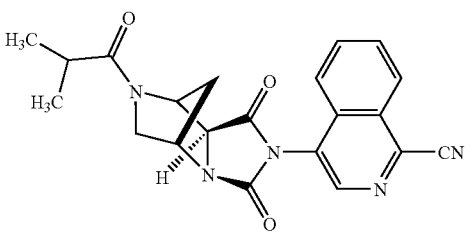<br>Chiral | [5S-(5α,8α,8aβ)]-2-(1-Cyano-4-isoquinolinyl) octahydro-7-(2-methyl-1-oxopropyl)-1,3-dioxo-5,8-methanoimidazo[1,5-a]pyrazine. | 1.32 LCMS [M + H]$^+$ = 390.22 | 221Ci | C |
| 455 | 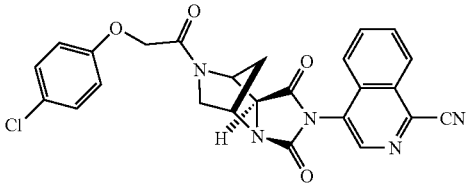<br>Chiral | [5S-(5α,8α,8aβ)]-7-[(4-Chlorophenoxy)acetyl]-2-(1-cyano-4-isoquinolinyl) octahydro-1,3-dioxo-5,8-methanoimidazo[1,5-a]pyrazine. | 1.68 LCMS [M + H]$^+$ = 488.18 | 221Ci | C |
| 456 | 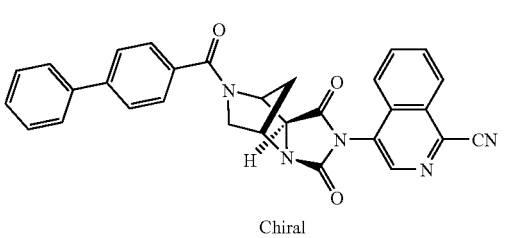<br>Chiral | [5S-(5α,8α,8aβ)]-7-([1,1'-Biphenyl]-4-ylcarbonyl)-2-(1-cyano-4-isoquinolinyl) octahydro-1,3-dioxo-5,8-methanoimidazo[1,5-a]pyrazine. | 1.80 LCMS [M + H]$^+$ = 500.22 | 221Ci | C |
| 457 | 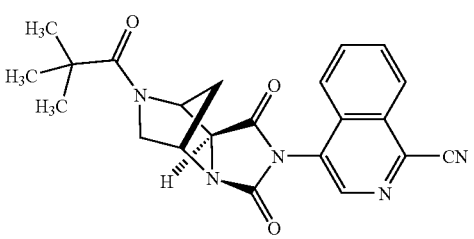<br>Chiral | [5S-(5α,8α,8aβ)]-2-(1-Cyano-4-isoquinolinyl)-7-(2,2-dimethyl-1-oxopropyl)octahydro-1,3-dioxo-5,8-methanoimidazo[1,5-a]pyrazine. | 1.43 LCMS [M + H]$^+$ = 404.22 | 221Ci | C |
| 458 | 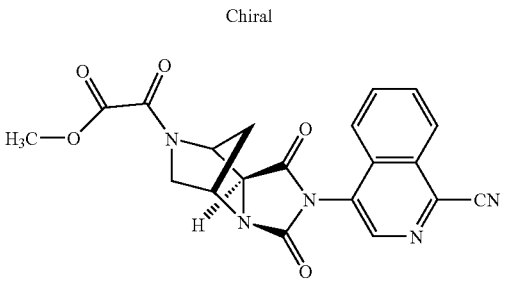<br>Chiral | [5S-(5α,8α,8aβ)]-2-(1-Cyano-4-isoquinolinyl) hexahydro-alpha,1,3-trioxo-5,8-methanoimidazo[1,5-a]pyrazine-7(1H)-acetic acid, methyl ester | 1.12 LCMS [M + H]$^+$ = 406.15 | 221Ci | C |

-continued

| | | | | | |
|---|---|---|---|---|---|
| 459 | | [5S-(5α,8α,8aβ)]-2-(1-Cyano-4-isoquinolinyl) octahydro-7-(3-methylbenzoyl)-1,3-dioxo-5,8-methanoimidazo[1,5-a]pyrazine. | 1.53 LCMS [M + H]$^+$ = 438.19 | 221Ci | C |
| 460 | | [5S-(5α,8α,8aβ)]-2-(1-Cyano-4-isoquinolinyl) octahydro-1,3-dioxo-7-[(phenylthio)acetyl]-5,8-methanoimidazo[1,5-a]pyrazine. | 1.55 LCMS [M + H]$^+$ = 470.22 | 221Ci | C |
| 461 | | [5S-(5α,8α,8aβ)]-2-(1-Cyano-4-isoquinolinyl) hexahydro-1,3-dioxo-5,8-methanoimidazo[1,5-a]pyrazine-7(1H)-carboxylic acid, (2-chlorophenyl) methyl ester. | 1.80 LCMS [M + H]$^+$ = 488.18 | 221Cii | C |
| 462 | | [5S-(5α,8α,8aβ)]-2-(1-Cyano-4-isoquinolinyl) hexahydro-N-(2-methylpropyl)-1,3-dioxo-5,8-methanoimidazo[1,5-a]pyrazine-7(1H)-carbothioamide. | 1.57 LCMS [M + H]$^+$ = 435.21 | 221Bi | C |
| 463 | | [5S-(5α,8α,8aβ)]-2-(1-Cyano-4-isoquinolinyl) hexahydro-1,3-dioxo-N-2-propynyl-5,8-methanoimidazo[1,5-a]pyrazine-7(1H)-carbothioamide. | 1.11 LCMS [M + H]$^+$ = 417.13 | 221Bi | C |
| 464 | | [5S-(5α,8α,8aβ)]-2-(1-Cyano-4-isoquinolinyl)-N-(2,6-difluorophenyl)-hexahydro-1,3-dioxo-5,8-methanoimidazo[1,5-a]pyrazine-7(1H)-carbothioamide. | 1.51 LCMS [M + H]$^+$ = 491.17 | 221Bi | C |

-continued

| | | | | | |
|---|---|---|---|---|---|
| 465 | (structure) Chiral | [5S-(5α,8α,8aβ)]-2-(1-Cyano-4-isoquinolinyl)hexahydro-N-[3-(4-morpholinyl)propyl]-1,3-dioxo-5,8-methanoimidazo[1,5-a]pyrazine-7(1H)-carbothioamide. | 1.18 LCMS $[M + H]^+$ = 506.25 | 221Bi | C |
| 466 | (structure) Chiral | [5S-(5α,8α,8aβ)]-2-(1-Cyano-4-isoquinolinyl)-N-[2-(3,4-dimethoxyphenyl)ethyl]hexahydro-1,3-dioxo-5,8-methanoimidazo[1,5-a]pyrazine-7(1H)-carbothioamide. | 1.70 LCMS $[M + H]^+$ = 543.26 | 221Bi | C |
| 467 | (structure) Chiral | [5S-(5α,8α,8aβ)]-N-1,3-Benzodioxol-5-yl-2-(1-cyano-4-isoquinolinyl)hexahydro-1,3-dioxo-5,8-methanoimidazo[1,5-a]pyrazine-7(1H)-carbothioamide. | 1.47 LCMS $[M + H]^+$ = 499.17 | 221Bi | C |
| 468 | (structure) Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, methyl ester. | 1.01 LCMS $[M + H]^+$ = 342.15 | 221Cii | C |
| 469 | (structure) Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, 2-propynyl ester. | 1.07 LCMS $[M + H]^+$ = 366.20 | 221Cii | C |
| 470 | (structure) Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, 3-butynyl ester. | 1.17 LCMS $[M + H]^+$ = 380.21 | 221Cii | C |

| | | | | | |
|---|---|---|---|---|---|
| 471 | 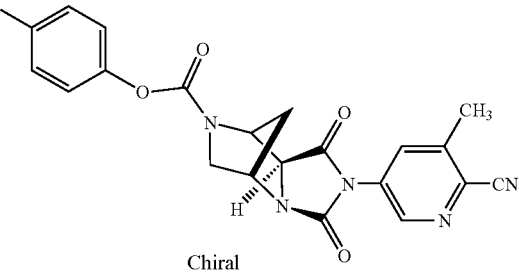 Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, 4-fluorophenyl ester. | 1.45 LCMS [M + H]$^+$ = 422.13 | 221Cii | C |
| 472 | 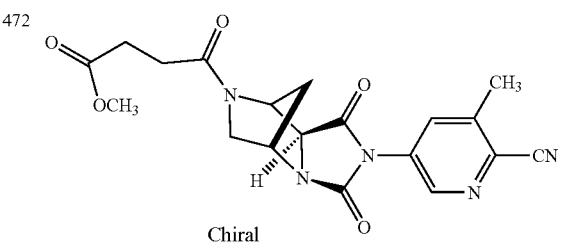 Chiral | [5S-(5α,8α,8aβ)]-2-(6-Cyano-5-methyl-3-pyridinyl)hexahydro-gamma,1,3-trioxo-5,8-methanoimidazo[1,5-a]pyrazine-7(1H)-butanoic acid, methyl ester. | 1.02 LCMS [M + H]$^+$ = 398.20 | 221Ci | C |
| 473 | 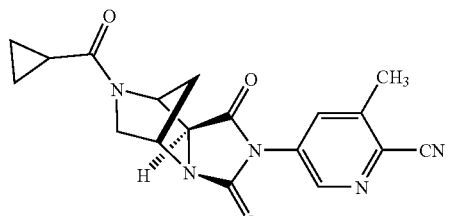 Chiral | [5S-(5α,8α,8aβ)]-2-(6-Cyano-5-methyl-3-pyridinyl)-7-(cyclo-propylcarbonyl)-octahydro-1,3-dioxo-5,8-methanoimidazo[1,5-a]pyrazine. | 1.00 LCMS [M + H]$^+$ = 352.19 | 221Ci | C |
| 474 | 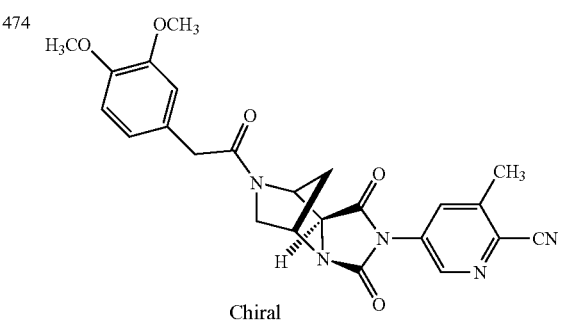 Chiral | [5S-(5α,8α,8aβ)]-2-(6-Cyano-5-methyl-3-pyridinyl)-7-[(3,4-dimethoxyphenyl)acetyl]-octahydro-1,3-dioxo-5,8-methanoimidazo[1,5-a]pyrazine. | 1.16 LCMS [M + H]$^+$ = 462.26 | 221Ci | C |
| 475 | 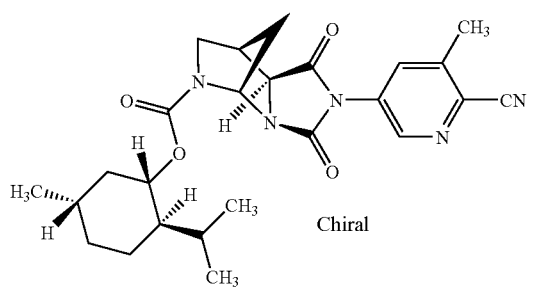 Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, (1S,2R,5S)-5-methyl-2-(1-methylethyl)cyclohexyl ester. | 1.96 LCMS [M + H]$^+$ = 466.34 | 221Cii | D |

-continued

| | | | | | |
|---|---|---|---|---|---|
| 476 | 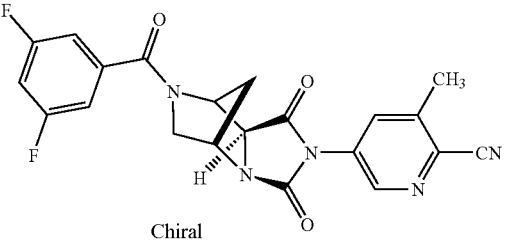 Chiral | [5S-(5α,8α,8aβ)]-2-(6-Cyano-5-methyl-3-pyridinyl)-7-(3,5-difluorobenzoyl)octahydro-1,3-dioxo-5,8-methanoimidazo[1,5-a]pyrazine. | 1.39 LCMS [M + H]$^+$ = 424.14 | 221Ci | C |
| 477 | 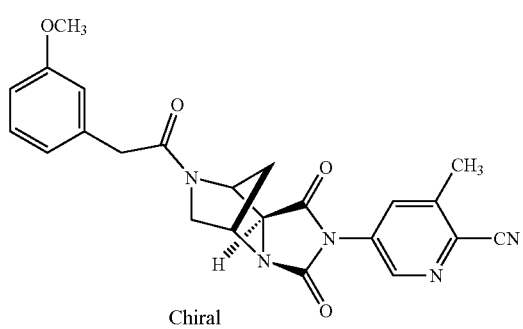 Chiral | [5S-(5α,8α,8aβ)]-2-(6-Cyano-5-methyl-3-pyridinyl)octahydro-7-[(3-methoxy-phenyl)acetyl]-1,3-dioxo-5,8-methanoimidazo[1,5-a]pyrazine. | 1.31 LCMS [M + H]$^+$ = 432.20 | 221Ci | C |
| 478 | 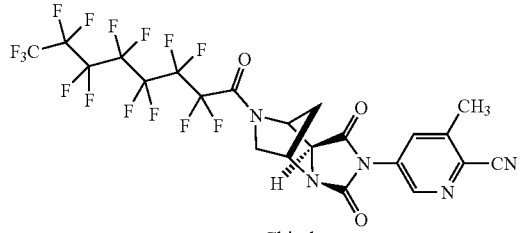 Chiral | [5S-(5α,8α,8aβ)]-2-(6-Cyano-5-methyl-3-pyridinyl)octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.01 LCMS [M + H]$^+$ = 680.15 | 221Ci | C |
| 479 | 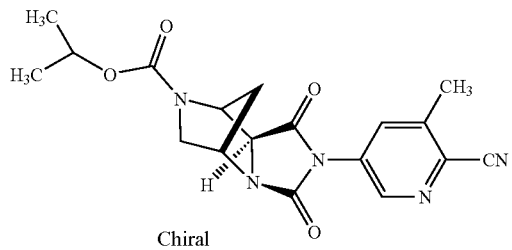 Chiral | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, 1-methylethyl ester. | 1.30 LCMS [M + H]$^+$ = 370.22 | 221Cii | C |
| 480 | 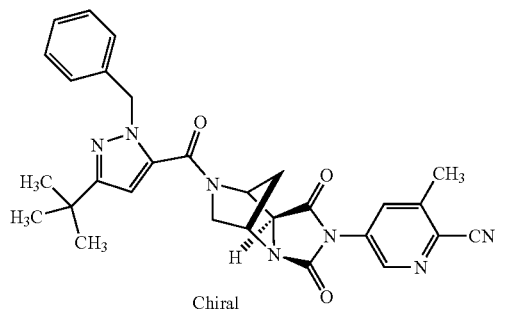 Chiral | [5S-(5α,8α,8aβ)]-2-(6-Cyano-5-methyl-3-pyridinyl)-7-[[3-(1,1-dimethylethyl)-1-(phenylmethyl)-1H-pyrazol-5-yl]carbonyl]octahydro-1,3-dioxo-5,8-methanoimidazo[1,5-a]pyrazine. | 1.82 LCMS [M + H]$^+$ = 524.27 | 221Ci | C |

| | | | | | |
|---|---|---|---|---|---|
| 481 | 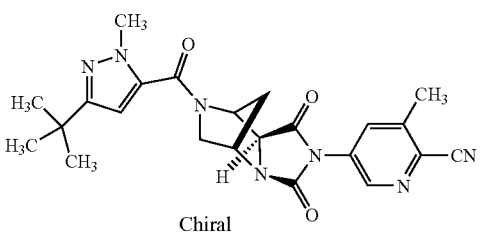 Chiral | [5S-(5α,8α,8aβ)]-2-(6-Cyano-5-methyl-3-pyridinyl)-7-[[3-(1,1-dimethylethyl)-1-methyl-1H-pyrazol-5-yl]carbonyl]-octahydro-1,3-dioxo-5,8-methanoimidazo[1,5-a]pyrazine. | 1.57 LCMS [M + H]⁺ = 448.26 | 221Ci | C |
| 482 | 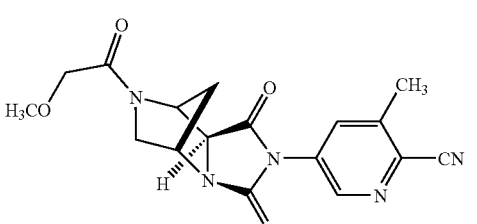 Chiral | [5S-(5α,8α,8aβ)]-2-(6-Cyano-5-methyl-3-pyridinyl)octahydro-7-(methoxyacetyl)-1,3-dioxo-5,8-methanoimidazo[1,5-a]pyrazine. | 0.89 LCMS [M + H]⁺ = 356.20 | 221Ci | C |
| 483 | 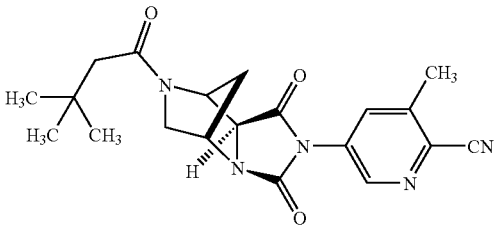 Chiral | [5S-(5α,8α,8aβ)]-2-(6-Cyano-5-methyl-3-pyridinyl)-7-(3,3-dimethyl-1-oxobutyl)octahydro-1,3-dioxo-5,8-methanoimidazo[1,5-a]pyrazine. | 1.41 LCMS [M + H]⁺ = 382.26 | 221Ci | C |
| 484 | 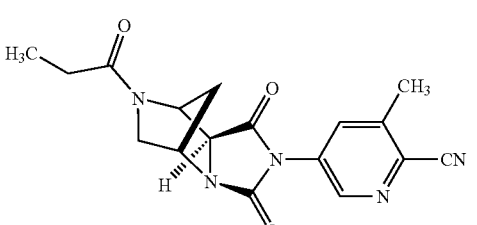 Chiral | [5S-(5α,8α,8aβ)]-2-(6-Cyano-5-methyl-3-pyridinyl)octahydro-1,3-dioxo-7-(1-oxopropyl)-5,8-methanoimidazo[1,5-a]pyrazine. | 0.97 LCMS [M + H]⁺ = 340.17 | 221Ci | C |
| 485 | 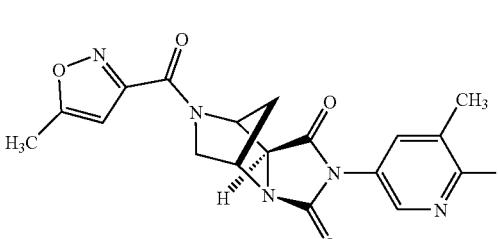 Chiral | [5S-(5α,8α,8aβ)]-2-(6-Cyano-5-methyl-3-pyridinyl)octahydro-7-[(5-methyl-3-isoxazolyl)carbonyl]-1,3-dioxo-5,8-methanoimidazo[1,5-a]pyrazine. | 1.12 LCMS [M + H]⁺ = 393.19 | 221Ci | D |

-continued

| | | | | | |
|---|---|---|---|---|---|
| 486 | 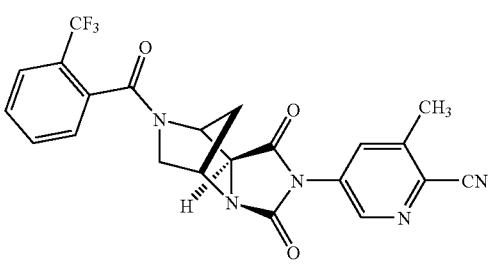 Chiral | [5S-(5α,8α,8aβ)]-2-(6-Cyano-5-methyl-3-pyridinyl)octahydro-1,3-dioxo-7-[2-(trifluoromethyl)-benzoyl]-5,8-methanoimidazo[1,5-a]pyrazine. | 1.46 LCMS [M + H]⁺ = 456.20 | 221Ci | C |
| 487 | 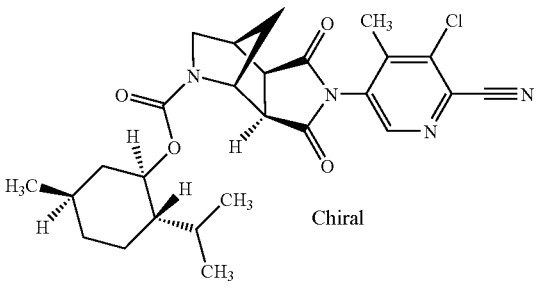 Chiral | [5S-(5α,8α,8aβ)]-2-(3-Chloro-4-cyano-2-methylphenyl)-hexahydro-1,3-dioxo-5,8-methanoimidazo[1,5-a]pyrazine-7(1H)-carboxylic acid, 5-methyl-2-(1-methylethyl)cyclohexyl ester. | 2.13 LCMS [M + H]⁺ = 521.21 | 221Cii | E |
| 488 | 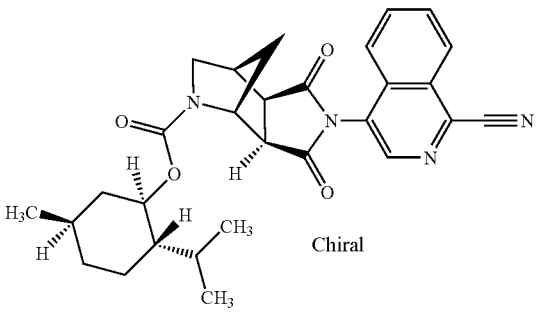 Chiral | [5S-(5α,8α,8aβ)]-2-(1-Cyano-4-isoquinolinyl)hexahydro-1,3-dioxo-5,8-methanoimidazo[1,5-a]pyrazine-7(1H)-carboxylic acid, 5-methyl-2-(1-methylethyl)cyclohexyl ester. | 2.05 LCMS [M + H]⁺ = 502.30 | 221Cii | C |
| 489 | 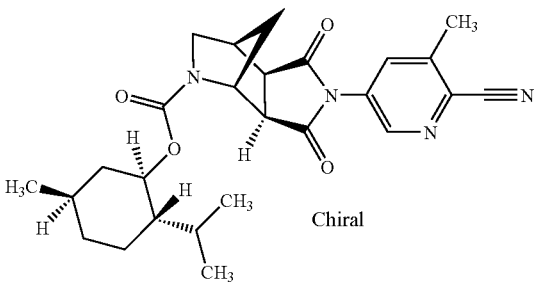 Chiral | [5S-(5α,8α,8aβ)]-2-(6-Cyano-5-methyl-3-pyridinyl)-hexahydro-1,3-dioxo-5,8-methanoimidazo[1,5-a]pyrazine-7(1H)-carboxylic acid, (1R,2S,5R)-5-methyl-2-(1-methylethyl)-cyclohexyl ester. | 1.94 LCMS [M + H]⁺ = 466.33 | 221Cii | D |
| 490 | 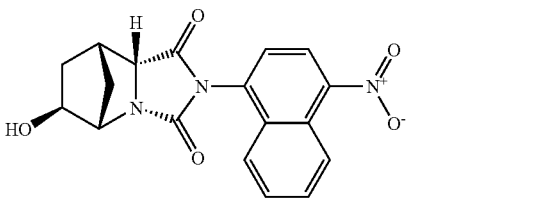 | (5α,6α,8α,8aα)-Tetrahydro-6-hydroxy-2-(4-nitro-1-naphthalenyl)-5,8-methanoimidazo[1,5-a]pyridine-1,3(2H,5H)-dione | LCMS [M + H]⁺ = | 222i | G |

| 491 | 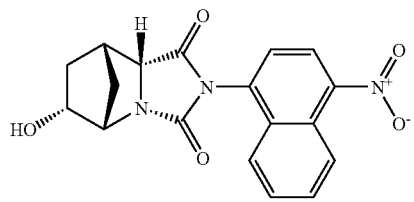 | (5α,6β,8α,8aα)-Tetrahydro-6-hydroxy-2-(4-nitro-1-naphthalenyl)-5,8-methanoimidazo[1,5-a]pyridine-1,3(2H,5H)-dione | LCMS [M + H]$^+$ = | 222ii | G |

We claim:

1. A compound having the formula (Ia) or (Ib):

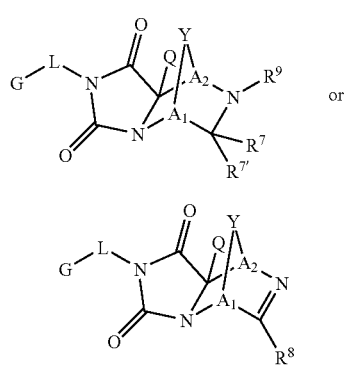

or a pharmaceutically acceptable salt thereof;
wherein the symbols have the following meanings and are, for each occurrence, independently selected:

G is an aryl, substituted aryl, heterocyclo group, or substituted heterocyclo group, where said group is mono- or polycyclic;

$A_1$ is $CR^7$;

$A_2$ is $CR^7$;

Y is $(CR^7R^{7'})_n$ and n=1 or 2;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo, halo, CN, —C(=O)OR$^1$, —C(=O)R$^4$, —C(=O)NR$^5$R$^6$, —C(R$^7$R$^{7'}$)—OH, nitro, —(CH$_2$)—OR$^1$, —OR$^1$, —C(=O)SR$^1$, —SO$_2$R$^1$, —NH$_2$, or NR$^4$R$^5$;

L is a bond, $(CR^7R^{7'})_n$, NH, NR$^5$ or N(CR$^7$R$^{7'})_n$, where n=0-2;

R$^1$ and R$^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, and/or arylalkyl or substituted arylalkyl, provided, however, that R$^1$ and R$^{1'}$ are not hydrogen when attached to —SO$_2$O— or SO$_2$—;

R$^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloal kylalkyl, cycloalkenylal kyl or substituted cycloalkenylalkyl, heterocycloal kyl or substituted heterocycloalkyl, aryl or substituted aryl, or arylalkyl or substituted arylalkyl;

R$^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloal kylalkyl, cycloalkenylal kyl or substituted cycloalkenylalkyl, heterocycloal kyl or substituted heterocycloalkyl, aryl or substituted aryl, arylalkyl or substituted arylalkyl, —C(=O)R$^1$, —C(=O)OR$^1$, —C(=O)NHR$^1$, —SO$_2$OR$^1$, —SO$_2$R$^1$ or —SO$_2$NR$^1$R$^1$;

R$^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloal kylalkyl, cycloalkenylal kyl or substituted cycloalkenylalkyl, heterocycloal kyl or substituted heterocycloalkyl, aryl or substituted aryl, arylalkyl or substituted arylalkyl, —C(=O)R$^1$, —C(=O)NHR$^1$, —SO$_2$OR$^1$, —SO$_2$R$^1$ or —SO$_2$NR$^1$R$^1$;

R$^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloal kylalkyl, cycloalkenylal kyl or substituted cycloalkenylalkyl, heterocycloal kyl or substituted heterocycloalkyl, aryl or substituted aryl, arylalkyl or substituted arylalkyl, CN, —OR$^1$, —C(=O)R$^1$, —C(=O)NHR$^1$, —SO$_2$R$^1$, —SO$_2$OR1 or —SO$_2$NR$^1$ R$^{1'}$;

R$^7$ and R$^{7'}$ are each independently at each occurrence H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylal kyl or substituted cycloalkylal kyl, cycloalkenylal kyl or substituted cycloalkenylalkyl, heterocycloalkyl or substituted heterocycloalkyl, aryl or substituted aryl, arylalkyl or substituted arylalkyl, halo, CN, OR$^1$, nitro, hydroxylamine, hydroxylamide, NHR$^4$, —NR$^2$R$^5$, —NHOR$^1$, thiol, alkylthio or substituted alkylthio, —C(=O)R$^1$, —OC(=O)R$^1$, —C(=O)OR$^1$, —PO$_3$R$^1$ R$^{1'}$, —C(=O)NR$^1$ R$^{1'}$, —C(=O)SR$^1$, —C(=O)NHSO$_2$R$^1$, —SOR$^1$, —SO$_2$R$^1$, —SO$_2$OR$^1$ and/or —SO$^2$NR$^1$ R$^{1'}$;

or two groups R$^7$ and R$^{7'}$ attached to the same carbon atom may be joined to form a spiro ring, or groups R$^7$ and R$^{7'}$ attached to two adjacent carbon atoms may be joined to form a fused, optionally-substituted monocyclic or bicyclic heterocyclic or carbocyclic ring;

$R^8$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, $OR^1$, nitro, $NHR^4$, $-NR^2R^5$, $-NHOR^1$, alkylthio or substituted alkylthio, $-C(=O)R^1$, $-OC(=O)R^1$, $-C(=O)OR^1$, $-PO_3R^1R^{1\prime}$, $-C(=O)NR^1R^{1\prime}$, $-C(=O)SR^1$, $-C(=O)NHSO_2R^1$, $-SOR^1$, $-SO_2R^1$, $-SO_2OR^1$, or $-SO_2NR^1R^{1\prime}$;

$R^9$ is selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, $OR^1$, $-C(=O)R^1$, $-C(=O)OR^1$, $-C(=O)NR^1R^{1\prime}$, $SO_2R^1$, $-SO_2OR^1$ and $-SO_2NR^1R^{1\prime}$;

wherein substituted alkyl, substituted cycloalkyl, substituted cycloalkylalkyl, substituted alkenyl, substituted cycloalkenyl, substituted cycloalkenylalkyl, substituted alkynyl, substituted arylalkyl, substituted heterocycloalkyl, and substituted alkylthio are substituted with one or more substituents selected from alkyl, halo, alkoxy, alkylthio, hydroxy, $-C(=O)OH$, alkoxycarbonyl, alkylcarbonyloxy, $-NH_2$, carbamoyl, carbamate, urea, amidinyl, thiol, aryl, heterocycle, cycloalkyl, heterocycloalkyl, -S-aryl, -S-heterocycle, $-S(=O)$-aryl, $-S(=O)$-heterocycle, $-S(=O)_2$-aryl, $-S(=O)_2$-heterocycle, $-NHS(=O)_2$-aryl, $-NHS(=O)_2$-heterocycle, $-NHS(=O)_2NH$-aryl, $-NHS(=O)_2NH$-heterocycle, -O-aryl, -O-heterocycle, $-NH$-aryl, $-NH$-heterocycle, $-NHC(=O)$-aryl, $-NHC(=O)$-heterocycle, $-OC(=O)$-aryl, $-OC(=O)$-heterocycle, $-NHC(=O)NH$-aryl, $-NHC(=O)NH$-heterocycle, $-OC(=O)O$-aryl, $-OC(=O)O$-heterocycle, $-OC(=O)NH$-aryl, $-OC(=O)NH$-heterocycle, $-NHC(=O)O$-aryl, $-NHC(=O)O$-heterocycle, $-C(=O)NH$-aryl, $-C(=O)NH$-heterocycle, $-C(=O)O$-aryl, $-C(=O)O$-heterocycle, $-N(alkyl)S(=O)_2$-aryl, -N(alkyl)S(=O)_2$- heterocycle, $-N(alkyl)S(=O)_2NH$-aryl, $N(alkyl)S(=O)_2NH$-heterocycle, $-N(alkyl)$-aryl, $-N(alkyl)$-heterocycle, $-N(alkyl)C(=O)$-aryl, $-N(alkyl)C(=O)$-heterocycle, $-N(alkyl)C(=O)NH$-aryl, $-N(alkyl)C(=O)NH$-heterocycle, $-OC(=O)N(alkyl)$-aryl, $-OC(=O)N(alkyl)$-heterocycle, $-N(alkyl)C(=O)O$-aryl, $-N(alkyl)C(=O)O$-heterocycle, $-C(=O)N(alkyl)$-aryl, $-C(=O)N(alkyl)$-heterocycle, $-NHS(=O)_2N(alkyl)$-aryl, $NHS(=O)_2N(alkyl)$-heterocycle, $-NHC(=O)N(alkyl)$-aryl, $-NHC(=O)N(alkyl)$-heterocycle, $-N(alkyl)S(=O)_2N(alkyl)$-aryl, $-N(alkyl)S(=O)_2N(alkyl)$-heterocycle, $-N(alkyl)C(=O)N(alkyl)$-aryl, and $-N(alkyl)C(=O)N(alkyl)$-heterocycle;

wherein substituted aryl and substituted heterocyclo are substituted with one or more substituents selected from alkyl, halo, $-CF_3$, cyano, nitro, alkoxy, alkylthio, hydroxy, $-C(=O)OH$, alkoxycarbonyl, alkylcarbonyloxy, $-NH_2$, carbamoyl, carbamate, urea, amidinyl, thiol, aryl, heterocycle, cycloalkyl, heterocycloalkyl, $-S$-aryl, $-S$-heterocycle, $-S(=O)$-aryl, $-S(=O)$-heterocycle, $-S(=O)_2$-aryl, $-S(=O)_2$-heterocycle, $-NHS(=O)_2$-aryl, $-NHS(=O)_2$-heterocycle, $-NHS(=O)_2NH$-aryl, $-NHS(=O)_2NH$-heterocycle, $-O$-aryl, $-O$-heterocycle, $-NH$-aryl, $-NH$-heterocycle, $-NHC(=O)$-aryl, $-NHC(=O)$-heterocycle, $-OC(=O)$-aryl, $-OC(=O)$-heterocycle, $-NHC(=O)NH$-aryl, $-NHC(=O)NH$-heterocycle, $-OC(=O)O$-aryl, $-OC(=O)O$-heterocycle, $-OC(=O)NH$-aryl, $-OC(=O)NH$-heterocycle, $-NHC(=O)O$-aryl, $-NHC(=O)O$-heterocycle, $-C(=O)NH$-aryl, $-C(=O)NH$-heterocycle, $-C(=O)O$-aryl, $-C(=O)O$-heterocycle, $-N(alkyl)S(=O)_2$-aryl, $-N(alkyl)S(=O)_2$-heterocycle, $-N(alkyl)S(=O)_2NH$-aryl, $N(alkyl)S(=O)_2NH$-heterocycle, $-N(alkyl)$-aryl, $-N(alkyl)$-heterocycle, $-N(alkyl)C(=O)$-aryl, $-N(alkyl)C(=O)$-heterocycle, $-N(alkyl)C(=O)NH$-aryl, $-N(alkyl)C(=O)NH$-heterocycle, $-OC(=O)N(alkyl)$-aryl, $-OC(=O)N(alkyl)$-heterocycle, $-N(alkyl)C(=O)O$-aryl, $-N(alkyl)C(=O)O$-heterocycle, $-C(=O)N(alkyl)$-aryl, $-C(=O)N(alkyl)$-heterocycle, $-NHS(=O)_2N(alkyl)$-aryl, $NHS(=O)_2N(alkyl)$-heterocycle, $-NHC(=O)N(alkyl)$-aryl, $-NHC(=O)N(alkyl)$-heterocycle, $-N(alkyl)S(=O)_2N(alkyl)$-aryl, $-N(alkyl)S(=O)_2N(alkyl)$-heterocycle, $-N(alkyl)C(=O)N(alkyl)$-aryl, and $-N(alkyl)C(=O)N(alkyl)$-heterocycle:

with the provisos that:

(a) when $A_1$ and $A_2$ are both OH, Q is H, $CH_3$, or $-CO_2CH_3$, and $R^7$, $R^{7\prime}$, and $R^8$ are at each occurrence hydrogen, then G-L considered together are not unsubstituted phenyl, 4-chlorophenyl, 4-methoxyphenyl, or benzyl;

(b) when $A_1$ and $A_2$ are both CH, Q is H, and $R_7$ and $R_7'$ of the group Y are taken together to form phenyl, then G-L is not 4-chlorophenyl or benzyl; and (c) when Q is H, Y is $-CH_2-CH_2-$, $R^7$, $R^{7\prime}$, and $R^8$ are at each occurrence hydrogen, then G-L- is not 4-chlorophenyl when (i) $A_1$ and $A_2$ are both $C-CH_3$; and (ii) when A1 is C-isopropyl and $A_2$ is $C-CH_3$.

2. The compound according to claim 1, or a pharmaceutically acceptable salt thereof, wherein, Y is $(CH_2)_n$ and n=1 or 2;

Q is H, alkyl or substituted alkyl;

L is a bond;

$R^1$ and $R^{1\prime}$ are each independently H, alkyl or substituted alkyl, alkenyl or substituted alkenyl, cycloalkyl or substituted cycloalkyl, heterocyclo or substituted heterocyclo, and/or aryl or substituted aryl;

$R^2$ is alkyl or substituted alkyl, alkenyl or substituted alkenyl, cycloalkyl or substituted cycloalkyl, heterocyclo or substituted heterocyclo, or aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, $-C(=O)R^1$, $-C(=O)OR^1$, $-C(=O)NHR^1$, $-SO_2R^1$ or $-SO_2NR^1R^{1\prime}$;

$R^5$ is alkyl or substituted alkyl, cycloalkyl or substituted cycloalkyl, heterocyclo or substituted heterocyclo, aryl or substituted aryl, $-C(=O)R^1$, $-SO_2R^1$, or $-SO_2NR^1R^{1\prime}$;

$R^7$ and $R^{7\prime}$ are independently at each occurrence H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, $OR^1$, —NHR⁴, —NR²R⁵, —C(=O)R¹, —OC(=O)R¹, —C(=O)OR¹, —C(=O)NR¹R¹', —SO₂R¹, and/or —SO₂NR¹R¹'; and R⁹ is selected from H, alkyl or substituted alkyl, alkenyl or substituted alkenyl, cycloalkyl or substituted cycloalkyl, heterocyclo or substituted heterocyclo, aryl or substituted aryl, CN, OR¹, —C(=O)R¹, C(=O)NR¹R¹, SO₂R¹, and —SO₂NR¹R¹'.

3. The compound according to claim 1, or a pharmaceutically acceptable salt thereof, having the formula (Ia):
wherein,
G is a di-substituted or tri-substituted phenyl or napthyl group;
Q is H, alkyl or substituted alkyl;
R¹ and R¹ are each independently H, alkyl or substituted alkyl, alkenyl or substituted alkenyl, cycloalkyl or substituted cycloalkyl, heterocyclo or substituted heterocyclo, and/or aryl or substituted aryl;
R² is alkyl or substituted alkyl, alkenyl or substituted alkenyl, cycloalkyl or substituted cycloalkyl, heterocyclo or substituted heterocyclo, or aryl or substituted aryl;
R⁴ is H, alkyl or substituted alkyl, alkenyl or substituted alkenyl, cycloalkylalkyl or substituted cycloalkylalkyl, arylalkyl or substituted arylalkyl, —C(=O)R¹, —C(=O)OR¹, C(=O)NHR¹, —SO₂R¹ or —SO₂NR¹R¹';
R⁵ is alkyl or substituted alkyl, cycloalkyl or substituted cycloalkyl, heterocyclo or substituted heterocyclo, aryl or substituted aryl, —C(=O)R¹, —SO₂R¹, or —SO₂NR¹R¹';
R⁷ and R⁷' are independently at each occurrence H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, OR¹, —NHR⁴, —NR²R⁵, —C(=O)R¹, —OC(=O)R¹, —C(=O)OR¹, —C(=O)NR¹R¹', —SO₂R¹, and/or —SO₂NR¹R¹'; and
R⁹ is selected from H, alkyl or substituted alkyl, alkenyl or substituted alicenyl, cycloalkyl or substituted cycloalkyl, heterocyclo or substituted heterocyclo, aryl or substituted aryl, CN, OR¹, —C(=O)R¹, C(=O)NR¹R¹', SO₂R¹, and —SO₂NR¹R¹'.

4. A compound according to claim 3, or a pharmaceutically acceptable salt thereof, wherein,
at least one of A₁ and A₂ is C(alkyl) or C(substituted alkyl); and
Y is (CR⁷R⁷')ₙ wherein n=1.

5. The compound according to claim 4, or a pharmaceutically acceptable salt thereof, wherein,
G is

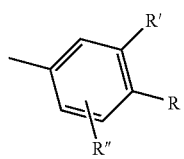

wherein R, R' and R" are independently hydrogen, trifluoromethyl, methyl, halogen, cyano, nitro, OH, O(alkyl), alkyl, and/or cycloalkyl.

6. The compound according to claim 1, or a pharmaceutically acceptable salt thereof, havIng the formula (lb),
wherein,
G is a di-substituted or tri-substituted phenyl or napthyl group;
Q is H, alkyl or substituted alkyl;
R¹ and R¹' are each independently H, alkyl or substituted alkyl, alkenyl or substituted alkenyl, cycloalkyl or substituted cycloalkyl, heterocyclo or substituted heterocyclo, and/or aryl or substituted aryl;
R² is alkyl or substituted alkyl, alkenyl or substituted alkenyl, cycloalkyl or substituted cycloalkyl, heterocyclo or substituted heterocyclo, or aryl or substituted aryl;
R⁴ is H, alkyl or substituted alkyl, alkenyl or substituted alkenyl, cycloalkylalkyl or substituted cycloalkylalkyl, arylalkyl or substituted arylalkyl, —C(=O)R¹, —C(=O)OR¹, —C(0)NHR¹, —SO₂R¹ or —SO₂NR¹R¹';
R⁵ is alkyl or substituted alkyl, cycloalkyl or substituted cycloalkyl, heterocyclo or substituted heterocyclo, aryl or substituted aryl, —C(=O)R¹, —SO₂R¹, or —SO₂NR¹R¹'; and
R⁷ and R⁷' are at each occurrence independently H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, OR¹, —NHR⁴, —NR²R⁵, —C(=O)R¹, —OC(=O)R¹, —C(=O)OR¹, —C(=O)NR¹ R¹', —SO₂R¹, and/or —SO₂NR¹R¹'.

7. The compound according to claim 6, or a pharmaceutically acceptable salt thereof, wherein,
A₁ and A₂ are independently CH, C(alkyl) and/or C(substituted alkyl); and
Y is (CR⁷R⁷')ₙ wherein n=1.

8. The compound according to claim 6, or a pharmaceutically acceptable salt thereof, wherein A₁ and A₂ are independently CH and/or CCH₃.

9. The compound according to claim 8, or a pharmaceutically acceptable salt thereof, wherein,
G is

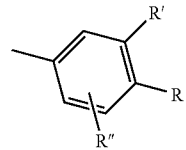

wherein R, R' and R" are independently hydrogen, trifluoromethyl, methyl, halogen, cyano, nitro, OH, O(alkyl), alkyl, and/or cycloalkyl.

10. A compound selected from (i) the group consisting of: (5S,8S,8aR)-4-[Octahydro-7-[(1,1-dimethylethoxy)carbonyl]-1,3-dioxo-5,8-methanoimidazo[1,5-a]pyrazin-2-yl]-2-(trifluoromethyl)benzonitrile; (5R,8R,8aR)-4-[Octahydro-7-[(1,1-dimethylethoxy)carbonyl]-1,3-dioxo-5,8-methanoimidazo[1,5-a]pyrazin-2-yl]-2-(trifluoromethyl) benzonitrile; (5S-(5α,8α,8aα)]-4-(Hexahydro-1,3-dioxo-5,8-methanoimidazo[1,5-a]pyrazin-2(3H)-yl)-2-(trifluoromethyl)benzonitrile; (5R,8R,8aR)-4-[Octahydro-7-[(1,1-dimethylethoxy)carbonyl]-1,3-dioxo-5,8-methanoimidazo[1,5-a]pyrazin-2-yl]-2-(trifluoromethyl) benzonitrile; (5S,8S,8aR)-4-[Octahydro-7-[(1,1-dimethylethoxy)carbonyl]-1,3-dioxo-5,8-methanoimidazo

[1,5-a]pyrazin-2-yl]-2-(trifluoromethyl)benzonitrile; [5S-(5α,8α,8aα)]Hexahydro-2-(4-nitro-1-naphthalenyl)-1,3-dioxo-5,8-methanoimidazo[1,5-a]pyrazine-7(8H)-carboxylic acid, 1,1-dimethylethyl ester; [5S-(5α,8α,8aα)]-Tetrahydro-2-(4-nitro-1-naphthalenyl)-5,8 methanoimidazo [1,5-a]pyrazine-1,3(2H,5H)-dione; [5S-(5α,8α,8aα)]-7-[(4-Fluorophenyl)sulfonyl]tetrahydro-2-(4-nitro-1-naphthalenyl)-5,8-methanoimidazo[1,5-a]pyrazine-1,3(2H,5H)-dione; [5S-(5α,8α,8aα)]-2-[4-Cyano-3-(trifluoromethyl)phenyl]hexahydro-8a-methyl-1,3-dioxo-5, 8-methanoimidazo[1,5-a]pyrazine-7(8H)-carboxylic acid, 1,1-dimethylethyl-ester; [5S-(5α,8α,8aα)]-4-(Hexahydro-1, 4-dioxo-8a-methyl-5,8-methanoimidazo [1,5-a]pyrazin-2 (3H)-yl)-2-(trifluoromethyl)benzonitrile; [5S-(5α,8α,8aα)]-4-(7-Benzoylhexahydro-8a-methyl-1,3-dioxo-5,8-methanoimidazo[1,5-a]pyrazin-2(3H)-yl)-2-(trifluoromethyl)benzonitrile; [5S-(5α,8α,8aα)]-7-(4-Fluorobenzoyl)tetrahydro-2-(4-nitro-1-naphthalenyl)-5,8-methanoimidazo[1,5-a]pyrazine-1,3(2H,5H)-dione; [5S-(5α,8α,8aα)]-2-(4-Cyano-1-naphthalenyl)tetrahydro-7-(5-isoxazolylcarbonyl)-5,8-methanoimidazo[1,5-a]pyrazine-1,3(2H,5H)-dione (1 02A), [5S-(5α,8α,8aα)]-2-(4-Cyano-1-naphthalenyl)hexahydro-1,3-dioxo-5,8-methanoimidazo[1, 5-a]pyrazine-7(8H)-carboxylic acid, 4-fluorophenyl ester (102B), [5S-(5a8a,8a,a)]-2-(4-Cyan-1-naphthalenyl)tetrahydro-7-[(1-methyl-1H-imidazol-4-yl)sulfonyl]-5,8-methanoimidazo[1,5-a]pyrazine-1,3(2H,5H)-dione (102C); [5S-(5α, 8α,8aα)]-2-(4-Cyano-1-naphthalenyl)-N-(4-fluorophenyl) hexahydro-1,3-dioxo-5,8-methanoimidazo[1,5-a]pyrazine-7 (8H)-carboxamide; [5S-(5α,8α,8aβ)]-Tetrahydro-2-(4-nitro-1-naphthalenyl)-7-(phenylmethyl)-5,8-methanoimidazo[1,5-a]pyrazine-1,3(2H,5H)-dione; [5R-(5α,8α,8aα)]-2-[4-Cyano-3-(trifluoromethyl)phenyl] hexahydro-1,3-dioxo-5,8-methanoimidazo[1,5-a] pyrazine-7(8H)-carboxylic acid, 1,1-dimethylethyl ester; [5R-(5α,8α, 8aα)]-Hexahydro-2-(4-nitro-1-naphthalenyl)-1,3-dioxo-5,8-methanoimidazo[1,5-a]pyrazine-7(8H) -carboxylic acid, 1,1-dimethylethyl ester; [5R-(5α,8α,8aα)]-Tetrahydro-2-(4-nitro-1-naphthalenyl)-5,8-methanoimidazo[1,5-a]pyrazine-1,3(2H,5H)-dione; [5R-(5α,8α,8aα)]-4-(Hexahydro-1,3-dioxo-5,8-methanoimidazo[1,5-a]pyrazin-2(3H)-yl)-2-(trifluoromethyl)benzonitrile; [5S-(5α,8α,8aα)]-4-(7-Benzoylhexahydro-1,3-dioxo-5,8-methanoimidazo[1,5-a] pyrazin-2(3H)-yl)-2-(trifluoromethyl)benzonitrile; [5S-(5α, 8α,8aα)]-2-[4-Cyano-3-(trifluoromethyl)phenyl] hexahydro-1,3-dioxo-5,8-methanoimidazo[1,5-a]pyrazine-7 (8H)-carboxylic acid, phenylmethyl ester; [5S-(5α,8α,8aα)]-4-(Hexahydro-7-methyl-1,3-dioxo-5,8-methanoimidazo[1, 5-a]pyrazin-2(3H)-yl)-2-(trifluoromethyl)benzonitrile; [5S-(5α,8α,8aα)]-7-Benzoyltetrahydro-2-(4-nitro-1-naphthalenyl)-5,8-methanoimidazo [1,5-a]pyrazine-1,3(2H, 5H)-dione; [5S-(5α,8α,8aα)]-Hexahydro-2-(4-nitro-1-naphthalenyl)-1,3-dioxo-5,8-methanoimidazo[1,5-a] pyrazine-7(8H) -carboxylic acid, phenylmethyl ester; [5S-(5α,8α,8aα)]-Tetrahydro-2-(4-nitro-1-naphthalenyl)-7-(2-propenyl)-5,8-methano-imidazo[1,5-a]pyrazine-1,3(2H, 5H)-dione; [5S-(5α,8α,8aα)]-4-[Hexahydro-dioxo-7-(phenylmethyl)-5,8-methanoimidazo[1,5-a]pyrazin-2(3H)-yl]-2-(trifluoromethyl)benzonitrile; [5R-(5α,8α,8aα)]-Tetrahydro-2-(4-nitro-1-naphthalenyl)-7-(2-propenyl)-5,8-methanoimidazo[1,5-a]pyrazine-1,3(2H,5H)-dione; [5R-(5α,8α,8aα)]-7-[(4-Fluorophenyl)sulfonyl]tetrahydro-2-(4-nitro-1-naphthalenyl)-5,8-methanoimidazo[1,5-a]pyrazine-1,3(2H,5H)-dione; [5R-(5α,8α,8aα)]-7-Benzoyltetrahydro-2-(4-nitro-1-naphthalenyl)-5,8-methanoimidazo[1,5-a]pyrazine-1,3(2H,5H)-dione; [5S-(5α,8α,8aα)]-Tetrahydro-2-(4-nitro-1-naphthalenyl)-7-[(phenylmethyl)sulfonyl]-5,8-methanoimidazo[1,5-a]pyrazine-1,3(2H,5H)-dione; [5S-(5α,8α,8aα)]-Tetrahydro-2-(4-nitro-1-naphthalenyl)-7-(phenylacetyl)-5,8-methanoimidazo[1,5-a]pyrazine-1,3(2H, 5H)-dione; [5S-(5α,8α,8aα)]-Tetrahydro-2-(4-nitro-1-naphthalenyl)-7-(3-phenyl-1-oxopropyl)-5,8-methanoimidazo[1,5-a]pyrazine-1,3(2H,5H)-dione; [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester; [5S-(5α,8α,8aα)]-4-(Hexahydro-1,3-dioxo-5,8-methanoimidazo[1,5-a] pyrazin-2(3H)-yl)-1-naphthalenecarbonitrile; [5S-(5α,8α, 8aα)]-4-[Hexahydro-7-(2-methyl-1-oxopropyl)-1,3-dioxo-5,8-methanoimidazo[1,5-a]pyrazin-2(3H)-yl]-1-naphthalenecarbonitrile; [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 1,1-dimethylethyl ester; [5S-(5α,8α,8aα)]-4-(Hexahydro-1,3-dioxo-5,8-methanoimidazo[1,5-a]pyrazin-2(3H)-yl-2-iodobenzonitrile; [5S-(5α,8α,8aα)]-7-Acetyltetrahydro-2-(4-nitro-1-naphthalenyl)-5,8-methanoimidazo[1,5-a]pyrazine-1,3(2H,5H)-dione; [5S-(5α,8α,8aα)]-Tetrahydro-7-(2-methyl-1-oxopropyl)-2-(4-nitro-1-naphthalenyl)-5,8-methanoimidazo [1,5-a]pyrazine-1,3(2H,5H)-dione; [5S-(5α,8α,8aα)]-7-[4-Fluoro-3-(trifluoromethyl)-benzoyl]tetrahydro-2-(4-nitro-1-naphthalenyl)-5,8-methanoimidazo[1,5-a]pyrazine-1,3 (2H,5H)-dione; [5S-(5α,8α,8aα)]-7-(4-Chloro-3-nitrobenzoyl)tetrahydro-2-(4-nitro-1-naphthalenyl)-5,8-methanoimidazo[1,5-a]pyrazine-1,3(2H,5H)-dione; [5S-(5α,8α,8aα)]-Tetrahydro-7-(5-isoxazolylcarbonyl)-2-(4-nitro-1-naphthalenyl)-5,8-methanoimidazo[1,5-a]pyrazine-1,3(2H,5H)-dione; [5S-(5α,8α,8aα)]-7-(4-Butylbenzoyl)tetrahydro-2-(4-nitro-1-naphthalenyl)-5,8-methanoimidazo [1,5-a]pyrazine-1,3(2H,5H)-dione; [5S-(5α,8α,8aα)]-N-(3-Chloro-4-fluorophenyl)-hexahydro-2-(4-nitro-1-naphthalenyl)-1,3-dioxo-5,8-methanoimidazo[1,5-a] pyrazine-7(8H)-carboxamide; [5S-(5α,8α,8aα)]-Tetrahydro-2-(4-nitro-1-naphthalenyl)-7-[4-(trifluoromethyl)benzoyl]-5,8-methanoimidazo[1,5-a] pyrazine-1,3(2H,5H)-dione; [5S-(5α,8α,8aα)]-Hexahydro-N-(1-methylethyl)-2-(4-nitro-1-naphthalenyl)-1,3-dioxo-5, 8-methanoimidazo[1,5-a]pyrazine-7(8H)-carboxamide; [5S-(5α,8α,8aα)]-N-(4-Fluorophenyl)hexahydro-2-(4-nitro-1-naphthalenyl)-1,3-dioxo-5,8-methanoimidazo[1,5-a] pyrazine-7(8H)-carboxamide; [5S-(5α,8α,8aα)]-N-[(4-Fluorophenyl)methyl]hexahydro-2-(4-nitro-1-naphthalenyl)-1,3-dioxo-5,8-methanoimidazo[1,5-a] pyrazine-7(8H)-carboxamide; [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-nitrophenyl ester; [5S-(5α,8α,8aα)]-Hexahydro-2-(4-nitro-1-naphthalenyl)-1,3-dioxo-5,8-methanoimidazo[1,5-a] pyrazine-7(8H)-carboxylic acid, 4-fluorophenyl ester; [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-(nitrophenyl)-methyl ester; [5S-(5α,8α, 8aα)]-Hexahydro-2-(4-nitro-1-naphthalenyl)-1,3-dioxo-5,8-methanoimidazo[1,5-a]pyrazine-7(8H)-carboxylic acid, butyl ester; [5S-(5α,8α,8aα)]-Tetrahydro-7-[(1-methyl-iH-imidazol-4-yl)sulfonyl]-2-(4-nitro-1-naphthalenyl)-5,8-methanoimidazo[1,5-a]pyrazine-1,3(2H,5H)-dione; [5S-(5α,8α,8aα)]-7-[(4-Chloro-3-nitrophenyl)sulfonyl]tetrahydro-2-(4-nitro-1-naphthalenyl)-5,8-methanoimidazo[1,5-a] pyrazine-1,3(2H,5H)-dione; [5S-(5α,8α,8aα)]-Tetrahydro-2-(4-nitro-1-naphthalenyl)-7-[(2,2,2-trifluoroethyl) sulfonyl]-5,8-methanoimidazo[1,5-a]pyrazine-1,3(2H,5H)-dione; [5S-(5α,8α,8aα)]-7-Acetyl-2-(4-cyano-1-naphthalenyl)tetrahydro-5,8-methanoimidazo[1,5-a]

pyrazine-1,3(2H,5H)-dione; [5S-(5α,8α,8aα)]-2-(4-Cyano-1-naphthalenyl)tetrahydro-7-(2-methyl-1-oxopropyl)-5,8-methanoimidazo[1,5-a]pyrazine-1,3(2H,5H)-dione; [5S-(5α,8α,8aα)]-2-(4-Cyano-1-naphthalenyl)-7-[4-fluoro-3-(trifluoromethyl)benzoyl]tetrahydro-5,8-methanoimidazo[1,5-a]pyrazine-1,3(2H,5H)-dione; [5S-(5α,8α,8aα)]-7-(4-Chloro-3-nitrobenzoyl)-2-(4-cyano-1-naphthalenyl)tetrahydro-5,8-methanoimidazo[1,5-a]pyrazine-1,3(2H,5H)-dione; [5S-(5α,8α,8aα)]-7-(4-Butylbenzoyl)-2-(4-cyano-1-naphthalenyl)tetrahydro-5,8-methanoimidazo[1,5-a]pyrazine-1,3(2H,5H)-dione; [5S-(5α,8α,8aα)]-N-(3-Chloro-4-fluorophenyl)-2-(4-cyano-1-naphthalenyl)hexahydro-1,3-dioxo-5,8-methanoimnidazo-[1,5-a]pyrazine-7(8H)-carboxamide; [5S-(5α,8α,8aα)]-2-(4-Cyano-1-naphthalenyl)-hexahydro-1,3-dioxo-N-[4-(trifluoromethyl)phenyl]-5,8-methanoimidazo[1,5-a]pyrazine-7(8H)-carboxamide; [5S-(5α,8α,8aα)]-2-(4-Cyano-1-naphthalenyl)-hexahydro-N-(1-methylethyl)-1,3-dioxo-5,8-methanoimidazo[1,5-a]pyrazine-7(8H)-carboxamide; [5S-(5α,8α,8aα)]-2-(4-Cyano-1-naphthalenyl)-N-[(4-fluorophenyl)methyl]hexahydro-1,3-dioxo-5,8-methanoimnidazo[1,5-a]pyrazine-7(8H)-carboxamide; [5S-(5α,8α,8αa)]-2-(4-Cyano-1-naphthalenyl)hexahydro-1,3-dioxo-5,8-methanoimidazo[1,5-a]pyrazine-7(8H)-carboxylic acid, 4-(nitrophenyl)-methyl ester; [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, butyl ester; [5S-(5α,8α,8aα)]-7-[(4-Chloro-3-nitrophenyl)sulfonyl]-2-(4-cyano-1-naphthalenyl)tetrahydro-5,8-methanoimidazo[1,5-a]pyrazine-1,3(2H,5H)-dione; [5S-(5ax8x,8a,a)]-2-(4-Cyano-1-naphthalenyl)tetrahydro-7-[(2,2,2-trifluoroethyl)sulfonyl]-5,8-methanoimidazo[1,5-a]pyrazine-1,3(2H,5H)-dione; [5S-(5α,8α,8aα)]-7-Acetyl-2-[4-cyano-3-(trifluoro-methyl)phenyl]tetrahydro-5,8-methanoimidazo[1,5-a]pyrazine-1,3(2H,5H)-dione; [5S-(5α,8α,8aα)]-2-[4-Cyano-3-(trifluoromethyl)phenyl]tetrahydro-7-(2-methyl-1-oxopropyl)-5,8-methanoimidazo[1,5-a]pyrazine-1,3(2H,5H)-dione; [5S-(5α,8α,8aα)]-2-[4-Cyano-3-(trifluoromethyl)phenyl]-7-[4-fluoro-3-(trifluoromethyl)benzoyl]-tetrahydro-5,8-methanoimidazo[1,5-a]pyrazine-1,3(2H,5H)-dione; [5S-(5α,8α,8aα)]-7-(4-Chloro-3-nitrobenzoyl)-2-[4-cyano-3-(trifluoromethyl)phenyl]tetrahydro-5,8-methanoimidazo[1,5-a]pyrazine-1,3(2H,5H)-dione; [5S-(5α,8α,8aα)]-2-[4-Cyano-3-(trifluoromethyl)phenyl]tetrahydro-7-(5-isoxazolylcarbonyl)-5,8-methano-imidazo[1,5-a]pyrazine-1,3(2H,5H)-dione; [5S-(5α,8α,8aα)]-7-(4-Butylbenzoyl)-2-[4-cyano-3-(trifluoromethyl)phenyl]tetrahydro-5,8-methanoimidazo[1,5-a]pyrazine-1,3(2H,5H)-dione; [5S-(5α,8α,8aα)]-N-(3-Chloro-4-fluorophenyl)-2-[4-cyano-3-(trifluoromethyl)phenyl]hexahydro-1,3-dioxo-5,8-methanoimidazo[1,5-a]pyrazine-7(8H)-carboxamide; [5S-(5α,8α,8aα)]-2-[4-Cyano-3-(trifluoromethyl)phenyl]-hexahydro-1,3-dioxo-N-[4-(trifluoromethyl)phenyl]-5,8-methanoimidazo[1,5-a]pyrazine-7(8H)-carboxamide; [5S-(5α,8α,8aα)]-2-[4-Cyano-3-(trifluoromethyl)-phenyl]hexahydro-N-(1-methylethyl)-1,3-dioxo-5,8-methanoimidazo[1,5-a]pyrazine-7(8H)-carboxamide; [5S-(5α,8α,8aα)]-2-[4-Cyano-3-(trifluoromethyl)phenyl]-N-(4-fluorophenyl)hexahydro-1,3-dioxo-5,8-methanoimidazo[1,5-a]pyrazine-7(8H)-carboxamide; [5S-(5α,8α,8aα)]-2-[4-Cyano-3-(trifluoromethyl)phenyl]-N-[(4-fluorophenyl)methyl]hexahydro-1,3-dioxo-5,8-methanoimidazo[1,5-a]pyrazine-7(8H)-carboxamide; [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-nitrophenyl ester; [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-fluorophenyl ester; [5S-(5α,8α,8aα)]-2-[4-Cyano-3-(trifluoromethyl)phenyl]-hexahydro-1,3-dioxo-5,8-methanoimidazo[1,5-a]pyrazine-7(8H)-carboxylic acid, 4-(nitrophenyl)methyl ester; [5S-(5α,8α,8aα)]-2-[4-Cyano-3-(trifluoromethyl)-phenyl]hexahydro-1,3-dioxo-5,8-methanoimidazo[1,5-a]pyrazine-7(8H)-carboxylic acid, butyl ester; [5S-(5α,8α,8aα)]-2-[4-Cyano-3-(trifluoromethyl)phenyl]tetrahydro-7-[(1-methyl-iH-imidazol-4-yl)sulfonyl]-5,8-methanoimidazo[1,5-a]pyrazine-1,3(2H,5H)-dione; [5S-(5α,8α,8aα)]-7-[(4-Chloro-3-nitrophenyl)sulfonyl]-cyano-3-(trifluoromethyl)phenyl]tetrahydro-5,8-methanoimidazo[1,5-a]pyrazine-1,3(2H,5H)-dione; [5S-(5α,8α,8aα)]-2-[4-Cyano-3-(trifluoromethyl)-phenyl]tetrahydro-7-[(2,2,2-trifluoroethyl)sulfonyl]-5,8-methanoimidazo[1,5-a]pyrazine-1,3(2H,5H)-dione; [5S-(5α,8α,8aα)]-7-Acetyl-2-(4-cyano-3-iodophenyl)tetrahydro-5,8-methanoimidazo[1,5-a]pyrazine-1,3(2H,5H)-dione; [5S-(5α,8α,8aα)]-2-(4-Cyano-3-iodophenyl)tetrahydro-7-(2-methyl-1-oxopropyl)-5,8-methanoimidazo[1,5-a]pyrazine-1,3(2H,5H)-dione; [5S-(5α,8α,8aα)]-2-(4-Cyano-3-iodophenyl)-7-[4-fluoro-3-(trifluoromethyl)benzoyl]tetrahydro-5,8-methanoimidazo[1,5-a]pyrazine-1,3(2H,5H)-dione; [5S-(5α,8α,8aα)]-7-(4-Chloro-3-nitrobenzoyl)-2-(4-cyano-3-iodophenyl)tetrahydro-5,8-methanoimidazo[1,5-a]pyrazine-1,3(2H,5H)-dione; [5S-(5α,8α,8aα)]-2-(4-Cyano-3-iodophenyl)tetrahydro-7-(5-isoxazolylcarbonyl)-5,8-methanoimidazo[1,5-a]pyrazine-1,3(2H,5H)-dione; [5S-(5α,8α,8aα)]-7-(4-Butylbenzoyl)-2-(4-cyano-3-iodophenyl)tetrahydro-5,8-methanoimidazo[1,5-a]pyrazine-1,3(2H,5H)-dione; [5S-(5α,8α,8aα)]-N-(3-Chloro-4-fluorophenyl)-2-(4-cyano-3-iodophenyl)hexahydro-1,3-dioxo-5,8-methanoimidazo[1,5-a]pyrazine-7(8H)-carboxamide; [5S-(5α,8α,8aα)]-2-(4-Cyano-3-iodophenyl)hexahydro-1,3-dioxo-N-[4-(trifluoromethyl)phenyl]-5,8-methanoimidazo[1,5-a]pyrazine-7(8H)-carboxamide; [5S-(5α,8α,8aα)]-2-(4-Cyano-3-iodophenyl)hexahydro-N-(1-methylethyl)-1,3-dioxo-5,8-methanoimidazo[1,5-a]pyrazine-7(8H)-carboxamide; [5S-(5α,8α,8aα)]-2-(4-Cyano-3-iodophenyl)-N-(4-fluorophenyl)hexahydro-1,3-dioxo-5,8-methanoimidazo[1,5-a]pyrazine-7(8H)-carboxamide; [5S-(5α,8α,8aα)]-2-(4-Cyano-3-iodophenyl)-N-[(4-fluorophenyl)methyl]hexahydro-1,3-dioxo-5,8-methanoimidazo[1,5-a]pyrazine-7(8H)-carboxamide; [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 4-nitrophenyl ester; [5S-(5α,8α,8aα)]-2-(4-Cyano-3-iodophenyl)hexahydro-1,3-dioxo-5,8-methano-imidazo[1,5-a]pyrazine-7(8H)-carboxylic acid, 4-fluorophenyl ester; [5S-(5α,8α,8aα)]-2-(4-Cyano-3-iodophenyl)hexahydro-1,3-dioxo-5,8-methano-imidazo[1,5-a]pyrazine-7(8H)-carboxylic acid, (4-nitrophenyl)methyl ester; [5S-(5α,8α,8aα)]-2-(4-Cyano-3-iodophenyl)hexahydro-1,3-dioxo-5,8-methanoimidazo[1,5-a]pyrazine-7(8H)-carboxylic acid, butyl ester; [5S-(5α,8α,8aα)]-2-(4-Cyano-3-iodophenyl)tetrahydro-7-[(1-methyl-iH-imidazol-4-yl)sulfonyl]-5,8-methanoimidazo[1,5-a]pyrazine-1,3(2H,5H)-dione; [5S-(5a,88a,a)]-7-[(4-Chloro-3-nitrophenyl)sulfonyl]-2-(4-cyano-3-iodophenyl)tetrahydro-5,8-methanoimidazo[1,5-a]pyrazine-1,3(2H,5H)-dione; [5S-(5α,8α,8aα)]-2-(4-Cyano-3-iodophenyl)tetrahydro-7-(methylsulfonyl)-5,8-methanoimidazo[1,5-a]pyrazine-1,3(2H,5H)-dione; [5S-(5α,8α,8aα)]-4-(Hexahydro-1,3-dioxo-5,8-methanoimidazo[1,5-a]pyrazin-2(3H)-yl)-2-(trifluoromethyl)benzonitrile; [5R-(5α,8α,8aα)]-

Hexahydro-2-(4-nitro-1-naphthalenyl)-1,3-dioxo-5,8-methanoimidazo[1,5-a]pyrazine-7(8H)-carboxylic acid, 1,1-dimethylethyl ester; [5S-(5α,8α,8α)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester; [5S-(5α,8α,8aα)]-Tetrahydro-2-(4-nitro-1-naphthalenyl)-5,8-methanoimidazo[1,5-a]pyrazine-1,3(2H,5H)-dione, trifluoroacetate; [5R-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester; [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester; [5R-(5α,8α,8aβ)]-4-(Hexahydro-1,3-dioxo-5,8-methanoimidazo[1,5-a]pyrazin-2(1H)-yl)-2-(trifluoromethyl)benzonitrile; [5S-(5α,8α,8aβ)]-4-(7-Benzoylhexahydro-1,3-dioxo-5,8-methanoimidazo[1,5-a]pyrazin-2(3H)-yl)-2-(trifluoromethyl)benzonitrile; [5S-(5α,8α,8aβ)]-7-Benzoyltetrahydro-2-(4-nitro-1-naphthalenyl)-5,8-methanoimidazo[1,5-a]pyrazine-1,3(2H,5H)-dione; [5S-(5α,8α,8aβ)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester; [5S-(5α,8α,8aβ)]-2-(4-Cyano-3-iodophenyl)hexahydro-1,3-dioxo-5,8-methano-imidazo[1,5-a]pyrazine-7(8H)-carboxylic acid, 1,1-dimethylethyl ester; and [5S-(5α,8α,8aβ)]-2-(3,5-Dichlorophenyl)hexahydro-1,3-dioxo-5,8-methanoimidazo[1,5-a]pyrazine-7(8H)-carboxylic acid, 1,1-dimethylethyl ester; or (ii) a pharmaceutically acceptable salt thereof.

11. A compound having the formula (Ia*) or (Ib*),

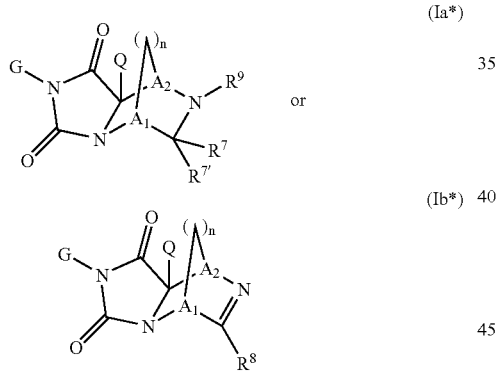

or a pharmaceutically acceptable salt thereof;

wherein the symbols have the following meanings and are, for each occurrence, independently selected:

G is an aryl, substituted aryl, heterocyclo group, or substituted heterocyclo group, where said group is mono- or polycyclic, provided that G is not 4-chiorophenyl;

$A_1$ is $CR^7$;

$A_2$ is $CR^7$;

Q is H, alkyl or substituted alkyl;

$R^1$ and $R^{1'}$ are each independently H, alkyl or substituted alkyl, alkenyl or substituted alkenyl, cycloalkyl or substituted cycloalkyl, heterocyclo or substituted heterocyclo, and/or aryl or substituted aryl;

$R^2$ is alkyl or substituted alkyl, alkenyl or substituted alkenyl, cycloalkyl or substituted cycloalkyl, heterocyclo or substituted heterocyclo, or aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2R^1$ or —SO$_2$N$R^1R^{1'}$;

$R^5$ is alkyl or substituted alkyl, cycloalkyl or substituted cycloalkyl, heterocyclo or substituted heterocyclo, aryl or substituted aryl, —C(=O)$R^1$, —SO$_2R^1$, or —SO$_2$N$R^1R^{1'}$;

$R^7$ and $R^{7'}$ are independently at each occurrence H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, O$R^1$, —NH$R^4$, —N$R^2R^5$, —C(=O)$R^1$, —OC(=O)$R^1$, —C(=O)O$R^1$, —C(=O)N$R^1R^{1'}$, —SO$_2R^1$, and/or —SO$_2$N$R^1R^{1'}$, provided, however, that every group $R^7$, $R^{7'}$ is not simultaneously hydrogen;

$R^8$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, O$R^1$, nitro, NH$R^4$, —N$R^2R^5$, —NHO$R^1$, alkylthio or substituted alkylthio, —C(=O)$R^1$, —OC(=O)$R^1$, —C(=O)O$R^1$, —PO$_3R^1R^{1'}$, —C(=O)N$R^1R^{1'}$, —C(=O)S$R^1$, —C(=O)NHSO$_2R^1$, —SO$R^1$, —SO$_2R^1$, —SO$_2$O$R^1$, or —SO$_2$N$R^1R^{1'}$;

$R^9$ is selected from H, alkyl or substituted alkyl, alkenyl or substituted alkenyl, cycloalkyl or substituted cycloalkyl, heterocyclo or substituted heterocyclo, aryl or substituted aryl, ON, O$R^1$, —C(=O)$R^1$, C(=O)N$R^1R^{1'}$, —SO$_2R^1$, and SO2N$R^1R^{1'}$; and n=1 or 2;

wherein substituted alkyl, substituted cycloalkyl, substituted cycloalkylalkyl, substituted alkenyl, substituted cycloalkenyl, substituted cycloalkenylalkyl, substituted alkynyl, substituted arylalkyl, substituted heterocycloalkyl, and substituted alkylthio are substituted with one or more substituents selected from alkyl, halo, alkoxy, alkylthio, hydroxy, —C(=O)OH, alkoxycarbonyl, alkylcarbonyloxy, —NH$_2$, carbamoyl, carbamate, urea, amidinyl, thiol, aryl, heterocycle, cycloalkyl, heterocycloalkyl, —S-aryl, —S-heterocycle, —S(=O)-aryl, —S(=O)-heterocycle, —S(=O)$_2$-aryl, —S(=O)$_2$-heterocycle, —NHS(=O)$_2$-aryl, —NHS(=O)$_2$-heterocycle, —NHS(=O)$_2$NH-aryl, —NHS(=O)$_2$NH-heterocycle, —O-aryl, —O-heterocycle, —NH-aryl, —NH-heterocycle, —NHC(=O)-aryl, —NHC(=O)-heterocycle, —OC(=O)-aryl, —OC(=O)-heterocycle, —NHC(=O)NH-aryl, —NHC(=O)NH-heterocycle, —OC(=O)O-aryl, —OC(=O)O-heterocycle, —OC(=O)NH-aryl, —OC(=O)NH-heterocycle, —NHC(=O)O-aryl, —NHC(=O)O—N(alkyl)S(=O)$_2$-aryl, —N(alkyl)S(=O)$_2$-heterocycle, —N(alkyl)S(=O)$_2$NH-aryl, N(alkyl)S(=O)$_2$NH-heterocycle, —N(alkyl)-aryl, —N(alkyl)-heterocycle, —N(alkyl)C(=O)-aryl, —N(alkyl)C(=O)-heterocycle, —N(alkyl)C(=O)NH-aryl, —N(alkyl)C(=O)NH-heterocycle, —OC(=O)N(alkyl)-aryl, —OC(=O)N(alkyl)-heterocycle, —N(alkyl)C(=O)O-aryl, —N(alkyl)C(=O)O-heterocycle, —C(=O)N(alkyl)-aryl, —C(=O)N(alkyl)-heterocycle, —NHS(=O)$_2$N(alkyl)-aryl, NHS(=O)$_2$N(alkyl)-heterocycle, —NHC(=O)N(alkyl)-aryl, —N(alkyl)-heterocycle, —N(alkyl)S(=O)$_2$N(alkyl)-aryl, —N(alkyl)S(=O)$_2$N(alkyl)-heterocycle, —N(alkyl)C(=O)N(alkyl)-aryl, and —N(alkyl)C(=O)N(alkyl)-heterocycle;

wherein substituted aryl and substituted heterocyclo are substituted with one or more substituents selected from alkyl, halo, —CF$_3$, cyano, nitro, alkoxy, alkylthio, hydroxy, —C(=O)OH, alkoxycarbonyl, alkylcarbonyloxy, —NH$_2$, carbamoyl, carbamate, urea, amidinyl, thiol, aryl, heterocycle, cycloalkyl, heterocycloalkyl, —S-aryl, —S-heterocycle, —S(=O)-aryl, —S(=O)-heterocycle, —S(=O)$_2$-aryl, —S(=O)$_2$-heterocycle, —NHS(=O)$_2$-aryl, —NHS(=O)$_2$-heterocycle, —NHS(=O)$_2$NH-aryl, —NHS(=O)$_2$NH-heterocycle, —O-aryl, —O-heterocycle, —NH-aryl, —NH-heterocycle, —NHC(=O)-aryl, —NHC(=O)-heterocycle, —OC(=O)-aryl, —OC(=O)-heterocycle, —NHC(=O)NH-aryl, —NHC(=O)NH-heterocycle, —OC(=O)O-aryl, —OC(=O)O-heterocycle, —N(alkyl)S(=O)$_2$-heterocycle, —N(alkyl)S(=O)$_2$NH-aryl, N(alkyl)S(=O)$_2$NH-heterocycle, -N(alkyl)-aryl, —N(alkyl)-heterocycle, -N(alkyl)C(=O)-aryl, —N(alkyl)C(=O)-heterocycle, —N(alkyl)C(=O)NH-aryl, —N(alkyl)C(=O)NH-heterocycle, —OC(=O)N(alkyl)-aryl, —OC(=O)N(alkyl)-heterocycle, —N(alkyl)C(=O)O-aryl, —N(alkyl)C(=O)O-heterocycle, —C(=O)N(alkyl)-aryl, —C(=O)N(alkyl)-heterocycle, —NHS(=O)$_2$N(alkyl)-aryl, NHS(=O)$_2$N(alkyl)-heterocycle, —NHC(=O)N(alkyl)-aryl, —NHC(=O)N(alkyl)-heterocycle, —N(alkyl)S(=O)$_2$N(alkyl)-aryl, —N(alkyl)S(=O)$_2$N(alkyl)-heterocycle, —N(alkyl)C(=O)N(alkyl)-aryl, and —N(alkyl)C(=O)N(alkyl)-heterocycle.

12. The compound according to claim 11, wherein, G is

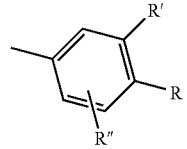

wherein R, R' and R" are selected from hydrogen, trifluoromethyl, methyl, halogen, cyano, nitro, OH, O(alkyl), alkyl, and cycloalkyl.

13. A pharmaceutical composition comprising a compound according to claim 1, and a pharmaceutically-acceptable carrier.

14. The pharmaceutical composition comprising a compound according to claim 11, and a pharmaceutically-acceptable carrier.

\* \* \* \* \*

UNITED STATES PATENT AND TRADEMARK OFFICE
CERTIFICATE OF CORRECTION

PATENT NO.       : 7,432,267 B2
APPLICATION NO.  : 11/168223
DATED            : October 7, 2008
INVENTOR(S)      : Mark E. Salvati et al.

It is certified that error appears in the above-identified patent and that said Letters Patent is hereby corrected as shown below:

In the Specification:

Col. 77, Ex. No. 121,

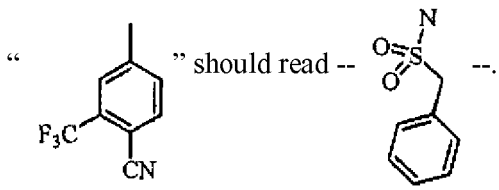

Col. 77, Ex. No. 201,

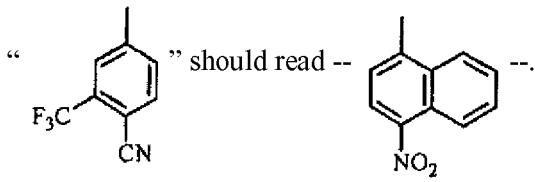

Col. 159, Ex. No. 351,

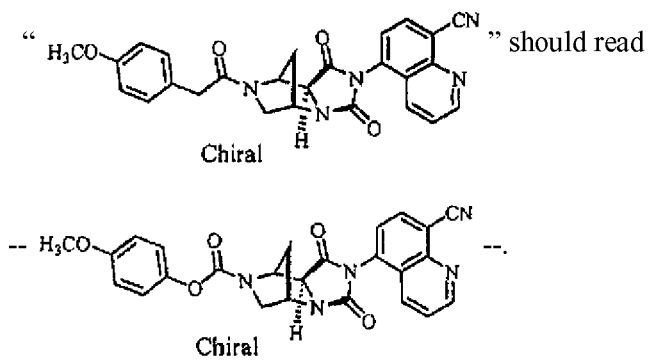

UNITED STATES PATENT AND TRADEMARK OFFICE
CERTIFICATE OF CORRECTION

PATENT NO. : 7,432,267 B2
APPLICATION NO. : 11/168223
DATED : October 7, 2008
INVENTOR(S) : Mark E. Salvati et al.

It is certified that error appears in the above-identified patent and that said Letters Patent is hereby corrected as shown below:

In the Specification:

Col. 163, Ex. No. 359,

" 359  [5$S$-(5α,8α,8aβ)]-   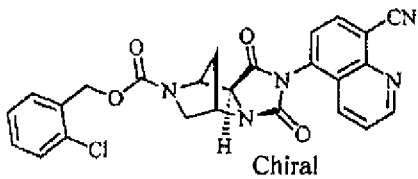   2-(8-Cyano-5-quinolinyl)- "
hexahydro-1,3-  1.57  221Cii  B
dioxo-  LCMS
5,8-  $[M+H]^+ =$
metha  488.39
noimi-
dazo[1,
5-
a]pyra-
zine-7
(1H)-
car-
boxylic
acid,
(2-
chlo-
rophe-
nyl)
methyl
ester should read -- 359  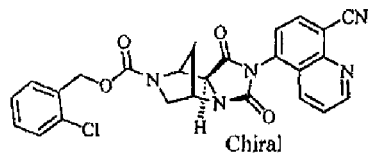  [5$S$-5α,8α,8aβ)] -2-(8-  1.57  221Cii  B --.
Cyano-5-quinolinyl)  LCMS
hexahydro-1,3-dioxo-  $[M+H]^+=$
5,8-methanoimidazo  488.39
[1,5-a]pyrazine-7(1H)-
carboxylic acid, (2-
chlorophenyl)methyl
ester.

UNITED STATES PATENT AND TRADEMARK OFFICE
CERTIFICATE OF CORRECTION

PATENT NO.      : 7,432,267 B2
APPLICATION NO. : 11/168223
DATED           : October 7, 2008
INVENTOR(S)     : Mark E. Salvati et al.

It is certified that error appears in the above-identified patent and that said Letters Patent is hereby corrected as shown below:

In the Specification:

Col. 165, Ex. No. 365,

" 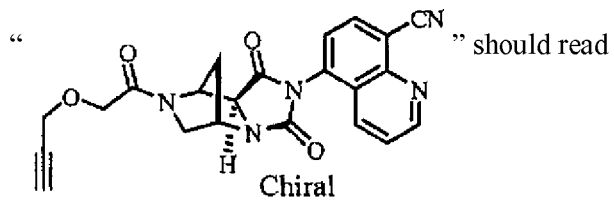 " should read

-- 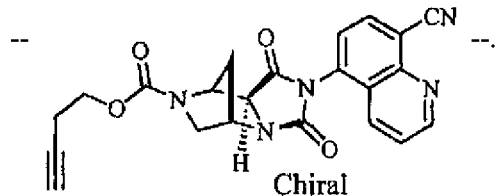 --.

Col. 167, Ex. No. 370,

" 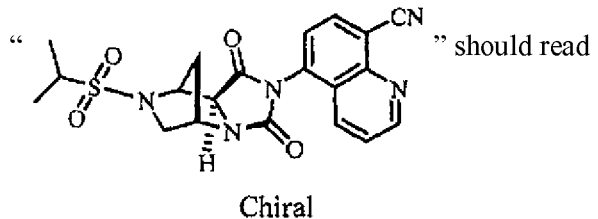 " should read

-- 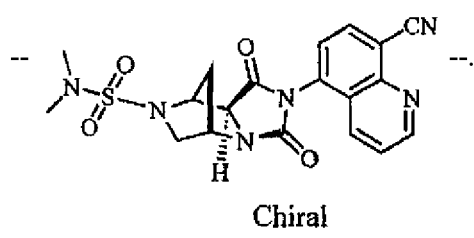 --.

UNITED STATES PATENT AND TRADEMARK OFFICE
CERTIFICATE OF CORRECTION

PATENT NO.        : 7,432,267 B2
APPLICATION NO. : 11/168223
DATED             : October 7, 2008
INVENTOR(S)       : Mark E. Salvati et al.

It is certified that error appears in the above-identified patent and that said Letters Patent is hereby corrected as shown below:

In the Specification:

Col. 187, Ex. No. 429,

" 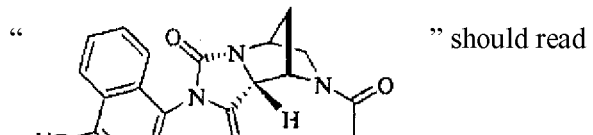 " should read

-- 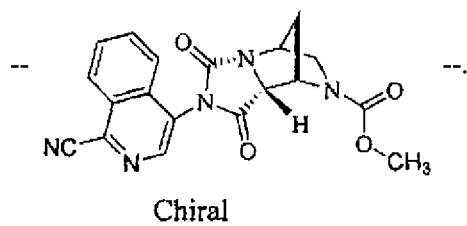 --.

Col. 203, Ex. No. 475,

" 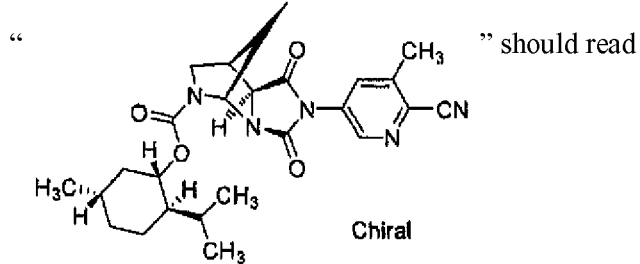 " should read

-- 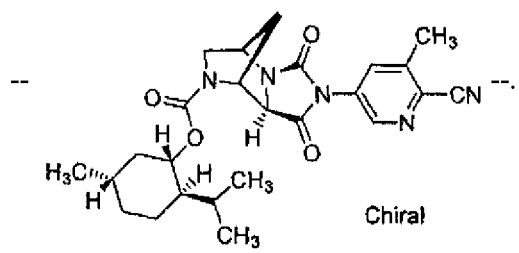 --.

UNITED STATES PATENT AND TRADEMARK OFFICE
CERTIFICATE OF CORRECTION

PATENT NO.       : 7,432,267 B2
APPLICATION NO.  : 11/168223
DATED            : October 7, 2008
INVENTOR(S)      : Mark E. Salvati et al.

It is certified that error appears in the above-identified patent and that said Letters Patent is hereby corrected as shown below:

In the Specification:

Col. 209, Ex. No. 487,

" 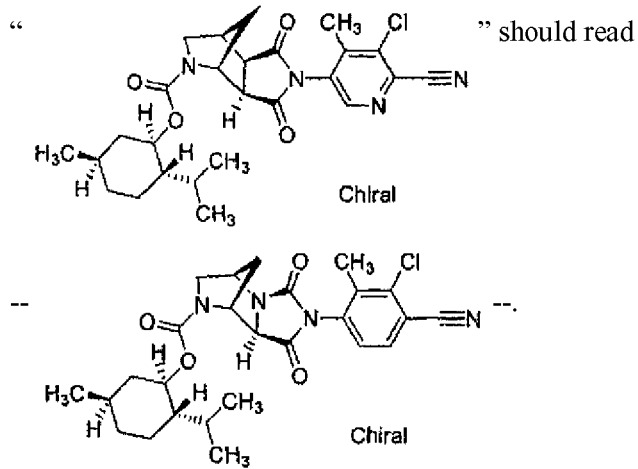 " should read

Col. 209, Ex. No. 488,

" 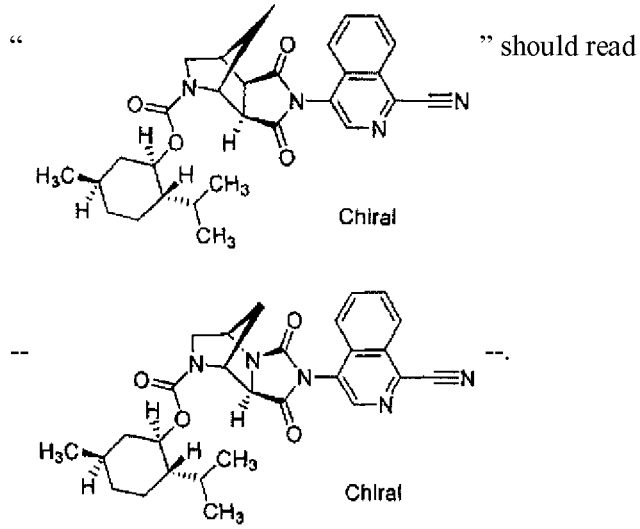 " should read

UNITED STATES PATENT AND TRADEMARK OFFICE
CERTIFICATE OF CORRECTION

| | | |
|---|---|---|
| PATENT NO. | : 7,432,267 B2 | |
| APPLICATION NO. | : 11/168223 | |
| DATED | : October 7, 2008 | |
| INVENTOR(S) | : Mark E. Salvati et al. | |

It is certified that error appears in the above-identified patent and that said Letters Patent is hereby corrected as shown below:

In the Specification:

Col. 209, Ex. No. 489,

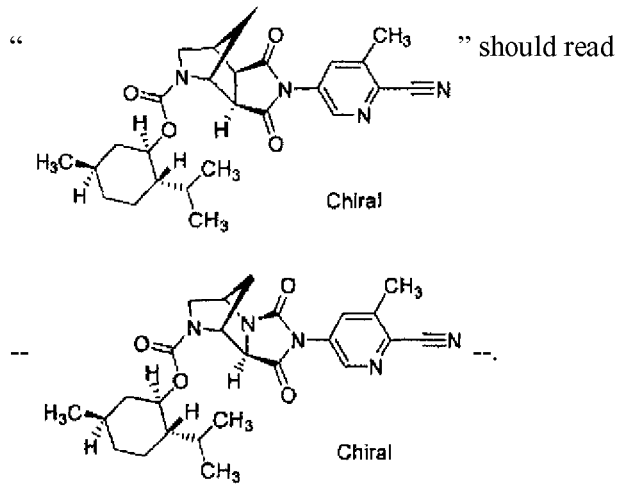

In the Claims:

Col. 211, line 45, "substituted cycloal kenyl," should read -- substituted cycloalkenyl --.

Col. 212, lines 16-17, "cycloalkylalkyl or substituted cycloal kyalkyl, cycloalkenylal kyl or substituted cycloalkenylalkyl, heterocycloal kyl or substituted heterocycloalkyl, aryl or" should read -- cycloalkylalkyl or substituted cycloalkyalkyl, cycloalkenylalkyl or substituted cycloalkenylalkyl, heterocycloalkyl or substituted heterocycloalkyl, aryl or --.

Col. 212, lines 23-25, "cycloalkylalkyl or substituted cycloal kylalkyl, cycloalkenylal kyl or substituted cycloalkenylalkyl, heterocycloal kyl or substituted heterocycloalkyl, aryl or" should read -- cycloalkylalkyl or substituted cycloalkylalkyl, cycloalkenylalkyl or substituted cycloalkenylalkyl, heterocycloalkyl or substituted heterocycloalkyl, aryl or --.

UNITED STATES PATENT AND TRADEMARK OFFICE
CERTIFICATE OF CORRECTION

PATENT NO. : 7,432,267 B2
APPLICATION NO. : 11/168223
DATED : October 7, 2008
INVENTOR(S) : Mark E. Salvati et al.

It is certified that error appears in the above-identified patent and that said Letters Patent is hereby corrected as shown below:

In the Claims:

Col. 212, line 28, "or -SO$_2$NR$^1$R$^1$;" should read -- or -SO$_2$NR$^1$R$^{1'}$; --.

Col. 212, lines 33-35, "cycloalkylalkyl or substituted cycloal kylalkyl, cycloalkenylal kyl or substituted cycloalkenylalkyl, heterocycloal kyl or substituted heterocycloalkyl, aryl or" should read -- cycloalkylalkyl or substituted cycloalkylalkyl, cycloalkenylalkyl or substituted cycloalkenylalkyl, heterocycloalkyl or substituted heterocycloalkyl, aryl or --.

Col. 212, line 49, "-SO$_2$OR1 or -SO$_2$NR$^1$R$^{1t}$;" should read -- -SO$_2$OR$^1$ or -SO$_2$NR$^1$R$^{1'}$; --.

Col. 212, line 50, "R$^7$ and R$^{7t}$ are each" should read -- R$^7$ and R$^{7'}$ are each --.

Col. 212, lines 54-55, "heterocyclo or substituted heterocyclo, cycloalkylal kyl or substituted cycloalkylal kyl, cycloalkenylal kyl or" should read -- heterocyclo or substituted heterocyclo, cycloalkylalkyl or substituted cycloalkylalkyl, cycloalkenylalkyl or --.

Col. 212, lines 61-64, "–C(=O)R$^1$, –OC(=O)R$^1$, –C(=O)OR$^1$, –PO$_3$R$^1$R$^{1t}$, –C(=O)NR$^1$ R$^{1t}$, –C(=O)SR$^1$, –C(=O)NHSO$_2$R$^1$, –SOR$^1$, –SO$_2$R$^1$, –SO$_2$OR$^1$ and/or –SO$^2$NR$^1$R$^{1t}$;" should read -- –C(=O)R$^1$, –OC(=O)R$^1$, –C(=O)OR$^1$, –PO$_3$R$^1$R$^{1'}$, –C(=O)NR$^1$R$^{1'}$, –C(=O)SR$^1$, –C(=O)NHSO$_2$R$^1$, –SOR$^1$, –SO$_2$R$^1$, –SO$_2$OR$^1$ and/or –SO$_2$NR$^1$R$^{1'}$; --.

Col. 212, line 65, "or two groups R$^7$ and R$^{7t}$attached" should read -- or two groups R$^7$ and R$^{7'}$ attached --.

Col. 213, lines 7-9, "cycloalkylalkyl or substituted cycloal kylalkyl, cycloalkenylal kyl or substituted cycloalkenylalkyl, heterocycloal kyl or substituted heterocycloalkyl, aryl or" should read -- cycloalkylalkyl or substituted cycloalkylalkyl, cycloalkenylalkyl or substituted cycloalkenylalkyl, heterocycloalkyl or substituted heterocycloalkyl, aryl or --.

UNITED STATES PATENT AND TRADEMARK OFFICE
CERTIFICATE OF CORRECTION

PATENT NO. : 7,432,267 B2
APPLICATION NO. : 11/168223
DATED : October 7, 2008
INVENTOR(S) : Mark E. Salvati et al.

It is certified that error appears in the above-identified patent and that said Letters Patent is hereby corrected as shown below:

In the Claims:

Col. 213, lines 13-15, "-$C(=O)OR^1$, -$PO_3R^1R^{1t}$, -$C(=O)NR^1R^{1t}$, -$C(=O)SR^1$, -$C(=O)NHSO_2R^1$, -$SOR^1$, -$SO_2R^1$, -$SO_2OR^1$, or -$SO_2NR^1 R^{1t}$;" should read -- -$C(=O)OR^1$, -$PO_3R^1R^{1'}$, -$C(=O)NR^1R^{1'}$, -$C(=O)SR^1$, -$C(=O)NHSO_2R^1$, -$SOR^1$, -$SO_2R^1$, -$SO_2OR^1$, or -$SO_2NR^1R^{1'}$; --.

Col. 213, lines 17-28, "substituted alkenyl, alkynyl or substituted al kynyl, cycloal kyl or substituted cycloalkyl, cycloalkenyl or substituted cycloalkenyl, heterocyclo or substituted heterocyclo, cycloal kylalkyl or substituted cycloalkylalkyl, cycloalkenylalkyl or substituted cycloalkenylalkyl, heterocycloal kyl or substituted heterocycloalkyl, aryl or substituted aryl, arylalkyl or substituted arylalkyl, CN, $OR^1$, –$C(=O)R^1$, –$C(O)OR^1$, –$C(=O)NR^1R^{1t}$, $SO_2R^1$, –$SO_2OR^1$ and –$SO_2NR^1R^{1t}$;" should read -- substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, $OR^1$, –$C(=O)R^1$, –$C(=O)OR^1$, –$C(=O)NR^1R^{1'}$, $SO_2R^1$, –$SO_2OR^1$ and –$SO_2NR^1R^{1'}$; --.

Col. 213, lines 48-49, "-N (alkyl)S(=O)$_2$-aryl, -N(alkyl)S(=O)$_2$- heterocycle, -N(alkyl)S(=O)$_2$NH-aryl," should read -- -N(alkyl)S(=O)$_2$-aryl, -N(alkyl)S(=O)$_2$-heterocycle, -N(alkyl)S(=O)$_2$NH-aryl, --.

Col. 213, lines 59-60, "-NHC(=O)N(alkyl)-heterocycle, -N(alkyl)S(=O)$_2$N(alkyl)-aryl, -N(alkyl)S(=O)$_2$N(alkyl)-heterocycle," should read -- -NHC(=O)N(alkyl)-heterocycle, -N(alkyl)S(=O)$_2$N(alkyl)-aryl, -N(alkyl)S(=O)$_2$N(alkyl)-heterocycle, --.

Col. 214, lines 30-31, "(a) when $A_1$ and $A_2$ are both OH, Q is H, $CH_3$, or –$CO_2CH_3$, and $R^7$, $R^{7t}$, and $R^8$ are at each occurrence" should read -- (a) when $A_1$ and $A_2$ are both CH, Q is H, $CH_3$, or –$CO_2CH_3$, and $R^7$, $R^{7'}$, and $R^8$ are at each occurrence --.

Col. 214, line 35, "(b) when $A_1$ and $A_2$ are both CH, Q is H, and $R_7$ and $R_7^{t}$ of" should read -- (b) when $A_1$ and $A_2$ are both CH, Q is H, and $R^7$ and $R^{7'}$ of --.

UNITED STATES PATENT AND TRADEMARK OFFICE
CERTIFICATE OF CORRECTION

PATENT NO.         : 7,432,267 B2
APPLICATION NO.    : 11/168223
DATED              : October 7, 2008
INVENTOR(S)        : Mark E. Salvati et al.

It is certified that error appears in the above-identified patent and that said Letters Patent is hereby corrected as shown below:

In the Claims:

Col. 214, lines 38-41, "(c) when Q is H, Y is -CH$_2$-CH$_2$-, R$^7$, R$^{7t}$, and R$^8$ are at each occurrence hydrogen, then G-L- is not 4-chiorophenyl when (i) A$_1$ and A$_2$ are both C-CH$_3$; and (ii) when A1 is C-isopropyl and A$_2$ is C-CH$_3$." should read -- (c) when Q is H, Y is -CH$_2$-CH$_2$-, R$^7$, R$^{7'}$, and R$^8$ are at each occurrence hydrogen, then G-L- is not 4-chlorophenyl when (i) A$_1$ and A$_2$ are both C-CH$_3$; and (ii) when A$_1$ is C-isopropyl and A$_2$ is C-CH$_3$. --.

Col. 214, line 47, "R$^1$ and R$^1$ are each independently H, alkyl or substituted" should read -- R$^1$ and R$^{1'}$ are each independently H, alkyl or substituted --.

Col. 214, line 58, "–SO$_2$R$^1$R1$^t$;" should read -- –SO$_2$NR$^1$R$^{1'}$; --.

Col. 214, line 62, "–SO$_2$NR$^1$R$^{1t}$;" should read -- –SO$_2$NR$^1$R$^{1'}$; --.

Col. 214, lines 63-64, "R$^7$ and R$^{7t}$ are independently at each occurrence H, alkyl or substituted alkyl, alkenyl or substituted al kenyl," should read -- R$^7$ and R$^{7'}$ are independently at each occurrence H, alkyl or substituted alkyl, alkenyl or substituted alkenyl, --.

Col. 215, lines 2-3, "–C(=O)OR$^1$, –C(=O)NR$^1$R$^{1t}$, –SO$_2$R$^1$, and/or –SO$_2$NR$^1$R$^{1t}$; and" should read -- –C(=O)OR$^1$, –C(=O)NR$^1$R$^{1'}$, –SO$_2$R$^1$, and/or –SO$_2$NR$^1$R$^{1'}$; and --.

Col. 215, lines 8-9, "CN, OR$^1$, –C(=O)R$^1$, C(=O)NR$^1$R$^1$, SO$_2$R$^1$, and –SO$_2$NR$^1$R$^{1t}$." should read -- CN, OR$^1$, –C(=O)R$^1$, C(=O)NR$^1$R$^{1'}$, SO$_2$R$^1$, and –SO$_2$NR$^1$R$^{1'}$. --.

Col. 215, line 13, "G is a di-substituted or tn-substituted phenyl or napthyl" should read -- G is a di-substituted or tri-substituted phenyl or napthyl --.

Col. 215, line 16, "R$^1$ and R$^1$ are each independently H, alkyl or substituted" should read -- R$^1$ and R$^{1'}$ are each independently H, alkyl or substituted --.

Col. 215, lines 27-28, "–C(O)OR$^1$, C(=O)NHR$^1$, –SO$_2$R$^1$ or –SO$_2$NR$^1$R$^{1t}$;" should read -- –C(=O)OR$^1$, –C(=O)NHR$^1$, –SO$_2$R$^1$ or –SO$_2$NR$^1$R$^{1'}$; --.

UNITED STATES PATENT AND TRADEMARK OFFICE
CERTIFICATE OF CORRECTION

PATENT NO. : 7,432,267 B2
APPLICATION NO. : 11/168223
DATED : October 7, 2008
INVENTOR(S) : Mark E. Salvati et al.

It is certified that error appears in the above-identified patent and that said Letters Patent is hereby corrected as shown below:

In the Claims:

Col. 215, line 32, "$-SO_2NR^1R^{1t}$;" should read -- $-SO_2NR^1R^{1'}$; --.

Col. 215, lines 33-34, "$R^7$ and $R^7$ are independently at each occurrence H, alkyl or substituted alkyl, alkenyl or substituted al kenyl," should read -- $R^7$ and $R^7$ are independently at each occurrence H, alkyl or substituted alkyl, alkenyl or substituted alkenyl, --.

Col. 215, lines 39-40, "$-C(=O)OR^1$, $-C(=O)NR^1R^{1t}$, $-SO_2R^1$, and/or $-SO_2NR^1R^{1t}$; and" should read -- $-C(=O)OR^1$, $-C(=O)NR^1R^{1'}$, $-SO_2R^1$, and/or $-SO_2NR^1R^{1'}$; and --.

Col. 215, line 42, "substituted alicenyl, cycloalkyl or substituted" should read -- substituted alkenyl, cycloalkyl, or substituted --.

Col. 215, lines 44-45, "or substituted aryl, CN, $OR^1$, $-C(=O)R^1$, $C(=O)NR^1R^{1t}$, $SO_2R^1$, and $-SO_2NR^1R^{1t}$." should read -- or substituted aryl, CN, $OR^1$, $-C(=O)R^1$, $C(=O)NR^1R^{1'}$, $SO_2R^1$, and $-SO_2NR^1R^{1'}$. --.

Col. 215, line 49, "at least one of $A_1$ and $A_2$ is C(alkyl) or C(substltuted alkyl);" should read -- at least one of $A_1$ and $A_2$ is C(alkyl) or C(substituted alkyl); --.

Col. 215, line 51, "Y is $(CR^7R^{7t})_n$ wherein $n = 1$." should read -- Y is $(CR^7R^{7'})_n$ wherein $n = 1$. --.

Col. 215, line 66, "methyl, halogen, cyano, nitro, OH, O(aikyl), alkyl," should read -- methyl, halogen, cyano, nitro, OH, O(alkyl), alkyl, --.

Col. 216, line 2, "acceptable salt thereof, havIng the formula (Ib)," should read -- acceptable salt thereof, having the formula (Ib), --.

Col. 216, line 7, "$R^1$ and $R^{1t}$ are each independently H, alkyl or substituted" should read -- $R^1$ and $R^{1'}$ are each independently H, alkyl or substituted --.

Col. 216, lines 17-18, "$-C(=O)OR^1$, $-C(0)NHR^1$, $-SO_2R^1$ or $-SO_2NR^1R^{1t}$;" should read -- $-C(=O)OR^1$, $-C(=O)NHR^1$, $-SO_2R^1$ or $-SO_2NR^1R^{1'}$; --.

UNITED STATES PATENT AND TRADEMARK OFFICE
CERTIFICATE OF CORRECTION

PATENT NO.       : 7,432,267 B2
APPLICATION NO.  : 11/168223
DATED            : October 7, 2008
INVENTOR(S)      : Mark E. Salvati et al.

It is certified that error appears in the above-identified patent and that said Letters Patent is hereby corrected as shown below:

In the Claims:

Col. 216, line 22, "$-SO_2NR^1R^{1t}$; and" should read -- $-SO_2NR^1R^{1'}$; and --.

Col. 216, line 23, "$R^7$ and $R^{7t}$ are at each occurrence independently H, alkyl or substituted alkyl, alkenyl or substituted al kenyl," should read -- $R^7$ and $R^{7'}$ are at each occurrence independently H, alkyl or substituted alkyl, alkenyl or substituted alkenyl, --.

Col. 216, lines 29-30, "$-C(=O)OR^1$, $-C(=O)NR^1 R^{1t}$, $-SO_2R^1$, and/or $-SO_2NR^1R^{1t}$." should read -- $-C(=O)OR^1$, $-C(=O)NR^1R^{1'}$, $-SO_2R^1$, and/or $-SO_2R^1R^{1'}$. --.

Col. 216, line 36, "Y is $(CR^7R^{7t})_n$ wherein $n = 1$." should read -- Y is $(CR^7R^{7'})_n$ wherein $n = 1$. --.

Col. 221, line 54, "polycyclic, provided that G is not 4-chiorophenyl;" should read -- polycyclic, provided that G is not 4-chlorophenyl; --.

Col. 221, line 59, "$R^1$ and $R^1$ are each independently H, alkyl or substituted" should read -- $R^1$ and $R^{1'}$ are each independently H, alkyl or substituted --.

Col. 222, lines 3 and 7, "$-SO_2NR^1R^{1t}$;" should read -- $-SO_2NR^1R^{1'}$; --.

Col. 222, line 8, "$R^7$ and $R^7$ are independently at each occurrence H, alkyl or substituted alkyl, alkenyl or substituted al kenyl," should read -- $R^7$ and $R^{7'}$ are independently at each occurrence H, alkyl or --.

Col. 222, lines 14-16, "$-C(=O)OR^1$, $-C(=O)NR^1 R^{1t}$, $-SO_2R^1$, and/or $-SO_2NR^1R^{1t}$, provided, however, that every group $R^7$, $R^{7t}$ is not simultaneously hydrogen;" should read -- $-C(=O)OR^1$, $-C(=O)NR^1R^{1'}$, $-SO_2R^1$, and/or $-SO_2NR^1R^{1'}$, provided, however, that every group $R^7$, $R^{7'}$ is not simultaneously hydrogen; --.

Col. 222, lines 21-23, "cycloalkylalkyl or substituted cycloal kylalkyl, cycloalkenylal kyl or substituted cycloalkenylalkyl, heterocycloal kyl or substituted heterocycloalkyl, aryl or" should read -- cycloalkylalkyl or substituted cycloalkylalkyl, cycloalkenylalkyl or substituted cycloalkenylalkyl, heterocycloalkyl or substituted heterocycloalkyl, aryl or --.

UNITED STATES PATENT AND TRADEMARK OFFICE
CERTIFICATE OF CORRECTION

PATENT NO. : 7,432,267 B2
APPLICATION NO. : 11/168223
DATED : October 7, 2008
INVENTOR(S) : Mark E. Salvati et al.

It is certified that error appears in the above-identified patent and that said Letters Patent is hereby corrected as shown below:

In the Claims:

Col. 222, lines 27-29, "-C(=O)OR$^1$, -PO$_3$R$^1$R$^{1t}$, -C(=O)NR$^1$R$^1$, -C(=O)SR$^1$, -C(=O)NHSO$_2$R$^1$, -SOR$^1$, -SO$_2$R$^1$, -SO$_2$OR$^1$, or -SO$_2$NR$^1$R$^{1t}$;" should read -- -C(=O)OR$^1$, -PO$_3$R$^1$R$^{1'}$, -C(=O)NR$^1$R$^{1'}$, -C(=O)SR$^1$, -C(=O)NHSO$_2$R$^1$, -SOR$^1$, -SO$_2$R$^1$, -SO$_2$OR$^1$, or -SO$_2$NR$^1$R$^{1'}$; --.

Col. 222, lines 33-34, "ON, OR$^1$, –C(=O)R$^1$, C(=O)NR$^1$R$^{1t}$, SO$_2$R$^1$, and –SO2NR$^1$R$^{1t}$; and" should read -- CN, OR$^1$, –C(=O)R$^1$, C(=O)NR$^1$R$^{1'}$, SO$_2$R$^1$, and –SO$_2$NR$^1$R$^{1'}$; and --.

Col. 222, line 37, "cycloalkylalkyl, substituted al kenyl substituted" should read -- cycloalkylalkyl, substituted alkenyl substituted --.

Col. 222, lines 48-49, "-NHS(=O)$_2$NH-aryl, -NHS(=O)$_2$ NH-heterocycle, -O-aryl, -O-heterocycle," should read -- -NHS(=O)$_2$NH-aryl, -NHS(=O)$_2$NH-heterocycle, -O-aryl, -O-heterocycle, --.

Col. 222, lines 55-56, "-NHC(=O)O-aryl, -NHC(=O)O -N(alkyl)S(=O)$_2$-aryl," should read -- -NHC(=O)O-aryl, -NHC(=O)O-heterocycle, -C(=O)NH-aryl, -C(=O)NH-heterocycle, -C(=O)O-aryl, -C(=O)O-heterocycle, -N(alkyl)S(=O)$_2$-aryl, --.

UNITED STATES PATENT AND TRADEMARK OFFICE
CERTIFICATE OF CORRECTION

PATENT NO.        : 7,432,267 B2
APPLICATION NO.   : 11/168223
DATED             : October 7, 2008
INVENTOR(S)       : Mark E. Salvati et al.

It is certified that error appears in the above-identified patent and that said Letters Patent is hereby corrected as shown below:

In the Claims:

Col. 223, lines 18-19, "-OC(=O)O-heterocycle, -N(alkyl)S(=O)$_2$-heterocycle, -N(alkyl)S(=O)$_2$NH-aryl," should read -- -OC(=O)O-heterocycle, -OC(=O)NH-aryl, -OC(=O)NH-heterocycle, -NHC(=O)O-aryl, -NHC(=O)O-heterocycle, -C(=O)NH-aryl, -C(=O)NH-heterocycle, -C(=O)O-aryl, -C(=O)O-heterocycle, -N(alkyl)S(=O)$_2$-aryl, -N(alkyl)S(=O)$_2$-heterocycle, -N(alkyl)S(=O)$_2$NH-aryl, --.

Signed and Sealed this

Second Day of June, 2009

JOHN DOLL
*Acting Director of the United States Patent and Trademark Office*